United States Patent
Bhamidipati et al.

(10) Patent No.: US 9,624,229 B2
(45) Date of Patent: Apr. 18, 2017

(54) PYRIMIDINE-2-AMINE COMPOUNDS AND THEIR USE AS INHIBITORS OF JAK KINASES

(71) Applicant: Rigel Pharmaceuticals, Inc., South San Francisco, CA (US)

(72) Inventors: Somasekhar Bhamidipati, Foster City, CA (US); Jeffrey Clough, Redwood City, CA (US); Ankush Argade, Foster City, CA (US); Rajinder Singh, Belmont, CA (US); Vadim Markovtsov, San Mateo, CA (US); Pingyu Ding, Foster City, CA (US); Jiaxin Yu, Foster City, CA (US); Andy Atuegbu, Dublin, CA (US); Hui Hong, Foster City, CA (US); Ihab Darwish, San Carlos, CA (US); Sambaiah Thota, Fremont, CA (US)

(73) Assignee: Rigel Pharmaceuticals, Inc., South San Francisco, CA (US)

(*) Notice: Subject to any disclaimer, the term of this patent is extended or adjusted under 35 U.S.C. 154(b) by 164 days.

(21) Appl. No.: 14/243,579

(22) Filed: Apr. 2, 2014

(65) Prior Publication Data
US 2014/0213585 A1     Jul. 31, 2014

Related U.S. Application Data

(60) Continuation of application No. 13/619,843, filed on Sep. 14, 2012, now Pat. No. 8,735,418, which is a division of application No. 12/371,550, filed on Feb. 13, 2009, now Pat. No. 8,309,566.

(60) Provisional application No. 61/029,265, filed on Feb. 15, 2008, provisional application No. 61/038,672, filed on Mar. 21, 2008, provisional application No. 61/112,046, filed on Nov. 6, 2008.

(51) Int. Cl.
| C07D 487/08 | (2006.01) |
| C07D 451/00 | (2006.01) |
| C07D 451/04 | (2006.01) |
| C07D 491/08 | (2006.01) |
| C07D 519/00 | (2006.01) |

(52) U.S. Cl.
CPC ......... *C07D 487/08* (2013.01); *C07D 451/00* (2013.01); *C07D 451/04* (2013.01); *C07D 491/08* (2013.01); *C07D 519/00* (2013.01)

(58) Field of Classification Search
None
See application file for complete search history.

(56) References Cited

U.S. PATENT DOCUMENTS

| 4,788,195 | A  | 11/1988 | Torley et al. |
| 4,876,252 | A  | 10/1989 | Torley et al. |
| 5,521,184 | A  | 5/1996  | Zimmermann |
| 5,728,536 | A  | 3/1998  | Ihle et al. |
| 6,080,747 | A  | 6/2000  | Uckun et al. |
| 6,080,748 | A  | 6/2000  | Uckun et al. |
| 6,093,716 | A  | 7/2000  | Davis et al. |
| 6,103,737 | A  | 8/2000  | Cocuzza et al. |
| 6,114,333 | A  | 9/2000  | Davis et al. |
| 6,133,305 | A  | 10/2000 | Tang et al. |
| 6,177,433 | B1 | 1/2001  | Uckun et al. |
| 6,210,654 | B1 | 4/2001  | Ihle et al. |
| 6,313,130 | B1 | 11/2001 | Uckun et al. |
| 6,316,635 | B1 | 11/2001 | Tang et al. |
| 6,433,018 | B1 | 8/2002  | Siddiqui et al. |
| 6,486,185 | B1 | 11/2002 | McMahon et al. |
| 6,506,763 | B2 | 1/2003  | Tang et al. |
| 6,528,509 | B1 | 3/2003  | Hale et al. |
| 6,552,029 | B1 | 4/2003  | Davis et al. |

(Continued)

FOREIGN PATENT DOCUMENTS

| WO | WO 95/03701 A1 | 2/1995 |
| WO | WO 95/10506 A1 | 4/1995 |

(Continued)

OTHER PUBLICATIONS

SHIDE. Blood, 2011, 117(25), 6866-74.*

(Continued)

*Primary Examiner* — Noble Jarrell
(74) *Attorney, Agent, or Firm* — Seed IP Law Group LLP; Travis Young

(57) ABSTRACT

This invention is directed to methods of treating diseases or conditions associated with JAK2 activity in a mammal comprising the administration of a compound of formula (I):

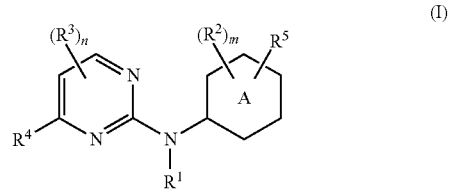

where

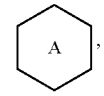

n, m, Y, $R^1$, $R^2$, $R^3$, $R^4$ and $R^5$ are disclosed herein, or a pharmaceutically acceptable salt.

8 Claims, No Drawings

(56) References Cited

U.S. PATENT DOCUMENTS

| | | |
|---|---|---|
| 6,593,357 B1 | 7/2003 | Green et al. |
| 6,600,037 B1 | 7/2003 | Davis et al. |
| 6,608,048 B2 | 8/2003 | Tsou et al. |
| 6,610,688 B2 | 8/2003 | Liang et al. |
| 6,635,651 B2 | 10/2003 | Uckun |
| 6,677,368 B2 | 1/2004 | Cui et al. |
| 6,683,082 B2 | 1/2004 | Tang et al. |
| 6,696,448 B2 | 2/2004 | Tang et al. |
| 6,699,865 B2 | 3/2004 | Hale et al. |
| 6,777,417 B2 | 8/2004 | Liang et al. |
| 6,784,195 B2 | 8/2004 | Hale et al. |
| 6,815,439 B2 | 11/2004 | Harris et al. |
| 6,825,190 B2 | 11/2004 | Moon et al. |
| 6,949,544 B2 | 9/2005 | Bethiel et al. |
| 6,949,580 B2 | 9/2005 | Hale et al. |
| 6,969,760 B2 | 11/2005 | Ihle et al. |
| 6,998,391 B2 | 2/2006 | Lyons et al. |
| 7,056,944 B2 | 6/2006 | Hale et al. |
| 7,074,793 B2 | 7/2006 | Hudkins et al. |
| 7,081,532 B2 | 7/2006 | Buerger et al. |
| 7,105,529 B2 | 9/2006 | Davis et al. |
| 7,449,458 B2 | 11/2008 | Bhamidipati et al. |
| 7,538,108 B2 | 5/2009 | Singh et al. |
| 7,557,207 B2 | 7/2009 | Cooper et al. |
| 7,563,892 B1 | 7/2009 | Singh et al. |
| 7,709,482 B2 | 5/2010 | Goff et al. |
| 7,872,000 B2 | 1/2011 | Goff et al. |
| 7,879,856 B2 | 2/2011 | Goff et al. |
| 7,884,119 B2 | 2/2011 | Singh et al. |
| 7,935,693 B2 | 5/2011 | Singh et al. |
| 8,012,965 B2 | 9/2011 | Goff et al. |
| 8,097,630 B2 | 1/2012 | Singh et al. |
| 8,168,636 B2 | 5/2012 | Goff et al. |
| 8,288,382 B2 | 10/2012 | Goff et al. |
| 8,349,838 B2 | 1/2013 | Singh et al. |
| 8,389,557 B2 | 3/2013 | Singh et al. |
| 8,431,594 B2 | 4/2013 | Singh et al. |
| 8,492,373 B2 | 7/2013 | Goff et al. |
| 8,546,433 B2 | 10/2013 | Hitoshi et al. |
| 8,563,559 B2 | 10/2013 | Singh et al. |
| 8,609,650 B2 | 12/2013 | Goff et al. |
| 8,618,331 B2 | 12/2013 | Goff et al. |
| 8,658,669 B2 | 2/2014 | Singh et al. |
| 8,741,898 B2 | 6/2014 | Goff et al. |
| 8,796,259 B2 | 8/2014 | Ding et al. |
| 8,809,364 B2 | 8/2014 | Singh et al. |
| 2001/0007033 A1 | 7/2001 | Tang et al. |
| 2002/0115173 A1 | 8/2002 | Ben-Sasson |
| 2002/0137141 A1 | 9/2002 | Ben-Sasson |
| 2003/0212269 A1 | 11/2003 | Davis et al. |
| 2003/0236244 A1 | 12/2003 | Ledford |
| 2004/0029902 A1 | 2/2004 | Singh et al. |
| 2004/0097504 A1 | 5/2004 | Bethiel et al. |
| 2004/0102455 A1 | 5/2004 | Burns et al. |
| 2004/0142404 A1 | 7/2004 | Wilks et al. |
| 2004/0147507 A1 | 7/2004 | Ledeboer et al. |
| 2004/0176271 A1 | 9/2004 | Bethiel et al. |
| 2004/0214817 A1 | 10/2004 | Pierce et al. |
| 2004/0235876 A1 | 11/2004 | Davis et al. |
| 2004/0248918 A1 | 12/2004 | Kim et al. |
| 2005/0171134 A1 | 8/2005 | Davis et al. |
| 2005/0209224 A1 | 9/2005 | Singh et al. |
| 2005/0234049 A1 | 10/2005 | Singh et al. |
| 2006/0009453 A1 | 1/2006 | Geuns-Meyer et al. |
| 2007/0060603 A1 | 3/2007 | Singh et al. |
| 2008/0182862 A1 | 7/2008 | Ding et al. |
| 2008/0188474 A1 | 8/2008 | Goff et al. |
| 2009/0062270 A1 | 3/2009 | Cooper et al. |
| 2009/0124580 A1 | 5/2009 | Singh et al. |
| 2013/0109695 A1 | 5/2013 | Singh et al. |
| 2014/0213585 A1 | 7/2014 | Bhamidipati et al. |
| 2014/0323490 A1 | 10/2014 | Goff et al. |

FOREIGN PATENT DOCUMENTS

| | | |
|---|---|---|
| WO | WO 98/11095 A1 | 3/1998 |
| WO | WO 98/18782 A1 | 5/1998 |
| WO | WO 99/15500 A1 | 4/1999 |
| WO | WO 00/00202 A1 | 1/2000 |
| WO | WO 00/010981 A1 | 3/2000 |
| WO | WO 00/47583 A1 | 8/2000 |
| WO | WO 00/51587 A2 | 9/2000 |
| WO | WO 00/55159 A2 | 9/2000 |
| WO | WO 01/12621 A1 | 2/2001 |
| WO | WO 01/29009 A1 | 4/2001 |
| WO | WO 01/42246 A2 | 6/2001 |
| WO | WO 01/45641 A2 | 6/2001 |
| WO | WO 01/52892 A2 | 7/2001 |
| WO | WO 01/56993 A2 | 8/2001 |
| WO | WO 01/57022 A2 | 8/2001 |
| WO | WO 01/72758 A1 | 10/2001 |
| WO | WO 02/00661 A1 | 1/2002 |
| WO | WO 02/22597 A1 | 3/2002 |
| WO | WO 02/43735 A2 | 6/2002 |
| WO | WO 02/46184 A1 | 6/2002 |
| WO | WO 02/48336 A2 | 6/2002 |
| WO | WO 02/060492 A1 | 8/2002 |
| WO | WO 02/060927 A1 | 8/2002 |
| WO | WO 02/064586 A2 | 8/2002 |
| WO | WO 02/066480 A2 | 8/2002 |
| WO | WO 02/079197 A1 | 10/2002 |
| WO | WO 02/083667 A2 | 10/2002 |
| WO | WO 02/096905 A1 | 12/2002 |
| WO | WO 02/096909 A1 | 12/2002 |
| WO | WO 02/102800 A1 | 12/2002 |
| WO | WO 03/004492 A1 | 1/2003 |
| WO | WO 03/011837 A1 | 2/2003 |
| WO | WO 03/020698 A2 | 3/2003 |
| WO | WO 03/030909 A1 | 4/2003 |
| WO | WO 03/048162 A1 | 6/2003 |
| WO | WO 03/051886 A1 | 6/2003 |
| WO | WO 03/063794 A2 | 8/2003 |
| WO | WO 03/101989 A1 | 12/2003 |
| WO | WO 2004/005282 A1 | 1/2004 |
| WO | WO 2004/005283 A1 | 1/2004 |
| WO | WO 2004/014382 A1 | 2/2004 |
| WO | WO 2004/016597 A2 | 2/2004 |
| WO | WO 2004/041789 A1 | 5/2004 |
| WO | WO 2004/041810 A1 | 5/2004 |
| WO | WO 2004/041814 A1 | 5/2004 |
| WO | WO 2004/043953 A1 | 5/2004 |
| WO | WO 2004/046112 A2 | 6/2004 |
| WO | WO 2004/046120 S2 | 6/2004 |
| WO | WO 2004/047843 A1 | 6/2004 |
| WO | WO 2004/058749 A1 | 7/2004 |
| WO | WO 2004/058753 A1 | 7/2004 |
| WO | WO 2004/085388 A2 | 10/2004 |
| WO | WO 2004/087698 A2 | 10/2004 |
| WO | WO 2004/087699 A2 | 10/2004 |
| WO | WO 2004/092154 A1 | 10/2004 |
| WO | WO 2004/096810 A1 | 11/2004 |
| WO | WO 2005/009957 A1 | 2/2005 |
| WO | WO 2005/012262 A1 | 2/2005 |
| WO | WO 2005/012294 A1 | 2/2005 |
| WO | WO 2005/012298 A1 | 2/2005 |
| WO | WO 2005/016344 A1 | 2/2005 |
| WO | WO 2005/016893 A2 | 2/2005 |
| WO | WO 2005/028475 A2 | 3/2005 |
| WO | WO 2005/033107 A1 | 4/2005 |
| WO | WO 2005/040154 A1 | 5/2005 |
| WO | WO 2005/075461 A1 | 8/2005 |
| WO | WO 2005/075468 A2 | 8/2005 |
| WO | WO 2005/116025 A2 | 12/2005 |
| WO | WO 2006/021458 A2 | 3/2006 |
| WO | WO 2006/068826 A2 | 6/2006 |
| WO | WO 2006/095159 A1 | 9/2006 |
| WO | WO 2007/018941 A2 | 2/2007 |
| WO | WO 2007/024843 A2 | 3/2007 |
| WO | WO 2007/033780 A2 | 3/2007 |
| WO | WO 2007/042786 A2 | 4/2007 |
| WO | WO 2007/053776 A1 | 5/2007 |
| WO | WO 2007/067506 A2 | 6/2007 |

(56) References Cited

FOREIGN PATENT DOCUMENTS

| WO | WO 2007/089768 A2 | 8/2007 |
| WO | WO 2007/132221 A1 | 11/2007 |
| WO | WO 2008/003766 A1 | 1/2008 |
| WO | WO 2008/109943 A1 | 9/2008 |
| WO | WO 2008/150799 A1 | 12/2008 |
| WO | WO 2009/103032 A1 | 8/2009 |

OTHER PUBLICATIONS

"Myelofibrosis", http://www.mayoclinic.org/diseases-conditions/myelofibrosis/basics/causes/con-20027210, accessed May 2, 2016.*
("Myeloproliferative disorders", https://www.nlm.nih.gov/cgi/mesh/2016/MB_cgi?mode=&index=9215&field=all&HM=&II=&PA=&form=&input=, accessed May 2, 2016.*
"Bone marrow transplant", http://www.hopkinsmedicine.org/healthlibrary/conditions/hematology_and_blood_disorders . . ., accessed May 2, 2016.*
Myelofibrosis, http://www.mayoclinic.org/diseases-conditions/myelofibrosis/basics/definition/con-20027210, accessed May 2, 2016.*
WARSCH. Blood, 2013, 122(13), 2167-75.*
U.S. Appl. No. 14/540,323, Goff et al., filed Nov. 13, 2014.
Abraham et al., "IL-23 and autoimmunity. New Insights into the Pathogenesis of Inflammatory Bowel Disease," *Annu. Rev. Med* 60: 97-110, 2009.
Atallah et al., "Prospect of JAK2 inhibitor therapy in myeloproliferative neoplasms," *Expert Rev. Anticancer Ther.* 9(5): 663-670, 2009.
Bean-Knudsen et al., "Porcine Mast Cell Leukemia with Systemic Mastocytosis," *Vet. Pathol.* 26: 90-92, 1989.
Carreras et al., "Activated T cells in an animal model of allergic conjunctivitis," *British Journal of Ophthalmology* 77: 509-514, 1993.
Cetkovic-Cvrlje and Tibbles, "Therapeutic Potential of Janus Kinase 3 (JAK3) Inhibitors," *Current Pharmaceutical Design* 10(15): 1767-1784, 2004.
Chan et al., "Expression of Interleukin-4 in the Epidermis of Transgenic Mice Results in a Pruritic Inflammatory Skin Disease: An Experimental Animal Model to Study Atopic Dermatitis," *The Journal of Investigative Dermatology* 117(4): 977-983, Oct. 2001.
Changelian et al., "Prevention of Organ Allograft Rejection by a Specific Janus Kinase 3 Inhibitor," *Science* 302: 875-878, Oct. 31, 2003.
Claman and Spiegelberg, "Immunoglobulin Dysregulation in Murine Graft-vs-Host Disease: A Hyper-IgE Syndrome," *Clinical Immunology and Immunopathology* 56: 46-53, 1990.
Dugan et al., "A Selective, Orally Bioavailable 1,2,4-Triazolo[1,5-α]pyridine-Based Inhibitor of Janus Kinase 2 for Use in Anticancer Therapy: Discovery of CEP-33779," *J. Med. Chem.* 55: 5243-5254, 2012.
Foster, "The Pathophysiology of Ocular Allergy: Current Thinking," *Allergy* 50(suppl 21): 6-9, 1995.
Hakim et al., "A Nine-Amino Acid Peptide from IL-1β Augments Antitumor Immune Responses Induced by Protein and DNA Vaccines," *The Journal of Immunology* 157: 5503-5511, 1996.
Hexner et al., "Lestaurtinib (CEP701) is a JAK2 inhibitor that suppresses JAK2/STAT5 signaling and the proliferation of primary erythroid cells from patients with myeloproliferative disorders," *Blood* 111(12): 5663-5671, Jun. 15, 2008.
Hough et al., "A model for spontaneous B-lineage lymphomas in $IgH_\mu$-HOX11 transgenic mice," *Proc. Natl. Acad. Sci. USA* 95: 13853-13858, Nov. 1998.
Ihle et al., "Jak2: normal function and role in hematopoietic disorders," *Current Opinion in Genetics & Development* 17: 8-14, 2007.
Kawaguchi et al., "Nasal mast cells in experimentally induced allergic rhinitis in guinea-pigs," *Clinical and Experimental Allergy* 24: 238-244, 1994.
Kiladjian, "The spectrum of JAK2-positive myeloproliferative neoplasms," *Hematology* 561-566, 2012.
Kunert et al., "Alteration in Goblet Cell Numbers and Mucin Gene Expression in a Mouse Model of Allergic Conjunctivitis," *Investigative Ophthalmology & Visual Science* 42(11): 2483-2489, Oct. 2001.
Lacout et al., "$JAK2^{V617F}$ expression in murine hematopoietic cells leads to MPD mimicking human PV with secondary myelofibrosis," *Blood* 108(5): 1652-1660, Sep. 1, 2006.
Lee et al., "Discovery of 4-Amino-5-(3-bromophenyl)-7-(6-morpholino-pyridin-3-yl)pyrido[2,3-*d*]pyrimidine, an Orally Active, Non-Nucleoside Adenosine Kinase Inhibitor," *J. Med. Chem* 44(13): 2133-2138, 2001.
Levine et al., "Role of JAK2 in the pathogenesis and therapy of myeloproliferative disorders," *Nature Reviews: Cancer* 7: 673-678, Sep. 2007.
Mascareno et al., "The role of Jak/STAT signaling in heart tissue renin-angiotension system," *Molecular and Cellular Biochemistry* 212: 171-175, 2000.
Mascareno et al., "JAK/STAT Signaling Is Associated With Cardiac Dysfunction During Ischemia and Reperfusion," *Circulation* 104: 325-329, 2001, 6 pages.
Meydan et al., "Inhibition of acute lymphoblastic leukaemia by a Jak-2 inhibitor," *Nature* 379: 645-648, Feb. 15, 1996.
O'Keefe et al., "Systemic Mastocytosis in 16 Dogs," *Journal of Veterinary Internal Medicine* 1(2): 75-80, 1987.
O'Shea et al., "A New Modality for Immunosuppression: Targeting the JAK/STAT Pathway," *Nature Reviews: Drug Discovery* 3: 555-564, Jul. 2004.
Pardanani et al., "TG101209, a small molecule JAK2-selective kinase inhibitor potently inhibits myeloproliferative disorder-associated *JAK2*V617F and *MPL*W515L/K mutations," *Leukemia* 1-11, 2007.
Paul et al., "Preparation of Substituted *N*-Phenyl-4-aryl-2-pyrimidinamines as Mediator Release Inhibitors," *J. Med. Chem.* 36(19): 2716-2725, 1993.
"Polycythemia Vera—How Can Polycythemia Vera Be Prevented?" URL=http://www.nhlbi.nih.gov/health//dci/Diseases/poly/poly_prevention.html, download date Jan. 18, 2012, 1 page.
Saiga et al., "Clinical and Cytologic Aspects of Ocular Late-Phase Reaction in the Guinea Pig," *Ophthalmic Res.* 24: 45-50, 1992.
Shide et al., "Development of ET, primary myelofibrosis and PV in mice expressing JAK2 V617F," *Leukemia* 22: 87-95, 2008.
Sugimoto et al., "A new model of allergic rhinitis in rats by topical sensitization and evaluation of $H_1$-receptor antagonists," *Immunopharmacology* 48: 1-7, 2000.
Suto et al., "NC/Nga Mice: A Mouse Model for Atopic Dermatitis," *Int. Arch. Allergy Immunol.* 120(suppl 1): 70-75, 1999.
Szelenyi et al., "Animal Models of Allergic Rhinitis," *Arzneim.-Forsch/Drug Res.* 50(II)(11): 1037-1042, 2000.
Tumas et al., "Anti-IgE efficacy in murine asthma models is dependent on the method of allergen sensitization," *J. Allergy Clin. Immunol.* 107(6): 1025-1033, Jun. 2001.
Wernig et al., "Expression of Jak2V617F causes a polycythemia vera-like disease with associated myelofibrosis in a murine bone marrow transplant model," *Blood* 107(11): 4274-4281, Jun. 1, 2006.
Wilks, "The JAK kinases: Not just another kinase drug discovery target," *Seminars in Cell & Developmental Biology* 19: 319-328, 2008.
Zimmermann et al., "Phenylamino-Pyrimidine (PAP) Derivatives: A New Class of Potent and Selective Inhibitors of Protein Kinase C (PKC)," *Arch. Pharm. Pharm. Med. Chem.* 329: 371-376, 1996.

* cited by examiner

PYRIMIDINE-2-AMINE COMPOUNDS AND THEIR USE AS INHIBITORS OF JAK KINASES

CROSS-REFERENCE TO RELATED APPLICATIONS

This application is a continuation of U.S. patent application Ser. No. 13/619,843, filed Sep. 14, 2012, now allowed; which is a divisional of U.S. patent application Ser. No. 12/371,550, filed Feb. 13, 2009, now U.S. Pat. No. 8,309,566; which claims the benefit under 37 U.S.C. §119(e) of U.S. Provisional Patent Application No. 61/029,265, filed Feb. 15, 2008; U.S. Provisional Patent Application No. 61/038,672, filed Mar. 21, 2008; and U.S. Provisional Patent Application No. 61/112,046, filed Nov. 6, 2008. These applications are incorporated herein by reference in their entireties.

FIELD OF THE INVENTION

The present invention relates to compounds, or pharmaceutically acceptable salts thereof, and pharmaceutical compositions comprising the compounds or salts which are useful as modulators of the JAK pathway or as inhibitors of JAK kinases, particularly JAK2. This invention is also directed to methods of using the compounds or pharmaceutically acceptable salts and pharmaceutical compositions thereof in treating diseases and conditions associated with JAK activity.

BACKGROUND OF THE INVENTION

Protein kinases constitute a large family of structurally related enzymes that are responsible for the control of a variety of signal transduction processes within cells (see, e.g., Hardie and Hanks, *The Protein Kinase Facts Book*, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), *FASEB J.* 9:576-596; Knighton et al., (1991), *Science* 253:407-414; Hiles et al., (1992), *Cell* 70:419-429; Kunz et al., (1993), *Cell* 73:585-596; Garcia-Bustos et al., (1994), *EMBO J.* 13:2352-2361).

JAK kinases (JAnus Kinases) are a family of cytoplasmic protein tyrosine kinases including JAK1, JAK2, JAK3 and TYK2. Each of the JAK kinases is selective for the receptors of certain cytokines, though multiple JAK kinases can be affected by particular cytokine or signaling pathways. Studies suggest that JAK3 associates with the common gamma (γc) chain of the various cytokine receptors. JAK3, in particular, selectively binds to receptors and is part of the cytokine signaling pathway for IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), *J. Allergy Clin. Immunol.* 105:877-888). JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), *Mol. Med.* 5:432:456 and Seidel et al., (2000), *Oncogene* 19:2645-2656.

As described above, JAK's are crucial components of diverse signal transduction pathways that govern important cellular functions, including cell survival, proliferation, differentiation and apoptosis. Interfering with JAK activity may lead to the loss of a vital signal transduction pathway, thereby disrupting normal cellular processes needed for cell survival. Therefore, it is important to selectively inhibit particular JAK's that are involved in various disease states.

JAK2 associates with cytokine receptors and is essential for signal transduction by mediating tyrosine phosphorylation. JAK2 activity is regulated by a series of interactions, beginning with binding to specific domains in receptors, suppression of activation by the pseudokinase domain, and the requirement for phosphorylation within the activation loop. Recent studies have implicated deregulation of JAK2 kinase activity by chromosomal translocations in hematopoietic tumors and mutations within the pseudokinase domain in a spectrum of myeloproliferative diseases (Ihle, J N et al., *Current Opinion in Genetics and Development* (2007) 17:1, 8-14.

In addition, JAK2 has been suggested to be involved in the upregulation of angiotensinogen promoter activity in hypertrophy and ischemia (Mascareno E, et al. (2000) *Mol. Cell. Biochem.*, 212:171-175; and Mascareno E, et al. (2001) *Circulation*, 104:1). One particular tyrphostin, AG490, selectively inhibits JAK2 and has been proposed for treating cancer (Meydan N, et al. (1996) *Nature*, 379:645). Administration of tyrphostin AG490 has been suggested to afford cardioprotection to hearts subjected to ischemia/reperfusion (Mascareno E, et al. (2000) *Mol. Cell. Biochem.*, 212:171 and Mascareno E, et al. (2001) *Circulation*, 104:1). TG101209, a JAK2-selective compound, has been recently shown to be effective in inhibiting mutations in myeloproliferative disorders (Pardanani A, et al. (2007) *Leukemia*, 1-11).

JAK3, in particular, has been implicated in a variety of biological processes. For example, the proliferation and survival of murine mast cells induced by IL-4 and IL-9 have been shown to be dependent on JAK3- and gamma chain-signaling (Suzuki et al., (2000), *Blood* 96:2172-2180). JAK3 also plays a crucial role in IgE receptor-mediated mast cell degranulation responses (Malaviya et al., (1999), *Biochem. Biophys. Res. Commun.* 257:807-813), and inhibition of JAK3 kinase has been shown to prevent type I hypersensitivity reactions, including anaphylaxis (Malaviya et al., (1999), *J. Biol. Chem.* 274:27028-27038). JAK3 inhibition has also been shown to result in immune suppression for allograft rejection (Kirken, (2001), *Transpl. Proc.* 33:3268-

3270). JAK3 kinases have also been implicated in the mechanism involved in early and late stages of rheumatoid arthritis (Muller-Ladner et al., (2000), *J. Immunol.* 164: 3894-3901); familial amyotrophic lateral sclerosis (Trieu et al., (2000), *Biochem Biophys. Res. Commun.* 267:22-25); leukemia (Sudbeck et al., (1999), *Clin. Cancer Res.* 5:1569-1582); mycosis fungoides, a form of T-cell lymphoma (Nielsen et al., (1997), *Prac. Natl. Acad. Sci. USA* 94:6764-6769); and abnormal cell growth (Yu et al., (1997), *J. Immunol.* 159:5206-5210; Catlett-Falcone et al., (1999), *Immunity* 10:105-115).

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), *Mol. Cell. Biol.* 16:4710-6; Jurlander et al., (1997), *Blood.* 89:4146-52; Kaneko et al., (1997), *Clin. Exp. Immun.* 109:185-193; and Nakamura et al., (1996), *J. Biol. Chem.* 271:19483-8). They are also known to be important to lymphocyte differentiation, function and survival. JAK-3, in particular, plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) *Am. J. Transplant* 4:51-57; Changelian (2003) *Science* 302:875-878). Conditions in which targeting of the JAK pathway or modulation of the JAK kinases, particularly JAK3, are contemplated to be therapeutically useful include leukemia, lymphoma, transplant rejection (e.g., pancreas islet transplant rejection), bone marrow transplant applications (e.g., graft-versus-host disease), autoimmune diseases (e.g., RA, type I diabetes), and inflammation (e.g., asthma, allergic reactions). Conditions which can benefit for inhibition of JAK2 are discussed in greater detail below.

In view of the numerous conditions that are contemplated to benefit by treatment involving modulation of the JAK pathway, it is immediately apparent that new compounds that modulate JAK pathways and methods of using these compounds should provide substantial therapeutic benefits to a wide variety of patients.

RELATED DISCLOSURES

Patents and patent applications related to modulation of the JAK pathway include: U.S. Pat. Nos. 5,728,536; 6,080,747; 6,080,748; 6,133,305; 6,177,433; 6,210,654; 6,313,130; 6,316,635; 6,433,018; 6,486,185; 6,506,763; 6,528,509; 6,593,357; 6,608,048; 6,610,688; 6,635,651; 6,677,368; 6,683,082; 6,696,448; 6,699,865; 6,777,417; 6,784,195; 6,825,190; 6,506,763; 6,784,195; 6,528,509; 6,608,048; 7,105,529; 6,699,865; 6,825,190; 6,815,439; 6,949,580; 7,056,944; 6,998,391; 7,074,793; 6,969,760; U.S. Pat. App. Pub. Nos. 2001/0007033 A1; 2002/0115173 A1; 2002/0137141 A1; 2003/0236244 A1; 2004/0102455 A1; 2004/0142404 A1; 2004/0147507 A1; and 2004/0214817 A1; and International Published Patent Application Nos. WO 95/03701A1; WO 99/15500A1; WO 00/00202A1; WO 00/10981A1; WO 00/47583A1; WO 00/51587A2; WO 00/55159A2; WO 01/42246A2; WO 01/45641A2; WO 01/52892A2; WO 01/56993A2; WO 01/57022A2; WO 01/72758A1; WO 02/00661A1; WO 02/43735A1; WO 02/48336A2; WO 02/060492A1; WO 02/060927A1; WO 02/096909A1; WO 02/102800A1; WO 03/020698A2; WO 03/048162A1; WO 03/101989A1; WO 2004/016597A2; WO 2004/041789A1; WO 2004/041810A1; WO 2004/041814A1; WO 2004/046112A2; WO 2004/046120A2; WO 2004/047843A1; WO 2004/058749A1; WO 2004/058753A1; WO 2004/085388A2; WO 2004/092154A1; WO 2005/009957A1; WO 2005/016344A1; WO 2005/028475A2; and WO 2005/033107A1.

All of the above publications are herein incorporated by reference in their entireties to the same extent as if each individual publication was specifically and individually indicated to be incorporated by reference in its entirety.

SUMMARY OF THE INVENTION

This invention is directed to 2-pyrimidineamine compounds, or pharmaceutically acceptable salts thereof, and pharmaceutical compositions comprising the compounds or pharmaceutically acceptable salts thereof, for use in the treatment of conditions in which modulation of the JAK pathway or inhibition of JAK kinases, particularly JAK2, can be therapeutically useful.

Accordingly, in one aspect, this invention is directed to compounds of formula (I):

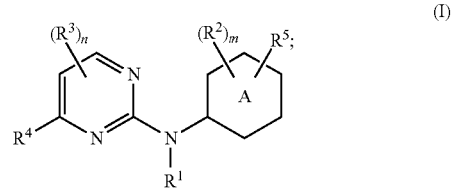

and pharmaceutically acceptable salts thereof, wherein:

is selected from the group consisting of a six-membered aryl and a six-membered heteroaryl;

n is 0, 1 or 2;

m is 0, 1, 2, 3 or 4;

$R^1$ is selected from the group consisting of hydrogen, alkyl, alkenyl, alkynyl, haloalkyl, haloalkenyl, haloalkenyl, optionally substituted cycloalkyl, optionally substituted cycloalkylalkyl, optionally substituted cycloalkylalkenyl, optionally substituted cycloalkylalkynyl, optionally substituted aryl, optionally substituted aralkyl, optionally substituted aralkenyl, optionally substituted aralkynyl, $-R^8-C(O)OR^6$, $-R^9-N(R^6)R^7$ and $-R^9-OR^6$;

each $R^2$, when present, is independently selected from the group consisting of optionally substituted alkyl, halo, haloalkyl, cyano, nitro, $-OR^6$, $-N(R^6)_2$, $-C(O)OR^6$ and $-C(O)N(R^6)_2$;

each $R^3$, when present, is independently selected from the group consisting of alkyl, halo and haloalkyl;

$R^4$ is selected from the group consisting of aryl and heteroaryl, where the aryl and the heteroaryl are each independently optionally substituted by one or more substituents selected from the group consisting of oxo, alkyl, halo, haloalkyl, cyano, N-heterocyclyl, N-heteroaryl, aryl, $-R^8-OR^{6a}$, $-R^8-S(O)_pR^{6a}$ (where p is 0, 1 or 2), $-R^8-C(O)R^{6a}$, $-R^8-C(O)OR^{6a}$, $-R^8-C(O)N(R^{6a})$ $R^{7a}$, $-R^8-N(R^{6a})R^{7a}$, $-R^8-N(R^{6a})-R^9-N(R^{6a})R^{7a}$, $-R^8-N(R^{6a})-R^9-OR^{7a}$, $-R^8-N(R^{6a})C(O)R^{7a}$, $-R^8-N(R^{6a})S(O)_2R^{7a}$, $-R^8-N(R^{6a})C(O)-R^8-N(R^{6a})R^{7a}$, and $-R^8-N(R^{6a})-R^9-N(R^{6a})S(O)_2R^{7a}$, where each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl and optionally substituted aralkyl, and where the N-heterocyclyl, the N-heteroaryl and the aryl are each independently optionally substituted by one or more substituents selected from the group consisting of $-C(O)R^6$, $-R^8-N(R^6)R^7$, $-R^8-C(O)N(R^6)R^7$, alkyl, halo and optionally substituted aryl;

$R^5$ is an N-heterocyclyl, wherein a nitrogen atom in the N-heterocyclyl is optionally substituted by a substituent selected from the group consisting of alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^8-OR^6$, $-R^8-C(O)R^6$, $-R^8-C(O)OR^6$, $-R^9-N(R^6)R^7$, $-R^8-C(O)N(R^6)R^7$, $-R^8-C(N=R^6)N(R^6)R^7$, $-R^8-S(O)_2N(R^6)R^7$, and $-R^8-S(O)_tR^6$ (where t is 1 or 2); and a carbon atom in the N-heterocyclyl is optionally substituted by a substituent selected from the group consisting of alkyl, alkenyl, alkynyl, halo, haloalkyl, haloalkenyl, haloalkynyl, oxo, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^8-OR^6$, $-R^8-C(O)R^6$, $-R^8-C(O)OR^6$, $-R^9-N(R^6)R^7$, $-R^8-C(O)N(R^6)R^7$, $-R^8-S(O)_2N(R^6)R^7$, and $-R^8-S(O)_pR^6$ (where p is 0, 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain; and each $R^9$ is independently selected from the group consisting of an optionally substituted straight or branched alkylene chain, an optionally substituted straight or branched alkenylene chain and an optionally substituted straight or branched alkynylene chain;

provided at least one of $R^5$ and a substituent on $R^4$ is a bridged N-heterocyclyl;

as an isolated stereoisomer or a mixture thereof and when comprising one or more stereoisomeric substituents.

In another aspect, this invention is directed to pharmaceutical compositions comprising a pharmaceutically acceptable excipient and a compound of the invention, as described herein, as an isolated stereoisomer or mixture thereof, or a pharmaceutically acceptable salt thereof.

In another aspect, this invention is directed to methods of treating a disease or condition associated with JAK activity in a mammal, particularly JAK2, wherein the methods comprise administering to the mammal a therapeutically effective amount of a compound of the invention, as described above, as an isolated stereoisomer or mixture thereof, or a pharmaceutically acceptable salt thereof, or a therapeutically effective amount of a pharmaceutical composition comprising a pharmaceutically acceptable excipient and a compound of the invention, as described herein, as an isolated stereoisomer or mixture thereof, or a pharmaceutically acceptable salt thereof.

In another aspect, this invention provides assays to determine the effectiveness of a compound of the invention in inhibiting JAK activity, particularly JAK2 activity, in a cell-based assay.

In another aspect, this invention provides a method of inhibiting an activity of a JAK kinase comprising contacting the JAK kinase with an amount of a compound effective to inhibit an activity of the JAK kinase, wherein the compound is selected from the compounds of this invention, or pharmaceutically acceptable salts thereof, as described herein.

In another aspect, this invention provides a method of inhibiting an activity of a JAK kinase comprising contacting in vitro a JAK2 kinase with an amount of a compound effective to inhibit an activity of the JAK kinase, wherein the compound is selected from the compounds of this invention, or pharmaceutically acceptable salts thereof, as described herein.

In another aspect, this invention provides a method of inhibiting an activity of a JAK kinase comprising contacting in a cell a JAK2 kinase with an amount of a compound effective to inhibit an activity of the JAK2 kinase, wherein the compound is selected from the compounds of this invention, or pharmaceutically acceptable salts thereof, as described herein.

In another aspect, this invention provides a method of treating a T-cell mediated autoimmune disease comprising administering to a patient suffering from such an autoimmune disease an amount of a compound effective to treat the autoimmune disease, wherein the compound is selected from the compounds of this invention, or pharmaceutically acceptable salts thereof, as described herein.

In another aspect, this invention provides a method of treating allograft transplant rejection in a mammal, preferably a transplant recipient, comprising administering to the mammal a therapeutically effective amount of a compound of the invention, or a pharmaceutically acceptable salt thereof, as described herein.

In another aspect, this invention provides a method of treating a Type IV hypersensitivity reaction in a mammal comprising administering to the mammal in need thereof a therapeutically effective amount of a compound of the invention, or a pharmaceutically acceptable salt thereof, as described herein.

In another aspect, this invention provides a method of inhibiting a signal transduction cascade in which JAK2 kinase plays a role comprising contacting a cell expressing a receptor involved in such a signaling cascade with an inhibitory amount of a compound of the invention, or a pharmaceutically acceptable salt thereof, as described herein.

In another aspect, this invention provides a method of treating a JAK kinase-mediated disease or condition in a mammal comprising administering to the mammal in need thereof a therapeutically effective amount of a compound of the invention, or a pharmaceutically acceptable salt thereof, as described herein.

In another aspect, this invention provides a method of treating a JAK2 kinase-mediated myeloproliferative disorder (MPD), such as polycythemia vera (PV), essential thrombocythemia (ET) and primary myelofibrosis (PMF) or JAK-dependent malignancies in a mammal, comprising administering to the mammal in need thereof a therapeutically effective amount of a compound of the invention, or a pharmaceutically acceptable salt thereof, as described herein.

In another aspect, this invention provides a kit comprising a compound selected from the compounds of this invention, or pharmaceutically acceptable salts thereof, packaging, and instructions for use.

DETAILED DESCRIPTION OF THE INVENTION

Definitions

As used in the specification and appended claims, unless specified to the contrary, the following terms have the meaning indicated:

"Ring A" refers to

in compounds of formula (I), as described above in the Summary of the Invention.

"Amino" refers to the —NH$_2$ radical.
"Carboxy" refers to the —C(O)OH radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Alkyl" refers to a fully saturated, straight or branched hydrocarbon chain radical consisting solely of carbon and hydrogen atoms, having from one to twelve carbon atoms, one to eight carbon atoms or one to six carbon atoms and which is attached to the rest of a molecule by a single bond, for example, methyl, ethyl, n-propyl, 1-methylethyl(isopropyl), n-butyl, n-pentyl, 1,1-dimethylethyl(t-butyl), 3-methylhexyl, 2-methylhexyl, and the like. For purposes of this invention, the term "lower alkyl" refers to an alkyl radical having one to six carbon atoms.

"Optionally substituted alkyl" refers to an alkyl radical, as defined above, which is optionally substituted by one or more substituents selected from the group consisting of halo, cyano, nitro, oxo, thioxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{20}$, —N(R$^{20}$)C(O)R$^{20}$, —N(R$^{20}$)S(O)$_2$R$^{20}$, —S(O)$_t$OR$^{20}$ (where t is 1 or 2), —S(O)$_p$R$^{20}$ (where p is 0, 1 or 2), and —S(O)$_2$N(R$^{20}$)$_2$ where each R$^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{20}$'s, together with the common nitrogen to which they are both attached, form an optionally substituted N-heterocyclyl or an optionally substituted N-heteroaryl.

"Alkenyl" refers to a straight or branched hydrocarbon chain radical consisting solely of carbon and hydrogen atoms, containing at least one double bond, having from one to twelve carbon atoms, or one to eight carbon atoms, and which is attached to the rest of a molecule by a single bond or a double bond, for example, ethenyl, prop-1-enyl, but-1-enyl, pent-1-enyl, penta-1,4-dienyl, and the like.

"Optionally substituted alkenyl" refers to an alkenyl radical, as defined above, which is optionally substituted by one or more substituents selected from the group consisting of halo, cyano, nitro, oxo, thioxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{20}$, —N(R$^{20}$)C(O)R$^{20}$, —N(R$^{20}$)S(O)$_2$R$^{20}$, —S(O)$_t$OR$^{20}$ (where t is 1 or 2), —S(O)$_p$R$^{20}$ (where p is 0, 1 or 2), and —S(O)$_2$N(R$^{20}$)$_2$ where each R$^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{20}$'s, together with the common nitrogen to which they are both attached, form an optionally substituted N-heterocyclyl or an optionally substituted N-heteroaryl.

"Alkynyl" refers to a straight or branched hydrocarbon chain radical consisting solely of carbon and hydrogen atoms, containing at least one triple bond, optionally containing at least one double bond, having from two to twelve carbon atoms, or two to eight carbon atoms, and which is attached to the rest of a molecule by a single bond or a double bond, for example, ethynyl, propynyl, butynyl, pentynyl, hexynyl, and the like.

"Optionally substituted alkynyl" refers to an alkynyl radical, as defined above, which is optionally substituted by one or more substituents selected from the group consisting of halo, cyano, nitro, oxo, thioxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{20}$, —N(R$^{20}$)C(O)R$^{20}$, —N(R$^{20}$)S(O)$_2$R$^{20}$, —S(O)$_t$OR$^{20}$ (where t is 1 or 2), —S(O)$_p$R$^{20}$ (where p is 0, 1 or 2), and —S(O)$_2$N(R$^{20}$)$_2$ where each R$^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

"Straight or branched alkylene chain" refers to a straight or branched divalent hydrocarbon chain linking the rest of a molecule to a radical group, consisting solely of carbon and hydrogen, containing no unsaturation and having from one to twelve carbon atoms, for example, methylene, ethylene, propylene, n-butylene, and the like. The alkylene chain is attached to the rest of a molecule through a single bond and to the radical group through a single bond. The points of attachment of the alkylene chain to the rest of a molecule and to the radical group can be through one carbon in the alkylene chain or through any two carbons within the chain.

"Optionally substituted straight or branched alkylene chain" refers to an alkylene chain, as defined above, which is optionally substituted by one or more substituents selected from the group consisting of halo, cyano, nitro, aryl, cycloalkyl, heterocyclyl, heteroaryl, oxo, thioxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{20}$, —$N(R^{20})C(O)R^{20}$, —$N(R^{20})S(O)_2R^{20}$, —$S(O)_tOR^{20}$ (where t is 1 or 2), —$S(O)_pR^{20}$ (where p is 0, 1 or 2), and —$S(O)_2N(R^{20})_2$ where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

"Straight or branched alkenylene chain" refers to a straight or branched divalent hydrocarbon chain linking the rest of a molecule to a radical group, consisting solely of carbon and hydrogen, containing at least one double bond and having from one to twelve carbon atoms, for example, ethenylene, propenylene, n-butenylene, and the like. The alkenylene chain is attached to the rest of a molecule through a double bond or a single bond and to the radical group through a double bond or a single bond. The points of attachment of the alkenylene chain to the rest of the molecule and to the radical group can be through one carbon or any two carbons within the chain.

"Optionally substituted straight or branched alkenylene chain" refers to an alkenylene chain, as defined above, which is optionally substituted by one or more substituents selected from the group consisting of halo, cyano, nitro, aryl, cycloalkyl, heterocyclyl, heteroaryl, oxo, thioxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{20}$, —$N(R^{20})C(O)R^{20}$, —$N(R^{20})S(O)_2R^{20}$, —$S(O)_tOR^{20}$ (where t is 1 or 2), —$S(O)_pR^{20}$ (where p is 0, 1 or 2), and —$S(O)_2N(R^{20})_2$ where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

"Straight or branched alkynylene chain" refers to a straight or branched divalent hydrocarbon chain linking the rest of a molecule to a radical group, consisting solely of carbon and hydrogen, containing at least one triple bond and having from two to twelve carbon atoms, for example, propynylene, n-butynylene, and the like. The alkynylene chain is attached to the rest of a molecule through a single bond and to the radical group through a double bond or a single bond. The points of attachment of the alkynylene chain to the rest of a molecule and to the radical group can be through one carbon or any two carbons within the chain.

"Optionally substituted straight or branched alkynylene chain" refers to an alkynylene chain, as defined above, which is optionally substituted by one or more substituents selected from the group consisting of alkyl, alkenyl, halo, haloalkenyl, cyano, nitro, aryl, cycloalkyl, heterocyclyl, heteroaryl, oxo, thioxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{20}$, —$N(R^{20})C(O)R^{20}$, —$N(R^{20})S(O)_2R^{20}$, —$S(O)_tOR^{20}$ (where t is 1 or 2), —$S(O)_pR^{20}$ (where p is 0, 1 or 2), and —$S(O)_2N(R^{20})_2$ where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

"Aryl" refers to a hydrocarbon ring system radical comprising hydrogen, 6 to 14 carbon atoms and at least one aromatic ring. For purposes of this invention, the aryl radical may be a monocyclic, bicyclic, or tricyclic system and which may include spiro ring systems. An aryl radical is commonly, but not necessarily, attached to a parent molecule via an aromatic ring of the aryl radical. Aryl radicals include, but are not limited to, aryl radicals derived from acenaphthylene, anthracene, azulene, benzene, 6,7,8,9-tetrahydro-5H-benzo[7]annulene, fluorene, as-indacene, s-indacene, indane, indene, naphthalene, phenalene, and phenanthrene.

"Optionally substituted aryl" refers to an aryl radical, as defined above, which is optionally substituted by one or more substituents selected from the group consisting of alkyl, alkenyl, alkynyl, halo, haloalkyl, haloalkenyl, haloalkynyl, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—O—$R^{22}$—$C(O)N(R^{20})_2$, —$R^{21}$—$N(R^{20})C(O)OR^{20}$, —$R^{21}$—$N(R^{20})C(O)R^{20}$, —$R^{21}$—$N(R^{20})S(O)_2R^{20}$, —$R^{21}$—$C(=NR^{20})N(R^{20})_2$, —$R^{21}$—$S(O)_tOR^{20}$ (where t is 1 or 2), —$R^{21}$—$S(O)_pR^{20}$ (where p is 0, 1 or 2), and —$R^{21}$—$S(O)_2N(R^{20})_2$, where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl, each $R^{21}$ is independently a direct bond or a straight or branched alkylene or alkenylene chain, and $R^{22}$ is a straight or branched alkylene or alkenylene chain.

"Aralkyl" refers to a radical of the formula $-R_b-R_c$ where $R_b$ is an alkylene chain as defined above and $R_c$ is one or more aryl radicals as defined above, for example, benzyl, diphenylmethyl and the like.

"Optionally substituted aralkyl" refers to an aralkyl radical, as defined above, wherein the alkylene chain of the aralkyl radical is an optionally substituted alkylene chain, as defined above, and each aryl radical of the aralkyl radical is an optionally substituted aryl radical, as defined above.

"Aralkenyl" refers to a radical of the formula $-R_d-R_c$ where $R_d$ is an alkenylene chain as defined above and $R_c$ is one or more aryl radicals as defined above.

"Optionally substituted aralkenyl" refers to an aralkenyl radical, as defined above, wherein the alkenylene chain of the aralkenyl radical is an optionally substituted alkenylene chain, as defined above, and each aryl radical of the aralkenyl radical is an optionally substituted aryl radical, as defined above.

"Aralkynyl" refers to a radical of the formula $-R_eR_c$, where $R_e$ is an alkynylene chain as defined above and $R_c$ is one or more aryl radicals as defined above.

"Optionally substituted aralkynyl" refers to an aralkynyl radical, as defined above, wherein the alkynylene chain of the aralkynyl radical is an optionally substituted alkynylene chain, as defined above, and each aryl radical of the aralkynyl radical is an optionally substituted aryl radical, as defined above.

"Cycloalkyl" refers to a stable non-aromatic monocyclic or polycyclic hydrocarbon radical consisting solely of carbon and hydrogen atoms, which includes fused, spiro or bridged ring systems, having from three to fifteen carbon atoms, or having from three to ten carbon atoms, or from five to seven carbons and which is saturated or unsaturated and attached to the rest of a molecule by a single bond. For purposes of this invention, a bridged ring system is a system wherein two non-adjacent ring atoms thereof are connected through an atom or a group of atoms, wherein the atom or the group of atoms are the bridging element. An example of a bridged cycloalkyl (monovalent) radical is norbornanyl (also called bicyclo[2.2.1]heptanyl). For purposes of this invention, a non-bridged ring system is a system which does not contain a bridging element, as described above. For purposes of this invention, a fused ring system is a system wherein two adjacent ring atoms thereof are connected through an atom or a group of atoms. An example of a fused cycloalkyl (monovalent) radical is decahydronaphthalenyl (also called decalinyl). For purposes of this invention, a spiro ring system is a system wherein two rings are joined via a single carbon (quaternary) atom. An example of a spiro cycloalkyl (monovalent) radical is spiro[5.5]undecanyl. Monocyclic cycloalkyl radicals do not include spiro, fused or bridged cycloalkyl radicals, but do include for example, cyclopropyl, cyclobutyl, cyclopentyl, cyclohexyl, cycloheptyl, and cyclooctyl. Polycyclic radicals include fused, spiro or bridged cycloalkyl radicals, for example, $C_{10}$ radicals such as adamantanyl (bridged) and decalinyl (fused), and $C_7$ radicals such as bicyclo[3.2.0]heptanyl (fused), norbornanyl and norbornenyl (bridged), as well as substituted polycyclic radicals, for example, substituted $C_7$ radicals such as 7,7-dimethylbicyclo[2.2.1]heptanyl (bridged), and the like.

"Optionally substituted cycloalkyl" refers to a cycloalkyl radical, as defined above, which is optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{21}-OR^{20}$, $-R^{21}-OC(O)-R^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{20}$, $-R^{21}-N(R^{20})C(O)R^{20}$, $-R^{21}-N(R^{20})S(O)_2R^{20}$, $-R^{21}-C(=NR^{20})N(R^{20})_2$, $-R^{21}-S(O)_tOR^{20}$ (where t is 1 or 2), $-R^{21}-S(O)_pR^{20}$ (where p is 0, 1 or 2), and $-R^{21}-S(O)_2N(R^{20})_2$, where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl, and each $R^{21}$ is independently a direct bond or a straight or branched alkylene or alkenylene chain.

"Cycloalkylalkyl" refers to a radical of the formula $-R_bR_g$ where $R_b$ is an alkylene chain as defined above and $R_g$ is a cycloalkyl radical as defined above.

"Optionally substituted cycloalkylalkyl" refers to a cycloalkylalkyl radical, as defined above, wherein the alkylene chain of the cycloalkylalkyl radical is an optionally substituted alkylene chain, as defined above, and the cycloalkyl radical of the cycloalkylalkyl radical is an optionally substituted cycloalkyl radical, as defined above.

"Cycloalkylalkenyl" refers to a radical of the formula $-R_dR_g$ where $R_d$ is an alkenylene chain as defined above and $R_g$ is a cycloalkyl radical as defined above.

"Optionally substituted cycloalkylalkenyl" refers to a cycloalkylalkenyl radical, as defined above, wherein the alkenylene chain of the cycloalkylalkenyl radical is an optionally substituted alkenylene chain, as defined above, and the cycloalkyl radical of the cycloalkylalkenyl radical is an optionally substituted cycloalkyl radical as defined above.

"Cycloalkylalkynyl" refers to a radical of the formula $-R_eR_g$ where $R_e$ is an alkynylene radical as defined above and $R_g$ is a cycloalkyl radical as defined above.

"Optionally substituted cycloalkylalkynyl" refers to a cycloalkylalkynyl radical, as defined above, wherein the alkynylene chain of the cycloalkylalkynyl radical is an optionally substituted alkynylene chain, as defined above, and the cycloalkyl radical of the cycloalkylalkynyl radical is an optionally substituted cycloalkyl radical as defined above.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkenyl" refers to an alkenyl radical, as defined above, that is substituted by one or more halo radicals, as defined above.

"Haloalkynyl" refers to an alkynyl radical, as defined above, that is substituted by one or more halo radicals, as defined above.

"Heterocyclyl" refers to a stable 3- to 18-membered non-aromatic ring system radical which comprises one to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of a bridged heterocyclyl include, but are not limited to, azabicyclo[2.2.1]heptanyl, diazabicyclo[2.2.1]heptanyl, oxazabicyclo[2.2.1]heptanyl, diazabicyclo[2.2.2]octanyl, azabicyclo[3.2.1]octanyl, diazabicyclo[3.2.1]octanyl, azabicyclo[3.3.1]nonanyl, diazabicyclo[3.3.1]nonanyl, azabicyclo[3.2.2.]nonanyl, diazabicyclo[3.2.2]nonanyl, 6,9-methanooctahydropyrido[1,2-a]pyrazinyl, azabicyclo[3.3.2]decanyl and diazabicyclo[3.3.2]decanyl. A "bridged N-heterocyclyl" is a bridged heterocyclyl containing at least one nitrogen, but which optionally contains up to four additional heteroatoms selected from O, N and S. For purposes of this invention, a non-bridged ring system is a system wherein no two non-adjacent ring atoms thereof are connected through an atom or a group of atoms. Examples of heterocyclyl radicals include, but are not limited to, dioxolanyl, 1,4-diazepanyl, decahydroisoquinolyl, imidazolinyl, imidazolidinyl, isothiazolidinyl, isoxazolidinyl, morpholinyl, octahydroindolyl, octahydroisoindolyl, octahydro-1H-pyrrolo[3,2-c]pyridinyl, octahydro-1H-pyrrolo[2,3-d]pyridinyl, octahydro-1H-pyrrolo[2,3-b]pyridinyl, octahydro-1H-pyrrolo[3,4-b]pyridinyl, octahydropyrrolo[3,4-c]pyrrolyl, octahydro-1H-pyrido[1,2-a]pyrazinyl, 2-oxopiperazinyl, 2-oxopiperidinyl, 2-oxopyrrolidinyl, oxazolidinyl, 3,7-diazabicyclo[3.3.1]nonan-3-yl, piperidinyl, piperazinyl, 4-piperidonyl, pyrrolidinyl, pyrazolidinyl, quinuclidinyl, thiazolidinyl, tetrahydrofuranyl, thienyl[1,3]dithianyl, trithianyl, tetrahydropyranyl, thiomorpholinyl, thiamorpholinyl, 1-oxo-thiomorpholinyl, 1,1-dioxo-thiomorpholinyl, azetidinyl, octahydropyrrolo[3,4-c]pyrrolyl, octahydropyrrolo[3,4-b]pyrrolyl, decahydroprazino[1,2-a]azepinyl, azepanyl, azabicyclo[3.2.1]octyl, and 2,7-diazaspiro[4.4]nonanyl.

"Optionally substituted heterocyclyl" refers to a heterocyclyl radical, as defined above, which is optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—$N(R^{20})C(O)OR^{20}$, —$R^{21}$—$N(R^{20})C(O)R^{20}$, —$R^{21}$—$N(R^{20})S(O)_2R^{20}$, —$R^{21}$—$C(=NR^{20})N(R^{20})_2$, —$R^{21}$—$S(O)_tOR^{20}$ (where t is 1 or 2), —$R^{21}$—$S(O)_pR^{20}$ (where p is 0, 1 or 2), and —$R^{21}$—$S(O)_2N(R^{20})_2$, where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl, and each $R^{21}$ is independently a direct bond or a straight or branched alkylene or alkenylene chain.

"N-heterocyclyl" refers to a heterocyclyl radical as defined above containing at least one nitrogen and where the point of attachment of the N-heterocyclyl radical to the rest of a molecule may be through a nitrogen atom in the N-heterocyclyl radical or through a carbon in the N-heterocyclyl radical.

"Optionally substituted N-heterocyclyl" refers to an N-heterocyclyl, as defined above, which is optionally substituted by one or more substituents as defined above for optionally substituted heterocyclyl.

"Heterocyclylalkyl" refers to a radical of the formula —$R_bR_h$ where $R_b$ is an alkylene chain as defined above and $R_h$ is a heterocyclyl radical as defined above, and when the heterocyclyl is a nitrogen-containing heterocyclyl, the heterocyclyl may be attached to the alkylene chain at the nitrogen atom.

"Optionally substituted heterocyclylalkyl" refers to a heterocyclylalkyl radical, as defined above, wherein the alkylene chain of the heterocyclylalkyl radical is an optionally substituted alkylene chain, as defined above, and the heterocyclyl radical of the heterocyclylalkyl radical is an optionally substituted heterocyclyl radical, as defined above.

"Heterocyclylalkenyl" refers to a radical of the formula —$R_dR_h$ where $R_d$ is an alkenylene chain as defined above and $R_h$ is a heterocyclyl radical as defined above, and when the heterocyclyl is a nitrogen-containing heterocyclyl, the heterocyclyl may be attached to the alkenylene chain at the nitrogen atom.

"Optionally substituted heterocyclylalkenyl" refers to a heterocyclylalkenyl radical, as defined above, wherein the alkenylene chain of the heterocyclylalkenyl radical is an optionally substituted alkenylene chain, as defined above, and the heterocyclyl radical of the heterocyclylalkenyl radical is an optionally substituted heterocyclyl radical, as defined above.

"Heterocyclylalkynyl" refers to a radical of the formula —$R_eR_h$ where $R_e$ is an alkynylene chain as defined above and $R_h$ is a heterocyclyl radical as defined above, and when the heterocyclyl is a nitrogen-containing heterocyclyl, the heterocyclyl may be attached to the alkynylene chain at the nitrogen atom.

"Optionally substituted heterocyclylalkynyl" refers to a heterocyclylalkynyl radical, as defined above, wherein the alkynylene chain of the heterocyclylalkynyl radical is an optionally substituted alkynylene chain, as defined above, and the heterocyclyl radical of the heterocyclylalkynyl radical is an optionally substituted heterocyclyl radical, as defined above.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. A heteroaryl radical is commonly, but not necessarily, attached to the parent molecule via an aromatic ring of the heteroaryl radical. For purposes of this invention, the heteroaryl radical may be a monocyclic, bicyclic or tricyclic ring system, which may include spiro or bridged ring systems; and the nitrogen, carbon or sulfur atoms in the heteroaryl radical may be optionally oxidized and the nitrogen atom may be optionally quaternized. For purposes of this invention, the aromatic ring of the heteroaryl radical need not contain a heteroatom, as long as one ring of the heteroaryl radical contains a heteroatom. For example benzo-fused heterocyclyls, like 1,2,3,4-tetrahydroisoquinolin-7-yl, are considered a "heteroaryl" for the purposes of this invention. Examples of heteroaryl radicals include, but are not limited to, azepinyl, acridinyl, benzimidazolyl, benzindolyl, 1,3-benzodioxolyl, benzofuranyl, benzoxazolyl, benzothiazolyl, benzothiadiazolyl, benzo[b][1,4]dioxepinyl, benzo[b][1,4]oxazinyl, benzo[b]azepinyl, 2,3,4,5-tetrahydro-1H-benzo[b]azepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 3,4-dihydro-2H-benzo[b][1,4]dioxepinyl, cyclopenta[4,5]thieno[2,3-d]pyrimidinyl such as 6,7-dihydro-5H-cyclopenta[4,5]thieno[2,3-d]pyrimidinyl, 5,6-dihydrobenzo[h]quinazolinyl, 3,4-dihydro-2H-benzo[b][1,4]thiazinyl, 5,6-dihydrobenzo[h]cinnolinyl, 7',8'-dihydro-5'H-spiro[[1,3]dioxolane-2,6'-quinoline]-3'-yl, 6,7-dihydro-5H-benzo[6,7]cyclohepta[1,2-c]pyridazinyl, 2,3-dihydro-1H-pyrido[2,3-b][1,4]oxazinyl, 3',4'-dihydrospiro[cyclobutane-1,2'-pyrido[3,2-b][1,4]oxazinyl, dihydropyridooxazinyl such as 3,4-dihydro-2H-pyrido[3,2-b][1,4]oxazinyl, dihydropyridothiazinyl such as 3,4-dihydro-2H-pyrido[3,2-b][1,4]thiazinyl, dibenzofuranyl, dibenzothiophenyl, furanyl, furanonyl, furo[3,2-c]pyridinyl, furopyrimidinyl, furopyridazinyl, furopyrazinyl, isothiazolyl, imidazolyl, imidazopyrimidinyl, imidazopyridazinyl, imidazopyrazinyl, imidazo[1,2-a]pyridinyl, indazolyl, indolyl, indazolyl, isoindolyl, indolinyl, isoindolinyl, isoquinolinyl (isoquinolyl), indolizinyl, isoxazolyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 3'-oxo-3',4'-dihydrospiro[cyclobutane-1,2'-pyrido[3,2-b][1,4]oxazine]yl, 7-oxo-5,6,7,8-tetrahydro-1,8-naphthyridinyl, 1-phenyl-1H-pyrrolyl, phenazinyl, phenothiazinyl, phenoxazinyl, phthalazinyl, phenanthridinyl, pteridinyl, purinyl, pyrrolyl, pyrazolyl, pyrazolo[3,4-d]pyrimidinyl, pyridinyl (pyridyl), pyrido[3,2-d]pyrimidinyl, pyrido[3,4-d]pyrimidinyl, pyrazinyl, pyrimidinyl, pyridazinyl (pyridazyl), pyrrolyl, pyrrolopyrimidinyl, pyrrolopyridazinyl, pyrrolopyrazinyl, 2H-pyrido[3,2-b][1,4]oxazinonyl, 1H-pyrido[2,3-b][1,4]oxazinonyl, pyrrolopyridinyl such as 1H-pyrrolo[2,3-b]pyridinyl, quinazolinyl, quinoxalinyl, quinolinyl, quinuclidinyl, tetrahydroquinolinyl, 5,6,7,8-tetrahydroquinazolinyl, 2,3,4,5-tetrahydrobenzo[b]oxepinyl, 6,7,8,9-tetrahydro-5H-pyrido[2,3-b]indolyl, 6,7,8,9-tetrahydro-5H-cyclohepta[b]pyridinyl, 6,7,8,9-tetrahydro-5H-pyrido[3,2-c]azepinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-d]pyridazinyl, 7,8,9,9a-tetrahydro-5H-pyrido[2,3-e]pyrrolo[1,2-a][1,4]diazepin-10(11H)-onyl, thiazolyl, thiadiazolyl, triazolyl, tetrazolyl, 1,2,3,4-tetrahydroisoquinolin-7-yl, triazinyl, thieno[2,3-d]pyrimidinyl, thienopyrimidinyl (e.g., thieno[3,2-d]pyrimidinyl), thieno[2,3-c]pyridinyl, thienopyridazinyl, thienopyrazinyl, and thiophenyl (thienyl).

"Optionally substituted heteroaryl" refers to a heteroaryl radical, as defined above, which is optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—$N(R^{20})C(O)OR^{20}$, —$R^{21}$—$N(R^{20})C(O)R^{20}$, —$R^{21}$—$N(R^{20})S(O)_2R^{20}2$, —$R^{21}$—$C(=NR^{20})N(R^{20})_2$, —$R^{21}$—$S(O)_tOR^{20}$ (where t is 1 or 2), —$R^{21}$—$S(O)_pR^{20}$ (where p is 0, 1 or 2), and —$R^{21}$—$S(O)_2N(R^{20})_2$, where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl, and each $R^{21}$ is independently a direct bond or a straight or branched alkylene or alkenylene chain.

"N-heteroaryl" refers to a heteroaryl radical as defined above containing at least one nitrogen and where the point of attachment of the N-heteroaryl radical to the rest of the molecule may be through a nitrogen atom in the N-heteroaryl radical or through a carbon atom in the N-heteroaryl radical.

"Optionally substituted N-heteroaryl" refers to an N-heteroaryl, as defined above, which is optionally substituted by one or more substituents as defined above for optionally substituted heteroaryl.

"Heteroarylalkyl" refers to a radical of the formula —$R_bR_i$ where $R_b$ is an alkylene chain as defined above and $R_i$ is a heteroaryl radical as defined above, and when the heteroaryl is a nitrogen-containing heteroaryl, the heteroaryl may be attached to the alkylene chain at the nitrogen atom.

"Optionally substituted heteroarylalkyl" refers to a heteroarylalkyl radical, as defined above, wherein the alkylene chain of the heteroarylalkyl radical is an optionally substituted alkylene chain, as defined above, and the heteroaryl radical of the heteroarylalkyl radical is an optionally substituted heteroaryl radical, as defined above.

"Heteroarylalkenyl" refers to a radical of the formula —$R_dR_i$ where $R_d$ is an alkenylene chain as defined above and $R_i$ is a heteroaryl radical as defined above, and when the heteroaryl is a nitrogen-containing heteroaryl, the heteroaryl may be attached to the alkenylene chain at the nitrogen atom.

"Optionally substituted heteroarylalkenyl" refers to a heteroarylalkenyl radical, as defined above, wherein the alkenylene chain of the heteroarylalkenyl radical is an optionally substituted alkenylene chain, as defined above, and the heteroaryl radical of the heteroarylalkenyl radical is an optionally substituted heteroaryl radical, as defined above.

"Heteroarylalkynyl" refers to a radical of the formula —$R_eR_i$ where $R_e$ is an alkynylene chain as defined above and $R_i$ is a heteroaryl radical as defined above, and when the heteroaryl is a nitrogen-containing heteroaryl, the heteroaryl may be attached to the alkynylene chain at the nitrogen atom.

"Optionally substituted heteroarylalkynyl" refers to a heteroarylalkynyl radical, as defined above, wherein the alkynylene chain of the heteroarylalkynyl radical is an optionally substituted alkynylene chain, as defined above, and the heteroaryl radical of the heteroarylalkynyl radical is an optionally substituted heteroaryl radical, as defined above.

"Hydroxyalkyl" refers to an alkyl radical as defined above which is substituted by one or more hydroxy radicals (—OH).

"Hydroxyalkenyl" refers to an alkenyl radical as defined above which is substituted by one or more hydroxy radicals (—OH).

"Hydroxyalkenyl" refers to an alkynyl radical as defined above which is substituted by one or more hydroxy radicals (—OH).

Certain chemical groups named herein may be preceded by a shorthand notation indicating the total number of carbon atoms that are to be found in the indicated chemical group. For example; $C_7$-$C_{12}$alkyl describes an alkyl group, as defined above, having a total of 7 to 12 carbon atoms, and $C_4$-$C_{12}$cycloalkylalkyl describes a cycloalkylalkyl group, as defined above, having a total of 4 to 12 carbon atoms. The total number of carbons in the shorthand notation does not include carbons that may exist in substituents of the group described.

"Stable compound" and "stable structure" are meant to indicate a compound that is sufficiently robust to survive isolation to a useful degree of purity from a reaction mixture, and formulation into an efficacious therapeutic agent.

"Mammal" means any vertebrate of the class Mammalia. Humans and domestic animals, such as cats, dogs, swine, cattle, sheep, goats, horses, rabbits, and the like are a particular focus. Frequently, for purposes of this invention, the mammal is a human.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. However, when a first functional group is described as "optionally substituted," and in turn, substituents on the first functional group are also "optionally substituted" and so forth, for the purposes of this invention, such iterations for a radical to be optionally substituted are limited to three. Thus, groups described as substituents on the third iteration are not themselves optionally substituted. For example, if an R group herein is defined as being "optionally substituted aryl" (the first iteration) and the optional substituents for the "optionally substituted aryl" include "optionally substituted heteroaryl" (the second iteration) and the optional substituents for the "optionally substituted heteroaryl" include "optionally substituted cycloalkyl" (the third iteration), the optional substituents on the cycloalkyl can not be optionally substituted.

"Para" for the purposes of this invention refers to the position of a substituent on a phenyl or a six-membered heteroaryl ring relative to another substituent on the ring; the relative position being 1,4-substitution. That is, starting from one substituent as being attached to a first atom of the phenyl or six-membered heteroaryl ring and, counting atoms in the ring from the first atom, another substituent is on atom 4 of the phenyl or the six-membered heteroaryl ring, the substituents' relative orientation about the phenyl or six-membered heteroaryl ring is "para." For example, a compound of formula (I), as set forth above in the Summary of the Invention, depicted below as a compound of formula (Ia-1), where $R^5$ is on a first atom of the phenyl ring, and the nitrogen bearing $R^1$ is on the fourth atom, then $R^5$ and the nitrogen bearing $R^1$ are "para" in relative orientation.

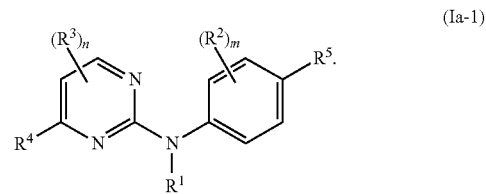

(Ia-1)

"Meta" for the purposes of this invention refers to the position of a substituent on a phenyl or a six-membered heteroaryl ring relative to another substituent on the ring; the relative position being 1,3-substitution. That is, starting from one substituent as being attached to a first atom of the phenyl or six-membered heteroaryl ring and, counting atoms in the ring from the first atom, another substituent is on the third atom of the phenyl or the six-membered heteroaryl ring, the substituents' relative orientation about the phenyl or the six-membered heteroaryl ring is "meta." For example, a compound of formula (I), as set forth above in the Summary of the Invention, depicted below as a compound of formula (Ia-1c), where $R^2$ is on a first atom of the phenyl ring, and the nitrogen bearing hydrogen is on a third atom, then $R^2$ and the nitrogen bearing hydrogen are "para" in relative orientation.

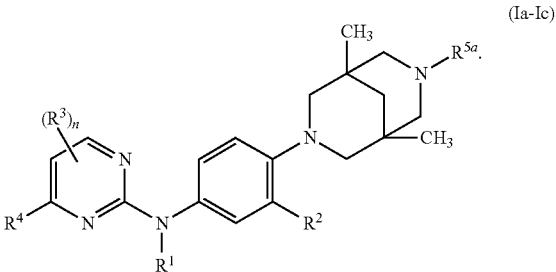

(Ia-Ic)

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfonic acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of a compound of the invention which, when administered to a mammal, for example a human, is sufficient to effect treatment, as defined below, of a disease or condition of interest in the mammal, preferably a human. The amount of a compound of the invention which constitutes a "therapeutically effective amount" will vary depending on the compound, the disease or condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, for example a human, having the disease or condition of interest, and includes:

(i) preventing the disease or condition or one of its manifestations or symptoms from occurring in a mammal, in particular, when such mammal is predisposed to the condition but has not yet been diagnosed as having it;

(ii) inhibiting the disease or condition, i.e., arresting its development or one or more of its manifestations or symptoms;

(iii) relieving the disease or condition, i.e., causing regression of the disease or condition or one if its manifestations or symptoms; or (iv) stabilizing the disease or condition or one of its manifestations or symptoms.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Likewise, all tautomeric forms of the specifically described structures are also intended to be included. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centres of geometric asymmetry, and unless specified otherwise, it is intended that the compounds include both E and Z geometric isomers. Similarly, with reference to bicyclic ring systems present in particular embodiments, such moieties often may have substituents attached in an "endo" or "exo" relative configuration. The stereochemical descriptor "endo" refers to a bridge substituent that points toward the larger of the two remaining bridges. If the substituent points toward the smaller remaining bridge, it is referred to as an "exo" substituent.

When used herein in a formula to indicate a chemical bond and not to indicate the point of attachment of a substituent to the rest of a molecule (as shown in Tables 2 and 3 below), the bond symbol ∽ indicates that the chemical bond may be attached in any relative or absolute configuration, for example, the chemical bond may be in an endo or exo relative configuration. Similarly, the chemical bond may be attached in the R or S absolute configuration.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

"Atropisomers" are stereoisomers resulting from hindered rotation about single bonds where the barrier to rotation is high enough to allow for the isolation of the conformers (Eliel, E. L.; Wilen, S. H. *Stereochemistry of Organic Compounds*; Wiley & Sons: New York, 1994; Chapter 14). Atropisomerism is significant because it introduces an element of chirality in the absence of stereogenic atoms. The invention is meant to encompass atropisomers, for example in cases of limited rotation around the single bonds emanating from the core pyrimidine structure, atropisomers are also possible and are also specifically included in the compounds of the invention.

The chemical naming protocol and structure diagrams used herein are a modified form of the I.U.P.A.C. nomenclature system wherein the compounds of the invention are named herein as derivatives of the central core structure, i.e., the pyrimidine-2-amine structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms which are assumed to be bonded to sufficient hydrogen atoms to complete the valency.

For example, a compound of formula (I), as set forth above in the Summary of the Invention, wherein n is 0, m is 1,

is phenyl, $R^1$ is hydrogen, $R^2$ is fluoro at the meta position, $R^4$ is 6-(4-acetylpiperazin-1-yl)pyridin-3-yl and $R^5$ is (1S,4S)-5-methyl-2,5-diazabicyclo[2.2.1]heptan-2-yl at the para position relative to the nitrogen bearing hydrogen, i.e., a compound of the following formula (wherein the positions of the pyrimidinyl ring are indicated):

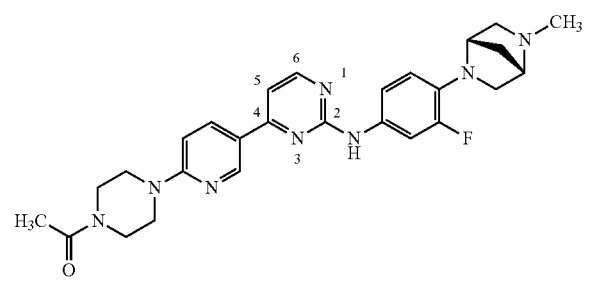 [SMILES: CC(=O)N1CCN(c2ccc(-c3ccnc(Nc4ccc(N5C[C@@H]6C[C@H]5CN6C)c(F)c4)n3)cn2)CC1]

is named herein as 4-(6-(4-acetylpiperazin-1-yl)pyridin-3-yl)-N-(3-fluoro-4-((1S,4S)-5-methyl-2,5-diazabicyclo[2.2.1]heptan-2-yl)phenyl)pyrimidin-2-amine.

EMBODIMENTS OF THE INVENTION

One aspect of the invention are compounds of formula (I), as set forth above in the Summary of the Invention, as an isolated stereoisomer or a mixture thereof, or as a pharmaceutically acceptable salt thereof. Of this aspect, certain embodiments of the compounds of formula (I) are preferred.

In one embodiment, ring A in the compounds of formula (I) is a phenyl or pyridinyl ring. Of this embodiment, one embodiment is wherein $R^5$ is a bridged N-heterocyclyl. Of this embodiment, a preferred embodiment is wherein the bridged N-heterocyclyl is selected from the group consisting of:

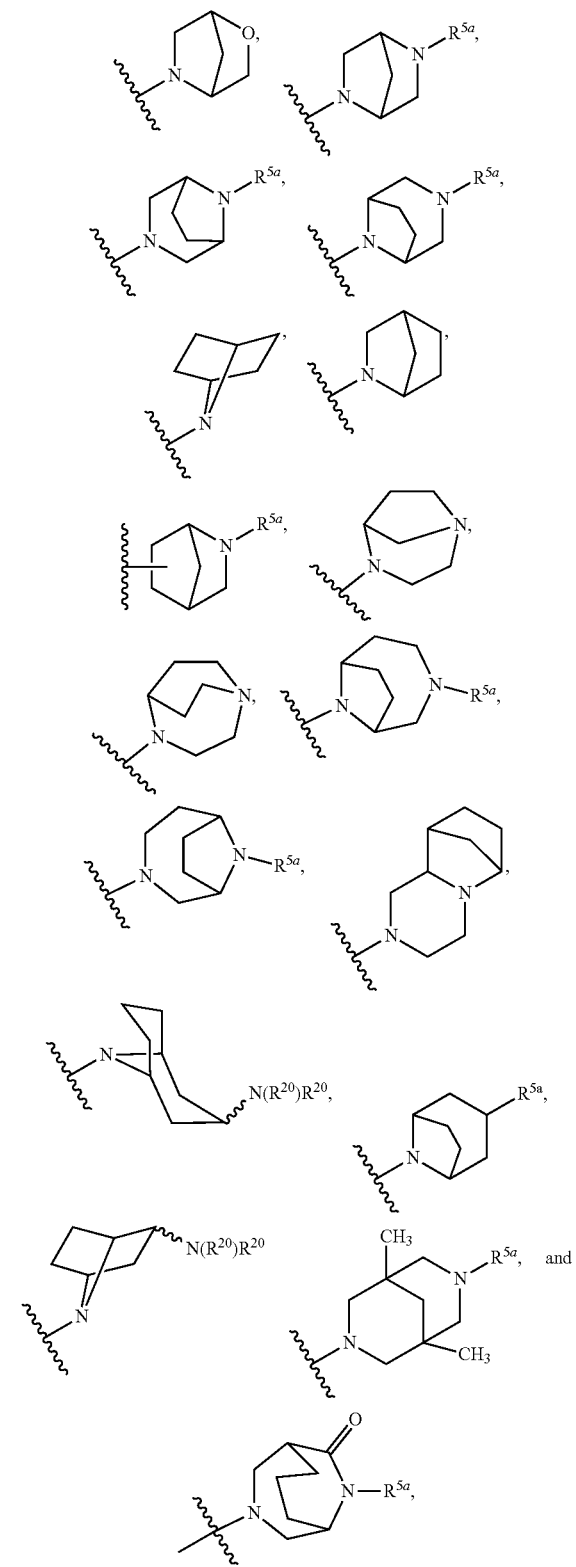

where each $R^{5a}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^8$—$OR^6$, —$R^8$—C(O)$R^6$, —$R^8$—C(O)O$R^6$, —$R^9$—N($R^6$)$R^7$, —$R^8$—C(O)N($R^6$)$R^7$, —$R^8$—C(N=$R^6$)N($R^6$)$R^7$, —$R^8$—S(O)$_2$N($R^6$)$R^7$, and —$R^8$—S(O)$_t R^6$ where t is 1 or 2 and each $R^6$, $R^7$, $R^8$ and $R^9$ is as defined above in the Summary of the Invention for compounds of formula (I), and where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

Another embodiment of the compounds of formula (I), as set forth above in the Summary of the Invention, are compounds wherein $R^5$ is a bridged N-heterocyclyl, or wherein a $R^4$ substituent is a bridged N-heterocyclyl, or wherein $R^5$ and a $R^4$ substitutent are both bridged N-heterocyls. In certain embodiments of this invention, $R^5$ is a bridged N-heterocyclyl.

In the compounds of formula (I) wherein $R^5$ is a bridged N-heterocyclyl or the $R^4$ substituent is a N-heterocyclyl, $R^5$ and the $R^4$ substituent need not be attached to ring A or $R^4$, respectively, via a ring nitrogen of the bridged N-heterocyclyl, but rather can be attached via a ring carbon, for example. In some embodiments, a bridged N-heterocyclyl as $R^5$ or as a $R^4$ substituent is fused to another ring, part of a spiro ring system or both. In certain embodiments, a bridged N-heterocyclyl as $R^5$ or as a $R^4$ substituent, alone or as part of a larger fused, spiro or combination ring system, comprises a substructure geometry selected from the group consisting of [4.4.0], [4.3.0], [4.2.0], [4.1.0], [3.3.0], [3.2.0], [3.1.0], [3.3.3], [3.3.2], [3.3.1], [3.2.2], [3.2.1], [2.2.2] and [2.2.1].

In one embodiment, the bridged N-heterocyclyl as $R^5$ or as an $R^4$ substituent, independently if more than one, is selected from the group consisting of:

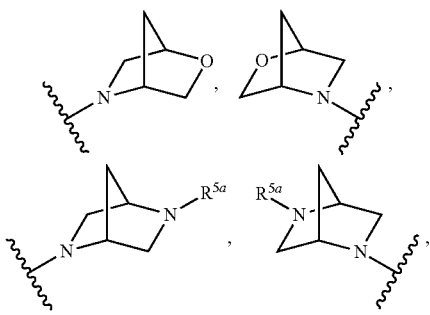

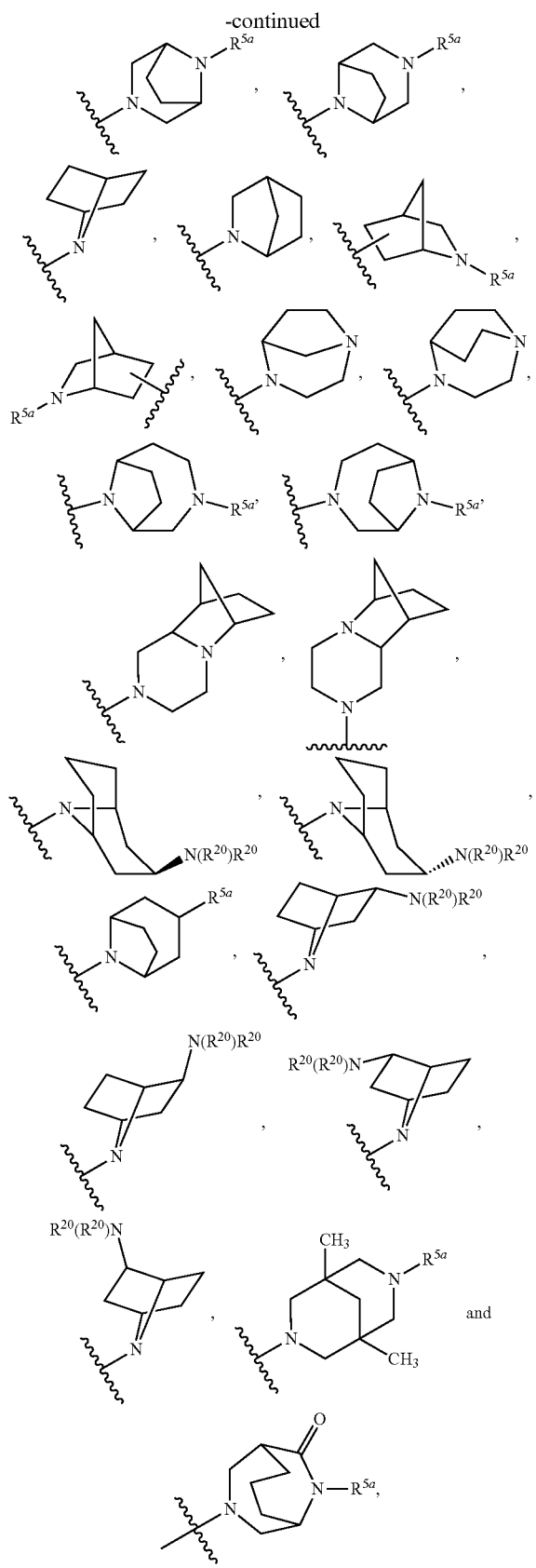

where each $R^{5a}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^8$—$OR^6$, —$R^8$—$C(O)R^6$, —$R^8$—$C(O)OR^6$, —$R^9$—$N(R^6)R^7$, —$R^8$—$C(O)N(R^6)R^7$, —$R^8$—$C(N=R^6)N(R^6)R^7$, —$R^8$—$S(O)_2N(R^6)R^7$, and —$R^8$—$S(O)_tR^6$ where t is 1 or 2 and each $R^6$, $R^7$, $R^8$ and $R^9$ is as defined above in the Summary of the Invention for compounds of formula (I) and where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

In a particular embodiment, $R^5$ is a bridged N-heterocyclyl and $R^4$ is a heteroaryl optionally substituted with a bridged N-heterocyclyl. In exemplary compounds of the invention for this embodiment, $R^5$ is a bridged N-heterocyclyl containing an additional nitrogen, $R^4$ is a 5- or 6-membered heteroaryl and n is 0. In a specific embodiment, $R^5$ and the nitrogen bearing $R^1$ are in a para regiochemical relationship with each other and $R^4$ is selected from pyridyl, pyridazinyl, pyrimidinyl, pyrazinyl, triazinyl triazolyl, tetrazinyl, tetrazolyl, pyrazolyl, pyrrolyl, imidazolyl and pyrazolyl. In certain embodiments, $R^4$ is substituted with an amino-containing group, e.g., —$R^8$—$N(R^{6a})R^{7a}$, —$R^8$—$N(R^{6a})$—$R^9$—$N(R^{6a})R^{7a}$ or —$R^8$—$N(R^{6a})$—$R^9$—$OR^{7a}$, where each $R^{6a}$, $R^{7a}$, $R^8$ and $R^9$ are as described above in the Summary of the Invention for compounds of formula (I), or $R^4$ is substituted with an optionally substituted heterocyclyl, e.g. an optionally substituted piperidinyl, optionally substituted piperazinyl, optionally substituted morpholinyl, and optionally substituted thiomorpholinyl. In some examples of this embodiment, $R^4$ is substituted with a bridged N-heterocyclyl. In further examples, ring A and/or $R^4$ are substituted with up to three additional substituents selected from the group consisting of halo, alkyl, haloalkyl, cyano, nitro, hydroxy, —$OR^{25}$, —$N(R^{25})_2$, —$C(O)OR^{25}$, —$C(O)N(R^{25})_2$ and combinations thereof; where each $R^{25}$ is independently selected from the group consisting of hydrogen, alkyl, haloalkyl, cycloalkyl and cycloalkylalkyl.

Another embodiment of the invention is a compound of formula (I), as set forth above in the Summary of the Invention, according to formula (Ia):

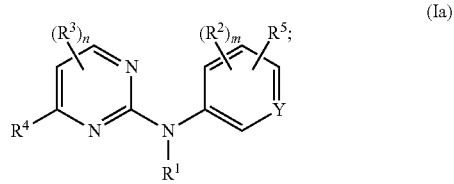

(Ia)

wherein:
n is 0, 1 or 2;
m is 0, 1 or 2;
Y is selected from the group consisting of =$C(R^6)$— and =N—;
$R^1$ is selected from the group consisting of hydrogen, alkyl, alkenyl, alkynyl, haloalkyl, haloalkenyl, haloalkenyl, optionally substituted cycloalkyl, optionally substituted cycloalkylalkyl, optionally substituted cycloalkylalkenyl, optionally substituted cycloalkylalkynyl, optionally substituted aryl, optionally substituted aralkyl, optionally substituted aralkenyl, optionally substituted aralkynyl, —$R^8$—$C(O)OR^6$, —$R^9$—$N(R^6)R^7$ and —$R^9$—$OR^6$;
each $R^2$, when present, is independently selected from the group consisting of optionally substituted alkyl, halo, cyano and —$OR^6$;
each $R^3$, when present, is independently selected from the group consisting of alkyl, halo and haloalkyl;
$R^4$ is selected from the group consisting of aryl and heteroaryl, where the aryl and the heteroaryl are each independently optionally substituted by one or more substituents selected from the group consisting of oxo, alkyl, halo, haloalkyl, cyano, N-heterocyclyl, N-heteroaryl, aryl, —$R^8$—$OR^{6a}$, —$R^8$—$S(O)_pR^{6a}$ (where p is 0, 1 or 2), —$R^8$—$C(O)R^{6a}$, —$R^8$—$C(O)OR^{6a}$, —$R^8$—$C(O)N(R^{6a})R^{7a}$, —$R^8$—$N(R^{6a})R^{7a}$, —$R^8$—$N(R^{6a})$—$R^9$—$N(R^{6a})R^{7a}$, —$R^8$—$N(R^{6a})$—$R^9$—$OR^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$, and —$R^8$—$N(R^{6a})$—$R^9$—$N(R^{6a})S(O)_2R^{7a}$, where each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl and optionally substituted aralkyl, and where the N-heterocyclyl, the N-heteroaryl and the aryl are each independently optionally substituted by one or more substituents selected from the group consisting of —$C(O)R^6$, —$R^8$—$N(R^6)R^7$, —$R^8$—$C(O)N(R^6)R^7$, alkyl, halo and optionally substituted aryl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;
$R^5$ is an N-heterocyclyl, wherein a nitrogen atom in the N-heterocyclyl is optionally substituted by a substituent selected from the group consisting of alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^8$—$OR^6$, —$R^8$—$C(O)R^6$, —$R^8$—$C(O)OR^6$, —$R^9$—$N(R^6)R^7$, —$R^8$—$C(O)N(R^6)R^7$, —$R^8$—$C(N=R^6)N(R^6)R^7$, —$R^8$—$S(O)_2N(R^6)R^7$, and —$R^8$—$S(O)_tR^6$ (where t is 1 or 2); and a carbon atom in the N-heterocyclyl is optionally substituted by a substituent selected from the group consisting of alkyl, alkenyl, alkynyl, halo, haloalkyl, haloalkenyl, haloalkynyl, oxo, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^8-OR^6$, $-R^8-C(O)R^6$, $-R^8-C(O)OR^6$, $-R^9-N(R^6)R^7$, $-R^8-C(O)N(R^6)R^7$, $-R^8-S(O)_2N(R^6)R^7$, and $-R^8-S(O)_pR^6$ (where p is 0, 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain; and each $R^9$ is independently selected from the group consisting of an optionally substituted straight or branched alkylene chain, an optionally substituted straight or branched alkenylene chain and an optionally substituted straight or branched alkynylene chain;

provided at least one of $R^5$ and a substituent on $R^4$ is a bridged N-heterocyclyl;

as an isolated stereoisomer or a mixture thereof, or as a pharmaceutically acceptable salt thereof.

One embodiment of the compounds of formula (Ia) is a compound of formula (Ia), as set forth above, wherein:
m is 0 or 1;
$R^2$, when present, is in a meta position relative to the nitrogen bearing $R^1$; and
$R^5$ is in the para position relative to the nitrogen bearing $R^1$.

One embodiment of the compounds of formula (Ia) is a compound of formula (Ia), as set forth above, wherein:
n is 0 or 1; and
$R^3$, when present, is at the 5-position of the pyrimidinyl ring.

One embodiment of the compounds of formula (Ia) is a compound of formula (Ia), as set forth above, wherein:
m is 0 or 1;
n is 0 or 1;
$R^2$, when present, is in a meta position relative to the nitrogen bearing $R^1$;
$R^3$, when present, is at the 5-position of the pyrimidinyl ring; and
$R^5$ is in the para position relative to the nitrogen bearing $R^1$.

One embodiment of the invention is a compound of formula (I), as set forth above in the Summary of the Invention, according to formula (Ia-1):

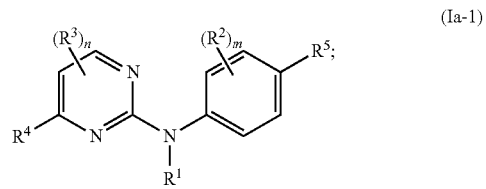

wherein:
n is 0, 1 or 2;
m is 0, 1 or 2;
$R^1$ is selected from the group consisting of hydrogen, alkyl, alkenyl, alkynyl, haloalkyl, haloalkenyl, haloalkenyl, optionally substituted cycloalkyl, optionally substituted cycloalkylalkyl, optionally substituted cycloalkylalkenyl, optionally substituted cycloalkylalkynyl, optionally substituted aryl, optionally substituted aralkyl, optionally substituted aralkenyl, optionally substituted aralkynyl, $-R^8-C(O)OR^6$, $-R^9-N(R^6)R^7$ and $-R^9-OR^6$;
each $R^2$, when present, is independently selected from the group consisting of optionally substituted alkyl, halo, cyano and $-OR^6$;
each $R^3$, when present, is independently selected from the group consisting of alkyl, halo and haloalkyl;
$R^4$ is selected from the group consisting of aryl and heteroaryl, where the aryl and the heteroaryl are each independently optionally substituted by one or more substituents selected from the group consisting of oxo, alkyl, halo, haloalkyl, cyano, N-heterocyclyl, N-heteroaryl, aryl, $-R^8-OR^{6a}$, $-R^8-S(O)_pR^{6a}$ (where p is 0, 1 or 2), $-R^8-C(O)R^{6a}$, $-R^8-C(O)OR^{6a}$, $-R^8-C(O)N(R^{6a})R^{7a}$, $-R^8-N(R^{6a})R^{7a}$, $-R^8-N(R^{6a})-R^9-N(R^{6a})R^{7a}$, $-R^8-N(R^{6a})-R^9-OR^{7a}$, $-R^8-N(R^{6a})C(O)R^{7a}$, $-R^8-N(R^{6a})S(O)_2R^{7a}$, $-R^8-N(R^{6a})C(O)-R^8-N(R^{6a})R^{7a}$, and $-R^8-N(R^{6a})-R^9-N(R^{6a})S(O)_2R^{7a}$, where each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl and optionally substituted aralkyl, and where the N-heterocyclyl, the N-heteroaryl and the aryl are each independently optionally substituted by one or more substituents selected from the group consisting of $-C(O)R^6$, $-R^8-N(R^6)R^7$, $-R^8-C(O)N(R^6)R^7$, alkyl, halo and optionally substituted aryl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;
$R^5$ is an N-heterocyclyl, wherein a nitrogen atom in the N-heterocyclyl is optionally substituted by a substituent selected from the group consisting of alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^8-OR^6$, $-R^8-C(O)R^6$, $-R^8-C(O)OR^6$, $-R^9-N(R^6)R^7$, $-R^8-C(O)N$ $(R^6)R^7$, —$R^8$—$C(N=R^6)N(R^6)R^7$, —$R^8$—$S(O)_2N(R^6)$ $R^7$, and —$R^8$—$S(O)_tR^6$ (where t is 1 or 2); and a carbon atom in the N-heterocyclyl is optionally substituted by a substituent selected from the group consisting of alkyl, alkenyl, alkynyl, halo, haloalkyl, haloalkenyl, haloalkynyl, oxo, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^8$—$OR^6$, —$R^8$—$C(O)R^6$, —$R^8$—$C(O)OR^6$, —$R^9$—$N(R^6)R^7$, —$R^8$—$C(O)N(R^6)R^7$, —$R^8$—$S(O)_2N(R^6)R^7$, and —$R^8$—$S(O)_pR^6$ (where p is 0, 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain; and each $R^9$ is independently selected from the group consisting of an optionally substituted straight or branched alkylene chain, an optionally substituted straight or branched alkenylene chain and an optionally substituted straight or branched alkynylene chain;

provided at least one of $R^5$ and a substituent on $R^4$ is a bridged N-heterocyclyl.

Of the compounds of formula (Ia-1), as set forth above, one embodiment is a compound selected from the following formulae:

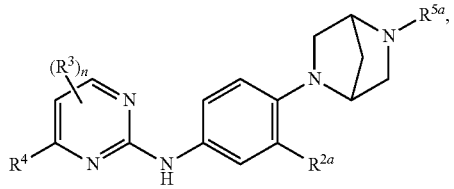
(Ia-1a)

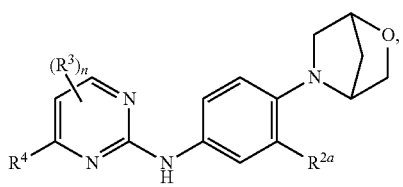
(Ia-1b)

-continued

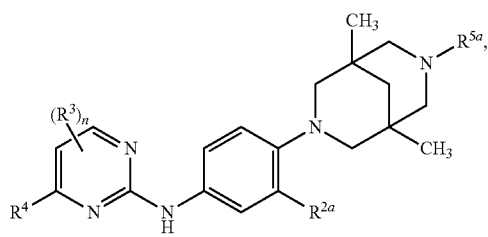
(Ia-1c)

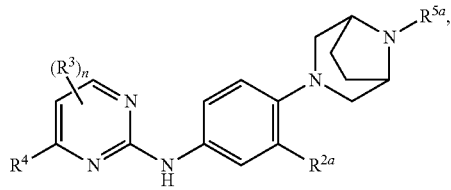
(Ia-1d)

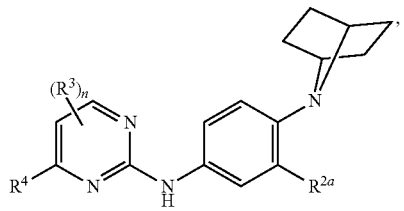
(Ia-1e)

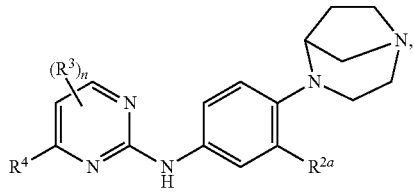
(Ia-1f)

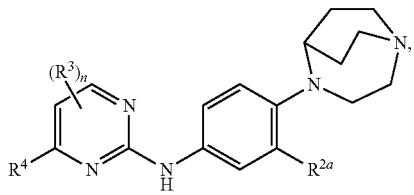
(Ia-1g)

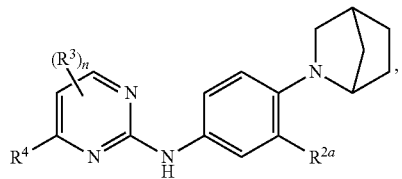
(Ia-1h)

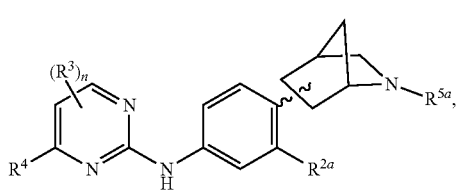
(Ia-1i)

-continued

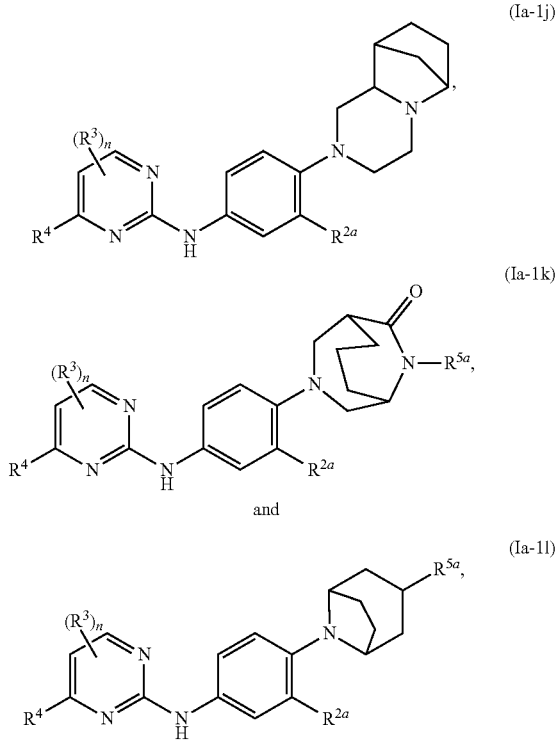

wherein:
each n is 0, 1 or 2;
each $R^{22}$ is independently selected from the group consisting of hydrogen, optionally substituted alkyl, halo, cyano and —$OR^6$;
each $R^3$, when present, is independently selected from the group consisting of alkyl, halo and haloalkyl;
each $R^4$ is independently selected from the group consisting of aryl and heteroaryl, where the aryl and the heteroaryl are each independently optionally substituted by one or more substituents selected from the group consisting of oxo, alkyl, halo, haloalkyl, cyano, N-heterocyclyl, N-heteroaryl, aryl, —$R^8$—$OR^{6a}$, —$R^8$—$S(O)_pR^{6a}$ (where p is 0, 1 or 2), —$R^8$—$C(O)R^{6a}$, —$R^8$—$C(O)OR^{6a}$, —$R^8$—$C(O)N(R^{6a})R^{7a}$, —$R^8$—$N(R^{6a})R^{7a}$, —$R^8$—$N(R^{6a})$—$R^9$—$N(R^{6a})R^{7a}$, —$R^8$—$N(R^{6a})$—$R^9$—$OR^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$, and —$R^8$—$N(R^{6a})$—$R^9$—$N(R^{6a})S(O)_2R^{7a}$, where each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl and optionally substituted aralkyl, and where the N-heterocyclyl, the N-heteroaryl and the aryl are each independently optionally substituted by one or more substituents selected from the group consisting of —$C(O)R^6$, —$R^8$—$N(R^6)R^7$, —$R^8$—$C(O)N(R^6)R^7$, alkyl, halo and optionally substituted aryl, and when any $R^{6a}$ and $R^{7a}$ are bonded to a common nitrogen, $R_{6a}$ and $R^{7a}$ together with the common nitrogen to which they are both attached, may form an optionally substituted N-heteroaryl or an optionally substituted N-heterocyclyl;
each $R^{5a}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^8$—$OR^6$, —$R^8$—$C(O)R^6$, —$R^8$—$C(O)OR^6$, —$R^9$—$N(R^6)R^7$, —$R^8$—$C(O)N(R^6)R^7$, —$R^8$—$C(N=R^6)N(R^6)R^7$, —$R^8$—$S(O)_2N(R^6)R^7$, and —$R^8$—$S(O)_tR^6$ (where t is 1 or 2);
each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;
each $R^8$ is independently selected from the group consisting of a direct bond, an optionally substituted straight or branched alkylene chain, an optionally substituted straight or branched alkenylene chain and an optionally substituted straight or branched alkynylene chain; and
each $R^9$ is independently selected from the group consisting of an optionally substituted straight or branched alkylene chain, an optionally substituted straight or branched alkenylene chain and an optionally substituted straight or branched alkynylene chain.

Of this embodiment, one embodiment is a compound selected from the formulae above wherein:
each n is 0 or 1;
each $R^4$ is independently selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —$R^8$—$OR^{6a}$, —$R^8$—$S(O)_pR^{6a}$ (where p is 0, 1 or 2), —$R^8$—$C(O)R^{6a}$, —$R^8$—$C(O)OR^{6a}$, —$R^8$—$C(O)N(R^{6a})R^{7a}$, —$R^8$—$N(R^{6a})R^{7a}$, —$R^8$—$N(R^{6a})$—$R^9$—$N(R^{6a})R^{7a}$, —$R^8$—$N(R^{6a})$—$R^9$—$OR^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$, and —$R^8$—$N(R^{6a})$—$R^9$—$N(R^{6a})S(O)_2R^{7a}$, where the N-heterocyclyl, the N-heteroaryl and the aryl are each independently optionally substituted by one or more substituents selected from the group consisting of —C(O)R⁶, —R⁸—N(R⁶)R⁷, —R⁸—C(O)N(R⁶)R⁷, alkyl, halo and optionally substituted aryl;

each R⁶ and each R⁷ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any R⁶ and R⁷, together with the common nitrogen to which they are both attached, form an optionally substituted N-heteroaryl or an optionally substituted N-heterocyclyl;

R⁶ᵃ and R⁷ᵃ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any R⁶ᵃ and R⁷ᵃ are bonded to a common nitrogen, R⁶ᵃ and R⁷ᵃ together with the common nitrogen to which they are both attached, may form an optionally substituted N-heteroaryl or an optionally substituted N-heterocyclyl;

each R⁸ is independently selected from the group consisting of a direct bond and an optionally substituted straight or branched alkylene chain; and each R⁹ is an optionally substituted straight or branched alkylene chain.

One embodiment of the compounds of formula (Ia-1), as set forth above, is a compound according to formula (Ia-1a):

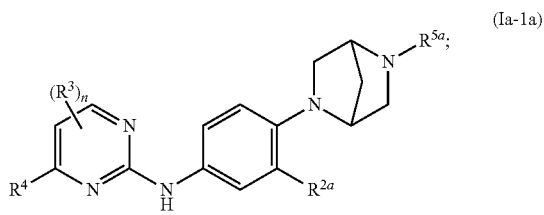

(Ia-1a)

wherein:

n is 0 or 1;

R²ᵃ is independently selected from the group consisting of hydrogen, optionally substituted alkyl, halo, cyano and —OR⁶;

R³, when present, is independently selected from the group consisting of alkyl, halo and haloalkyl;

R⁴ is selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —R⁸—OR⁶ᵃ, —R⁸—S(O)ₚR⁶ᵃ (where p is 0, 1 or 2), —R⁸—C(O)R⁶ᵃ, —R⁸—C(O)OR⁶ᵃ, —R⁸—C(O)N(R⁶ᵃ)R⁷ᵃ, —R⁸—N(R⁶ᵃ)R⁷ᵃ, —R⁸—N(R⁶ᵃ—R⁹—N(R⁶ᵃ)R⁷ᵃ, —R⁸—N(R⁶ᵃ)—R⁹—OR⁷ᵃ, —R⁸—N(R⁶ᵃ)C(O)R⁷ᵃ, —R⁸—N(R⁶ᵃ)S(O)₂R⁷ᵃ, —R⁸—N(R⁶ᵃ)C(O)—R⁸—N(R⁶ᵃ)R⁷ᵃ, and —R⁸—N(R⁶ᵃ)—R⁹—N(R⁶ᵃ)S(O)₂R⁷ᵃ, where the N-heterocyclyl, the N-heteroaryl and the aryl are each independently optionally substituted by one or more substituents selected from the group consisting of —C(O)R⁶, —R⁸—N(R⁶)R⁷, —R⁸—C(O)N(R⁶)R⁷, alkyl, halo and optionally substituted aryl;

R⁵ᵃ is selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R⁸—OR⁶, —R⁸—C(O)R⁶, —R⁸—C(O)OR⁶, —R⁹—N(R⁶)R⁷, —R⁸—C(O)N(R⁶)R⁷, —R⁸—C(N=R⁶)N(R⁶)R⁷, —R⁸—S(O)₂N(R⁶)R⁷, and —R⁸—S(O)ₜR⁶ (where t is 1 or 2);

each R⁶ and each R⁷ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any R⁶ and R⁷, together with the common nitrogen to which they are both attached, form an optionally substituted N-heteroaryl or an optionally substituted N-heterocyclyl;

R⁶ᵃ and R⁷ᵃ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any R⁶ᵃ and R⁷ᵃ are bonded to a common nitrogen, R⁶ᵃ and R⁷ᵃ together with the common nitrogen to which they are both attached, may form an optionally substituted N-heteroaryl or an optionally substituted N-heterocyclyl;

each R⁸ is independently selected from the group consisting of a direct bond and an optionally substituted straight or branched alkylene chain; and each R⁹ is an optionally substituted straight or branched alkylene chain.

Of this embodiment, one embodiment is a compound of formula (Ia-1a), as set forth above, wherein:

n is 0 or 1;

R²ᵃ is independently selected from the group consisting of hydrogen, optionally substituted alkyl, halo, cyano and —OR⁶;

R³, when present, is independently selected from the group consisting of alkyl, halo and haloalkyl;

R⁴ is pyridinyl substituted by one or more substituents selected from the group consisting of alkyl, haloalkyl, cyano, —R⁸—OR⁶ᵃ, —R⁸—N(R⁶ᵃ)R⁷ᵃ, —R⁸—N(R⁶ᵃ)—R⁹—N(R⁶ᵃ)R⁷ᵃ and —R⁸—N(R⁶ᵃ)—R⁹—OR⁷ᵃ;

R⁵ᵃ is independently selected from the group consisting of hydrogen, alkyl, optionally substituted cycloalkyl, —R⁸—C(O)R⁶ and —R⁸—S(O)ₜR⁶ (where t is 1 or 2);

each R⁶ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

R⁶ᵃ and R⁷ᵃ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any R⁶ᵃ and R⁷ᵃ are bonded to a common nitrogen, R⁶ᵃ and R⁷ᵃ together with the common nitrogen to which they are both attached, may form an optionally substituted N-heteroaryl or an optionally substituted N-heterocyclyl;

each R⁸ is independently selected from the group consisting of a direct bond and an optionally substituted straight or branched alkylene chain; and each R⁹ is an optionally substituted straight or branched alkylene chain.

A specific embodiment of this embodiment is a compound of formula (Ia-1a), as set forth above, selected from the group consisting of:

4-(6-(N,N-dimethylamino)pyridin-3-yl)-N-(3-methyl-4-((1S,4S)-5-methyl-2,5-diazabicyclo[2.2.1]heptan-2-yl)phenyl)pyrimidin-2-amine;

4-(6-(N,N-dimethylamino)pyridin-3-yl)-5-methyl-N-(3-methyl-4-((1S,4S)-5-methyl-2,5-diazabicyclo[2.2.1]heptan-2-yl)phenyl)pyrimidin-2-amine;

4-(6-(N,N-dimethylamino)pyridin-3-yl)-5-trifluoromethyl-N-(3-methyl-4-((1S,4S)-5-methyl-2,5-diazabicyclo[2.2.1]heptan-2-yl)phenyl)pyrimidin-2-amine;

4-(6-(N,N-dimethylamino)pyridin-3-yl)-5-fluoro-N-(3-methyl-4-((1S,4S)-5-methyl-2,5-diazabicyclo[2.2.1]heptan-2-yl)phenyl)pyrimidin-2-amine;

4-(6-(N,N-dimethylamino)pyridin-3-yl)-5-fluoro-N-(3-fluoro-4-((1S,4S)-5-methyl-2,5-diazabicyclo[2.2.1]heptan-2-yl)phenyl)pyrimidin-2-amine;

4-(6-(N,N-dimethylamino)pyridin-3-yl)-5-methyl-N-(3-fluoro-4-((1S,4S)-5-methyl-2,5-diazabicyclo[2.2.1]heptan-2-yl)phenyl)pyrimidin-2-amine;

4-(6-(N,N-dimethylamino)pyridin-3-yl)-N-(3-fluoro-4-((1S,4S)-5-methyl-2,5-diazabicyclo[2.2.1]heptan-2-yl)phenyl)pyrimidin-2-amine;

4-(6-(dimethylamino)pyridin-3-yl)-N-(3-methyl-4-((1S,4S)-5-ethyl-2,5-diazabicyclo[2.2.1]heptan-2-yl)phenyl)pyrimidin-2-amine;

4-(6-(2-(morpholin-4-yl)ethyl)aminopyridin-3-yl)-N-(4-((1S,4S)-5-methyl-2,5-diazabicyclo[2.2.1]heptan-2-yl)phenyl)pyrimidin-2-amine;

4-(6-(2-(morpholin-4-yl)ethyl)aminopyridin-3-yl)-N-(3-fluoro-4-((1S,4S)-5-methyl-2,5-diazabicyclo[2.2.1]heptan-2-yl)phenyl)pyrimidin-2-amine;

4-(6-(cyclohexylamino)pyridin-3-yl)-N-(3-methyl-4-((1S,4S)-5-methyl-2,5-diazabicyclo[2.2.1]heptan-2-yl)phenyl)pyrimidin-2-amine;

4-(6-(cyclohexylamino)pyridin-3-yl)-N-(3-fluoro-4-((1S,4S)-5-methyl-2,5-diazabicyclo[2.2.1]heptan-2-yl)phenyl)pyrimidin-2-amine;

4-(6-(benzylamino)pyridin-3-yl)-N-(3-methyl-4-((1S,4S)-5-methyl-2,5-diazabicyclo[2.2.1]heptan-2-yl)phenyl)pyrimidin-2-amine;

4-(6-(benzylamino)pyridin-3-yl)-N-(3-fluoro-4-((1S,4S)-5-methyl-2,5-diazabicyclo[2.2.1]heptan-2-yl)phenyl)pyrimidin-2-amine;

4-(6-(cyclohexylamino)pyridin-3-yl)-N-(3-trifluoromethyl-4-((1S,4S)-5-methyl-2,5-diazabicyclo[2.2.1]heptan-2-yl)phenyl)pyrimidin-2-amine;

4-(6-(dimethylamino)pyridin-3-yl)-N-(3-trifluoromethyl-4-((1S,4S)-5-methyl-2,5-diazabicyclo[2.2.1]heptan-2-yl)phenyl)pyrimidin-2-amine;

4-(6-cyanopyridin-3-yl)-N-(3-methyl-4-((1S,4S)-5-methyl-2,5-diazabicyclo[2.2.1]heptan-2-yl)phenyl)pyrimidin-2-amine;

4-(5-cyanopyridin-3-yl)-N-(3-methyl-4((1S,4S)-5-methyl-2,5-diazabicyclo[2.2.1]heptan-2-yl)phenyl)pyrimidin-2-amine;

4-(6-aminopyridin-3-yl)-N-(3-methyl-4-((1S,4S)-5-ethylcarbonyl-2,5-diazabicyclo[2.2.1]heptan-2-yl)phenyl)pyrimidin-2-amine;

4-(6-aminopyridin-3-yl)-N-(3-methyl-4-((1S,4S)-5-methylsulfonyl-2,5-diazabicyclo[2.2.1]heptan-2-yl)phenyl)pyrimidin-2-amine;

4-(6-ethoxypyridin-3-yl)-N-(3-methyl-4-((1S,4S)-5-methyl-2,5-diazabicyclo[2.2.1]heptan-2-yl)phenyl)pyrimidin-2-amine;

4-(6-ethoxypyridin-3-yl)-N-(3-fluoro-4-((1S,4S)-5-methyl-2,5-diazabicyclo[2.2.1]heptan-2-yl)phenyl)pyrimidin-2-amine;

4-(6-(dimethylamino)pyridin-3-yl)-N-(4-((1S,4S)-5-methyl-2,5-diazabicyclo[2.2.1]heptan-2-yl)phenyl)pyrimidin-2-amine;

4-(6-(3-ethoxypropyl)aminopyridin-3-yl)-N-(3-methyl-4-((1S,4S)-5-methyl-2,5-diazabicyclo[2.2.1]heptan-2-yl)phenyl)pyrimidin-2-amine;

4-(6-(propylamino)pyridin-3-yl)-N-(3-methyl-4-((1S,4S)-5-methyl-2,5-diazabicyclo[2.2.1]heptan-2-yl)phenyl)pyrimidin-2-amine;

4-(6-(2-(morpholin-4-yl)ethyl)aminopyridin-3-yl)-N-(3-methyl-4-((1S,4S)-5-ethylcarbonyl-2,5-diazabicyclo[2.2.1]heptan-2-yl)phenyl)pyrimidin-2-amine;

4-(6-(3-dimethylamino)propylaminopyridin-3-yl)-N-(3-methyl-4-((1S,4S)-5-methyl-2,5-diazabicyclo[2.2.1]heptan-2-yl)phenyl)pyrimidin-2-amine;

4-(6-(3-methylbutyl)aminopyridin-3-yl)-N-(3-methyl-4-((1S,4S)-5-methyl-2,5-diazabicyclo[2.2.1]heptan-2-yl)phenyl)pyrimidin-2-amine;

4-(6-(3,3-dimethylbutyl)aminopyridin-3-yl)-N-(3-methyl-4-((1S,4S)-5-methyl-2,5-diazabicyclo[2.2.1]heptan-2-yl)phenyl)pyrimidin-2-amine;

4-(6-(2-methoxyethyl)(methyl)aminopyridin-3-yl)-N-(3-methyl-4-((1S,4S)-5-methyl-2,5-diazabicyclo[2.2.1]heptan-2-yl)phenyl)pyrimidin-2-amine;

4-(6-(propylamino)pyridin-3-yl)-N-(3-methyl-4-((1S,4S)-5-methylsulfonyl-2,5-diazabicyclo[2.2.1]heptan-2-yl)phenyl)pyrimidin-2-amine;

4-(2-(trifluoromethyl)pyridin-4-yl)-N-(3-methyl-4-((1S,4S)-5-methyl-2,5-diazabicyclo[2.2.1]heptan-2-yl)phenyl)pyrimidin-2-amine;
4-(6-(tetrahydropyran-4-yloxy)pyridin-3-yl)-N-(3-chloro-4-((1S,4S)-5-(methylsulfonyl)-2,5-diazabicyclo[2.2.1]heptan-2-yl)phenyl)pyrimidin-2-amine;
4-(6-(tetrahydropyran-4-yloxy)pyridin-3-yl)-N-(3-chloro-4-((1S,4S)-5-acetyl-2,5-diazabicyclo[2.2.1]heptan-2-yl)phenyl)pyrimidin-2-amine;
4-(6-(tetrahydropyran-4-yloxy)pyridin-3-yl)-N-(3-methyl-4-((1S,4S)-5-methyl-2,5-diazabicyclo[2.2.1]heptan-2-yl)phenyl)pyrimidin-2-amine; and
4-(6-(tetrahydropyran-4-yloxy)pyridin-3-yl)-N-(3-methyl-4-((1S,4S)-5-cyclopentyl-2,5-diazabicyclo[2.2.1]heptan-2-yl)phenyl)pyrimidin-2-amine.

Of this embodiment, another embodiment is a compound of formula (Ia-1a), as set forth above, wherein:
n is 0 or 1;
$R^{2a}$ is independently selected from the group consisting of hydrogen, optionally substituted alkyl, halo, cyano and —OR$^6$;
$R^3$, when present, is independently selected from the group consisting of alkyl, halo and haloalkyl;
$R^4$ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by one or more substituents selected from the group consisting of —C(O)R$^6$, —R$^8$—N(R$^6$)R$^7$, —R$^8$—C(O)N(R$^6$)R$^7$, alkyl, halo and optionally substituted aryl;
$R^{5a}$ is independently selected from the group consisting of hydrogen, alkyl, haloalkyl, optionally substituted cycloalkyl, optionally substituted cycloalkylalkyl, —R$^8$—C(O)R$^6$, —R$^8$—C(O)N(R$^6$)R$^7$, —R$^8$—C(N═R$^6$)N(R$^6$)R$^7$ and —R$^8$—S(O)$_t$R$^8$ (where t is 1 or 2);
each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and
each $R^8$ is independently selected from the group consisting of a direct bond and an optionally substituted straight or branched alkylene chain.

A specific embodiment of this embodiment is a compound of formula (Ia-1a), as set forth above, selected from the group consisting of:
4-(6-(morpholin-4-yl)pyridin-3-yl)-N-(3-methyl-4-((1S,4S)-5-methyl-2,5-diazabicyclo[2.2.1]heptan-2-yl)phenyl)pyrimidin-2-amine;
4-(6-(morpholin-4-yl)pyridin-3-yl)-N-(3-fluoro-4-((1S,4S)-5-methyl-2,5-diazabicyclo[2.2.1]heptan-2-yl)phenyl)pyrimidin-2-amine;
4-(6-(4-acetylpiperazin-1-yl)pyridin-3-yl)-N-(3-fluoro-4-((1S,4S)-5-methyl-2,5-diazabicyclo[2.2.1]heptan-2-yl)phenyl)pyrimidin-2-amine;
4-(6-(morpholin-4-yl)pyridin-3-yl)-N-(3-methyl-4-((1S,4S)-5-ethyl-2,5-diazabicyclo[2.2.1]heptan-2-yl)phenyl)pyrimidin-2-amine;
4-(6-(morpholin-4-yl)pyridin-3-yl)-N-(3-methyl-4-((1S,4S)-5-((ethylamino)carbonyl)-2,5-diazabicyclo[2.2.1]heptan-2-yl)phenyl)pyrimidin-2-amine;
4-(6-(morpholin-4-yl)pyridin-3-yl)-N-(3-methyl-4-((1S,4S)-5-(2,2,2-trifluoroethyl)-2,5-diazabicyclo[2.2.1]heptan-2-yl)phenyl)pyrimidin-2-amine;
4-(6-(morpholin-4-yl)pyridin-3-yl)-N-(3-methyl-4-((1S,4S)-5-(cyclopropyl)methyl-2,5-diazabicyclo[2.2.1]heptan-2-yl)phenyl)pyrimidin-2-amine;
4-(3-fluoro-2-(morpholin-4-yl)pyridin-4-yl)-N-(3-fluoro-4-((1S,4S)-5-methyl-2,5-diazabicyclo[2.2.1]heptan-2-yl)phenyl)pyrimidin-2-amine;
4-(5-methyl-6-(morpholin-4-yl)pyridin-3-yl)-N-(3-fluoro-4-((1S,4S)-5-methyl-2,5-diazabicyclo[2.2.1]heptan-2-yl)phenyl)pyrimidin-2-amine;
4-(5-methyl-6-(morpholin-4-yl)pyridin-3-yl)-N-(3-methyl-4-((1S,4S)-5-methyl-2,5-diazabicyclo[2.2.1]heptan-2-yl)phenyl)pyrimidin-2-amine;
5-methyl-4-(6-(morpholin-4-yl)pyridin-3-yl)-N-(3-methyl-4-((1S,4S)-5-methyl-2,5-diazabicyclo[2.2.1]heptan-2-yl)phenyl)pyrimidin-2-amine;
5-methyl-4-(6-(morpholin-4-yl)pyridin-3-yl)-N-(3-fluoro-4-((1S,4S)-5-methyl-2,5-diazabicyclo[2.2.1]heptan-2-yl)phenyl)pyrimidin-2-amine;
4-(6-(morpholin-4-yl)pyridin-3-yl)-N-(3-methyl-4-((1R,4R)-5-methyl-2,5-diazabicyclo[2.2.1]heptan-2-yl)phenyl)pyrimidin-2-amine;
4-(6-(morpholin-4-yl)pyridin-3-yl)-N-(3-fluoro-4-((1R,4R)-5-methyl-2,5-diazabicyclo[2.2.1]heptan-2-yl)phenyl)pyrimidin-2-amine;
4-(6-(morpholin-4-yl)pyridin-3-yl)-N-(3-trifluoromethyl-4-((1S,4S)-5-methyl-2,5-diazabicyclo[2.2.1]heptan-2-yl)phenyl)pyrimidin-2-amine;
4-(6-(morpholin-4-yl)pyridin-3-yl)-N-(3-cyano-4-((1S,4S)-5-acetyl-2,5-diazabicyclo[2.2.1]heptan-2-yl)phenyl)pyrimidin-2-amine;
4-(6-(morpholin-4-yl)pyridin-3-yl)-N-(3-cyano-4-((1S,4S)-5-methylsulfonyl-2,5-diazabicyclo[2.2.1]heptan-2-yl)phenyl)pyrimidin-2-amine;
4-(6-(morpholin-4-yl)pyridin-3-yl)-N-(3-cyano-4-((1S,4S)-5-methyl-2,5-diazabicyclo[2.2.1]heptan-2-yl)phenyl)pyrimidin-2-amine;
4-(6-(morpholin-4-yl)pyridin-3-yl)-N-(3-cyano-4-((1S,4S)-5-cyclopentyl-2,5-diazabicyclo[2.2.1]heptan-2-yl)phenyl)pyrimidin-2-amine;
4-(6-(morpholin-4-yl)pyridin-3-yl)-N-(4-((1S,4S)-5-methyl-2,5-diazabicyclo[2.2.1]heptan-2-yl)phenyl)pyrimidin-2-amine;
4-(6-(cis-2,6-dimethylmorpholin-4-yl)pyridin-3-yl)-N-(3-methyl-4-((1S,4S)-5-methyl-2,5-diazabicyclo[2.2.1]heptan-2-yl)phenyl)pyrimidin-2-amine;
4-(6-(2-(dimethylamino)methylmorpholin-4-yl)pyridin-3-yl)-N-(3-methyl-4-((1S,4S)-5-methyl-2,5-diazabicyclo[2.2.1]heptan-2-yl)phenyl)pyrimidin-2-amine;
4-(6-(piperidin-1-yl)pyridin-3-yl)-N-(3-methyl-4-((1S,4S)-5-methyl-2,5-diazabicyclo[2.2.1]heptan-2-yl)phenyl)pyrimidin-2-amine;
4-(6-(3-(aminocarbonyl)piperidin-1-yl)pyridin-3-yl)-N-(3-methyl-4-((1S,4S)-5-methyl-2,5-diazabicyclo[2.2.1]heptan-2-yl)phenyl)pyrimidin-2-amine;
4-(6-(morpholin-4-yl)pyridin-3-yl)-N-(3-methyl-4-((1S,4S)-5-methylsulfonyl-2,5-diazabicyclo[2.2.1]heptan-2-yl)phenyl)pyrimidin-2-amine;

4-(6-(morpholin-4-yl)pyridin-3-yl)-N-(3-methyl-4-((1S,4S)-5-ethylcarbonyl-2,5-diazabicyclo[2.2.1]heptan-2-yl)phenyl)pyrimidin-2-amine;

4-(6-(morpholin-4-yl)pyridin-3-yl)-N-(3-methyl-4-((1S,4S)-5-amidino-2,5-diazabicyclo[2.2.1]heptan-2-yl)phenyl)pyrimidin-2-amine;

4-(6-(morpholin-4-yl)pyridin-3-yl)-N-(3-methyl-4-((1S,4S)-5-isobutyl-2,5-diazabicyclo[2.2.1]heptan-2-yl)phenyl)pyrimidin-2-amine;

4-(6-(1,4-oxazepan-4-yl)pyridin-3-yl)-N-(3-methyl-4-((1S,4S)-5-methyl-2,5-diazabicyclo[2.2.1]heptan-2-yl)phenyl)pyrimidin-2-amine;

4-(6-((1S,4S)-2-oxa-5-azabicyclo[2.2.1]heptan-5-yl)pyridin-3-yl)-N-(3-methyl-4-((1S,4S)-5-methyl-2,5-diazabicyclo[2.2.1]heptan-2-yl)phenyl)pyrimidin-2-amine;

4-(6-(thiamorpholin-4-yl)pyridin-3-yl)-N-(3-methyl-4-((1S,4S)-5-methyl-2,5-diazabicyclo[2.2.1]heptan-2-yl)phenyl)pyrimidin-2-amine; and 4-(6-(morpholin-4-yl)pyridin-3-yl)-N-(3-methyl-4-((1S,4S)-5-methyl-2,5-diazabicyclo[2.2.1]heptan-2-yl)phenyl)pyrimidin-2-amine;

4-(6-(morpholin-4-yl)pyridin-3-yl)-N-(3-methyl-4-((1S,4S)-5-cyclopropyl-2,5-diazabicyclo[2.2.1]heptan-2-yl)phenyl)pyrimidin-2-amine;

4-(6-(morpholin-4-yl)pyridin-3-yl)-N-(3-chloro-4-((1S,4S)-5-methyl-2,5-diazabicyclo[2.2.1]heptan-2-yl)phenyl)pyrimidin-2-amine;

4-(6-(morpholin-4-yl)pyridin-3-yl)-N-(3-chloro-4-((1S,4S)-5-(methylsulfonyl)-2,5-diazabicyclo[2.2.1]heptan-2-yl)phenyl)pyrimidin-2-amine;

4-(6-(morpholin-4-yl)pyridin-3-yl)-N-(3-chloro-4-((1S,4S)-5-acetyl-2,5-diazabicyclo[2.2.1]heptan-2-yl)phenyl)pyrimidin-2-amine;

4-(6-(morpholin-4-yl)pyridin-3-yl)-N-(3-chloro-4-((1S,4S)-5-(1-methylethyl)-2,5-diazabicyclo[2.2.1]heptan-2-yl)phenyl)pyrimidin-2-amine;

4-(6-((1S,4S)-2-oxa-5-azabicyclo[2.2.1]heptan-5-yl)pyridin-3-yl)-N-(3-methyl-4-((1S,4S)-5-(methylsulfonyl)-2,5-diazabicyclo[2.2.1]heptan-2-yl)phenyl)pyrimidin-2-amine; and 4-(6-((1R,4R)-2-oxa-5-azabicyclo[2.2.1]heptan-5-yl)pyridin-3-yl)-N-(3-methyl-4-((1S,4S)-5-methyl-2,5-diazabicyclo[2.2.1]heptan-2-yl)phenyl)pyrimidin-2-amine.

Another embodiment is a compound of formula (Ia-1a), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is pyridinyl substituted by one or more substituents selected from the group consisting of —$R^8$—$C(O)R^{6a}$, —$R^8$—$C(O)OR^{6a}$, —$R^8$—$C(O)N(R^{6a})R^{7a}$, —$R^8$—$S(O)_pR^{6a}$ (where p is 0, 1 or 2), —$R^8$—$N(R^{6a})$—$R^9$—$N(R^{6a})S(O)_2R^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$ and tetrazolyl;

$R^{5a}$ is independently selected from the group consisting of hydrogen, alkyl, haloalkyl, optionally substituted cycloalkyl, optionally substituted cycloalkylalkyl, —$R^8$—$C(O)R^6$, —$R^8$—$C(O)N(R^6)R^7$, —$R^8$—$C(N$=$R^6)N(R^6)R^7$ and —$R^8$—$S(O)_tR^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;

each $R^8$ is independently selected from the group consisting of a direct bond and an optionally substituted straight or branched alkylene chain; and $R^9$ is an optionally substituted straight or branched alkylene chain.

A specific embodiment of this embodiment is a compound of formula (Ia-1a), as set forth above, selected from the group consisting of:

4-(6-(methylaminocarbonyl)pyridin-3-yl)-N-(3-methyl-4-((1S,4S)-5-methyl-2,5-diazabicyclo[2.2.1]heptan-2-yl)phenyl)pyrimidin-2-amine;

4-(5-((morpholin-4-yl)carbonyl)pyridin-3-yl)-N-(3-methyl-4-((1S,4S)-5-methyl-2,5-diazabicyclo[2.2.1]heptan-2-yl)phenyl)pyrimidin-2-amine. Bis TFA salt;

4-(5-(methyl)sulfonylpyridin-3-yl)-N-(3-methyl-4-((1S,4S)-5-methyl-2,5-diazabicyclo[2.2.1]heptan-2-yl)phenyl)pyrimidin-2-amine;

4-(6-((2-(cyclopropylsulfonyl)aminoethyl)-amino)pyridin-3-yl)-N-(3-methyl-4-((1S,4S)-5-methyl-2,5-diazabicyclo[2.2.1]heptan-2-yl)phenyl)pyrimidin-2-amine;

4-(6-(1H-tetrazol-5-yl)pyridin-3-yl)-N-(3-methyl-4((1S,4S)-5-methyl-2,5-diazabicyclo[2.2.1]heptan-2-yl)phenyl)pyrimidin-2-amine 4-(6-(acetamido)pyridin-3-yl)-N-(3-methyl-4-((1S,4S)-5-methyl-2,5-diazabicyclo[2.2.1]heptan-2-yl)phenyl)pyrimidin-2-amine;

4-(6-(2-(morpholin-4-yl)acetamido)pyridin-3-yl)-N-(3-methyl-4-((1S,4S)-5-methyl-2,5-diazabicyclo[2.2.1]heptan-2-yl)phenyl)pyrimidin-2-amine;

4-(6-(2-(morpholin-4-yl)acetamido)pyridin-3-yl)-N-(4-((1S,4S)-5-methyl-2,5-diazabicyclo[2.2.1]heptan-2-yl)phenyl)pyrimidin-2-amine;

4-(6-(2-(morpholin-4-yl)acetamido)pyridin-3-yl)-N-(3-fluoro-4-((1S,4S)-5-methyl-2,5-diazabicyclo[2.2.1]heptan-2-yl)phenyl)pyrimidin-2-amine;

4-(6-(acetamido)pyridin-3-yl)-N-(3-methyl-4-((1S,4S)-5-ethylcarbonyl-2,5-diazabicyclo[2.2.1]heptan-2-yl)phenyl)pyrimidin-2-amine;

4-(6-(methylsulfonylamino)pyridin-3-yl)-N-(3-methyl-4-((1S,4S)-5-methyl-2,5-diazabicyclo[2.2.1]heptan-2-yl)phenyl)pyrimidin-2-amine;

4-(6-(2-(dimethylamino)acetamido)-pyridin-3-yl)-N-(3-methyl-4-((1S,4S)-5-methyl-2,5-diazabicyclo[2.2.1]heptan-2-yl)phenyl)pyrimidin-2-amine; and 4-(6-(methylsulfonylamino)pyridin-3-yl)-N-(3-fluoro-4-((1S,4S)-5-methyl-2,5-diazabicyclo[2.2.1]heptan-2-yl)phenyl)pyrimidin-2-amine; and 4-(5-(1-methylethoxy)carbonylpropyl-6-aminopyridin-3-yl)-N-(3-methyl-4-((1S,4S)-5-methyl-2,5-diazabicyclo[2.2.1]heptan-2-yl)phenyl)pyrimidin-2-amine.

Another embodiment is a compound of formula (Ia-1a), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is selected from the group consisting of naphthyridinyl, benzo[b]azepinyl, 2,3,4,5-tetrahydro-1H-benzo[b]azepinyl, benzo[b][1,4]oxazinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]thiazinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, and 3,4-dihydro-2H-pyrido[3,2-b][1,4]oxazinyl, each optionally substituted by one or more substituents independently selected from the group consisting of alkyl and oxo;

$R^{5a}$ is independently selected from the group consisting of hydrogen, alkyl, haloalkyl, optionally substituted cycloalkyl, optionally substituted cycloalkylalkyl, —$R^8$—$C(O)R^6$, —$R^8$—$C(O)N(R^6)R^7$, —$R^8$—$C(N=R^6)N(R^6)R^7$, —$R^8$—$S(O)_tR^6$ (where t is 1 or 2), and —$R^8$—$S(O)_2N(R^6)R^7$;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and each $R^8$ is independently selected from the group consisting of a direct bond and an optionally substituted straight or branched alkylene chain.

A specific embodiment of this embodiment is a compound of formula (Ia-1a), as set forth above, selected from the group consisting of:

4-(4-methyl-3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine;

4-(4-methyl-3,4-dihydro-2H-pyrido[3,2-b][1,4]oxazin-7-yl)-N-(3-fluoro-4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-fluoro-4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-((1S,4S)-5-(ethylcarbonyl)-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-((1S,4S)-5-(methylsulfonyl)-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-((1S,4S)-5-ethyl-2,5-diazabicyclo[2.2.1]heptan-2-yl)phenyl)pyrimidin-2-amine;

4-(3'-oxo-3,4'-dihydrospiro[cyclobutane-1,2'-pyrido[3,2-b][1,4]oxazine]-7'-yl)-N-(3-methyl-4-((1S,4S)-5-methyl-2,5-diazabicyclo[2.2.1]heptan-2-yl)phenyl)pyrimidin-2-amine;

4-(3-oxo-3,4'-dihydrospiro[cyclobutane-1,2'-pyrido[3,2-b][1,4]oxazine]-7'-yl)-N-(3-methyl-4-((1S,4S)-5-ethyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-((1S,4S)-5-(aminosulfonyl)-2,5-diazabicyclo[2.2.1]heptan-2-yl)phenyl)pyrimidin-2-amine;

4-(7-oxo-5,6,7,8-tetahydro-1,8-naphthyridin-3-yl)-N-(3-methyl-4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-cyano-4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-((1R,4R)-5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-fluoro-4-((1R,4R)-5-methyl-2,5-diazabicyclo[2.2.1]heptan-2-yl)phenyl)pyrimidin-2-amine;

4-(3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine;

4-(3,4-dihydro-2H-pyrido[3,2-b][1,4]oxazin-7-yl)-N-(3-fluoro-4-((1S,4S)-5-methyl-2,5-diazabicyclo[2.2.1]heptan-2-yl)phenyl)pyrimidin-2-amine;

4-(3,4-dihydro-2H-pyrido[3,2-b][1,4]oxazin-7-yl)-N-(3-trifluoromethyl-4-((1S,4S)-5-methyl-2,5-diazabicyclo[2.2.1]heptan-2-yl)phenyl)pyrimidin-2-amine;

4-(2H-benzo[b][1,4]oxazin-3(4H)-on-6-yl)-N-(3-fluoro-4-((1S,4S)-5-methyl-2,5-diazabicyclo[2.2.1]heptan-2-yl)phenyl)pyrimidin-2-amine;

4-(2,2,4-trimethyl-3-oxo-3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine;

4-(2,2,4-trimethyl-3-oxo-3,4-dihydro-2H-pyrido[3,2-b][1,4]oxazin-7-yl)-N-(3-fluoro-4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-trifluoromethyl-4-((1S,4S)-2,5-diazabicyclo[2.2.1]heptan-2-yl)phenyl)pyrimidin-2-amine;

4-(4-methyl-3,4-dihydro-2H-pyrido[3,2-b][1,4]oxazin-7-yl)-N-(4-((1S,4S)-5-methyl-2,5-diazabicyclo[2.2.1]heptan-2-yl)phenyl)pyrimidin-2-amine;

4-(4-methyl-3,4-dihydro-2H-pyrido[3,2-b][1,4]oxazin-7-yl)-N-(3-methyl-4-((1S,4S)-5-methylsulfonyl-2,5-diazabicyclo[2.2.1]heptan-2-yl)phenyl)pyrimidin-2-amine;

4-(3-oxo-3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine;

4-(7-oxo-5,6,7,8-tetrahydro-1,8-naphthyridin-3-yl)-N-(3-methyl-4-((1S,4S)-5-methylsulfonyl-2,5-diazabicyclo[2.2.1]heptan-2-yl)phenyl)pyrimidin-2-amine;

4-(3-oxo-3,4-dihydro-2H-benzo[b][1,4]thiazin-7-yl)-N-(4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-benzo[b][1,4]oxazin-7-yl)-N-(3-methyl-4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-benzo[b][1,4]oxazin-7-yl)-N-(3-methyl-4-((1S,4S)-5-methylsulfonyl-2,5-diazabicyclo[2.2.1]heptan-2-yl)phenyl)pyrimidin-2-amine;

4-(2-oxo-2,3,4,5-tetrahydro-1H-benzo[b]azepin-7-yl)-N-(3-methyl-4-((1S,4S)-5-methyl-2,5-diazabicyclo[2.2.1]heptan-2-yl)phenyl)pyrimidin-2-amine;

4-(2-oxo-2,3,4,5-tetrahydro-1H-benzo[b]azepin-7-yl)-N-(3-methyl-4-((1S,4S)-5-methylsulfonyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-((1S,4S)-5-(1-methylethyl)-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-((1S,4S)-5-cyclopropyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-chloro-4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-chloro-4-((1S,4S)-5-(methylsulfonyl)-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-((1S,4S)-5-cyclopentyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-((1S,4S)-5-acetyl-2,5-diazabicyclo[2.2.1]heptan-2-yl)phenyl)pyrimidin-2-amine;

4-(6,7,8,9-tetrahydro-5H-pyrido[2,3-b]indol-3-yl)-N-(3-methyl-4-((1S,4S)-5-methyl-2,5-diazabicyclo[2.2.1]heptan-2-yl)phenyl)pyrimidin-2-amine;

4-(6,7,8,9-tetrahydro-5H-pyrido[2,3-b]indol-3-yl)-N-(3-methyl-4-((1S,4S)-5-(methylsulfonyl)-2,5-diazabicyclo[2.2.1]heptan-2-yl)phenyl)pyrimidin-2-amine;

4-(7,8,9,9a-tetrahydro-5H-pyrido[2,3-e]pyrrolo[1,2-a][1,4]diazepin-10(11H)-on-3-yl)-N-(3-methyl-4-((1S,4S)-5-methyl-2,5-diazabicyclo[2.2.1]heptan-2-yl)phenyl)pyrimidin-2-amine;

4-(2,2-dimethyl-3-oxo-3,4-dihydro-2H-benzo[b][1,4]oxazin-7-yl)-N-(3-cyano-4-((1S,4S)-5-methyl-2,5-diazabicyclo[2.2.1]heptan-2-yl)phenyl)pyrimidin-2-amine;

4-(2-oxo-2,3,4,5-tetrahydro-1H-benzo[b]azepin-7-yl)-N-(3-cyano-4-((1S,4S)-5-methyl-2,5-diazabicyclo[2.2.1]heptan-2-yl)phenyl)pyrimidin-2-amine;

4-(3-oxo-3,4-dihydro-2H-benzo[b][1,4]thiazin-7-yl)-N-(3-cyano-4-((1S,4S)-5-methyl-2,5-diazabicyclo[2.2.1]heptan-2-yl)phenyl)pyrimidin-2-amine; and 4-(3-oxo-3,4-dihydro-2H-benzo[b][1,4]thiazin-7-yl)-N-(3-methyl-4-((1S,4S)-5-methyl-2,5-diazabicyclo[2.2.1]heptan-2-yl)phenyl)pyrimidin-2-amine.

Another embodiment is a compound of formula (Ia-1a), as set forth above, wherein:

n is 0 or 1;

$R^{2a}$ is independently selected from the group consisting of hydrogen, optionally substituted alkyl, halo, cyano and —OR$^6$;

$R^3$, when present, is independently selected from the group consisting of alkyl, halo and haloalkyl;

$R^4$ is phenyl substituted by one or more substituents selected from the group consisting of alkyl, haloalkyl, —R$^8$—OR$^{6a}$, —R$^8$—N(R$^{6a}$)R$^{7a}$, —R$^8$—C(O)N(R$^{6a}$)R$^{7a}$, —R$^8$—N(R$^{6a}$)C(O)R$^{7a}$, —R$^8$—N(R$^{6a}$)S(O)$_2$R$^{7a}$, —R$^8$—N(R$^{6a}$)C(O)—R$^8$—N(R$^{6a}$)R$^{7a}$, N-heteroaryl and N-heterocyclyl, where the N-heterocyclyl and the N-heteroaryl are each independently optionally substituted by one or more substituents selected from the group consisting of —C(O)R$^6$, —R$^8$—N(R$^6$)R$^7$, —R$^8$—C(O)N(R$^6$)R$^7$, alkyl, halo and optionally substituted aryl;

$R^{5a}$ is independently selected from the group consisting of hydrogen, alkyl, —R$^8$—C(O)R$^6$ and —R$^8$—S(O)$_t$R$^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;

each $R^8$ is independently selected from the group consisting of a direct bond and an optionally substituted straight or branched alkylene chain.

A specific embodiment of this embodiment is a compound of formula (Ia-1a), as set forth above, selected from the group consisting of:

4-(4-(N,N-dimethylamino)phenyl)-N-(3-methyl-4-((1S,4S)-5-methyl-2,5-diazabicyclo[2.2.1]heptan-2-yl)phenyl)pyrimidin-2-amine;

4-(4-(N,N-dimethylamino)phenyl)-N-(3-fluoro-4-((1S,4S)-5-methyl-2,5-diazabicyclo[2.2.1]heptan-2-yl)phenyl)pyrimidin-2-amine;

4-(4-(4,5-dihydrothiazol-2-ylcarbamoyl)phenyl)-N-(3-methyl-4-((1S,4S)-5-methyl-2,5-diazabicyclo[2.2.1]heptan-2-yl)phenyl)pyrimidin-2-amine;

4-(4-(1,1-dimethylethyl)phenyl)-N-(3-methyl-4-((1S,4S)-5-methyl-2,5-diazabicyclo[2.2.1]heptan-2-yl)phenyl)pyrimidin-2-amine;

4-(4-(morpholin-4-yl)phenyl)-N-(3-fluoro-4-((1S,4S)-5-methyl-2,5-diazabicyclo[2.2.1]heptan-2-yl)phenyl)pyrimidin-2-amine.TFA salt;

4-(4-((methyl)aminocarbonylmethyl)-phenyl)-N-(3-methyl-4-((1S,4S)-5-methyl-2,5-diazabicyclo[2.2.1]heptan-2-yl)phenyl)pyrimidin-2-amine.TFA salt;

4-(4-((cyclopropyl)aminocarbonyl-methyl)phenyl)-N-(3-methyl-4-((1S,4S)-5-methyl-2,5-diazabicyclo[2.2.1]heptan-2-yl)phenyl)pyrimidin-2-amine;

4-(4-(5-(4-dimethylaminophenyl)oxazol-2-yl)phenyl)-N-(3-methyl-4-((1S,4S)-5-methyl-2,5-diazabicyclo[2.2.1]heptan-2-yl)phenyl)pyrimidin-2-amine;

4-(4-(t-butylcarbonylamino)phenyl)-N-(3-fluoro-4-((1S,4S)-5-methyl-2,5-diazabicyclo[2.2.1]heptan-2-yl)phenyl)pyrimidin-2-amine;

4-(4-(t-butylcarbonylamino)phenyl)-N-(3-methyl-4-((1S,4S)-5-methyl-2,5-diazabicyclo[2.2.1]heptan-2-yl)phenyl)pyrimidin-2-amine;

4-(4-((pyridin-2-yl)aminocarbonyl)phenyl)-N-(3-fluoro-4-((1S,4S)-5-methyl-2,5-diazabicyclo[2.2.1]heptan-2-yl)phenyl)pyrimidin-2-amine;

4-(4-((pyridin-2-yl)aminocarbonyl)phenyl)-N-(3-methyl-4-((1S,4S)-5-methyl-2,5-diazabicyclo[2.2.1]heptan-2-yl)phenyl)pyrimidin-2-amine;

4-(4-(methylsulfonylamino)phenyl)-N-(3-fluoro-4-((1S,4S)-5-methyl-2,5-diazabicyclo[2.2.1]heptan-2-yl)phenyl)pyrimidin-2-amine;

4-(4-(methylsulfonylamino)phenyl)-N-(3-methyl-4-((1S,4S)-5-methyl-2,5-diazabicyclo[2.2.1]heptan-2-yl)phenyl)pyrimidin-2-amine;

4-(4-(3-cyclopropylureido)phenyl)-N-(4-((1S,4S)-5-methyl-2,5-diazabicyclo[2.2.1]heptan-2-yl)phenyl)pyrimidin-2-amine;

4-(4-(1-ethoxyethyl)phenyl)-N-(3-methyl-4-((1S,4S)-5-methyl-2,5-diazabicyclo[2.2.1]heptan-2-yl)phenyl)pyrimidin-2-amine;

4-(4-(1-ethoxyethyl)phenyl)-N-(3-fluoro-4-((1S,4S)-5-methyl-2,5-diazabicyclo[2.2.1]heptan-2-yl)phenyl)pyrimidin-2-amine; and 4-(4-(trifluoromethyl)phenyl)-N-(3-methyl-4-((1S,4S)-5-methyl-2,5-diazabicyclo[2.2.1]heptan-2-yl)phenyl)pyrimidin-2-amine.

Another embodiment is a compound of formula (Ia-1a), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is selected from the group consisting of benzimidazolyl, imidazo[1,2-a]pyridinyl, indolyl, indolinyl, pyrazolyl, pyrazinyl, pyrimidinyl, pyrrolyl, 1H-pyrrolo[2,3-b]pyridinyl and thiazolyl, each independently substituted by one or more substituents selected from the group consisting of alkyl, cyano, oxo, —$R^8$—$OR^{6a}$, —$R^8$—$N(R^{6a})R^{7a}$, —$R^8$—$C(O)N(R^{6a})R^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$, aryl, N-heteroaryl and N-heterocyclyl, where the aryl, the N-heterocyclyl and the N-heteroaryl are each independently optionally substituted by one or more substituents selected from the group consisting of —$C(O)R^6$, —$R^8$—$N(R^6)R^7$, —$R^8$—$C(O)N(R^6)R^7$, alkyl, halo and optionally substituted aryl;

$R^{5a}$ is independently selected from the group consisting of hydrogen, alkyl, —$R^8$—$C(O)R^6$ and —$R^8$—$S(O)_tR^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl; and each $R^8$ is independently selected from the group consisting of a direct bond and an optionally substituted straight or branched alkylene chain.

A specific embodiment of this embodiment is a compound of formula (Ia-1a), as set forth above, selected from the group consisting of:

4-(1H-indol-6-yl)-N-(3-methyl-4-((1S,4S)-5-methyl-2,5-diazabicyclo[2.2.1]heptan-2-yl)phenyl)pyrimidin-2-amine;

4-(1H-pyrrolo[2,3-b]pyridin-5-yl)-N-(3-methyl-4-((1S,4S)-5-methyl-2,5-diazabicyclo[2.2.1]heptan-2-yl)phenyl)pyrimidin-2-amine;

4-(1H-pyrrolo[2,3-b]pyridin-5-yl)-N-(3-fluoro-4-((1S,4S)-5-methyl-2,5-diazabicyclo[2.2.1]heptan-2-yl)phenyl)pyrimidin-2-amine;

4-(1H-pyrrolo[2,3-b]pyridin-5-yl)-N-(3-methyl-4-((1S,4S)-5-(2,2,2-trifluoroethyl)-2,5-diazabicyclo[2.2.1]heptan-2-yl)phenyl)pyrimidin-2-amine;

4-(1H-pyrrolo[2,3-b]pyridin-5-yl)-N-(3-methyl-4-((1S,4S)-5-(cyclopropyl)methyl-2,5-diazabicyclo[2.2.1]heptan-2-yl)phenyl)pyrimidin-2-amine;

4-(2-(morpholin-4-yl)pyrimidin-5-yl)-N-(4-((1S,4S)-5-methyl-2,5-diazabicyclo[2.2.1]heptan-2-yl)phenyl)pyrimidin-2-amine;

4-(2-(morpholin-4-yl)pyrimidin-5-yl)-N-(3-methyl-4-((1S,4S)-5-methyl-2,5-diazabicyclo[2.2.1]heptan-2-yl)phenyl)pyrimidin-2-amine;

4-(2-(morpholin-4-yl)pyrimidin-5-yl)-N-(3-fluoro-4-((1S,4S)-5-methyl-2,5-diazabicyclo[2.2.1]heptan-2-yl)phenyl)pyrimidin-2-amine;

4-(2-((cyclopropyl)carbonylamino)-pyrimidin-5-yl)-N-(3-methyl-4-((1S,4S)-5-methyl-2,5-diazabicyclo[2.2.1]heptan-2-yl)phenyl)pyrimidin-2-amine;

4-(2-(propyl)aminopyrimidin-5-yl)-N-(3-methyl-4-((1S,4S)-5-methyl-2,5-diazabicyclo[2.2.1]heptan-2-yl)phenyl)pyrimidin-2-amine;

4-(2-(propyl)aminopyrimidin-5-yl)-N-(3-fluoro-4-((1S,4S)-5-methyl-2,5-diazabicyclo[2.2.1]heptan-2-yl)phenyl)pyrimidin-2-amine;

4-(imidazo[1,2-a]pyridin-6-yl)-N-(3-methyl-4-((1S,4S)-5-methyl-2,5-diazabicyclo[2.2.1]heptan-2-yl)phenyl)pyrimidin-2-amine;

4-(6-methoxy-1H-indol-2-yl)-N-(3-methyl-4-((1S,4S)-5-methyl-2,5-diazabicyclo[2.2.1]heptan-2-yl)phenyl)pyrimidin-2-amine;

4-(1-(3-chlorophenyl)-1H-pyrazol-4-yl)-N-(3-methyl-4-((1S,4S)-5-methyl-2,5-diazabicyclo[2.2.1]heptan-2-yl)phenyl)pyrimidin-2-amine;

4-(1-methylbenzimidazol-6-yl)-N-(3-methyl-4-((1S,4S)-5-methyl-2,5-diazabicyclo[2.2.1]heptan-2-yl)phenyl)pyrimidin-2-amine;

4-(5-cyano-1H-indol-2-yl)-N-(3-methyl-4-((1S,4S)-5-methyl-2,5-diazabicyclo[2.2.1]heptan-2-yl)phenyl)pyrimidin-2-amine;

4-(1-(4-fluorophenyl)-1H-pyrazol-4-yl)-N-(3-methyl-4-((1S,4S)-5-methyl-2,5-diazabicyclo[2.2.1]heptan-2-yl)phenyl)pyrimidin-2-amine;

4-(2-oxoindolin-5-yl)-N-(3-methyl-4((1S,4S)-5-methyl-2,5-diazabicyclo[2.2.1]heptan-2-yl)phenyl)pyrimidin-2-amine;

4-(5-(3-methylpiperidin-1-yl)pyrazin-2-yl)-N-(3-fluoro-4-((1S,4S)-5-methyl-2,5-diazabicyclo[2.2.1]heptan-2-yl)phenyl)pyrimidin-2-amine;

4-(2-(diethylamino)thiazol-4-yl)-N-(3-methyl-4-((1S,4S)-5-methyl-2,5-diazabicyclo[2.2.1]heptan-2-yl)phenyl)pyrimidin-2-amine;

4-(2-(diethylamino)thiazol-4-yl)-N-(3-fluoro-4-((1S,4S)-5-methyl-2,5-diazabicyclo[2.2.1]heptan-2-yl)phenyl)pyrimidin-2-amine;

4-(1H-pyrrol-3-yl)-N-(3-methyl-4-((1S,4S)-5-methyl-2,5-diazabicyclo[2.2.1]heptan-2-yl)phenyl)pyrimidin-2-amine;

4-(1H-pyrrol-3-yl)-N-(4-((1S,4S)-5-methyl-2,5-diazabicyclo[2.2.1]heptan-2-yl)phenyl)pyrimidin-2-amine;

4-(1H-pyrrol-3-yl)-N-(3-trifluoromethyl-4-((1S,4S)-5-methyl-2,5-diazabicyclo[2.2.1]heptan-2-yl)phenyl)pyrimidin-2-amine;

4-(2-(dimethylamino)thiazol-4-yl)-N-(3-methyl-4-((1S,4S)-5-methyl-2,5-diazabicyclo[2.2.1]heptan-2-yl)phenyl)pyrimidin-2-amine;

4-(2-(dimethylamino)thiazol-4-yl)-N-(3-fluoro-4-((1S,4S)-5-methyl-2,5-diazabicyclo[2.2.1]heptan-2-yl)phenyl)pyrimidin-2-amine;

4-(5-(morpholin-4-yl)pyrazin-2-yl)-N-(3-methyl-4-((1S,4S)-5-methyl-2,5-diazabicyclo[2.2.1]heptan-2-yl)phenyl)pyrimidin-2-amine;

4-(5-(morpholin-4-yl)pyrazin-2-yl)-N-(3-fluoro-4-((1S,4S)-5-methyl-2,5-diazabicyclo[2.2.1]heptan-2-yl)phenyl)pyrimidin-2-amine;

4-(1-(pyridin-4-yl)-1H-indol-5-yl)-N-(3-methyl-4-((1S,4S)-5-methyl-2,5-diazabicyclo[2.2.1]heptan-2-yl)phenyl)pyrimidin-2-amine;

4-(1-(pyridin-4-yl)-1H-indol-5-yl)-N-(3-fluoro-4-((1S,4S)-5-methyl-2,5-diazabicyclo[2.2.1]heptan-2-yl)phenyl)pyrimidin-2-amine;

4-(1-(pyridin-4-yl)-1H-indol-5-yl)-N-(3-methyl-4-((1S,4S)-5-ethyl-2,5-diazabicyclo[2.2.1]heptan-2-yl)phenyl)pyrimidin-2-amine; and 4-(1-(pyridin-4-yl)-1H-indol-5-yl)-N-(3-methyl-4-((1S,4S)-5-isobutyl-2,5-diazabicyclo[2.2.1]heptan-2-yl)phenyl)pyrimidin-2-amine.

Another embodiment of the compounds of formula (Ia-1), as set forth above, is a compound according to formula (Ia-1b):

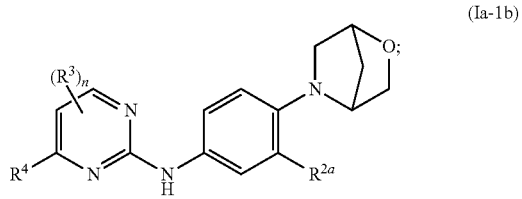

wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —$R^8$—$OR^{6a}$, —$R^8$—$S(O)_p R^{6a}$ (where p is 0, 1 or 2), —$R^8$—$C(O)R^{6a}$, —$R^8$—$C(O)OR^{6a}$, —$R^8$—$C(O)N(R^{6a})R^{7a}$, —$R^8$—$N(R^{6a})R^{7a}$, —$R^8$—$N(R^{6a})$—$R^9$—$N(R^{6a})R^{7a}$, —$R^8$—$N(R^{6a})$—$R^9$—$OR^{7a}$, —$R^8$—$N(R^{6a})C(O)R^{7a}$, —$R^8$—$N(R^{6a})S(O)_2 R^{7a}$, —$R^8$—$N(R^{6a})C(O)$—$R^8$—$N(R^{6a})R^{7a}$, and —$R^8$—$N(R^{6a})$—$R^9$—$N(R^{6a})S(O)_2 R^{7a}$, where the N-heterocyclyl, the N-heteroaryl and the aryl are each independently optionally substituted by one or more substituents selected from the group consisting of —$C(O)R^6$, —$R^8$—$N(R^6)R^7$, —$R^8$—$C(O)N(R^6)R^7$, alkyl, halo and optionally substituted aryl;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;
each $R^8$ is independently selected from the group consisting of a direct bond and an optionally substituted straight or branched alkylene chain; and
each $R^9$ is an optionally substituted straight or branched alkylene chain.

Of this embodiment, one embodiment is a compound of formula (I-1b), as set forth above, wherein:
n is 0 or 1;
$R^{2a}$ is independently selected from the group consisting of hydrogen, optionally substituted alkyl, halo, cyano and —$OR^6$;
$R^3$, when present, is independently selected from the group consisting of alkyl, halo and haloalkyl;
$R^4$ is pyridinyl substituted by one or more substituents selected from the group consisting of alkyl, cyano, —$R^8$—$OR^{6a}$, —$R^8$—$N(R^{6a})R^{7a}$, —$R^8$—$N(R^{6a})$—$R^9$—$N(R^{6a})R^{7a}$ and —$R^8$—$N(R^{6a})$—$R^9$—$OR^{7a}$;
$R^6$ is selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;
$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;
each $R^8$ is independently selected from the group consisting of a direct bond and an optionally substituted straight or branched alkylene chain; and
each $R^9$ is an optionally substituted straight or branched alkylene chain.

A specific embodiment of this embodiment is a compound of formula (Ia-1b), as set forth above, selected from the group consisting of:
4-(6-(3-ethoxypropyl)aminopyridin-3-yl)-N-(3-methyl-4-((1S,4S)-5-oxa-2-azabicyclo[2.2.1]heptan-2-yl)phenyl)pyrimidin-2-amine;
4-(6-(propylamino)pyridin-3-yl)-N-(3-methyl-4-((1S,4S)-5-oxa-2-azabicyclo[2.2.1]heptan-2-yl)phenyl)pyrimidin-2-amine;
4-(6-(3-dimethylamino)propylaminopyridin-3-yl)-N-(3-methyl-4-((1S,4S)-5-oxa-2-azabicyclo[2.2.1]heptan-2-yl)phenyl)pyrimidin-2-amine; and
4-(6-(2-methoxyethyl)(methyl)aminopyridin-3-yl)-N-(3-methyl-4-((1S,4S)-5-oxa-2-azabicyclo[2.2.1]heptan-2-yl)phenyl)pyrimidin-2-amine.

Another embodiment is a compound of formula (I-1b) wherein:
n is 0 or 1;
$R^{2a}$ is independently selected from the group consisting of hydrogen, optionally substituted alkyl, halo, cyano and —$OR^6$;
$R^3$, when present, is independently selected from the group consisting of alkyl, halo and haloalkyl;
$R^4$ is pyridinyl substituted by an N-heterocyclyl selected from the group consisting of morpholinyl, piperazinyl, piperidinyl, pyrrolidinyl, oxazepanyl, 5-oxa-2-azabicyclo[2.2.1]heptanyl and thiamorpholinyl, where the N-heterocyclyl is optionally substituted by one or more substituents selected from the group consisting of —$C(O)R^6$, —$R^8$—$N(R^6)R^7$, —$R^8$—$C(O)N(R^6)R^7$, alkyl, halo and optionally substituted aryl;
each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and
each $R^8$ is independently selected from the group consisting of a direct bond and an optionally substituted straight or branched alkylene chain.

A specific embodiment of this embodiment is a compound of formula (Ia-1b), as set forth above, selected from the group consisting of:
4-(6-(morpholin-4-yl)pyridin-3-yl)-N-(3-methyl-4-((1S,4S)-5-oxa-2-azabicyclo[2.2.1]heptan-2-yl)phenyl)pyrimidin-2-amine;
4-(6-cis-2,6-dimethylmorpholin-4-yl)pyridin-3-yl)-N-(3-methyl-4-((1S,4S)-5-oxa-2-azabicyclo[2.2.1]heptan-2-yl)phenyl)pyrimidin-2-amine;
4-(6-(1,4-oxazepan-4-yl)pyridin-3-yl)-N-(3-methyl-4-((1S,4S)-5-oxa-2-azabicyclo[2.2.1]heptan-2-yl)phenyl)pyrimidin-2-amine; and
4-(6-((1S,4S)-5-oxa-2-azabicyclo[2.2.1]heptan-2-yl)pyridin-3-yl)-N-(3-methyl-4-((1S,4S)-5-oxa-2-azabicyclo[2.2.1]heptan-2-yl)phenyl)pyrimidin-2-amine.

Another embodiment is a compound of formula (Ia-1b), as set forth above, wherein:
n is 0 or 1;
$R^{2a}$ is independently selected from the group consisting of hydrogen, optionally substituted alkyl, halo, cyano and —$OR^6$;
$R^3$, when present, is independently selected from the group consisting of alkyl, halo and haloalkyl;
$R^4$ is pyridinyl substituted by one or more substituents selected from the group consisting of —$R^8$—$C(O)R^{6a}$, —$R^8$—$C(O)N(R^{6a})R^{7a}$, —$R^8$—$S(O)_pR^{6a}$ (where p is 0, 1 or 2), —$R^8$—$N(R^{6a})$—$R^9$—$N(R^{6a})S(O)_2R^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$, and tetrazolyl;
$R^6$ is selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl; and each $R^8$ is independently selected from the group consisting of a direct bond and an optionally substituted straight or branched alkylene chain; and $R^9$ is an optionally substituted straight or branched alkylene chain.

A specific embodiment of this embodiment is a compound of formula (Ia-1b), as set forth above, selected from the group consisting of:

4-(6-((2-(cyclopropylsulfonyl)aminoethyl)-amino)pyridin-3-yl)-N-(3-methyl-4-((1S,4S)-5-oxa-2-azabicyclo[2.2.1]heptan-2-yl)phenyl)pyrimidin-2-amine;

4-(5-(methyl)sulfonylpyridin-3-yl)-N-(3-fluoro-4-((1S,4S)-5-methyl-2,5-diazabicyclo[2.2.1]heptan-2-yl)phenyl)pyrimidin-2-amine;

4-(5-(methyl)sulfonylpyridin-3-yl)-N-(3-trifluoromethyl-4-((1S,4S)-5-methyl-2,5-diazabicyclo[2.2.1]heptan-2-yl)phenyl)pyrimidin-2-amine; and 4-(6-(acetamido)pyridin-3-yl)-N-(3-methyl-4-((1S,4S)-5-oxa-2-azabicyclo[2.2.1]heptan-2-yl)phenyl)pyrimidin-2-amine.

Another embodiment is a compound of formula (Ia-1b), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is selected from the group consisting of naphthyridinyl, benzo[b]azepinyl, benzo[b][1,4]oxazinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]thiazinyl and 3,4-dihydro-2H-pyrido[3,2-b][1,4]oxazinyl, each optionally substituted by one or more substituents independently selected from the group consisting of alkyl and oxo; and $R^6$ is selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

A specific embodiment of this embodiment is a compound of formula (Ia-1b), as set forth above, selected from the group consisting of:

4-(2,2-dimethyl-3-oxo-3,4-dihydro-2H-pyrido[3,2-b][1,4]oxazin-7-yl)-N-(3-methyl-4-((1S,4S)-5-oxa-2-azabicyclo[2.2.1]heptan-2-yl)phenyl)pyrimidin-2-amine;

4-(4-methyl-3,4-dihydro-2H-pyrido[3,2-b][1,4]oxazin-7-yl)-N-(3-methyl-4-((1S,4S)-5-oxa-2-azabicyclo[2.2.1]heptan-2-yl)phenyl)pyrimidin-2-amine; and 4-(3-oxo-3,4-dihydro-2H-pyrido[3,2-b][1,4]oxazin-7-yl)-N-(3-methyl-4-((1S,4S)-5-oxa-2-azabicyclo[2.2.1]heptan-2-yl)phenyl)pyrimidin-2-amine.

Another embodiment is a compound of formula (Ia-1b), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is selected from the group consisting of benzimidazolyl, imidazo[1,2-a]pyridinyl, indolyl, indolinyl, pyrazolyl, pyridinyl, pyrazinyl, pyrimidinyl, pyrrolyl, 1H-pyrrolo[2,3-b]pyridinyl and thiazolyl, each independently substituted by one or more substituents selected from the group consisting of alkyl, cyano, oxo, —$R^8$—$OR^{6a}$, —$R^8$—$N(R^{6a})R^{7a}$, —$R^8$—$C(O)N(R^{6a})R^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$, aryl, N-heteroaryl and N-heterocyclyl, where the aryl, the N-heterocyclyl and the N-heteroaryl are each independently optionally substituted by one or more substituents selected from the group consisting of —$C(O)R^6$, —$R^8$—$N(R^6)R^7$, —$R^8$—$C(O)N(R^6)R^7$, alkyl, halo and optionally substituted aryl;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl; and each $R^8$ is independently selected from the group consisting of a direct bond and an optionally substituted straight or branched alkylene chain.

A specific embodiment of this embodiment is a compound of formula (Ia-1b), as set forth above, selected from the group consisting of:

4-(1H-pyrrolo[2,3-b]pyridin-5-yl)-N-(3-methyl-4-((1S,4S)-5-oxa-2-azabicyclo[2.2.1]heptan-2-yl)phenyl)pyrimidin-2-amine; and 4-(2-(morpholin-4-yl)pyrimidin-5-yl)-N-(3-methyl-4-((1S,4S)-5-oxa-2-azabicyclo[2.2.1]heptan-2-yl)phenyl)pyrimidin-2-amine.

Another embodiment of the compounds of formula (Ia-1), as set forth above, is a compound according to formula (Ia-1c):

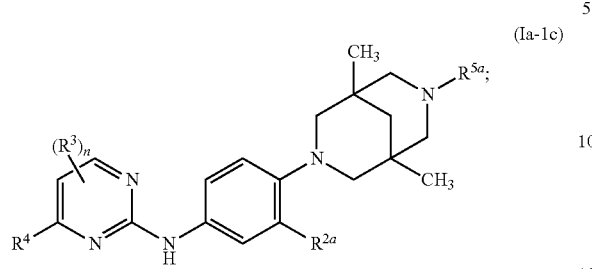

wherein:
n is 0 or 1;
$R^{2a}$ is independently selected from the group consisting of hydrogen, optionally substituted alkyl, halo, cyano and —$OR^6$;
$R^3$, when present, is independently selected from the group consisting of alkyl, halo and haloalkyl;
$R^4$ is selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —$R^8$—$OR^{6a}$, —$R^8$—$S(O)_pR^{6a}$ (where p is 0, 1 or 2), —$R^8$—$C(O)R^{6a}$, —$R^8$—$C(O)OR^{6a}$, —$R^8$—$C(O)N(R^{6a})R^{7a}$, —$R^8$—$N(R^{6a})R^{7a}$, —$R^8$—$N(R^{6a})$—$R^9$—$N(R^{6a})R^{7a}$, —$R^8$—$N(R^{6a})$—$R^9$—$OR^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$, and —$R^8$—$N(R^{6a})$—$R^9$—$N(R^{6a})S(O)_2R^{7a}$, where the N-heterocyclyl, the N-heteroaryl and the aryl are each independently optionally substituted by one or more substituents selected from the group consisting of —$C(O)R^6$, —$R^8$—$N(R^6)R^7$, —$R^8$—$C(O)N(R^6)R^7$, alkyl, halo and optionally substituted aryl;
$R^{5a}$ is selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^8$—$OR^6$, —$R^8$—$C(O)R^6$, —$R^8$—$C(O)OR^6$, —$R^9$—$N(R^6)R^7$, —$R^8$—$C(O)N(R^6)R^7$, —$R^8$—$C(N=R^6)N(R^6)R^7$, —$R^8$—$S(O)_2N(R^6)R^7$, and —$R^8$—$S(O)_tR^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;
$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl; and
each $R^8$ is independently selected from the group consisting of a direct bond and an optionally substituted straight or branched alkylene chain; and
each $R^9$ is an optionally substituted straight or branched alkylene chain.

Of this embodiment, one embodiment is a compound of formula (Ia-1c), as set forth above, wherein:
n is 0 or 1;
$R^{2a}$ is independently selected from the group consisting of hydrogen, optionally substituted alkyl, halo, cyano and —$OR^6$;
$R^3$, when present, is independently selected from the group consisting of alkyl, halo and haloalkyl;
$R^4$ is pyridinyl substituted by one or more substituents selected from the group consisting of alkyl, cyano, —$R^8$—$OR^{6a}$, —$R^8$—$N(R^{6a})R^{7a}$, —$R^8$—$N(R^{6a})$—$R^9$—$N(R^{6a})R^{7a}$ and —$R^8$—$N(R^{6a})$—$R^9$—$OR^{7a}$;
$R^{5a}$ is independently selected from the group consisting of hydrogen, alkyl, —$R^8$—$C(O)R^6$ and —$R^8$—$S(O)_tR^6$ (where t is 1 or 2);
$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;
each $R^6$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^8$ is independently selected from the group consisting of a direct bond and an optionally substituted straight or branched alkylene chain; and $R^9$ is an optionally substituted straight or branched alkylene chain.

A specific embodiment of this embodiment is a compound of formula (Ia-1c), as set forth above, selected from the group consisting of:

4-(6-(dimethylamino)pyridin-3-yl)-N-(3-methyl-4-(1,5,7-trimethyl-3,7-diazabicyclo[3.3.1]nonan-3-yl)phenyl)pyrimidin-2-amine;

4-(6-(cyclohexylamino)pyridin-3-yl)-N-(3-methyl-4-(1,5,7-trimethyl-3,7-diazabicyclo[3.3.1]nonan-3-yl)phenyl)pyrimidin-2-amine;

4-(6-(dimethylamino)pyridin-3-yl)-N-(3-fluoro-4-(1,5,7-trimethyl-3,7-diazabicyclo[3.3.1]nonan-3-yl)phenyl)pyrimidin-2-amine;

4-(4-(dimethylamino)phenyl)-N-(3-fluoro-4-(1,5,7-trimethyl-3,7-diazabicyclo[3.3.1]nonan-3-yl)phenyl)pyrimidin-2-amine;

4-(6-(benzyl)pyridin-3-yl)-N-(3-methyl-4-(1,5,7-trimethyl-3,7-diazabicyclo[3.3.1]nonan-3-yl)phenyl)pyrimidin-2-amine;

4-(6-(benzyl)pyridin-3-yl)-N-(3-fluoro-4-(1,5,7-trimethyl-3,7-diazabicyclo[3.3.1]nonan-3-yl)phenyl)pyrimidin-2-amine;

4-(6-(3-ethoxypropyl)aminopyridin-3-yl)-N-(3-methyl-4-(1,5,7-trimethyl-3,7-diazabicyclo[3.3.1]nonan-3-yl)phenyl)pyrimidin-2-amine;

4-(6-(propylamino)pyridin-3-yl)-N-(3-methyl-4-(1,5,7-trimethyl-3,7-diazabicyclo[3.3.1]nonan-3-yl)phenyl)pyrimidin-2-amine;

4-(6-(3-dimethylamino)propylaminopyridin-3-yl)-N-(3-methyl-4-(1,5,7-trimethyl-3,7-diazabicyclo[3.3.1]nonan-3-yl)phenyl)pyrimidin-2-amine; and 4-(6-(2-methoxyethyl)(methyl)aminopyridin-3-yl)-N-(3-methyl-4-(1,5,7-trimethyl-3,7-diazabicyclo[3.3.1]nonan-3-yl)phenyl)pyrimidin-2-amine.

Another embodiment is a compound of formula (Ia-1c), as set forth above, wherein:

n is 0 or 1;

$R^{2a}$ is independently selected from the group consisting of hydrogen, optionally substituted alkyl, halo, cyano and —OR$^6$;

$R^3$, when present, is independently selected from the group consisting of alkyl, halo and haloalkyl;

$R^4$ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by one or more substituents selected from the group consisting of —C(O)R$^6$, —R$^8$—N(R$^6$)R$^7$, —R$^8$—C(O)N(R$^6$)R$^7$, alkyl, halo and optionally substituted aryl;

$R^{5a}$ is independently selected from the group consisting of hydrogen, alkyl, haloalkyl, optionally substituted cycloalkyl, optionally substituted cycloalkylalkyl, —R$^8$—C(O)R$^6$, —R$^8$—C(O)N(R$^6$)R$^7$, —R$^8$—C(N=R$^6$)N(R$^6$)R$^7$ and —R$^8$—S(O)$_t$R$^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

each $R^8$ is independently selected from the group consisting of a direct bond and an optionally substituted straight or branched alkylene chain; and each $R^9$ is an optionally substituted straight or branched alkylene chain.

A specific embodiment of this embodiment is a compound of formula (Ia-1c), as set forth above, selected from the group consisting of:

4-(6-(morpholin-4-yl)pyridin-3-yl)-N-(3-methyl-4-(1,5,7-trimethyl-3,7-diazabicyclo[3.3.1]nonan-3-yl)phenyl)pyrimidin-2-amine;

4-(5-methyl-6-(morpholin-4-yl)pyridin-3-yl)-N-(3-fluoro-4-(1,5,7-trimethyl-3,7-diazabicyclo[3.3.1]nonan-3-yl)phenyl)pyrimidin-2-amine;

4-(6-(morpholin-4-yl)pyridin-3-yl)-N-(3-fluoro-4-(1,5,7-trimethyl-3,7-diazabicyclo[3.3.1]nonan-3-yl)phenyl)pyrimidin-2-amine; and 4-(6-((2S,6R)-2,6-dimethylmorpholin-4-yl)pyridin-3-yl)-N-(3-methyl-4-(1,5,7-trimethyl-3,7-diazabicyclo[3.3.1]nonan-3-yl)phenyl)pyrimidin-2-amine.

Another embodiment is a compound of formula (Ia-1c), as set forth above, wherein:

n is 0 or 1;

$R^{2a}$ is independently selected from the group consisting of hydrogen, optionally substituted alkyl, halo, cyano and —OR$^6$;

$R^3$, when present, is independently selected from the group consisting of alkyl, halo and haloalkyl;

$R^4$ is selected from the group consisting of naphthyridinyl, benzo[b]azepinyl, benzo[b][1,4]oxazinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]thiazinyl and 3,4-dihydro-2H-pyrido[3,2-b][1,4]oxazinyl, each optionally substituted by one or more substituents independently selected from the group consisting of alkyl and oxo;

$R^{5a}$ is independently selected from the group consisting of hydrogen, alkyl, haloalkyl, optionally substituted cycloalkyl, optionally substituted cycloalkylalkyl, —R$^8$—C(O)R$^6$, —R$^8$—C(O)N(R$^6$)R$^7$, —R$^8$—C(N=R$^6$)N(R$^6$)R$^7$, —R$^8$—S(O)$_t$R$^6$ (where t is 1 or 2), and —R$^8$—S(O)$_2$N(R$^6$)R$^7$;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and each R$^8$ is independently selected from the group consisting of a direct bond and an optionally substituted straight or branched alkylene chain.

A specific embodiment of this embodiment is a compound of formula (Ia-1c), as set forth above, selected from the group consisting of:

4-(3,4-dihydro-2H-pyrido[3,2-b][1,4]oxazin-7-yl)-N-(3-methyl-4-(1,5,7-trimethyl-3,7-diazabicyclo[3.3.1]nonan-3-yl)phenyl)pyrimidin-2-amine;

4-(3,4-dihydro-2H-pyrido[3,2-b][1,4]oxazin-7-yl)-N-(3-fluoro-4-(1,5,7-trimethyl-3,7-diazabicyclo[3.3.1]nonan-3-yl)phenyl)pyrimidin-2-amine; and 4-(2,2-dimethyl-3-oxo-3,4-dihydro-2H-pyrido[3,2-b][1,4]oxazin-7-yl)-N-(3-methyl-4-(1,5,7-trimethyl-3,7-diazabicyclo[3.3.1]nonan-3-yl)phenyl)pyrimidin-2-amine.

Another embodiment of the compounds of formula (Ia-1), as set forth above, is a compound according to formula (Ia-1d):

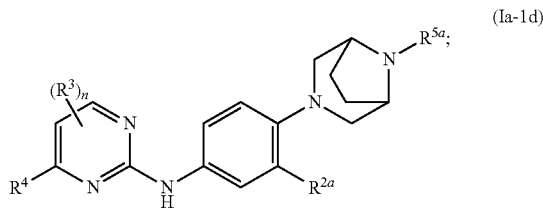

(Ia-1d)

wherein:

n is 0 or 1;

R$^{2a}$ is independently selected from the group consisting of hydrogen, optionally substituted alkyl, halo, cyano and —OR$^6$;

R$^3$, when present, is independently selected from the group consisting of alkyl, halo and haloalkyl;

R$^4$ is selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —R$^8$—OR$^{6a}$, —R$^8$—S(O)$_p$R$^{6a}$ (where p is 0, 1 or 2), —R$^8$—C(O)R$^{6a}$, —R$^8$—C(O)OR$^{6a}$, —R$^8$—C(O)N(R$^{6a}$)R$^{7a}$, —R$^8$—N(R$^{6a}$)R$^{7a}$, —R$^8$—N(R$^{6a}$)—R$^9$—N(R$^{6a}$)R$^{7a}$, —R$^8$—N(R$^{6a}$)—R$^9$—OR$^{7a}$, —R$^8$—N(R$^{6a}$)C(O)R$^{7a}$, —R$^8$—N(R$^{6a}$)S(O)$_2$R$^{7a}$, —R$^8$—N(R$^{6a}$)C(O)—R$^8$—N(R$^{6a}$)R$^{7a}$, and —R$^8$—N(R$^{6a}$)—R$^9$—N(R$^{6a}$)S(O)$_2$R$^{7a}$, where the N-heterocyclyl, the N-heteroaryl and the aryl are each independently optionally substituted by one or more substituents selected from the group consisting of —C(O)R$^6$, —R$^8$—N(R$^6$)R$^7$, —R$^8$—C(O)N(R$^6$)R$^7$, alkyl, halo and optionally substituted aryl;

R$^{5a}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^8$—OR$^6$, —R$^8$—C(O)R$^6$, —R$^8$—C(O)OR$^6$, —R$^9$—N(R$^6$)R$^7$, —R$^8$—C(O)N(R$^6$)R$^7$, —R$^8$—C(N═R$^6$)N(R$^6$)R$^7$, —R$^8$—S(O)$_2$N(R$^6$)R$^7$, and —R$^8$—S(O)$_t$R$^6$ (where t is 1 or 2);

each R$^6$ and each R$^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any R$^6$ and R$^7$, together with the common nitrogen to which they are both attached, form an optionally substituted N-heteroaryl or an optionally substituted N-heterocyclyl;

R$^{6a}$ and R$^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any R$^{6a}$ and R$^{7a}$ are bonded to a common nitrogen, R$^{6a}$ and R$^{7a}$ together with the common nitrogen to which they are both attached, may form an optionally substituted N-heteroaryl or an optionally substituted N-heterocyclyl;

each R$^9$ is independently selected from the group consisting of a direct bond and an optionally substituted straight or branched alkylene chain; and each R$^9$ is an optionally substituted straight or branched alkylene chain.

Of this embodiment, one embodiment is a compound of formula (Ia-1d), as set forth above, wherein:

n is 0 or 1;

R$^{2a}$ is independently selected from the group consisting of hydrogen, optionally substituted alkyl, halo, cyano and —OR$^6$;

R$^3$, when present, is independently selected from the group consisting of alkyl, halo and haloalkyl;

R$^4$ is pyridinyl substituted by one or more substituents selected from the group consisting of alkyl, cyano, —R$^8$—OR$^{6a}$, —R$^8$—N(R$^{6a}$)R$^{7a}$, —R$^8$—N(R$^{6a}$)—R$^9$—N(R$^{6a}$)R$^{7a}$ and —R$^8$—N(R$^{6a}$)—R$^9$—OR$^{7a}$;

R$^{5a}$ is independently selected from the group consisting of hydrogen, alkyl, —R$^8$—C(O)R$^6$ and —R$^8$—S(O)$_t$R$^6$ (where t is 1 or 2);

each R$^6$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;

each $R^8$ is independently selected from the group consisting of a direct bond and an optionally substituted straight or branched alkylene chain; and each $R^9$ is an optionally substituted straight or branched alkylene chain.

A specific embodiment of this embodiment is a compound of formula (Ia-1d), as set forth above, which is 4-(6-aminopyridin-3-yl)-N-(4-(8-methyl-3,8-diazabicyclo[3.2.1]octan-3-yl)phenyl)pyrimidin-2-amine.

Another embodiment is a compound of formula (Ia-1d), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by one or more substituents selected from the group consisting of —C(O)$R^6$, —$R^8$—N($R^6$)$R^7$, —$R^8$—C(O)N($R^6$)$R^7$, alkyl, halo and optionally substituted aryl;

$R^{5a}$ is independently selected from the group consisting of hydrogen, alkyl, haloalkyl, optionally substituted cycloalkyl, optionally substituted cycloalkylalkyl, —$R^8$—C(O)$R^6$, —$R^8$—C(O)N($R^6$)$R^7$, —$R^8$—C(N═$R^6$)N($R^6$)$R^7$ and —$R^8$—S(O)$_t$$R^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and each $R^8$ is independently selected from the group consisting of a direct bond and an optionally substituted straight or branched alkylene chain.

A specific embodiment of this embodiment is a compound of formula (Ia-1d), as set forth above, selected from the group consisting of:

4-(6-(morpholin-4-yl)pyridin-3-yl)-N-(4-(8-methyl-3,8-diazabicyclo[3.2.1]octan-3-yl)phenyl)pyrimidin-2-amine; and 4-(6-(morpholin-4-yl)pyridin-3-yl)-N-(3-methyl-4-(8-methyl-3,8-diazabicyclo[3.2.1]octan-3-yl)phenyl)pyrimidin-2-amine.

Another embodiment is a compound of formula (Ia-1d), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is pyridinyl substituted by one or more substituents selected from the group consisting of —$R^8$—C(O)$R^{6a}$, —$R^8$—C(O)N($R^{6a}$)$R^{7a}$, —$R^8$—S(O)$_p$$R^{6a}$ (where p is 0, 1 or 2), —$R^8$—N($R^{6a}$)—$R^9$—N($R^{6a}$)S(O)$_2$$R^{7a}$, —$R^8$—N($R^{6a}$)C(O)$R^{7a}$, —$R^8$—N($R^{6a}$)S(O)$_2$$R^{7a}$, —$R^8$—N($R^{6a}$)C(O)—$R^8$—N($R^{6a}$)$R^{7a}$, and tetrazolyl;

$R^{5a}$ is independently selected from the group consisting of hydrogen, alkyl, haloalkyl, optionally substituted cycloalkyl, optionally substituted cycloalkylalkyl, —$R^8$—C(O)$R^6$, —$R^8$—C(O)N($R^6$)$R^7$, —$R^8$—C(N═$R^6$)N($R^6$)$R^7$ and —$R^8$—S(O)$_t$$R^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;

each $R^8$ is independently selected from the group consisting of a direct bond and an optionally substituted straight or branched alkylene chain; and $R^9$ is an optionally substituted straight or branched alkylene chain.

A specific embodiment of this embodiment is a compound of formula (Ia-1d), as set forth above, selected from the group consisting of:

4-(6-(methylsulfonylamino)pyridin-3-yl)-N-(4-(8-methyl-3,8-diazabicyclo[3.2.1]octan-3-yl)phenyl)pyrimidin-2-amine;

4-(4-(acetamido)phenyl)-N-(4-(8-methyl-3,8-diazabicyclo[3.2.1]octan-3-yl)phenyl)pyrimidin-2-amine;

4-(6-(methylsulfonylamino)pyridin-3-yl)-N-(3-methyl-4-(8-methyl-3,8-diazabicyclo[3.2.1]octan-3-yl)phenyl)pyrimidin-2-amine; and 4-(4-(t-butylcarbonylamino)phenyl)-N-(3-methyl-4-(8-methyl-3,8-diazabicyclo[3.2.1]octan-3-yl)phenyl)pyrimidin-2-amine.

Another embodiment is a compound of formula (Ia-1d), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is selected from the group consisting of naphthyridinyl, benzo[b]azepinyl, benzo[b][1,4]oxazinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]thiazinyl and 3,4-dihydro-2H-pyrido[3,2-b][1,4]oxazinyl, each optionally substituted by one or more substituents independently selected from the group consisting of alkyl and oxo;

$R^{5a}$ is independently selected from the group consisting of hydrogen, alkyl, haloalkyl, optionally substituted cycloalkyl, optionally substituted cycloalkylalkyl, —$R^8$—$C(O)R^6$, —$R^8$—$C(O)N(R^6)R^7$, —$R^8$—$C(N=R^6)N(R^6)R^7$, —$R^8$—$S(O)_tR^6$ (where t is 1 or 2), and —$R^8$—$S(O)_2N(R^6)R^7$;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and each $R^8$ is independently selected from the group consisting of a direct bond and an optionally substituted straight or branched alkylene chain.

A specific embodiment of this embodiment is a compound of formula (Ia-1d), as set forth above, selected from the group consisting of:

4-(2,2-dimethyl-3-oxo-3,4-dihydro-2H-pyrido[3,2-b][1,4]oxazin-7-yl)-N-(4-(8-methyl-3,8-diazabicyclo[3.2.1]octan-3-yl)phenyl)pyrimidin-2-amine; and 4-(2,2-dimethyl-3-oxo-3,4-dihydro-2H-pyrido[3,2-b][1,4]oxazin-7-yl)-N-(3-methyl-4-(8-methyl-3,8-diazabicyclo[3.2.1]octan-3-yl)phenyl)pyrimidin-2-amine.

Another embodiment of the compounds of formula (Ia-1), as set forth above, is a compound according to formula (Ia-1e):

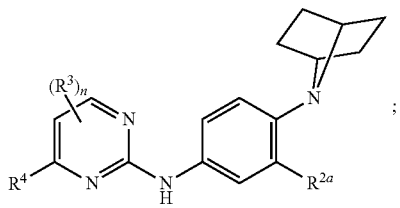

wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —$R^8$—$OR^{6a}$, —$R^8$—$S(O)_pR^{6a}$ (where p is 0, 1 or 2), —$R^8$—$C(O)R^{6a}$, —$R^8$—$C(O)OR^{6a}$, —$R^8$—$C(O)N(R^{6a})R^{7a}$, —$R^8$—$N(R^{6a})R^{7a}$, —$R^8$—$N(R^{6a})$—$R^9$—$N(R^{6a})R^{7a}$, —$R^8$—$N(R^{6a})$—$R^9$—$OR^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$, and —$R^8$—$N(R^{6a}$—$R^9$—$N(R^{6a})S(O)_2R^{7a}$, where the N-heterocyclyl, the N-heteroaryl and the aryl are each independently optionally substituted by one or more substituents selected from the group consisting of —$C(O)R^6$, —$R^8$—$N(R^6)R^7$, —$R^8$—$C(O)N(R^6)R^7$, alkyl, halo and optionally substituted aryl;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;

each $R^8$ is independently selected from the group consisting of a direct bond and an optionally substituted straight or branched alkylene chain; and each $R^9$ is an optionally substituted straight or branched alkylene chain.

Of this embodiment, one embodiment is a compound of formula (Ia-1e) wherein:

$R^4$ is pyridinyl substituted by one or more substituents selected from the group consisting of alkyl, cyano, —$R^8$—$OR^{6a}$, —$R^8$—$N(R^{6a})R^{7a}$, —$R^8$—$N(R^{6a})$—$R^9$—$N(R^{6a})R^{7a}$ and —$R^8$—$N(R^{6a})$—$R^9$—$OR^{7a}$; and $R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl.

A specific embodiment of this embodiment is a compound of formula (Ia-1e), as set forth above, which is 4-(6-cyanopyridin-3-yl)-N-(3-methyl-4-(7-azabicyclo[2.2.1]heptan-7-yl)phenyl)pyrimidin-2-amine.

Another embodiment is a compound of formula (Ia-1e), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by one or more substituents selected from the group consisting of —C(O)$R^6$, —$R^8$—N($R^6$)$R^7$, —$R^8$—C(O)N($R^6$)$R^7$, alkyl, halo and optionally substituted aryl;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and each $R^8$ is independently selected from the group consisting of a direct bond and an optionally substituted straight or branched alkylene chain.

A specific embodiment of this embodiment is a compound of formula (Ia-1e), as set forth above, which is 4-(6-(morpholin-4-yl)pyridin-3-yl)-N-(3-methyl-4-(7-azabicyclo[2.2.1]heptan-7-yl)phenyl)pyrimidin-2-amine.

Another embodiment of the compounds of formula (Ia-1), as set forth above, is a compound according to formula (Ia-1f):

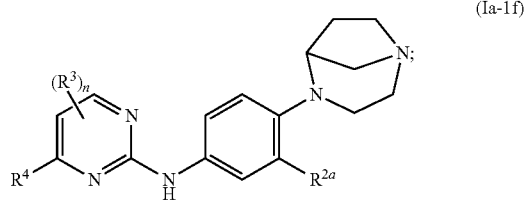

(Ia-1f)

wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —$R^8$—$OR^{6a}$, —$R^8$—S(O)$_p R^{6a}$ (where p is 0, 1 or 2), —$R^8$—C(O)$R^{6a}$, —$R^8$—C(O)$OR^{6a}$, —$R^8$—C(O)N($R^{6a}$)$R^{7a}$, —$R^8$—N($R^{6a}$)$R^{7a}$, —$R^8$—N($R^{6a}$)—$R^9$—N($R^{6a}$)$R^{7a}$, —$R^8$—N($R^{6a}$)—$R^9$—$OR^{7a}$, —$R^8$—N($R^{6a}$)C(O)$R^{7a}$, —$R^8$—N($R^{6a}$)S(O)$_2 R^{7a}$, —$R^8$—N($R^{6a}$)C(O)—$R^8$—N($R^{6a}$)$R^{7a}$, and —$R^8$—N($R^{6a}$)—$R^9$—N($R^{6a}$)S(O)$_2 R^{7a}$, where the N-heterocyclyl, the N-heteroaryl and the aryl are each independently optionally substituted by one or more substituents selected from the group consisting of —C(O)$R^6$, —$R^8$—N($R^6$)$R^7$, —$R^8$—C(O)N($R^6$)$R^7$, alkyl, halo and optionally substituted aryl;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;

each $R^8$ is independently selected from the group consisting of a direct bond and an optionally substituted straight or branched alkylene chain; and each $R^9$ is an optionally substituted straight or branched alkylene chain.

Of this embodiment, one embodiment is a compound of formula (Ia-1f), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is pyridinyl substituted by —$R^8$—$OR^{6a}$;

or $R^4$ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by —C(O)$R^6$; and each $R^6$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ is selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl; and $R^8$ is independently selected from the group consisting of a direct bond and an optionally substituted straight or branched alkylene chain.

A specific embodiment of this embodiment is a compound of formula (Ia-1f), as set forth above, selected from the group consisting of:

4-(6-(morpholin-4-yl)pyridin-3-yl)-N-(3-methyl-4-(1,4-diazabicyclo[3.2.1]octan-4-yl)phenyl)pyrimidin-2-amine;

4-(6-(tetrahydropyran-4-yloxy)pyridin-3-yl)-N-(3-methyl-4-(1,4-diazabicyclo[3.2.1]octan-4-yl)phenyl)pyrimidin-2-amine;

4-(6-(morpholin-4-yl)pyridin-3-yl)-N-(3-methyl-4-((R)-1,4-diazabicyclo[3.2.1]octan-4-yl)phenyl)pyrimidin-2-amine; and 4-(6-(morpholin-4-yl)pyridin-3-yl)-N-(3-methyl-4-((S)-1,4-diazabicyclo[3.2.1]octan-4-yl)phenyl)pyrimidin-2-amine.

Another embodiment is a compound of formula (Ia-1f), as set forth above, wherein:

n is 0 or 1;

$R^{2a}$ is independently selected from the group consisting of hydrogen, optionally substituted alkyl, halo, cyano and —O$R^6$;

$R^3$, when present, is independently selected from the group consisting of alkyl, halo and haloalkyl;

$R^4$ is selected from the group consisting of benzimidazolyl, imidazo[1,2-a]pyridinyl, indolyl, indolinyl, pyrazolyl, pyrazinyl, pyrimidinyl, pyrrolyl, 1H-pyrrolo[2,3-b]pyridinyl, 3,4-dihydro-2H-pyrido[3,2-b][1,4]oxazinyl and thiazolyl, each independently substituted by one or more substituents selected from the group consisting of alkyl, cyano, oxo, —$R^8$—O$R^{6a}$, —$R^8$—N($R^{6a}$)$R^{7a}$, —$R^8$—C(O)N($R^{6a}$)$R^{7a}$, —$R^8$—N($R^{6a}$)C(O)$R^{7a}$, —$R^8$—N($R^{6a}$)S(O)$_2R^{7a}$, —$R^8$—N($R^{6a}$)C(O)—$R^8$—N($R^{6a}$)$R^{7a}$, aryl, N-heteroaryl and N-heterocyclyl, where the aryl, the N-heterocyclyl and the N-heteroaryl are each independently optionally substituted by one or more substituents selected from the group consisting of —C(O)$R^6$, —$R^8$—N($R^6$)$R^7$, —$R^8$—C(O)N($R^6$)$R^7$, alkyl, halo and optionally substituted aryl;

$R^{5a}$ is independently selected from the group consisting of hydrogen, alkyl, —$R^8$—C(O)$R^6$ and —$R^8$—S(O)$_tR^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl; and each $R^8$ is independently selected from the group consisting of a direct bond and an optionally substituted straight or branched alkylene chain.

A specific embodiment of this embodiment is a compound of formula (Ia-1f), as set forth above, selected from the group consisting of:

4-(2-oxoindolin-5-yl)-N-(3-methyl-4-(1,4-diazabicyclo[3.2.1]octan-4-yl)phenyl)pyrimidin-2-amine;

(1-methylbenzimidazol-6-yl)-N-(3-methyl-4-(1,4-diazabicyclo[3.2.1]octan-4-yl)phenyl)pyrimidin-2-amine;

4-(imidazo[1,2-a]pyridin-6-yl)-N-(3-methyl-4-(1,4-diazabicyclo[3.2.1]octan-4-yl)phenyl)pyrimidin-2-amine; and 4-(2,2-dimethyl-3-oxo-3,4-dihydro-2H-pyrido[3,2-b][1,4]oxazin-7-yl)-N-(3-methyl-4-(1,4-diazabicyclo[3.2.1]octan-4-yl)phenyl)pyrimidin-2-amine.

Another embodiment of the compounds of formula (Ia-1), as set forth above, is a compound according to formula (Ia-1g):

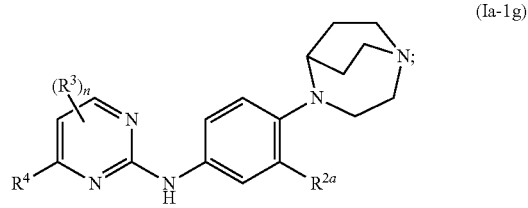

(Ia-1g)

wherein:

n is 0 or 1;

$R^{2a}$ is independently selected from the group consisting of hydrogen, optionally substituted alkyl, halo, cyano and —O$R^6$;

$R^3$, when present, is independently selected from the group consisting of alkyl, halo and haloalkyl;

$R^4$ is selected from the group consisting of phenyl, benzimidazolyl, benzo[b][1,4]oxazinyl, benzo[b]azepinyl, 2,3, 4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, $-R^8-OR^{6a}$, $-R^8-S(O)_pR^{6a}$ (where p is 0, 1 or 2), $-R^8-C(O)R^{6a}$, $-R^8-C(O)OR^{6a}$, $-R^8-C(O)N(R^{6a})R^{7a}$, $-R^8-N(R^{6a})R^{7a}$, $-R^8-N(R^{6a})-R^9-N(R^{6a})R^{7a}$, $-R^8-N(R^{6a})-R^9-OR^{7a}$, $-R^8-N(R^{6a})C(O)R^{7a}$, $-R^8-N(R^{6a})S(O)_2R^{7a}$, $-R^8-N(R^{6a})C(O)-R^9-N(R^{6a})R^{7a}$, and $-R^8-N(R^{6a})-R^9-N(R^{6a})S(O)_2R^{7a}$, where the N-heterocyclyl, the N-heteroaryl and the aryl are each independently optionally substituted by one or more substituents selected from the group consisting of $-C(O)R^6$, $-R^8-N(R^6)R^7$, $-R^8-C(O)N(R^6)R^7$, alkyl, halo and optionally substituted aryl;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;

each $R^8$ is independently selected from the group consisting of a direct bond and an optionally substituted straight or branched alkylene chain; and each $R^9$ is an optionally substituted straight or branched alkylene chain.

In one embodiment the compound has formula (Ia-1g), as set forth above, wherein:

n is 0 or 1;

$R^{2a}$ is independently selected from the group consisting of hydrogen, optionally substituted alkyl, halo, cyano and $-OR^6$;

$R^3$, when present, is independently selected from the group consisting of alkyl, halo and haloalkyl;

$R^4$ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by one or more substituents selected from the group consisting of $-C(O)R^6$, $-R^8-N(R^6)R^7$, $-R^8-C(O)N(R^6)R^7$, alkyl, halo and optionally substituted aryl;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and each $R^9$ is independently selected from the group consisting of a direct bond and an optionally substituted straight or branched alkylene chain.

A specific embodiment of this embodiment is a compound of formula (Ia-1g), as set forth above, selected from the group consisting of:

4-(6-(morpholin-4-yl)pyridin-3-yl)-N-(3-methyl-4-(1,4-diazabicyclo[3.2.2]nonan-4-yl)phenyl)pyrimidin-2-amine; and 4-(6-((1S,4S)-2-oxa-5-azabicyclo[2.2.1]heptan-5-yl)pyridin-3-yl)-N-(3-methyl-4-(1,4-diazabicyclo[3.2.2]nonan-4-yl)phenyl)pyrimidin-2-amine.

Another embodiment is a compound of formula (Ia-1g), as set forth above, wherein:

n is 0 or 1;

$R^{2a}$ is independently selected from the group consisting of hydrogen, optionally substituted alkyl, halo, cyano and $-OR^6$;

$R^3$, when present, is independently selected from the group consisting of alkyl, halo and haloalkyl;

$R^4$ is pyridinyl substituted by one or more substituents selected from the group consisting of $-R^8-C(O)R^{6a}$, $-R^8-C(O)N(R^{6a})R^{7a}$, $-R^8-S(O)_pR^{6a}$ (where p is 0, 1 or 2), $-R^8-N(R^{6a})-R^9-N(R^{6a})S(O)_2R^{7a}$, $-R^8-N(R^{6a})C(O)R^{7a}$, $-R^8-N(R^{6a})S(O)_2R^{7a}$, $-R^8-N(R^{6a})C(O)-R^8-N(R^{6a})R^{7a}$, and tetrazolyl;

$R^6$ is selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;

each R⁸ is independently selected from the group consisting of a direct bond and an optionally substituted straight or branched alkylene chain; and R⁹ is an optionally substituted straight or branched alkylene chain.

A specific embodiment of this embodiment is a compound of formula (Ia-1g), as set forth above, which is 4-(4-((pyridin-2-yl)aminocarbonyl)phenyl)-N-(3-methyl-4-(1,4-diazabicyclo[3.2.2]nonan-4-yl)phenyl)pyrimidin-2-amine.

Another embodiment is a compound of formula (Ia-1g), as set forth above, wherein:

n is 0 or 1;

R²ᵃ is independently selected from the group consisting of hydrogen, optionally substituted alkyl, halo, cyano and —OR⁶;

R³, when present, is independently selected from the group consisting of alkyl, halo and haloalkyl;

R⁴ is selected from the group consisting of naphthyridinyl, benzo[b]azepinyl, benzo[b][1,4]oxazinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]thiazinyl and 3,4-dihydro-2H-pyrido[3,2-b][1,4]oxazinyl, each optionally substituted by one or more substituents independently selected from the group consisting of alkyl and oxo; and R⁶ is selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl.

A specific embodiment of this embodiment is a compound of formula (Ia-1g), as set forth above, which is 4-(2,2-dimethyl-3-oxo-3,4-dihydro-2H-pyrido[3,2-b][1,4]oxazin-7-yl)-N-(3-methyl-4-(1,4-diazabicyclo[3.2.2]nonan-4-yl)phenyl)pyrimidin-2-amine.

Another embodiment of the compounds of formula (Ia-1), as set forth above, is a compound according to formula (Ia-1h):

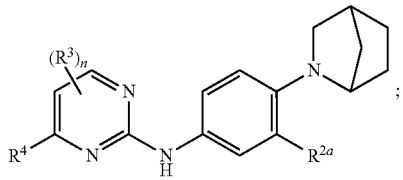

(Ia-1h)

wherein:

n is 0 or 1;

R²ᵃ is independently selected from the group consisting of hydrogen, optionally substituted alkyl, halo, cyano and —OR⁶;

R³, when present, is independently selected from the group consisting of alkyl, halo and haloalkyl;

R⁴ is selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1, 2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —R⁸—OR⁶ᵃ, —R⁸—S(O)ₚR⁶ᵃ (where p is 0, 1 or 2), —R⁸—C(O)R⁶ᵃ, —R⁸—C(O)OR⁶ᵃ, —R⁸—C(O)N(R⁶ᵃ)R⁷ᵃ, —R⁸—N(R⁶ᵃ)R⁷ᵃ, —R⁸—N(R⁶ᵃ)—R⁹—N(R⁶ᵃ)R⁷ᵃ, —R⁸—N(R⁶ᵃ)—R⁹—OR⁷ᵃ, —R⁸—N(R⁶ᵃ)C(O)R⁷ᵃ, —R⁸—N(R⁶ᵃ)S(O)₂R⁷ᵃ, —R⁸—N(R⁶ᵃ)C(O)—R⁸—N(R⁶ᵃ)R⁷ᵃ, and —R⁸—N(R⁶ᵃ)—R⁹—N(R⁶ᵃ)S(O)₂R⁷ᵃ, where the N-heterocyclyl, the N-heteroaryl and the aryl are each independently optionally substituted by one or more substituents selected from the group consisting of —C(O)R⁶, —R⁸—N(R⁶)R⁷, —R⁸—C(O)N(R⁶)R⁷, alkyl, halo and optionally substituted aryl;

each R⁶ and each R⁷ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any R⁶ and R⁷, together with the common nitrogen to which they are both attached, form an optionally substituted N-heteroaryl or an optionally substituted N-heterocyclyl;

R⁶ᵃ and R⁷ᵃ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any R⁶ᵃ and R⁷ᵃ are bonded to a common nitrogen, R⁶ᵃ and R⁷ᵃ together with the common nitrogen to which they are both attached, may form an optionally substituted N-heteroaryl or an optionally substituted N-heterocyclyl;

each R⁸ is independently selected from the group consisting of a direct bond and an optionally substituted straight or branched alkylene chain; and each R⁹ is an optionally substituted straight or branched alkylene chain.

In one embodiment the compound has formula (Ia-1h), as set forth above, wherein:

n is 0 or 1;

R²ᵃ is independently selected from the group consisting of hydrogen, optionally substituted alkyl, halo, cyano and —OR⁶;

R³, when present, is independently selected from the group consisting of alkyl, halo and haloalkyl;

R⁴ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by one or more substituents selected from the group consisting of —C(O)R⁶, —R⁸—N(R⁶)R⁷, —R⁸—C(O)N(R⁶)R⁷, alkyl, halo and optionally substituted aryl;

each R⁶ and each R⁷ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any R⁶ and R⁷, together with the common nitrogen to which they are both attached, form an optionally substituted N-heteroaryl or an optionally substituted N-heterocyclyl; and each R⁸ is independently selected from the group consisting of a direct bond and an optionally substituted straight or branched alkylene chain.

A specific embodiment of this embodiment is a compound of formula (Ia-1h), as set forth above, which is 4-(6-(morpholin-4-yl)pyridin-3-yl)-N-(3-methyl-4-((1S,4R)-2-azabicyclo[2.2.1]heptan-2-yl)phenyl)pyrimidin-2-amine.

Another embodiment is a compound of formula (Ia-1h), as set forth above, wherein:

n is 0 or 1;

R²ᵃ is independently selected from the group consisting of hydrogen, optionally substituted alkyl, halo, cyano and —OR⁶;

R³, when present, is independently selected from the group consisting of alkyl, halo and haloalkyl;

R⁴ is selected from the group consisting of naphthyridinyl, benzo[b]azepinyl, benzo[b][1,4]oxazinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]thiazinyl and 3,4-dihydro-2H-pyrido[3,2-b][1,4]oxazinyl, each optionally substituted by one or more substituents independently selected from the group consisting of alkyl and oxo; and R⁶ is selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl.

A specific embodiment of this embodiment is a compound of formula (Ia-1h) which is 4-(2,2-dimethyl-3-oxo-3,4-dihydro-2H-pyrido[3,2-b][1,4]oxazin-7-yl)-N-(3-methyl-4-((1S,4R)-2-azabicyclo[2.2.1]heptan-2-yl)phenyl)pyrimidin-2-amine.

Another embodiment of the compounds of formula (Ia-1), as set forth above, is a compound according to formula (Ia-1i):

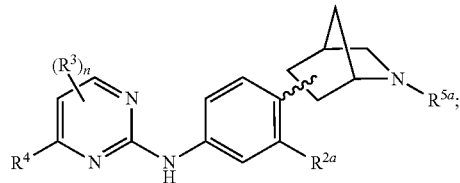

(Ia-1i)

wherein:

n is 0 or 1;

R²ᵃ is independently selected from the group consisting of hydrogen, optionally substituted alkyl, halo, cyano and —OR⁶;

R³, when present, is independently selected from the group consisting of alkyl, halo and haloalkyl;

R⁴ is selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —R⁸—OR⁶ᵃ, —R⁸—S(O)ₚR⁶ᵃ (where p is 0, 1 or 2), —R⁸—C(O)R⁶ᵃ, —R⁸—C(O)OR⁶ᵃ, —R⁸—C(O)N(R⁶ᵃ)R⁷ᵃ, —R⁸—N(R⁶ᵃ)R⁷ᵃ, —R⁸—N(R⁶ᵃ)—R⁹—N(R⁶ᵃ)R⁷ᵃ, —R⁸—N(R⁶ᵃ)—R⁹—OR⁷ᵃ, —R⁸—N(R⁶ᵃ)C(O)R⁷ᵃ, —R⁸—N(R⁶ᵃ)S(O)₂R⁷ᵃ, —R⁸—N(R⁶ᵃ)C(O)—R⁸—N(R⁶ᵃ)R⁷ᵃ, and —R⁸—N(R⁶ᵃ)—R⁹—N(R⁶ᵃ)S(O)₂R⁷ᵃ, where the N-heterocyclyl, the N-heteroaryl and the aryl are each independently optionally substituted by one or more substituents selected from the group consisting of —C(O)R⁶, —R⁸—N(R⁶)R⁷, —R⁸—C(O)N(R⁶)R⁷, alkyl, halo and optionally substituted aryl;

R⁵ᵃ is selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R⁸—OR⁶, —R⁸—C(O)R⁶, —R⁸—C(O)OR⁶, —R⁹—N(R⁶)R⁷, —R⁸—C(O)N(R⁶)R⁷, —R⁸—C(N=R⁶)N(R⁶)R⁷, —R⁸—S(O)₂N(R⁶)R⁷, and —R⁸—S(O)ₜR⁶ (where t is 1 or 2);

each R⁶ and each R⁷ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;

each $R^8$ is independently selected from the group consisting of a direct bond and an optionally substituted straight or branched alkylene chain; and each $R^9$ is an optionally substituted straight or branched alkylene chain.

Of this embodiment, one embodiment is a compound of formula (Ia-1i), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by one or more substituents selected from the group consisting of —C(O)$R^6$, —$R^8$—N($R^6$)$R^7$, —$R^8$—C(O)N($R^6$)$R^7$, alkyl, halo and optionally substituted aryl;

$R^{5a}$ is independently selected from the group consisting of hydrogen, alkyl, haloalkyl, optionally substituted cycloalkyl, optionally substituted cycloalkylalkyl, —$R^8$—C(O)$R^6$, —$R^8$—C(O)N($R^6$)$R^7$, —$R^8$—C(N=$R^6$)N($R^6$)$R^7$ and —$R^8$—S(O)$_t R^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and each $R^8$ is independently selected from the group consisting of a direct bond and an optionally substituted straight or branched alkylene chain.

A specific embodiment of this embodiment is a compound of formula (Ia-1i), as set forth above, selected from the group consisting of:

4-(6-(morpholin-4-yl)pyridin-3-yl)-N-(3-methyl-4-(2-methylsulfonyl-2-azabicyclo[2.2.1]heptan-5-yl)phenyl)pyrimidin-2-amine;

4-(6-(morpholin-4-yl)pyridin-3-yl)-N-(3-methyl-4-(2-methylsulfonyl-2-azabicyclo[2.2.1]heptan-6-yl)phenyl)pyrimidin-2-amine;

4-(6-(morpholin-4-yl)pyridin-3-yl)-N-(4-(2-methylsulfonyl-2-azabicyclo[2.2.1]heptan-5-yl)phenyl)pyrimidin-2-amine; and 4-(6-(morpholin-4-yl)pyridin-3-yl)-N-(4-(2-methylsulfonyl-2-azabicyclo[2.2.1]heptan-6-yl)phenyl)pyrimidin-2-amine.

Another embodiment is a compound of formula (Ia-1i), as set forth above, wherein:

n is 0 or 1;

$R^{2a}$ is independently selected from the group consisting of hydrogen, optionally substituted alkyl, halo, cyano and —$OR^6$;

$R^3$, when present, is independently selected from the group consisting of alkyl, halo and haloalkyl;

$R^4$ is selected from the group consisting of naphthyridinyl, benzo[b]azepinyl, benzo[b][1,4]oxazinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]thiazinyl and 3,4-dihydro-2H-pyrido[3,2-b][1,4]oxazinyl, each optionally substituted by one or more substituents independently selected from the group consisting of alkyl and oxo;

$R^{5a}$ is independently selected from the group consisting of hydrogen, alkyl, haloalkyl, optionally substituted cycloalkyl, optionally substituted cycloalkylalkyl, —$R^8$—C(O)$R^6$, —$R^8$—C(O)N($R^6$)$R^7$, —$R^8$—C(N=$R^6$)N($R^6$)$R^7$, —$R^8$—S(O)$_t R^6$ (where t is 1 or 2), and —$R^8$—S(O)$_2$N($R^6$)$R^7$;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and each $R^8$ is independently selected from the group consisting of a direct bond and an optionally substituted straight or branched alkylene chain.

A specific embodiment of this embodiment is a compound of formula (Ia-1i), as set forth above, selected from the group consisting of:

4-(2,2-dimethyl-3-oxo-3,4-dihydro-2H-pyrido[3,2-b][1,4]oxazin-7-yl)-N-(3-methyl-4-(2-methylsulfonyl-2-azabicyclo[2.2.1]heptan-5-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(2-methylsulfonyl-2-azabicyclo[2.2.1]heptan-6-yl)phenyl)pyrimidin-2-amine;

4-(2,2-dimethyl-3-oxo-3,4-dihydro-2H-pyrido[3,2-b][1,4]oxazin-7-yl)-N-(4-(2-methylsulfonyl-2-azabicyclo[2.2.1]heptan-5-yl)phenyl)pyrimidin-2-amine; and 4-(2,2-dimethyl-3-oxo-3,4-dihydro-2H-pyrido[3,2-b][1,4]
oxazin-7-yl)-N-(4-(2-methylsulfonyl-2-azabicyclo[2.2.1]
heptan-6-yl)phenyl)pyrimidin-2-amine.

Another embodiment of the compounds of formula (Ia-1),
as set forth above, is a compound according to formula
(Ia-1j):

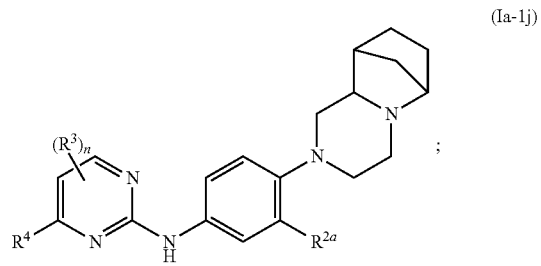

wherein n is 0 or 1;
$R^{2a}$ is independently selected from the group consisting of hydrogen, optionally substituted alkyl, halo, cyano and —$OR^6$;
$R^3$, when present, is independently selected from the group consisting of alkyl, halo and haloalkyl;
$R^4$ is selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —$R^8$—$OR^{6a}$, —$R^8$—$S(O)_pR^{6a}$ (where p is 0, 1 or 2), —$R^8$—$C(O)R^{6a}$, —$R^8$—$C(O)OR^{6a}$, —$R^8$—$C(O)N(R^{6a})R^{7a}$, —$R^8$—$N(R^{6a})R^{7a}$, —$R^8$—$N(R^{6a})$—$R^9$—$N(R^{6a})R^{7a}$, —$R^8$—$N(R^{6a})$—$R^9$—$OR^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$, and —$R^8$—N ($R^{6a}$—$R^9$—$N(R^{6a})S(O)_2R^{7a}$, where the N-heterocyclyl, the N-heteroaryl and the aryl are each independently optionally substituted by one or more substituents selected from the group consisting of —C(O)$R^6$, —$R^8$—$N(R^6)R^7$, —$R^8$—$C(O)N(R^6)R^7$, alkyl, halo and optionally substituted aryl;
each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;
each $R^8$ is independently selected from the group consisting of a direct bond and an optionally substituted straight or branched alkylene chain; and
each $R^9$ is an optionally substituted straight or branched alkylene chain.

Of this embodiment, one embodiment is a compound of formula (Ia-1j), as set forth above, wherein:
n is 0 or 1;
$R^{2a}$ is independently selected from the group consisting of hydrogen, optionally substituted alkyl, halo, cyano and —$OR^6$;
$R^3$, when present, is independently selected from the group consisting of alkyl, halo and haloalkyl;
$R^4$ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by one or more substituents selected from the group consisting of —C(O)$R^6$, —$R^8$—$N(R^6)R^7$, —$R^8$—$C(O)N(R^6)R^7$, alkyl, halo and optionally substituted aryl;
each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and
each $R^8$ is independently selected from the group consisting of a direct bond and an optionally substituted straight or branched alkylene chain.

A specific embodiment of this embodiment is a compound of formula (Ia-1j), as set forth above, which is 4-(6-(morpholin-4-yl)pyridin-3-yl)-N-(3-methyl-4-((6R,9S)-6,9-methanooctahydro-1H-pyrido[1,2-a]pyrazin-2-yl)phenyl)pyrimidin-2-amine.

Another embodiment is a compound of formula (Ia-1j), as set forth above, wherein:
n is 0 or 1;
$R^{2a}$ is independently selected from the group consisting of hydrogen, optionally substituted alkyl, halo, cyano and —$OR^6$;
$R^3$, when present, is independently selected from the group consisting of alkyl, halo and haloalkyl;
$R^4$ is selected from the group consisting of naphthyridinyl, benzo[b]azepinyl, 2,3,4,5-tetrahydro-1H-benzo[b]azepinyl, benzo[b][1,4]oxazinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]

thiazinyl and 3,4-dihydro-2H-pyrido[3,2-b][1,4]oxazinyl, each optionally substituted by one or more substituents independently selected from the group consisting of alkyl and oxo; and $R^6$ is selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl.

A specific embodiment of this embodiment is a compound of formula (Ia-1j) selected from the group consisting of:
4-(2,2-dimethyl-3-oxo-3,4-dihydro-2H-benzo[b][1,4]oxazin-7-yl)-N-(3-methyl-4-((6R,9S)-6,9-methanooctahydro-1H-pyrido[1,2-a]pyrazin-2-yl)phenyl)pyrimidin-2-amine;
4-(2-oxo-2,3,4,5-tetrahydro-1H-benzo[b]azepin-7-yl)-N-(3-methyl-4-((6R,9S)-6,9-methanooctahydro-1H-pyrido[1,2-a]pyrazin-2-yl)phenyl)pyrimidin-2-amine;
4-(3-oxo-3,4-dihydro-2H-benzo[b][1,4]thiazin-7-yl)-N-(3-methyl-4-((6R,9S)-6,9-methanooctahydro-1H-pyrido[1,2-a]pyrazin-2-yl)phenyl)pyrimidin-2-amine.

Another embodiment of the compounds of formula (Ia-1), as set forth above, is a compound according to formula (Ia-1k):

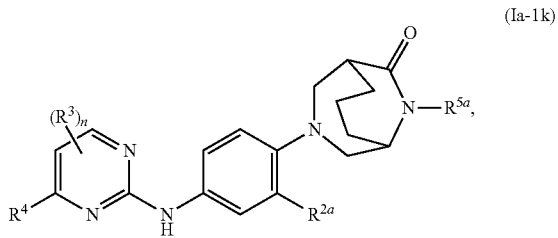

wherein n is 0 or 1;
$R^{2a}$ is independently selected from the group consisting of hydrogen, optionally substituted alkyl, halo, cyano and $-OR^6$;
$R^3$, when present, is independently selected from the group consisting of alkyl, halo and haloalkyl;
$R^4$ is selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, $-R^8-OR^{6a}$, $-R^8-S(O)_pR^{6a}$ (where p is 0, 1 or 2), $-R^8-C(O)R^{6a}$, $-R^8-C(O)OR^{6a}$, $-R^8-C(O)N(R^{6a})R^{7a}$, $-R^8-N(R^{6a})R^{7a}$, $-R^8-N(R^{6a})-R^9-N(R^{6a})R^{7a}$, $-R^8-N(R^{6a})-R^9-OR^{7a}$, $-R^8-N(R^{6a})C(O)R^{7a}$, $-R^8-N(R^{6a})S(O)_2R^{7a}$, $-R^8-N(R^{6a})C(O)-R^8-N(R^{6a})R^{7a}$, and $-R^8-N(R^{6a})-R^9-N(R^{6a})S(O)_2R^{7a}$, where the N-heterocyclyl, the N-heteroaryl and the aryl are each independently optionally substituted by one or more substituents selected from the group consisting of $-C(O)R^6$, $-R^8-N(R^6)R^7$, $-R^8-C(O)N(R^6)R^7$, alkyl, halo and optionally substituted aryl;

$R^{5a}$ is selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^8-OR^6$, $-R^8-C(O)R^6$, $-R^8-C(O)OR^6$, $-R^9-N(R^6)R^7$, $-R^8-C(O)N(R^6)R^7$, $-R^8-C(N=R^6)N(R^6)R^7$, $-R^8-S(O)_2N(R^6)R^7$, and $-R^8-S(O)_tR^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;

each $R^8$ is independently selected from the group consisting of a direct bond and an optionally substituted straight or branched alkylene chain; and each $R^9$ is an optionally substituted straight or branched alkylene chain.

Of this embodiment, one embodiment is a compound of formula (Ia-1k), as set forth above, wherein:
n is 0 or 1;
$R^{2a}$ is independently selected from the group consisting of hydrogen, optionally substituted alkyl, halo, cyano and $-OR^6$;
$R^3$, when present, is independently selected from the group consisting of alkyl, halo and haloalkyl;
$R^4$ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by one or more substituents selected from the group consisting of —C(O)R⁶, —R⁸—N(R⁶)R⁷, —R⁸—C(O)N(R⁶)R⁷, alkyl, halo and optionally substituted aryl;

R⁵ᵃ is independently selected from the group consisting of hydrogen, alkyl, haloalkyl, optionally substituted cycloalkyl, optionally substituted cycloalkylalkyl, —R⁸—C(O)R⁶, —R⁸—C(O)N(R⁶)R⁷, —R⁸—C(N═R⁶)N(R⁶)R⁷ and —R⁸—S(O)ₜR⁶ (where t is 1 or 2);

each R⁶ and each R⁷ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any R⁶ and R⁷, together with the common nitrogen to which they are both attached, form an optionally substituted N-heteroaryl or an optionally substituted N-heterocyclyl; and each R⁸ is independently selected from the group consisting of a direct bond and an optionally substituted straight or branched alkylene chain.

A specific embodiment of this embodiment is a compound of formula (Ia-1k) which is 4-(6-(morpholin-4-yl)pyridin-3-yl)-N-(3-cyano-4-(3,9-diazabicyclo[3.3.2]decan-10-on-3-yl)phenyl)pyrimidin-2-amine.

Another embodiment is a compound of formula (Ia-1k), as set forth above, wherein:

n is 0 or 1;

R²ᵃ is independently selected from the group consisting of hydrogen, optionally substituted alkyl, halo, cyano and —OR⁶;

R³, when present, is independently selected from the group consisting of alkyl, halo and haloalkyl;

R⁴ is selected from the group consisting of naphthyridinyl, benzo[b]azepinyl, 2,3,4,5-tetrahydro-1H-benzo[b]azepinyl, benzo[b][1,4]oxazinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]thiazinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, and 3,4-dihydro-2H-pyrido[3,2-b][1,4]oxazinyl, each optionally substituted by one or more substituents independently selected from the group consisting of alkyl and oxo;

R⁵ᵃ is independently selected from the group consisting of hydrogen, alkyl, haloalkyl, optionally substituted cycloalkyl, optionally substituted cycloalkylalkyl, —R⁸—C(O)R⁶, —R⁸—C(O)N(R⁶)R⁷, —R⁸—C(N═R⁶)N(R⁶)R⁷ and —R⁸—S(O)ₜR⁶ (where t is 1 or 2);

each R⁶ and each R⁷ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any R⁶ and R⁷, together with the common nitrogen to which they are both attached, form an optionally substituted N-heteroaryl or an optionally substituted N-heterocyclyl; and each R⁸ is independently selected from the group consisting of a direct bond and an optionally substituted straight or branched alkylene chain.

A specific embodiment of this embodiment is a compound of formula (Ia-1k) which is 4-(2,2-dimethyl-3-oxo-3,4-dihydro-2H-pyrido[3,2-b][1,4]oxazin-7-yl)-N-(3-cyano-4-(3,9-diazabicyclo[3.3.2]decan-10-on-3-yl)phenyl)pyrimidin-2-amine.

Another embodiment of the compounds of formula (Ia-1), as set forth above, is a compound according to formula (Ia-11):

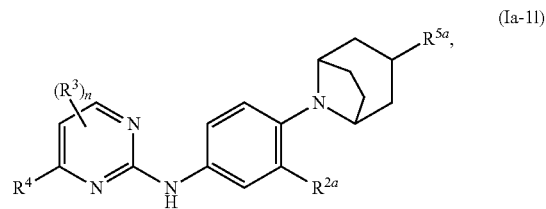

wherein n is 0 or 1;

R²ᵃ is independently selected from the group consisting of hydrogen, optionally substituted alkyl, halo, cyano and —OR⁶;

R³, when present, is independently selected from the group consisting of alkyl, halo and haloalkyl;

R⁴ is selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —R⁸—OR⁶ᵃ, —R⁸—S(O)ₚR⁶ᵃ (where p is 0, 1 or 2), —R⁸—C(O)R⁶ᵃ, —R⁸—C(O)OR⁶ᵃ, —R⁸—C(O)N(R⁶ᵃ)R⁷ᵃ, —R⁸—N(R⁶ᵃ)R⁷ᵃ, —R⁸—N(R⁶ᵃ)—R⁹—N(R⁶ᵃ)R⁷ᵃ, —R⁸—N(R⁶ᵃ)—R⁹—OR⁷ᵃ, —R⁸—N(R⁶ᵃ)C(O)R⁷ᵃ, —R⁸—N(R⁶ᵃ)S(O)₂R⁷ᵃ, —R⁸—N(R⁶ᵃ)C(O)—R⁸—N(R⁶ᵃ)R⁷ᵃ, and —R⁸—N(R⁶ᵃ)—R⁹—N(R⁶ᵃ)S(O)₂R⁷ᵃ, where the N-heterocyclyl, the N-heteroaryl and the aryl are each independently optionally substituted by one or more substituents selected from the group consisting of —C(O)R⁶, —R⁸—N(R⁶)R⁷, —R⁸—C(O)N(R⁶)R⁷, alkyl, halo and optionally substituted aryl;

R⁵ᵃ is selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^8$—$OR^6$, —$R^8$—$C(O)R^6$, —$R^8$—$C(O)OR^6$, —$R^8$—$N(R^6)R^7$, —$R^8$—$C(O)N(R^6)R^7$, —$R^8$—$C(N=R^6)N(R^6)R^7$, —$R^8$—$S(O)_2N(R^6)R^7$, and —$R^8$—$S(O)_tR^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl;

each $R^8$ is independently selected from the group consisting of a direct bond and an optionally substituted straight or branched alkylene chain; and each $R^9$ is an optionally substituted straight or branched alkylene chain.

Of this embodiment, one embodiment is a compound of formula (Ia-11), as set forth above, wherein:
n is 0 or 1;
$R^{2a}$ is independently selected from the group consisting of hydrogen, optionally substituted alkyl, halo, cyano and —$OR^6$;
$R^3$, when present, is independently selected from the group consisting of alkyl, halo and haloalkyl;
$R^4$ is pyridinyl substituted by one or more substituents selected from the group consisting of alkyl, haloalkyl, cyano, —$R^8$—$OR^{6a}$, —$R^8$—$N(R^{6a})R^{7a}$, —$R^8$—$N(R^{6a})$—$R^9$—$N(R^{6a})R^{7a}$ and —$R^8$—$N(R^{6a})$—$R^9$—$OR^{7a}$;
$R^{5a}$ is independently selected from the group consisting of hydrogen, alkyl, —$R^9$—$N(R^6)R^7$ and optionally substituted heterocyclyl;
each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

$R^{6a}$ and $R^{7a}$ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl, and when any $R^{6a}$ and $R^{7a}$ are bonded to a common nitrogen, $R^{6a}$ and $R^{7a}$ together with the common nitrogen to which they are both attached, may form an optionally substituted N-heteroaryl or an optionally substituted N-heterocyclyl;

each $R^8$ is independently selected from the group consisting of a direct bond and an optionally substituted straight or branched alkylene chain; and each $R^9$ is an optionally substituted straight or branched alkylene chain.

A specific embodiment of this embodiment is a compound of formula (Ia-11) selected from the group consisting of:
4-(6-(tetrahydropyran-4-yloxy)pyridin-3-yl)-N-(3-methyl-4-(3-(dimethylamino)-8-azabicyclo[3.2.1]octan-8-yl)phenyl)pyrimidin-2-amine; and
4-(6-(tetrahydropyran-4-yloxy)pyridin-3-yl)-N-(3-methyl-4-(3-(morpholin-4-yl)-8-azabicyclo[3.2.1]octan-8-yl)phenyl)pyrimidin-2-amine.

Another embodiment is a compound of formula (Ia-1 I), as set forth above, wherein:
n is 0 or 1;
$R^{2a}$ is independently selected from the group consisting of hydrogen, optionally substituted alkyl, halo, cyano and —$OR^6$;
$R^3$, when present, is independently selected from the group consisting of alkyl, halo and haloalkyl;
$R^4$ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by one or more substituents selected from the group consisting of —$C(O)R^6$, —$R^9$—$N(R^6)R^7$, —$R^9$—$C(O)N(R^6)R^7$, alkyl, halo and optionally substituted aryl;
$R^{5a}$ is independently selected from the group consisting of hydrogen, alkyl, —$R^9$—$N(R^6)R^7$ and optionally substituted heterocyclyl;
each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

each $R^8$ is independently selected from the group consisting of a direct bond and an optionally substituted straight or branched alkylene chain; and each $R^9$ is an optionally substituted straight or branched alkylene chain.

A specific embodiment of this embodiment is a compound of formula (Ia-11) selected from the group consisting of:

4-(6-(morpholin-4-yl)pyridin-3-yl)-N-(3-methyl-4-(3-(morpholin-4-yl)-8-azabicyclo[3.2.1]octan-8-yl)phenyl)pyrimidin-2-amine; and 4-(6-(morpholin-4-yl)pyridin-3-yl)-N-(3-methyl-4-(3-(dimethylamino)-8-azabicyclo[3.2.1]octan-8-yl)phenyl)pyrimidin-2-amine.

Of the compounds of formula (Ia-1), as set forth above, another embodiment is a compound wherein:

n is 0 or 1;
m is 0 or 1;
$R^1$ is selected from the group consisting of hydrogen or alkyl;
$R^2$, when present, is independently selected from the group consisting of optionally substituted alkyl, halo, cyano and —$OR^6$;
$R^3$, when present, is independently selected from the group consisting of alkyl, halo and haloalkyl;
$R^4$ is heteroaryl optionally substituted by a bridged N-heterocyclyl, where the bridged N-heterocyclyl is optionally substituted by one or more substituents selected from the group consisting of alkyl, halo and optionally substituted aryl;
$R^5$ is a non-bridged N-heterocyclyl, wherein a nitrogen atom in the non-bridged N-heterocyclyl is optionally substituted by a substituent selected from the group consisting of alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^8$—C(O)$R^6$, —$R^8$—C(O)O$R^6$, —$R^9$—N($R^6$)$R^7$, —$R^8$—C(O)N($R^6$)$R^7$, —$R^8$—S(O)$_2$N($R^6$)$R^7$, and —$R^8$—S(O)$_t$$R^6$ (where t is 1 or 2); and wherein a carbon atom in the non-bridged N-heterocyclyl is optionally substituted by a substituent selected from the group consisting of alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^8$—O$R^6$, —$R^8$—C(O)$R^6$, —$R^8$—C(O)O$R^6$, —$R^9$—N($R^6$)$R^7$, —$R^8$—C(O)N($R^6$)$R^7$, —$R^8$—S(O)$_2$N($R^6$)$R^7$, and —$R^8$—S(O)$_p$$R^6$ (where p is 0, 1 or 2);
each $R^6$ and each $R^7$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl; or any $R^6$ and $R^7$, together with the common nitrogen to which they are both attached, form an optionally substituted N-heteroaryl or an optionally substituted N-heterocyclyl;
each $R^8$ is independently selected from the group consisting of a direct bond and an optionally substituted straight or branched alkylene chain; and
each $R^9$ is an optionally substituted straight or branched alkylene chain.

Of this embodiment, one embodiment is a compound of formula (Ia-1) wherein:
n is 0 or 1;
m is 1;
$R^1$ is selected from the group consisting of hydrogen or alkyl;
$R^2$ is alkyl;

$R^3$, when present, is independently selected from the group consisting of alkyl, halo and haloalkyl;
$R^4$ is pyridinyl substituted by a bridged N-heterocyclyl, where the bridged N-heterocyclyl is optionally substituted by one or more substituents selected from the group consisting of alkyl, halo and optionally substituted aryl; and
$R^5$ is a non-bridged N-heterocyclyl selected from the group consisting of piperazinyl, piperidinyl and morpholinyl.

A specific embodiment of this embodiment is a compound of formula (Ia-1) selected from the group consisting of:
4-(6-((1S,4S)-5-methyl-2,5-diazabicyclo[2.2.1]heptan-2-yl)pyridin-3-yl)-N-(3-methyl-4-(4-methylpiperazin-1-yl)phenyl)pyrimidin-2-amine; and
4-(6-((1S,4S)-5-(4-fluorophenyl)-2,5-diazabicyclo[2.2.1]heptan-2-yl)pyridin-3-yl)-N-(3-methyl-4-(4-methylpiperazin-1-yl)phenyl)pyrimidin-2-amine.

Another embodiment of the invention is a compound of formula (Ia), as set forth above in the Summary of the Invention, according to formula (Ia-2):

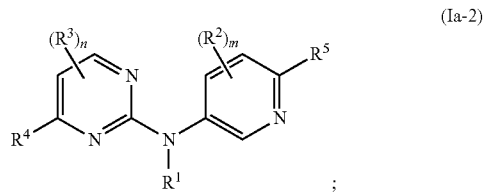

(Ia-2)

wherein:
n is 0, 1 or 2;
m is 0, 1 or 2;
$R^1$ is selected from the group consisting of hydrogen, alkyl, alkenyl, alkynyl, haloalkyl, haloalkenyl, haloalkenyl, optionally substituted cycloalkyl, optionally substituted cycloalkylalkyl, optionally substituted cycloalkylalkenyl, optionally substituted cycloalkylalkynyl, optionally substituted aryl, optionally substituted aralkyl, optionally substituted aralkenyl, optionally substituted aralkynyl, —$R^8$—C(O)O$R^6$, —$R^9$—N($R^6$)$R^7$ and —$R^9$—O$R^6$;
each $R^2$, when present, is independently selected from the group consisting of optionally substituted alkyl, halo, cyano and —$OR^6$;
each $R^3$, when present, is independently selected from the group consisting of alkyl, halo and haloalkyl;
$R^4$ is selected from the group consisting of aryl and heteroaryl, where the aryl and the heteroaryl are each independently optionally substituted by one or more substituents selected from the group consisting of oxo, alkyl, halo, haloalkyl, cyano, N-heterocyclyl, N-heteroaryl, aryl, —$R^8$—O$R^{6a}$, —$R^8$—S(O)$_p$$R^{6a}$ (where p is 0, 1 or 2), —$R^8$—C(O)$R^{6a}$, —$R^8$—C(O)O$R^{6a}$, —$R^8$—C(O)N($R^{6a}$)$R^{7a}$, —$R^8$—N($R^{6a}$)$R^{7a}$, —$R^8$—N($R^{6a}$)—$R^9$—N($R^{6a}$)$R^{7a}$, —$R^8$—N($R^{6a}$)—$R^9$—O$R^{7a}$, —$R^8$—N($R^{6a}$)C(O)$R^{7a}$, —$R^8$—N($R^{6a}$)S(O)$_2$$R^{7a}$, —$R^8$—N($R^{6a}$)C(O)—$R^8$—N($R^{6a}$)$R^{7a}$, and —$R^8$—N($R^{6a}$)—$R^9$—N($R^{6a}$)S(O)$_2$$R^{7a}$, where each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl and optionally substituted aralkyl, and where the N-heterocyclyl, the N-heteroaryl and the aryl are each independently optionally substituted by one or more substituents selected from the group consisting of —C(O)R⁶, —R⁸—N(R⁶)R⁷, —R⁸—C(O)N(R⁶)R⁷, alkyl, halo and optionally substituted aryl;
R⁵ is an N-heterocyclyl, wherein a nitrogen atom in the N-heterocyclyl is optionally substituted by a substituent selected from the group consisting of alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R⁸—OR⁶, —R⁸—C(O)R⁶, —R⁸—C(O)OR⁶, —R⁹—N(R⁶)R⁷, —R⁸—C(O)N(R⁶)R⁷, —R⁸—C(N=R⁶)N(R⁶)R⁷, —R⁸—S(O)₂N(R⁶)R⁷, and —R⁸—S(O)ₜR⁶ (where t is 1 or 2); and a carbon atom in the N-heterocyclyl is optionally substituted by a substituent selected from the group consisting of alkyl, alkenyl, alkynyl, halo, haloalkyl, haloalkenyl, haloalkynyl, oxo, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R⁸—OR⁶, —R⁸—C(O)R⁶, —R⁸—C(O)OR⁶, —R⁹—N(R⁶)R⁷, —R⁸—C(O)N(R⁶)R⁷, —R⁸—S(O)₂N(R⁶)R⁷, and —R⁸—S(O)ₚR⁶ (where p is 0, 1 or 2);

each R⁶ and each R⁷ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any R⁶ and R⁷, together with the common nitrogen to which they are both attached, form an optionally substituted N-heteroaryl or an optionally substituted N-heterocyclyl;

each R⁸ is independently selected from the group consisting of a direct bond, an optionally substituted straight or branched alkylene chain, an optionally substituted straight or branched alkenylene chain and an optionally substituted straight or branched alkynylene chain; and each R⁹ is independently selected from the group consisting of an optionally substituted straight or branched alkylene chain, an optionally substituted straight or branched alkenylene chain and an optionally substituted straight or branched alkynylene chain;

provided at least one of R⁵ and a substituent on R⁴ is a bridged N-heterocyclyl;

Of the compounds of formula (Ia-2), as set forth above, one embodiment is a compound selected from the following:

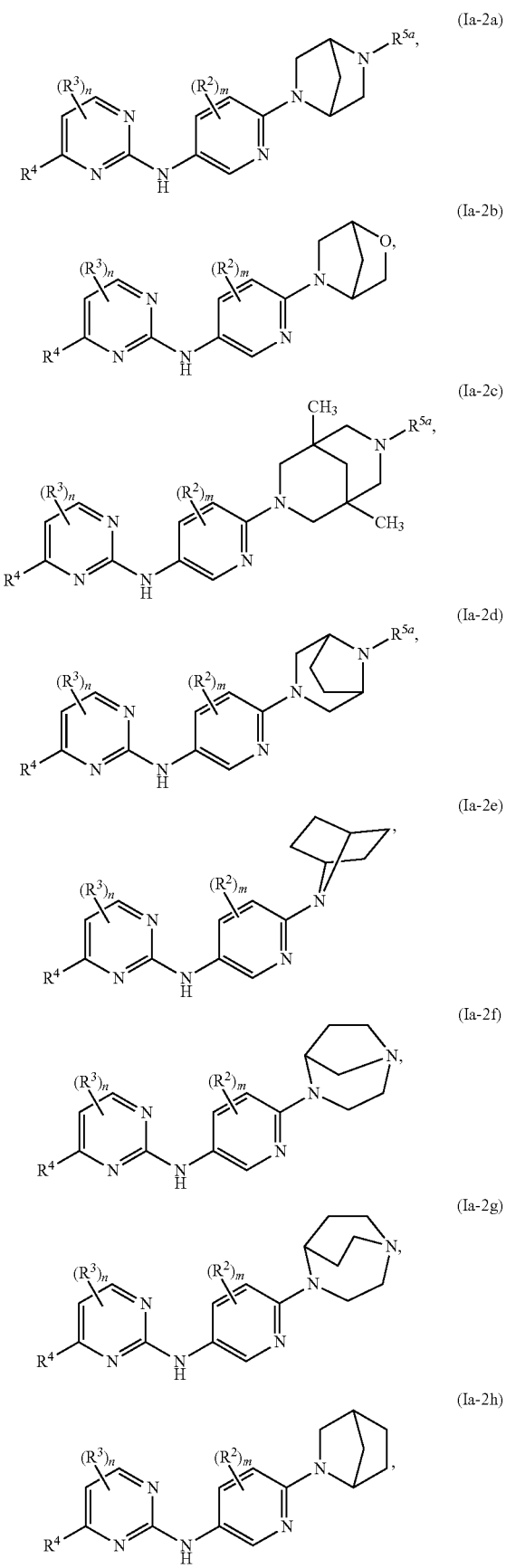

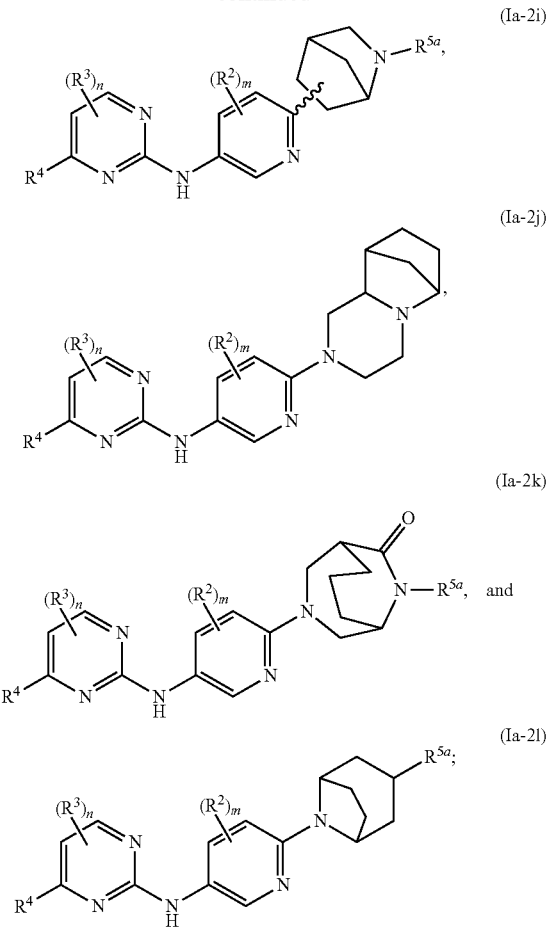

wherein:
each n is 0, 1 or 2;
each m is 0, 1 or 2;
each $R^2$, when present, is independently selected from the group consisting of optionally substituted alkyl, halo, cyano and —$OR^6$;
each $R^3$, when present, is independently selected from the group consisting of alkyl, halo and haloalkyl;
each $R^4$ is independently selected from the group consisting of aryl and heteroaryl, where the aryl and the heteroaryl are each independently optionally substituted by one or more substituents selected from the group consisting of oxo, alkyl, halo, haloalkyl, cyano, N-heterocyclyl, N-heteroaryl, aryl, —$R^8$—$OR^{6a}$, —$R^8$—$S(O)_pR^{6a}$ (where p is 0, 1 or 2), —$R^8$—$C(O)R^{6a}$, —$R^8$—$C(O)OR^{6a}$, —$R^8$—$C(O)N(R^{6a})R^{7a}$, —$R^8$—$N(R^{6a})R^{7a}$, —$R^8$—$N(R^{6a})$—$R^9$—$N(R^{6a})R^{7a}$, —$R^8$—$N(R^{6a})$—$R^9$—$OR^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$, and —$R^8$—$N(R^{6a})$—$R^9$—$N(R^{6a})S(O)_2R^{7a}$, where each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl and optionally substituted aralkyl, and where the N-heterocyclyl, the N-heteroaryl and the aryl are each independently optionally substituted by one or more substituents selected from the group consisting of —$C(O)R^6$, —$R^8$—$N(R^6)R^7$, —$R^8$—$C(O)N(R^6)R^7$, alkyl, halo and optionally substituted aryl;

each $R^{5a}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^8$—$OR^6$, —$R^8$—$C(O)R^6$, —$R^8$—$C(O)OR^6$, —$R^9$—$N(R^6)R^7$, —$R^8$—$C(O)N(R^6)R^7$, —$R^8$—$C(N$=$R^6)N(R^6)R^7$, —$R^8$—$S(O)_2N(R^6)R^7$, and —$R^8$—$S(O)_tR^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain; and each $R^9$ is independently selected from the group consisting of an optionally substituted straight or branched alkylene chain, an optionally substituted straight or branched alkenylene chain and an optionally substituted straight or branched alkynylene chain.

Of this embodiment, one embodiment is a compound selected from the formulae above wherein:
each n is 0 or 1;
each m is 0 or 1;
each $R^4$ is independently selected from the group consisting of phenyl, benzimidazolyl, benzo[b][1,4]oxazinyl, benzo[b]azepinyl, 2,3,4,5-tetrahydro-1H-benzo[b]azepinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]oxazinyl, 3,4-dihydro-2H-pyrido[3,2-b][1,4]thiazinyl, imidazo[1,2-a]pyridinyl, 6,7,8,9-tetrahydro-5H-pyrido[2,3-b]indolyl, 7,8,9,9a-tetrahydro-5H-pyrido[2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —$R^8$—$OR^{6a}$, —$R^8$—$S(O)_pR^{6a}$ (where p is 0, 1 or 2), —$R^8$—$C(O)R^{6a}$, —$R^8$—$C(O)OR^{6a}$, —$R^8$—$C(O)N(R^{6a})R^{7a}$, —$R^8$—$N(R^{6a})R^{7a}$, —$R^8$—$N(R^{6a})$—$R^9$—$N(R^{6a})R^{7a}$, —$R^8$—$N(R^{6a})$—$R^9$—$OR^{7a}$, —$R^8$—$N(R^{6a})C(O)R^{7a}$, —$R^8$—$N(R^{6a})S(O)_2R^{7a}$, —$R^8$—$N(R^{6a})C(O)$—$R^8$—$N(R^{6a})R^{7a}$, and —$R^8$—N ($R^{6a}$)—$R^9$—N($R^{6a}$)S(O)$_2$$R^{7a}$, where the N-heterocyclyl, the N-heteroaryl and the aryl are each independently optionally substituted by one or more substituents selected from the group consisting of —C(O)$R^6$, —$R^8$—N($R^6$)$R^7$, —$R^8$—C(O)N($R^6$)$R^7$, alkyl, halo and optionally substituted aryl;

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl;

each $R^8$ is independently selected from the group consisting of a direct bond and an optionally substituted straight or branched alkylene chain; and each $R^9$ is an optionally substituted straight or branched alkylene chain.

One embodiment of the compounds of formula (Ia-2), as set forth above, is a compound according to formula (Ia-2a):

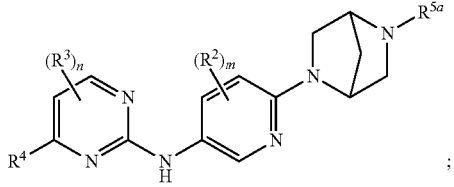

(Ia-2a)

n is 0 or 1;
m is 0 or 1;
$R^2$, when present, is independently selected from the group consisting of optionally substituted alkyl, halo, cyano and —O$R^6$;
$R^3$, when present, is independently selected from the group consisting of alkyl, halo and haloalkyl;
$R^4$ is selected from the group consisting of phenyl, benzimidazolyl, benzo[b][1,4]oxazinyl, benzo[b]azepinyl, 2,3, 4,5-tetrahydro-1H-benzo[b]azepinyl, 3,4-dihydro-2H-benzo[b][1,4]thiazinyl, 3',4'-dihydrospiro[cyclobutane-1, 2'-pyrido[3,2-b][1,4]oxazinyl, 3,4-dihydro-2H-pyrido[3, 2-b][1,4]oxazinyl, 3,4-dihydro-2H-pyrido[3,2-b][1,4] thiazinyl, imidazo[1,2-a]pyridinyl, 6,7,8,9-tetrahydro-5H-pyrido[2,3-b]indolyl, 7,8,9,9a-tetrahydro-5H-pyrido [2,3-e]pyrrolo[1,2-a][1,4]diazepin-10(11H)-onyl, indolyl, indolinyl, naphthyridinyl, pyrazolyl, pyridinyl, pyrazinyl, pyrimidinyl, pyrrolyl, 1H-pyrrolo[2,3-b]pyridinyl, and thiazolyl, each optionally substituted by one or more substituents independently selected from the group consisting of oxo, alkyl, halo, haloalkyl, cyano, N-heterocyclyl, N-heteroaryl, aryl, —$R^8$—O$R^{6a}$, —$R^8$—S(O)$_p$$R^{6a}$ (where p is 0, 1 or 2), —$R^8$—C(O)$R^{6a}$, —$R^8$—C(O)O$R^{6a}$, —$R^8$—C(O)N($R^{6a}$)$R^{7a}$, —$R^8$—N($R^{6a}$)$R^{7a}$, —$R^8$—N($R^{6a}$)—$R^9$—N($R^{6a}$)$R^{7a}$, —$R^8$—N($R^{6a}$)—$R^9$—O$R^{7a}$, —$R^8$—N($R^{6a}$)C(O)$R^{7a}$, —$R^8$—N($R^{6a}$)S(O)$_2$$R^{7a}$, —$R^8$—N($R^{6a}$)C(O)—$R^8$—N($R^{6a}$)$R^{7a}$, and —$R^8$—N ($R^{6a}$)—$R^9$—N($R^{6a}$)S(O)$_2$$R^{7a}$, where the N-heterocyclyl, the N-heteroaryl and the aryl are each independently optionally substituted by one or more substituents selected from the group consisting of —C(O)$R^6$, —$R^8$—N($R^6$)$R^7$, —$R^8$—C(O)N($R^6$)$R^7$, alkyl, halo and optionally substituted aryl;

$R^{5a}$ is selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^8$—O$R^6$, —$R^8$—C(O)$R^6$, —$R^8$—C(O)O$R^6$, —$R^9$—N($R^6$)$R^7$, —$R^8$—C(O)N($R^6$)$R^7$, —$R^8$—C(N=$R^6$)N($R^6$)$R^7$, —$R^8$—S(O)$_2$N($R^6$)$R^7$, and —$R^8$—S(O)$_t$$R^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl;

each $R^8$ is independently selected from the group consisting of a direct bond and an optionally substituted straight or branched alkylene chain; and each $R^9$ is an optionally substituted straight or branched alkylene chain.

Of this embodiment, one embodiment is a compound of formula (Ia-2a) wherein:
n is 0 or 1;
m is 0 or 1;
$R^2$, when present, is independently selected from the group consisting of optionally substituted alkyl, halo, cyano and —O$R^6$;
$R^3$, when present, is independently selected from the group consisting of alkyl, halo and haloalkyl;
$R^4$ is pyridinyl substituted by one or more substituents selected from the group consisting of alkyl, cyano, —R⁸—OR⁶ᵃ, —R⁸—N(R⁶ᵃ)R⁷ᵃ, —R⁸—N(R⁶ᵃ)—R⁹—N(R⁶ᵃ)R⁷ᵃ and —R⁸—N(R⁶ᵃ)—R⁹—OR⁷ᵃ;

R⁵ᵃ is independently selected from the group consisting of hydrogen, alkyl, —R⁸—C(O)R⁶ and —R⁸—S(O)ₜR⁶ (where t is 1 or 2); and each R⁶ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

R⁶ᵃ and R⁷ᵃ are each independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl;

each R⁸ is independently selected from the group consisting of a direct bond and an optionally substituted straight or branched alkylene chain; and each R⁹ is an optionally substituted straight or branched alkylene chain.

A specific embodiment of this embodiment is a compound of formula (Ia-2a) selected from the group consisting of:

4-(6-(dimethylamino)pyridin-3-yl)-N-(6-((1S,4S)-5-methyl-2,5-diazabicyclo[2.2.1]heptan-2-yl)pyridin-3-yl)pyrimidin-2-amine;

4-(6-(dimethylamino)pyridin-3-yl)-N-(5-methyl-6-((1S,4S)-5-methyl-2,5-diazabicyclo[2.2.1]heptan-2-yl)pyridin-3-yl)pyrimidin-2-amine; and 4-(6-aminopyridin-3-yl)-N-(5-methyl-6-((1S,4S)-5-methyl-2,5-diazabicyclo[2.2.1]heptan-2-yl)pyridin-3-yl)pyrimidin-2-amine.

Another embodiment is a compound of formula (Ia-2a) wherein:

n is 0 or 1;

m is 0 or 1;

R², when present, is independently selected from the group consisting of optionally substituted alkyl, halo, cyano and —OR⁶;

R³, when present, is independently selected from the group consisting of alkyl, halo and haloalkyl;

R⁴ is pyridinyl substituted by an N-heterocyclyl selected from the group consisting of morpholinyl, piperazinyl, piperidinyl, oxazepanyl, 5-oxa-2-azabicyclo[2.2.1]heptanyl and thiamorpholinyl, where the N-heterocyclyl is optionally substituted by one or more substituents selected from the group consisting of —C(O)R⁶, —R⁸—N(R⁶)R⁷, —R⁸—C(O)N(R⁶)R⁷, alkyl, halo and optionally substituted aryl;

R⁵ᵃ is independently selected from the group consisting of hydrogen, alkyl, haloalkyl, optionally substituted cycloalkyl, optionally substituted cycloalkylalkyl, —R⁸—C(O)R⁶, —R⁸—C(O)N(R⁶)R⁷, —R⁸—C(N=R⁶)N(R⁶)R⁷ and —R⁸—S(O)ₜR⁶ (where t is 1 or 2);

each R⁶ and each R⁷ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any R⁶ and R⁷, together with the common nitrogen to which they are both attached, form an optionally substituted N-heteroaryl or an optionally substituted N-heterocyclyl; and each R⁸ is independently selected from the group consisting of a direct bond and an optionally substituted straight or branched alkylene chain.

A specific embodiment of this embodiment is a compound of formula (Ia-2a) selected from the group consisting of:

4-(6-(4-acetylpiperazin-1-yl)pyridin-3-yl)-N-(6-((1S,4S)-5-methyl-2,5-diazabicyclo[2.2.1]heptan-2-yl)pyridin-3-yl)pyrimidin-2-amine;

4-(5-methyl-6-(morpholin-4-yl)pyridin-3-yl)-N-(6-((1S,4S)-5-methyl-2,5-diazabicyclo[2.2.1]heptan-2-yl)pyridin-3-yl)pyrimidin-2-amine;

4-(6-(4-acetylpiperazin-1-yl)pyridin-3-yl)-N-(5-methyl-6-((1S,4S)-5-methyl-2,5-diazabicyclo[2.2.1]heptan-2-yl)pyridin-3-yl)pyrimidin-2-amine;

4-(5-methyl-6-(morpholin-4-yl)pyridin-3-yl)-N-(5-methyl-6-((1S,4S)-5-methyl-2,5-diazabicyclo[2.2.1]heptan-2-yl)pyridin-3-yl)pyrimidin-2-amine;

4-(6-(morpholin-4-yl)pyridin-3-yl)-N-(5-methyl-6-((1S,4S)-5-methyl-2,5-diazabicyclo[2.2.1]heptan-2-yl)pyridin-3-yl)pyrimidin-2-amine;

4-(6-((1S,4S)-2-oxa-5-azabicyclo[2.2.1]heptan-5-yl)pyridin-3-yl)-N-(5-methyl-6-((1S,4S)-5-methyl-2,5-diazabicyclo[2.2.1]heptan-2-yl)pyridin-3-yl)pyrimidin-2-amine.

Another embodiment is a compound of formula (Ia-2a) wherein:

n is 0 or 1;

m is 0 or 1;

R², when present, is independently selected from the group consisting of optionally substituted alkyl, halo, cyano and —OR⁶;

R³, when present, is independently selected from the group consisting of alkyl, halo and haloalkyl;

R⁴ is pyridinyl substituted by one or more substituents selected from the group consisting of —R⁸—C(O)R⁶ᵃ, —R⁸—C(O)N(R⁶ᵃ)R⁷ᵃ, —R⁸—S(O)ₚR⁶ᵃ (where p is 0, 1 or 2), —R⁸—N(R⁶ᵃ)—R⁹—N(R⁶ᵃ)S(O)₂R⁷ᵃ, —R⁸—N(R⁶ᵃ)C(O)R⁷ᵃ, —R⁸—N(R⁶ᵃ)S(O)₂R⁷ᵃ, —R⁸—N(R⁶ᵃ)C(O)—R⁸—N(R⁶ᵃ)R⁷ᵃ, and tetrazolyl;

R⁵ᵃ is independently selected from the group consisting of hydrogen, alkyl, haloalkyl, optionally substituted cycloalkyl, optionally substituted cycloalkylalkyl, —R⁸—C(O)R⁶, —R⁸—C(O)N(R⁶)R⁷, —R⁸—C(N=R⁶)N(R⁶)R⁷ and —R⁸—S(O)ₜR⁶ (where t is 1 or 2);

each R⁶ and each R⁷ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any R⁶ and R⁷, together with the common nitrogen to which they are both attached, form an optionally substituted N-heteroaryl or an optionally substituted N-heterocyclyl;

each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl;

each $R^8$ is independently selected from the group consisting of a direct bond and an optionally substituted straight or branched alkylene chain; and each $R^9$ is an optionally substituted straight or branched alkylene chain.

A specific embodiment of this embodiment is a compound of formula (Ia-2a) selected from the group consisting of:
4-(6-(methylcarbonylamino)pyridin-3-yl)-N-(6-((1S,4S)-5-methyl-2,5-diazabicyclo[2.2.1]heptan-2-yl)pyridin-3-yl)pyrimidin-2-amine;
4-(6-(2-(morpholin-4-yl)acetamido)pyridin-3-yl)-N-(5-methyl-6-((1S,4S)-5-methyl-2,5-diazabicyclo[2.2.1]heptan-2-yl)pyridin-3-yl)pyrimidin-2-amine;
4-(6-(acetamido)pyridin-3-yl)-N-(5-methyl-6-((1S,4S)-5-methyl-2,5-diazabicyclo[2.2.1]heptan-2-yl)pyridin-3-yl)pyrimidin-2-amine; and
4-(6-(methylsulfonylamino)pyridin-3-yl)-N-(5-methyl-6-((1S,4S)-5-methyl-2,5-diazabicyclo[2.2.1]heptan-2-yl)pyridin-3-yl)pyrimidin-2-amine.

Another embodiment is a compound of formula (Ia-2a) wherein:
n is 0 or 1;
m is 0 or 1;
$R^2$, when present, is independently selected from the group consisting of optionally substituted alkyl, halo, cyano and —$OR^6$;
$R^3$, when present, is independently selected from the group consisting of alkyl, halo and haloalkyl;
$R^4$ is selected from the group consisting of naphthyridinyl, benzo[b]azepinyl, benzo[b][1,4]oxazinyl, 3,4-dihydro-2H-benzo[b][1,4]thiazinyl, 3',4'-dihydrospiro[cyclobutane-1,2'-pyrido[3,2-b][1,4]oxazinyl, 3,4-dihydro-2H-pyrido[3,2-b][1,4]thiazinyl and 3,4-dihydro-2H-pyrido[3,2-b][1,4]oxazinyl, each optionally substituted by one or more substituents independently selected from the group consisting of alkyl and oxo;
$R^{5a}$ is independently selected from the group consisting of hydrogen, alkyl, haloalkyl, optionally substituted cycloalkyl, optionally substituted cycloalkylalkyl, —$R^8$—C(O)$R^6$, —$R^8$—C(O)N($R^6$)$R^7$, —$R^8$—C(N=$R^6$)N($R^6$)$R^7$, —$R^8$—S(O)$_t R^6$ (where t is 1 or 2), and —$R^8$—S(O)$_2$N($R^6$)$R^7$;
each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl; and each $R^8$ is independently selected from the group consisting of a direct bond and an optionally substituted straight or branched alkylene chain.

A specific embodiment of this embodiment is a compound of formula (Ia-2a) selected from the group consisting of:
4-(4-methyl-3,4-dihydro-2H-pyrido[3,2-b][1,4]oxazin-7-yl)-N-(5-methyl-6-((1S,4S)-5-methyl-2,5-diazabicyclo[2.2.1]heptan-2-yl)pyridin-3-yl)pyrimidin-2-amine; and
4-(2,2-dimethyl-3-oxo-3,4-dihydro-2H-pyrido[3,2-b][1,4]oxazin-7-yl)-N-(5-methyl-6-((1S,4S)-5-methyl-2,5-diazabicyclo[2.2.1]heptan-2-yl)pyridin-3-yl)pyrimidin-2-amine.

Another embodiment is a compound of formula (Ia-2a) wherein:
n is 0 or 1;
m is 0 or 1;
$R^2$, when present, is independently selected from the group consisting of optionally substituted alkyl, halo, cyano and —$OR^6$;
$R^3$, when present, is independently selected from the group consisting of alkyl, halo and haloalkyl;
$R^4$ is phenyl substituted by one or more substituents selected from the group consisting of alkyl, —$R^8$—$OR^{6a}$, —$R^8$—N($R^{6a}$)$R^{7a}$, —$R^8$—C(O)N($R^{6a}$)$R^{7a}$, —$R^8$—N($R^{6a}$)C(O)$R^{7a}$, —$R^8$—N($R^{6a}$)S(O)$_2 R^{7a}$, —$R^8$—N($R^{6a}$)C(O)—$R^8$—N($R^{6a}$)$R^{7a}$, N-heteroaryl and N-heterocyclyl, where the N-heterocyclyl and the N-heteroaryl are each independently optionally substituted by one or more substituents selected from the group consisting of —C(O)$R^6$, —$R^8$—N($R^6$)$R^7$, —$R^8$—C(O)N($R^6$)$R^7$, alkyl, halo and optionally substituted aryl;
$R^{5a}$ is independently selected from the group consisting of hydrogen, alkyl, —$R^8$—C(O)$R^6$ and —$R^8$—S(O)$_t R^6$ (where t is 1 or 2);
each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl; and each $R^8$ is independently selected from the group consisting of a direct bond and an optionally substituted straight or branched alkylene chain.

A specific embodiment of this embodiment is a compound of formula (Ia-2a) selected from the group consisting of:
4-(4-(dimethylamino)phenyl)-N-(6-((1S,4S)-5-methyl-2,5-diazabicyclo[2.2.1]heptan-2-yl)pyridin-3-yl)pyrimidin-2-amine;
4-(4-(dimethylamino)phenyl)-N-(5-methyl-6-((1S,4S)-(5-methyl-2,5-diazabicyclo[2.2.1]heptan-2-yl)pyridin-3-yl)pyrimidin-2-amine;

4-(4-(t-butylcarbonylamino)phenyl)-N-(5-methyl-6-((1S,4S)-5-methyl-2,5-diazabicyclo[2.2.1]heptan-2-yl)pyridin-3-yl)pyrimidin-2-amine; and 4-(4-(3-cyclopropylureido)phenyl)-N-(5-methyl-6-((1S,4S)-5-methyl-2,5-diazabicyclo[2.2.1]heptan-2-yl)pyridin-3-yl)pyrimidin-2-amine.

Another embodiment is a compound of formula (Ia-2a) wherein:

n is 0 or 1;

m is 0 or 1;

$R^2$, when present, is independently selected from the group consisting of optionally substituted alkyl, halo, cyano and —$OR^6$;

$R^3$, when present, is independently selected from the group consisting of alkyl, halo and haloalkyl;

$R^4$ is selected from the group consisting of benzimidazolyl, imidazo[1,2-a]pyridinyl, indolyl, indolinyl, pyrazolyl, pyridinyl, pyrazinyl, pyrimidinyl, pyrrolyl, 1H-pyrrolo[2,3-b]pyridinyl and thiazolyl, each independently substituted by one or more substituents selected from the group consisting of alkyl, cyano, oxo, —$R^8$—$OR^{6a}$, —$R^8$—N($R^{6a}$)$R^{7a}$, —$R^8$—C(O)N($R^{6a}$)$R^{7a}$, —$R^8$—N($R^{6a}$)C(O)$R^{7a}$, —$R^8$—N($R^{6a}$)S(O)$_2R^{7a}$, —$R^8$—N($R^{6a}$)C(O)—$R^8$—N($R^{6a}$)$R^{7a}$, aryl, N-heteroaryl and N-heterocyclyl, where the aryl, the N-heterocyclyl and the N-heteroaryl are each independently optionally substituted by one or more substituents selected from the group consisting of —C(O)$R^6$, —$R^8$—N($R^6$)$R^7$, —$R^8$—C(O)N($R^6$)$R^7$, alkyl, halo and optionally substituted aryl;

$R^{5a}$ is independently selected from the group consisting of hydrogen, alkyl, —$R^8$—C(O)$R^6$ and —$R^8$—S(O)$_tR^6$ (where t is 1 or 2);

each $R^6$ and each $R^7$ is independently selected from the group consisting of hydrogen, alkyl, alkenyl, alkynyl, haloalkyl, haloalkenyl, haloalkynyl, optionally substituted cycloalkyl, optionally substituted cycloalkylalkyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl; or any $R^6$ and $R^7$, together with the common nitrogen to which they are both attached, form an optionally substituted N-heteroaryl or an optionally substituted N-heterocyclyl;

each $R^{6a}$ and $R^{7a}$ is independently selected from the group consisting of hydrogen, alkyl, optionally substituted cycloalkyl, optionally substituted heterocyclyl, optionally substituted heterocyclylalkyl, optionally substituted heteroaryl, and optionally substituted aralkyl; and each $R^8$ is independently selected from the group consisting of a direct bond and an optionally substituted straight or branched alkylene chain.

A specific embodiment of this embodiment is a compound of formula (Ia-2a) selected from the group consisting of:

4-(2-(dimethylamino)thiazol-4-yl)-N-(6-((1S,4S)-5-methyl-2,5-diazabicyclo[2.2.1]heptan-2-yl)pyridin-3-yl)pyrimidin-2-amine;

4-(5-(morpholin-4-yl)pyrazin-2-yl)-N-(6-((1S,4S)-5-methyl-2,5-diazabicyclo[2.2.1]heptan-2-yl)pyridin-3-yl)pyrimidin-2-amine; and 4-(1-(pyridin-4-yl)-1H-indol-5-yl)-N-(5-methyl-6-((1S,4S)-5-methyl-2,5-diazabicyclo[2.2.1]heptan-2-yl)pyridin-3-yl)pyrimidin-2-amine.

In certain embodiments of the compounds of the invention, n is 0 or 1.

In certain embodiments of the compounds of the invention, m is 0 or 1.

In certain embodiments of the compounds of the invention, Y is =C($R^6$)—.

In certain embodiments of the compounds of the invention Y is =N—.

In certain embodiments of the compounds of the invention, $R^1$ is selected from the group consisting of hydrogen, alkyl, haloalkyl, optionally substituted cycloalkyl, optionally substituted cycloalkylalkyl, optionally substituted aryl, optionally substituted aralkyl, —$R^8$—C(O)$OR^6$, —$R^9$—N($R^6$)$R^7$ and —$R^9$—$OR^6$;

In certain embodiments of the compounds of the invention, $R^5$ is an N-heterocyclyl, wherein a nitrogen atom in the N-heterocyclyl is optionally substituted by a substituent selected from the group consisting of alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^8$—$OR^6$, —$R^8$—C(O)$R^6$, —$R^8$—C(O)$OR^6$, —$R^9$—N($R^6$)$R^7$, —$R^8$—C(O)N($R^6$)$R^7$, —$R^8$—C(N=$R^6$)N($R^6$)$R^7$, —$R^8$—S(O)$_2$N($R^6$)$R^7$, and —$R^8$—S(O)$_tR^6$ (where t is 1 or 2); and a carbon atom in the N-heterocyclyl is optionally substituted by a substituent selected from the group consisting of alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^8$—$OR^6$, —$R^8$—C(O)$R^6$, —$R^8$—C(O)$OR^6$, —$R^9$—N($R^6$)$R^7$, —$R^8$—C(O)N($R^6$)$R^7$, —$R^8$—S(O)$_2$N($R^6$)$R^7$, and —$R^8$—S(O)$_pR^6$ (where p is 0, 1 or 2).

In certain embodiments of the compounds of the invention, each $R^6$ and each $R^7$ is independently selected from the group consisting of hydrogen, alkyl, haloalkyl, haloalkenyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl, optionally substituted heteroarylalkyl.

In one embodiment, the compounds of formula (I) are selected from the group consisting of:

4-(6-(N,N-dimethylamino)pyridin-3-yl)-N-(3-methyl-4-(5-methyl-2,5-diazabicyclo[2.2.1]heptan-2-yl)phenyl)pyrimidin-2-amine;

4-(6-(N,N-dimethylamino)pyridin-3-yl)-5-methyl-N-(3-methyl-4-(5-methyl-2,5-diazabicyclo[2.2.1]heptan-2-yl)phenyl)pyrimidin-2-amine;

4-(6-(N,N-dimethylamino)pyridin-3-yl)-5-trifluoromethyl-N-(3-methyl-4-(5-methyl-2,5-diazabicyclo[2.2.1]heptan-2-yl)phenyl)pyrimidin-2-amine;

4-(6-(N,N-dimethylamino)pyridin-3-yl)-5-fluoro-N-(3-methyl-4-(5-methyl-2,5-diazabicyclo[2.2.1]heptan-2-yl)phenyl)pyrimidin-2-amine;

4-(6-(N,N-dimethylamino)pyridin-3-yl)-5-fluoro-N-(3-fluoro-4-(5-methyl-2,5-diazabicyclo[2.2.1]heptan-2-yl)phenyl)pyrimidin-2-amine;

4-(6-(N,N-dimethylamino)pyridin-3-yl)-5-methyl-N-(3-fluoro-4-(5-methyl-2,5-diazabicyclo[2.2.1]heptan-2-yl)phenyl)pyrimidin-2-amine;

4-(6-(N,N-dimethylamino)pyridin-3-yl)-N-(3-fluoro-4-(5-methyl-2,5-diazabicyclo[2.2.1]heptan-2-yl)phenyl)pyrimidin-2-amine;

4-(4-methyl-3,4-dihydro-2H-pyrido[3,2-b][1,4]oxazin-7-yl)-N-(3-methyl-4-(5-methyl-2,5-diazabicyclo[2.2.1]heptan-2-yl)phenyl)pyrimidin-2-amine;

4-(4-methyl-3,4-dihydro-2H-pyrido[3,2-b][1,4]oxazin-7-yl)-N-(3-fluoro-4-(5-methyl-2,5-diazabicyclo[2.2.1]heptan-2-yl)phenyl)pyrimidin-2-amine;

4-(6-(morpholin-4-yl)pyridin-3-yl)-N-(3-methyl-4-(5-methyl-2,5-diazabicyclo[2.2.1]heptan-2-yl)phenyl)pyrimidin-2-amine;

4-(6-(morpholin-4-yl)pyridin-3-yl)-N-(3-fluoro-4-(5-methyl-2,5-diazabicyclo[2.2.1]heptan-2-yl)phenyl)pyrimidin-2-amine;

4-(6-(5-methyl-2,5-diazabicyclo[2.2.1]heptan-2-yl)pyridin-3-yl)-N-(3-methyl-4-(4-methylpiperazin-1-yl)phenyl)pyrimidin-2-amine;

4-(6-(5-(4-fluorophenyl)-2,5-diazabicyclo[2.2.1]heptan-2-yl)pyridin-3-yl)-N-(3-methyl-4-(4-methylpiperazin-1-yl)phenyl)pyrimidin-2-amine;

4-(4-(N,N-dimethylamino)phenyl)-N-(3-methyl-4-(5-methyl-2,5-diazabicyclo[2.2.1]heptan-2-yl)phenyl)pyrimidin-2-amine;

4-(4-(N,N-dimethylamino)phenyl)-N-(3-fluoro-4-(5-methyl-2,5-diazabicyclo[2.2.1]heptan-2-yl)phenyl)pyrimidin-2-amine;

4-(6-(4-acetylpiperazin-1-yl)pyridin-3-yl)-N-(3-fluoro-4-(5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-fluoro-4-(5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-methyl-2,5-diazabicyclo[2.2.1]heptan-2-yl)phenyl)pyrimidin-2-amine;

4-(1H-indol-6-yl)-N-(3-methyl-4-(5-methyl-2,5-diazabicyclo[2.2.1]heptan-2-yl)phenyl)pyrimidin-2-amine;

4-(1H-pyrrolo[2,3-b]pyridin-5-yl)-N-(3-methyl-4-(5-methyl-2,5-diazabicyclo[2.2.1]heptan-2-yl)phenyl)pyrimidin-2-amine;

4-(1H-pyrrolo[2,3-b]pyridin-5-yl)-N-(3-fluoro-4-(5-methyl-2,5-diazabicyclo[2.2.1]heptan-2-yl)phenyl)pyrimidin-2-amine;

4-(6-(dimethylamino)pyridin-3-yl)-N-(3-methyl-4-(5-ethyl-2,5-diazabicyclo[2.2.1]heptan-2-yl)phenyl)pyrimidin-2-amine;

4-(6-(morpholin-4-yl)pyridin-3-yl)-N-(3-methyl-4-(5-ethyl-2,5-diazabicyclo[2.2.1]heptan-2-yl)phenyl)pyrimidin-2-amine;

4-(6-(morpholin-4-yl)pyridin-3-yl)-N-(3-methyl-4-(5-((ethylamino)carbonyl)-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-oxa-2-azabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-(ethylcarbonyl)-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-(methylsulfonyl)-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-ethyl-2,5-diazabicyclo[2.2.1]heptan-2-yl)phenyl)pyrimidin-2-amine;

4-(3'-oxo-3,4'-dihydrospiro[cyclobutane-1,2'-pyrido[3,2-b][1,4]oxazine]-7-yl)-N-(3-methyl-4-(5-methyl-2,5-diazabicyclo[2.2.1]heptan-2-yl)phenyl)pyrimidin-2-amine;

4-(3-oxo-3,4'-dihydrospiro[cyclobutane-1,2'-pyrido[3,2-b][1,4]oxazine]-7-yl)-N-(3-methyl-4-(5-ethyl-2,5-diazabicyclo[2.2.1]heptan-2-yl)phenyl)pyrimidin-2-amine;

4-(1H-pyrrolo[2,3-b]pyridin-5-yl)-N-(3-methyl-4-(5-oxa-2-azabicyclo[2.2.1]heptan-2-yl)phenyl)pyrimidin-2-amine;

4-(1H-pyrrolo[2,3-b]pyridin-5-yl)-N-(3-methyl-4-(5-(2,2,2-trifluoroethyl)-2,5-diazabicyclo[2.2.1]heptan-2-yl)phenyl)pyrimidin-2-amine;

4-(1H-pyrrolo[2,3-b]pyridin-5-yl)-N-(3-methyl-4-(5-(cyclopropyl)methyl-2,5-diazabicyclo[2.2.1]heptan-2-yl)phenyl)pyrimidin-2-amine;

4-(6-(morpholin-4-yl)pyridin-3-yl)-N-(3-methyl-4-(5-(2,2,2-trifluoroethyl)-2,5-diazabicyclo[2.2.1]heptan-2-yl)phenyl)pyrimidin-2-amine;

4-(6-(morpholin-4-yl)pyridin-3-yl)-N-(3-methyl-4-(5-(cyclopropyl)methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-(aminosulfonyl)-2,5-diazabicyclo[2.2.1]heptan-2-yl)phenyl)pyrimidin-2-amine;

4-(3-fluoro-2-(morpholin-4-yl)pyridin-4-yl)-N-(3-fluoro-4-(5-methyl-2,5-diazabicyclo[2.2.1]heptan-2-yl)phenyl)pyrimidin-2-amine;

4-(2-(morpholin-4-yl)pyrimidin-5-yl)-N-(4-(5-methyl-2,5-diazabicyclo[2.2.1]heptan-2-yl)phenyl)pyrimidin-2-amine;

4-(2-(morpholin-4-yl)pyrimidin-5-yl)-N-(3-methyl-4-(5-methyl-2,5-diazabicyclo[2.2.1]heptan-2-yl)phenyl)pyrimidin-2-amine;

4-(2-(morpholin-4-yl)pyrimidin-5-yl)-N-(3-methyl-4-(5-oxa-2-azabicyclo[2.2.1]heptan-2-yl)phenyl)pyrimidin-2-amine;

4-(2-(morpholin-4-yl)pyrimidin-5-yl)-N-(3-fluoro-4-(5-methyl-2,5-diazabicyclo[2.2.1]heptan-2-yl)phenyl)pyrimidin-2-amine;

4-(2-((cyclopropyl)carbonylamino)-pyrimidin-5-yl)-N-(3-methyl-4-(5-methyl-2,5-diazabicyclo[2.2.1]heptan-2-yl)phenyl)pyrimidin-2-amine;

4-(4-(4,5-dihydrothiazol-2-ylcarbamoyl)phenyl)-N-(3-methyl-4-(5-methyl-2,5-diazabicyclo[2.2.1]heptan-2-yl)phenyl)pyrimidin-2-amine;

4-(4-(1,1-dimethylethyl)phenyl)-N-(3-methyl-4-(5-methyl-2,5-diazabicyclo[2.2.1]heptan-2-yl)phenyl)pyrimidin-2-amine;

4-(4-(morpholin-4-yl)phenyl)-N-(3-fluoro-4-(5-methyl-2,5-diazabicyclo[2.2.1]heptan-2-yl)phenyl)pyrimidin-2-amine.TFA salt;

4-(4-((methyl)aminocarbonylmethyl)-phenyl)-N-(3-methyl-4-(5-methyl-2,5-diazabicyclo[2.2.1]heptan-2-yl)phenyl)pyrimidin-2-amine.TFA salt;

4-(4-((cyclopropyl)aminocarbonyl-methyl)phenyl)-N-(3-methyl-4-(5-methyl-2,5-diazabicyclo[2.2.1]heptan-2-yl)phenyl)pyrimidin-2-amine;

4-(6-(methylaminocarbonyl)pyridin-3-yl)-N-(3-methyl-4-(5-methyl-2,5-diazabicyclo[2.2.1]heptan-2-yl)phenyl)pyrimidin-2-amine;

4-(7-oxo-5,6,7,8-tetrahydro-1,8-naphthyridin-3-yl)-N-(3-methyl-4-(5-methyl-2,5-diazabicyclo[2.2.1]heptan-2-yl)phenyl)pyrimidin-2-amine.TFA salt;

4-(5-((morpholin-4-yl)carbonyl)pyridin-3-yl)-N-(3-methyl-4-(5-methyl-2,5-diazabicyclo[2.2.1]heptan-2-yl)phenyl)pyrimidin-2-amine.Bis TFA salt;

4-(2,2-dimethyl-3-oxo-3,4-dihydro-2H-pyrido[3,2-b][1,4]oxazin-7-yl)-N-(3-cyano-4-(5-methyl-2,5-diazabicyclo[2.2.1]heptan-2-yl)phenyl)pyrimidin-2-amine;

4-(5-methyl-6-(morpholin-4-yl)pyridin-3-yl)-N-(3-fluoro-4-(5-methyl-2,5-diazabicyclo[2.2.1]heptan-2-yl)phenyl)pyrimidin-2-amine;

4-(5-methyl-6-(morpholin-4-yl)pyridin-3-yl)-N-(3-methyl-4-(5-methyl-2,5-diazabicyclo[2.2.1]heptan-2-yl)phenyl)pyrimidin-2-amine;

5-methyl-4-(6-(morpholin-4-yl)pyridin-3-yl)-N-(3-methyl-4-(5-methyl-2,5-diazabicyclo[2.2.1]heptan-2-yl)phenyl)pyrimidin-2-amine;

5-methyl-4-(6-(morpholin-4-yl)pyridin-3-yl)-N-(3-fluoro-4-(5-methyl-2,5-diazabicyclo[2.2.1]heptan-2-yl)phenyl)pyrimidin-2-amine;

4-(6-(2-(morpholin-4-yl)ethyl)aminopyridin-3-yl)-N-(4-(5-methyl-2,5-diazabicyclo[2.2.1]heptan-2-yl)phenyl)pyrimidin-2-amine;

4-(6-(2-(morpholin-4-yl)ethyl)aminopyridin-3-yl)-N-(3-fluoro-4-(5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-methyl-2,5-diazabicyclo[2.2.1]heptan-2-yl)phenyl)pyrimidin-2-amine;

4-(6-(morpholin-4-yl)pyridin-3-yl)-N-(3-methyl-4-(5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-fluoro-4-(5-methyl-2,5-diazabicyclo[2.2.1]heptan-2-yl)phenyl)pyrimidin-2-amine;

4-(6-(morpholin-4-yl)pyridin-3-yl)-N-(3-fluoro-4-(5-methyl-2,5-diazabicyclo[2.2.1]heptan-2-yl)phenyl)pyrimidin-2-amine;

4-(6-(morpholin-4-yl)pyridin-3-yl)-N-(3-methyl-4-(1,5,7-trimethyl-3,7-diazabicyclo[3.3.1]nonan-3-yl)phenyl)pyrimidin-2-amine;

4-(6-(dimethylamino)pyridin-3-yl)-N-(3-methyl-4-(1,5,7-trimethyl-3,7-diazabicyclo[3.3.1]nonan-3-yl)phenyl)pyrimidin-2-amine;

4-(6-(cyclohexylamino)pyridin-3-yl)-N-(3-methyl-4-(1,5,7-trimethyl-3,7-diazabicyclo[3.3.1]nonan-3-yl)phenyl)pyrimidin-2-amine;

4-(6-(cyclohexylamino)pyridin-3-yl)-N-(3-methyl-4-(5-methyl-2,5-diazabicyclo[2.2.1]heptan-2-yl)phenyl)pyrimidin-2-amine;

4-(6-(cyclohexylamino)pyridin-3-yl)-N-(3-fluoro-4-(5-methyl-2,5-diazabicyclo[2.2.1]heptan-2-yl)phenyl)pyrimidin-2-amine;

4-(6-(benzyl)pyridin-3-yl)-N-(3-methyl-4-(5-methyl-2,5-diazabicyclo[2.2.1]heptan-2-yl)phenyl)pyrimidin-2-amine;

4-(6-(benzyl)pyridin-3-yl)-N-(3-fluoro-4-(5-methyl-2,5-diazabicyclo[2.2.1]heptan-2-yl)phenyl)pyrimidin-2-amine;

4-(5-methyl-6-(morpholin-4-yl)pyridin-3-yl)-N-(3-fluoro-4-(1,5,7-trimethyl-3,7-diazabicyclo[3.3.1]nonan-3-yl)phenyl)pyrimidin-2-amine;

4-(6-(dimethylamino)pyridin-3-yl)-N-(3-fluoro-4-(1,5,7-trimethyl-3,7-diazabicyclo[3.3.1]nonan-3-yl)phenyl)pyrimidin-2-amine;

4-(4-(dimethylamino)phenyl)-N-(3-fluoro-4-(1,5,7-trimethyl-3,7-diazabicyclo[3.3.1]nonan-3-yl)phenyl)pyrimidin-2-amine;

4-(6-(morpholin-4-yl)pyridin-3-yl)-N-(3-fluoro-4-(1,5,7-trimethyl-3,7-diazabicyclo[3.3.1]nonan-3-yl)phenyl)pyrimidin-2-amine;

4-(3,4-dihydro-2H-pyrido[3,2-b][1,4]oxazin-7-yl)-N-(3-methyl-4-(5-methyl-2,5-diazabicyclo[2.2.1]heptan-2-yl)phenyl)pyrimidin-2-amine;

4-(3,4-dihydro-2H-pyrido[3,2-b][1,4]oxazin-7-yl)-N-(3-fluoro-4-(5-methyl-2,5-diazabicyclo[2.2.1]heptan-2-yl)phenyl)pyrimidin-2-amine;

4-(3,4-dihydro-2H-pyrido[3,2-b][1,4]oxazin-7-yl)-N-(3-methyl-4-(1,5,7-trimethyl-3,7-diazabicyclo[3.3.1]nonan-3-yl)phenyl)pyrimidin-2-amine;

4-(3,4-dihydro-2H-pyrido[3,2-b][1,4]oxazin-7-yl)-N-(3-fluoro-4-(1,5,7-trimethyl-3,7-diazabicyclo[3.3.1]nonan-3-yl)phenyl)pyrimidin-2-amine;

4-(6-(benzyl)pyridin-3-yl)-N-(3-methyl-4-(1,5,7-trimethyl-3,7-diazabicyclo[3.3.1]nonan-3-yl)phenyl)pyrimidin-2-amine;

4-(6-(benzyl)pyridin-3-yl)-N-(3-fluoro-4-(1,5,7-trimethyl-3,7-diazabicyclo[3.3.1]nonan-3-yl)phenyl)pyrimidin-2-amine;

4-(2-(propyl)aminopyrimidin-5-yl)-N-(3-methyl-4-(5-methyl-2,5-diazabicyclo[2.2.1]heptan-2-yl)phenyl)pyrimidin-2-amine;

4-(2-(propyl)aminopyrimidin-5-yl)-N-(3-fluoro-4-(5-methyl-2,5-diazabicyclo[2.2.1]heptan-2-yl)phenyl)pyrimidin-2-amine;

4-(6-(cyclohexylamino)pyridin-3-yl)-N-(3-trifluoromethyl-4-(5-methyl-2,5-diazabicyclo[2.2.1]heptan-2-yl)phenyl)pyrimidin-2-amine;

4-(5-(methyl)sulfonylpyridin-3-yl)-N-(3-methyl-4-(5-methyl-2,5-diazabicyclo[2.2.1]heptan-2-yl)phenyl)pyrimidin-2-amine;

4-(6-(dimethylamino)pyridin-3-yl)-N-(3-trifluoromethyl-4-(5-methyl-2,5-diazabicyclo[2.2.1]heptan-2-yl)phenyl)pyrimidin-2-amine;

4-(6-(morpholin-4-yl)pyridin-3-yl)-N-(3-trifluoromethyl-4-(5-methyl-2,5-diazabicyclo[2.2.1]heptan-2-yl)phenyl)pyrimidin-2-amine;

4-(3,4-dihydro-2H-pyrido[3,2-b][1,4]oxazin-7-yl)-N-(3-trifluoromethyl-4-(5-methyl-2,5-diazabicyclo[2.2.1]heptan-2-yl)phenyl)pyrimidin-2-amine;

4-(6-((2-(cyclopropylsulfonyl)aminoethyl)-amino)pyridin-3-yl)-N-(3-methyl-4-(5-methyl-2,5-diazabicyclo[2.2.1]heptan-2-yl)phenyl)pyrimidin-2-amine;

4-(6-((2-(cyclopropylsulfonyl)aminoethyl)-amino)pyridin-3-yl)-N-(3-methyl-4-(5-oxa-2-azabicyclo[2.2.1]heptan-2-yl)phenyl)pyrimidin-2-amine;

4-(5-(methyl)sulfonylpyridin-3-yl)-N-(3-fluoro-4-(5-methyl-2,5-diazabicyclo[2.2.1]heptan-2-yl)phenyl)pyrimidin-2-amine;

4-(5-(methyl)sulfonylpyridin-3-yl)-N-(3-trifluoromethyl-4-(5-methyl-2,5-diazabicyclo[2.2.1]heptan-2-yl)phenyl)pyrimidin-2-amine;

4-(imidazo[1,2-a]pyridin-6-yl)-N-(3-methyl-4-(5-methyl-2,5-diazabicyclo[2.2.1]heptan-2-yl)phenyl)pyrimidin-2-amine;

4-(4-(5-(4-dimethylaminophenyl)oxazol-2-yl)phenyl)-N-(3-methyl-4-(5-methyl-2,5-diazabicyclo[2.2.1]heptan-2-yl)phenyl)pyrimidin-2-amine;

4-(6-methoxy-1H-indol-2-yl)-N-(3-methyl-4-(5-methyl-2,5-diazabicyclo[2.2.1]heptan-2-yl)phenyl)pyrimidin-2-amine;

4-(1-(3-chlorophenyl)-1H-pyrazol-4-yl)-N-(3-methyl-4-(5-methyl-2,5-diazabicyclo[2.2.1]heptan-2-yl)phenyl)pyrimidin-2-amine;

4-(1-methylbenzimidazol-6-yl)-N-(3-methyl-4-(5-methyl-2,5-diazabicyclo[2.2.1]heptan-2-yl)phenyl)pyrimidin-2-amine;

4-(5-cyano-1H-indol-2-yl)-N-(3-methyl-4-(5-methyl-2,5-diazabicyclo[2.2.1]heptan-2-yl)phenyl)pyrimidin-2-amine;

4-(1-(4-fluorophenyl)-1H-pyrazol-4-yl)-N-(3-methyl-4-(5-methyl-2,5-diazabicyclo[2.2.1]heptan-2-yl)phenyl)pyrimidin-2-amine;

4-(6-(morpholin-4-yl)pyridin-3-yl)-N-(3-methyl-4-(7-azabicyclo[2.2.1]heptan-7-yl)phenyl)pyrimidin-2-amine;

4-(6-cyanopyridin-3-yl)-N-(3-methyl-4-(5-methyl-2,5-diazabicyclo[2.2.1]heptan-2-yl)phenyl)pyrimidin-2-amine;

4-(6-cyanopyridin-3-yl)-N-(3-methyl-4-(7-azabicyclo[2.2.1]heptan-7-yl)phenyl)pyrimidin-2-amine;

4-(2-oxoindolin-5-yl)-N-(3-methyl-4(5-methyl-2,5-diazabicyclo[2.2.1]heptan-2-yl)phenyl)pyrimidin-2-amine;

4-(5-cyanopyridin-3-yl)-N-(3-methyl-4(5-methyl-2,5-diazabicyclo[2.2.1]heptan-2-yl)phenyl)pyrimidin-2-amine;

4-(6-(1H-tetrazol-5-yl)pyridin-3-yl)-N-(3-methyl-4(5-methyl-2,5-diazabicyclo[2.2.1]heptan-2-yl)phenyl)pyrimidin-2-amine;

4-(6-(morpholin-4-yl)pyridin-3-yl)-N-(3-cyano-4-(5-acetyl-2,5-diazabicyclo[2.2.1]heptan-2-yl)phenyl)pyrimidin-2-amine;

4-(6-(morpholin-4-yl)pyridin-3-yl)-N-(3-cyano-4-(5-methylsulfonyl-2,5-diazabicyclo[2.2.1]heptan-2-yl)phenyl)pyrimidin-2-amine;

4-(6-(morpholin-4-yl)pyridin-3-yl)-N-(3-cyano-4-(5-methyl-2,5-diazabicyclo[2.2.1]heptan-2-yl)phenyl)pyrimidin-2-amine;

4-(6-(morpholin-4-yl)pyridin-3-yl)-N-(3-cyano-4-(5-cyclopentyl-2,5-diazabicyclo[2.2.1]heptan-2-yl)phenyl)pyrimidin-2-amine;

4-(6-(morpholin-4-yl)pyridin-3-yl)-N-(3-methyl-4-(1,4-diazabicyclo[3.2.1]octan-4-yl)phenyl)pyrimidin-2-amine;

4-(2-oxoindolin-5-yl)-N-(3-methyl-4-(1,4-diazabicyclo[3.2.1]octan-4-yl)phenyl)pyrimidin-2-amine;

(1-methylbenzimidazol-6-yl)-N-(3-methyl-4-(1,4-diazabicyclo[3.2.1]octan-4-yl)phenyl)pyrimidin-2-amine;

4-(imidazo[1,2-a]pyridin-6-yl)-N-(3-methyl-4-(1,4-diazabicyclo[3.2.1]octan-4-yl)phenyl)pyrimidin-2-amine;

4-(2H-benzo[b][1,4]oxazin-3(4H)-on-6-yl)-N-(3-fluoro-4-(5-methyl-2,5-diazabicyclo[2.2.1]heptan-2-yl)phenyl)pyrimidin-2-amine;

4-(2,2,4-trimethyl-3-oxo-3,4-dihydro-2H-pyrido[3,2-b][1,4]oxazin-7-yl)-N-(3-methyl-4-(5-methyl-2,5-diazabicyclo[2.2.1]heptan-2-yl)phenyl)pyrimidin-2-amine;

4-(2,2,4-trimethyl-3-oxo-3,4-dihydro-2H-pyrido[3,2-b][1,4]oxazin-7-yl)-N-(3-fluoro-4-(5-methyl-2,5-diazabicyclo[2.2.1]heptan-2-yl)phenyl)pyrimidin-2-amine;

4-(5-(3-methylpiperidin-1-yl)pyrazin-2-yl)-N-(3-fluoro-4-(5-methyl-2,5-diazabicyclo[2.2.1]heptan-2-yl)phenyl)pyrimidin-2-amine;

4-(4-(t-butylcarbonylamino)phenyl)-N-(3-fluoro-4-(5-methyl-2,5-diazabicyclo[2.2.1]heptan-2-yl)phenyl)pyrimidin-2-amine;

4-(4-(t-butylcarbonylamino)phenyl)-N-(3-methyl-4-(5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-methyl-2,5-diazabicyclo[2.2.1]heptan-2-yl)phenyl)pyrimidin-2-amine;

4-(6-(acetamido)pyridin-3-yl)-N-(3-methyl-4-(5-methyl-2,5-diazabicyclo[2.2.1]heptan-2-yl)phenyl)pyrimidin-2-amine;

4-(4-((pyridin-2-yl)aminocarbonyl)phenyl)-N-(3-fluoro-4-(5-methyl-2,5-diazabicyclo[2.2.1]heptan-2-yl)phenyl)pyrimidin-2-amine;

4-(4-((pyridin-2-yl)aminocarbonyl)phenyl)-N-(3-methyl-4-(5-methyl-2,5-diazabicyclo[2.2.1]heptan-2-yl)phenyl)pyrimidin-2-amine;

4-(4-(methylsulfonylamino)phenyl)-N-(3-fluoro-4-(5-methyl-2,5-diazabicyclo[2.2.1]heptan-2-yl)phenyl)pyrimidin-2-amine;

4-(4-(methylsulfonylamino)phenyl)-N-(3-methyl-4-(5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(4-(5-methyl-2,5-diazabicyclo[2.2.1]heptan-2-yl)phenyl)pyrimidin-2-amine;

4-(4-(3-cyclopropylureido)phenyl)-N-(4-(5-methyl-2,5-diazabicyclo[2.2.1]heptan-2-yl)phenyl)pyrimidin-2-amine;

4-(6-(2-(morpholin-4-yl)acetamido)pyridin-3-yl)-N-(3-methyl-4-(5-methyl-2,5-diazabicyclo[2.2.1]heptan-2-yl)phenyl)pyrimidin-2-amine;

4-(6-(2-(morpholin-4-yl)acetamido)pyridin-3-yl)-N-(4-(5-methyl-2,5-diazabicyclo[2.2.1]heptan-2-yl)phenyl)pyrimidin-2-amine;

4-(6-(2-(morpholin-4-yl)acetamido)pyridin-3-yl)-N-(3-fluoro-4-(5-methyl-2,5-diazabicyclo[2.2.1]heptan-2-yl)phenyl)pyrimidin-2-amine;

4-(6-(acetamido)pyridin-3-yl)-N-(3-methyl-4-(5-oxa-2-azabicyclo[2.2.1]heptan-2-yl)phenyl)pyrimidin-2-amine;

4-(6-aminopyridin-3-yl)-N-(3-methyl-4-(5-ethylcarbonyl-2,5-diazabicyclo[2.2.1]heptan-2-yl)phenyl)pyrimidin-2-amine;

4-(6-(acetamido)pyridin-3-yl)-N-(3-methyl-4-(5-ethylcarbonyl-2,5-diazabicyclo[2.2.1]heptan-2-yl)phenyl)pyrimidin-2-amine;

4-(6-aminopyridin-3-yl)-N-(3-methyl-4-(5-methylsulfonyl-2,5-diazabicyclo[2.2.1]heptan-2-yl)phenyl)pyrimidin-2-amine;

4-(6-(methylsulfonylamino)pyridin-3-yl)-N-(3-methyl-4-(5-methyl-2,5-diazabicyclo[2.2.1]heptan-2-yl)phenyl)pyrimidin-2-amine;

4-(6-(2-(dimethylamino)acetamido)-pyridin-3-yl)-N-(3-methyl-4-(5-methyl-2,5-diazabicyclo[2.2.1]heptan-2-yl)phenyl)pyrimidin-2-amine;

4-(6-(methylsulfonylamino)pyridin-3-yl)-N-(3-fluoro-4-(5-methyl-2,5-diazabicyclo[2.2.1]heptan-2-yl)phenyl)pyrimidin-2-amine;

4-(6-(morpholin-4-yl)pyridin-3-yl)-N-(4-(8-methyl-3,8-diazabicyclo[3.2.1]octan-3-yl)phenyl)pyrimidin-2-amine;

4-(6-(methylsulfonylamino)pyridin-3-yl)-N-(4-(8-methyl-3,8-diazabicyclo[3.2.1]octan-3-yl)phenyl)pyrimidin-2-amine;

4-(2,2-dimethyl-3-oxo-3,4-dihydro-2H-pyrido[3,2-b][1,4]oxazin-7-yl)-N-(4-(8-methyl-3,8-diazabicyclo[3.2.1]octan-3-yl)phenyl)pyrimidin-2-amine;

4-(6-aminopyridin-3-yl)-N-(4-(8-methyl-3,8-diazabicyclo[3.2.1]octan-3-yl)phenyl)pyrimidin-2-amine;

4-(6-(morpholin-4-yl)pyridin-3-yl)-N-(3-methyl-4-(1,4-diazabicyclo[3.2.2]nonan-4-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(1,4-diazabicyclo[3.2.2]nonan-4-yl)phenyl)pyrimidin-2-amine;

4-(4-((pyridin-2-yl)aminocarbonyl)phenyl)-N-(3-methyl-4-(1,4-diazabicyclo[3.2.2]nonan-4-yl)phenyl)pyrimidin-2-amine;

4-(4-(acetamido)phenyl)-N-(4-(8-methyl-3,8-diazabicyclo[3.2.1]octan-3-yl)phenyl)pyrimidin-2-amine;

4-(2-(diethylamino)thiazol-4-yl)-N-(3-methyl-4-(5-methyl-2,5-diazabicyclo[2.2.1]heptan-2-yl)phenyl)pyrimidin-2-amine;

4-(2-(diethylamino)thiazol-4-yl)-N-(3-fluoro-4-(5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(8-methyl-3,8-diazabicyclo[3.2.1]octan-3-yl)phenyl)pyrimidin-2-amine;

4-(6-(morpholin-4-yl)pyridin-3-yl)-N-(3-methyl-4-(8-methyl-3,8-diazabicyclo[3.2.1]octan-3-yl)phenyl)pyrimidin-2-amine;

4-(6-(methylsulfonylamino)pyridin-3-yl)-N-(3-methyl-4-(8-methyl-3,8-diazabicyclo[3.2.1]octan-3-yl)phenyl)pyrimidin-2-amine;

4-(4-(t-butylcarbonylamino)phenyl)-N-(3-methyl-4-(8-methyl-3,8-diazabicyclo[3.2.1]octan-3-yl)phenyl)pyrimidin-2-amine;

4-(1H-pyrrol-3-yl)-N-(3-methyl-4-(5-methyl-2,5-diazabicyclo[2.2.1]heptan-2-yl)phenyl)pyrimidin-2-amine;

4-(1H-pyrrol-3-yl)-N-(4-(5-methyl-2,5-diazabicyclo[2.2.1]heptan-2-yl)phenyl)pyrimidin-2-amine;

4-(1H-pyrrol-3-yl)-N-(3-trifluoromethyl-4-(5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-trifluoromethyl-4-(2,5-diazabicyclo[2.2.1]heptan-2-yl)phenyl)pyrimidin-2-amine;

4-(6-ethoxypyridin-3-yl)-N-(3-methyl-4-(5-methyl-2,5-diazabicyclo[2.2.1]heptan-2-yl)phenyl)pyrimidin-2-amine;

4-(6-ethoxypyridin-3-yl)-N-(3-fluoro-4-(5-methyl-2,5-diazabicyclo[2.2.1]heptan-2-yl)phenyl)pyrimidin-2-amine;

4-(2-(dimethylamino)thiazol-4-yl)-N-(3-methyl-4-(5-methyl-2,5-diazabicyclo[2.2.1]heptan-2-yl)phenyl)pyrimidin-2-amine;

4-(2-(dimethylamino)thiazol-4-yl)-N-(3-fluoro-4-(5-methyl-2,5-diazabicyclo[2.2.1]heptan-2-yl)phenyl)pyrimidin-2-amine;

4-(5-(morpholin-4-yl)pyrazin-2-yl)-N-(3-methyl-4-(5-methyl-2,5-diazabicyclo[2.2.1]heptan-2-yl)phenyl)pyrimidin-2-amine;

4-(5-(morpholin-4-yl)pyrazin-2-yl)-N-(3-fluoro-4-(5-methyl-2,5-diazabicyclo[2.2.1]heptan-2-yl)phenyl)pyrimidin-2-amine;

4-(4-(1-ethoxyethyl)phenyl)-N-(3-methyl-4-(5-methyl-2,5-diazabicyclo[2.2.1]heptan-2-yl)phenyl)pyrimidin-2-amine;

4-(4-(1-ethoxyethyl)phenyl)-N-(3-fluoro-4-(5-methyl-2,5-diazabicyclo[2.2.1]heptan-2-yl)phenyl)pyrimidin-2-amine;

4-(6-(dimethylamino)pyridin-3-yl)-N-(4-(5-methyl-2,5-diazabicyclo[2.2.1]heptan-2-yl)phenyl)pyrimidin-2-amine;

4-(6-(morpholin-4-yl)pyridin-3-yl)-N-(4-(5-methyl-2,5-diazabicyclo[2.2.1]heptan-2-yl)phenyl)pyrimidin-2-amine;

4-(4-methyl-3,4-dihydro-2H-pyrido[3,2-b][1,4]oxazin-7-yl)-N-(4-(5-methyl-2,5-diazabicyclo[2.2.1]heptan-2-yl)phenyl)pyrimidin-2-amine;

4-(6-(3-ethoxypropyl)aminopyridin-3-yl)-N-(3-methyl-4-(5-methyl-2,5-diazabicyclo[2.2.1]heptan-2-yl)phenyl)pyrimidin-2-amine;

4-(6-(cis-2,6-dimethylmorpholin-4-yl)pyridin-3-yl)-N-(3-methyl-4-(5-methyl-2,5-diazabicyclo[2.2.1]heptan-2-yl)phenyl)pyrimidin-2-amine;

4-(6-(propylamino)pyridin-3-yl)-N-(3-methyl-4-(5-methyl-2,5-diazabicyclo[2.2.1]heptan-2-yl)phenyl)pyrimidin-2-amine;

4-(6-(2-(dimethylamino)methylmorpholin-4-yl)pyridin-3-yl)-N-(3-methyl-4-(5-methyl-2,5-diazabicyclo[2.2.1]heptan-2-yl)phenyl)pyrimidin-2-amine;

4-(6-(piperidin-1-yl)pyridin-3-yl)-N-(3-methyl-4-(5-methyl-2,5-diazabicyclo[2.2.1]heptan-2-yl)phenyl)pyrimidin-2-amine;

4-(6-(3-(aminocarbonyl)piperidin-1-yl)pyridin-3-yl)-N-(3-methyl-4-(5-methyl-2,5-diazabicyclo[2.2.1]heptan-2-yl)phenyl)pyrimidin-2-amine;

4-(6-(morpholin-4-yl)pyridin-3-yl)-N-(3-methyl-4-(5-methylsulfonyl-2,5-diazabicyclo[2.2.1]heptan-2-yl)phenyl)pyrimidin-2-amine;

4-(4-methyl-3,4-dihydro-2H-pyrido[3,2-b][1,4]oxazin-7-yl)-N-(3-methyl-4-(5-methylsulfonyl-2,5-diazabicyclo[2.2.1]heptan-2-yl)phenyl)pyrimidin-2-amine;

4-(6-(morpholin-4-yl)pyridin-3-yl)-N-(3-methyl-4-(5-oxa-2-azabicyclo[2.2.1]heptan-2-yl)phenyl)pyrimidin-2-amine;

4-(4-methyl-3,4-dihydro-2H-pyrido[3,2-b][1,4]oxazin-7-yl)-N-(3-methyl-4-(5-oxa-2-azabicyclo[2.2.1]heptan-2-yl)phenyl)pyrimidin-2-amine;

4-(6-(morpholin-4-yl)pyridin-3-yl)-N-(3-methyl-4-(5-ethylcarbonyl-2,5-diazabicyclo[2.2.1]heptan-2-yl)phenyl)pyrimidin-2-amine;

4-(6-(2-(morpholin-4-yl)ethyl)aminopyridin-3-yl)-N-(3-methyl-4-(5-ethylcarbonyl-2,5-diazabicyclo[2.2.1]heptan-2-yl)phenyl)pyrimidin-2-amine;

4-(6-(3-dimethylamino)propylaminopyridin-3-yl)-N-(3-methyl-4-(5-methyl-2,5-diazabicyclo[2.2.1]heptan-2-yl)phenyl)pyrimidin-2-amine;

4-(6-(morpholin-4-yl)pyridin-3-yl)-N-(3-methyl-4-(5-amidino-2,5-diazabicyclo[2.2.1]heptan-2-yl)phenyl)pyrimidin-2-amine. TFA salt;

4-(6-(3-ethoxypropyl)aminopyridin-3-yl)-N-(3-methyl-4-(5-oxa-2-azabicyclo[2.2.1]heptan-2-yl)phenyl)pyrimidin-2-amine;

4-(6-cis-2,6-dimethylmorpholin-4-yl)pyridin-3-yl)-N-(3-methyl-4-(5-oxa-2-azabicyclo[2.2.1]heptan-2-yl)phenyl)pyrimidin-2-amine;

4-(6-(propylamino)pyridin-3-yl)-N-(3-methyl-4-(5-oxa-2-azabicyclo[2.2.1]heptan-2-yl)phenyl)pyrimidin-2-amine;

4-(6-(3-dimethylamino)propylaminopyridin-3-yl)-N-(3-methyl-4-(5-oxa-2-azabicyclo[2.2.1]heptan-2-yl)phenyl)pyrimidin-2-amine;

4-(6-(1,4-oxazepan-4-yl)pyridin-3-yl)-N-(3-methyl-4-(5-oxa-2-azabicyclo[2.2.1]heptan-2-yl)phenyl)pyrimidin-2-amine;

4-(6-(morpholin-4-yl)pyridin-3-yl)-N-(3-methyl-4-(5-isobutyl-2,5-diazabicyclo[2.2.1]heptan-2-yl)phenyl)pyrimidin-2-amine;

4-(6-(1,4-oxazepan-4-yl)pyridin-3-yl)-N-(3-methyl-4-(5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(1,5,7-trimethyl-3,7-diazabicyclo[3.3.1]nonan-3-yl)phenyl)pyrimidin-2-amine;

4-(2,2-dimethyl-3-oxo-3,4-dihydro-2H-pyrido[3,2-b][1,4]oxazin-7-yl)-N-(3-fluoro-4-(1,5,7-trimethyl-3,7-diazabicyclo[3.3.1]nonan-3-yl)phenyl)pyrimidin-2-amine;

4-(3-oxo-3,4-dihydro-2H-pyrido[3,2-b][1,4]oxazin-7-yl)-N-(3-methyl-4-(5-methyl-2,5-diazabicyclo[2.2.1]heptan-2-yl)phenyl)pyrimidin-2-amine;

4-(3-oxo-3,4-dihydro-2H-pyrido[3,2-b][1,4]oxazin-7-yl)-N-(3-methyl-4-(5-oxa-2-azabicyclo[2.2.1]heptan-2-yl)phenyl)pyrimidin-2-amine;

4-(6-(3-ethoxypropyl)aminopyridin-3-yl)-N-(3-methyl-4-(1,5,7-trimethyl-3,7-diazabicyclo[3.3.1]nonan-3-yl)phenyl)pyrimidin-2-amine;

4-(6-((2S,6R)-2,6-dimethylmorpholin-4-yl)pyridin-3-yl)-N-(3-methyl-4-(1,5,7-trimethyl-3,7-diazabicyclo[3.3.1]nonan-3-yl)phenyl)pyrimidin-2-amine;

4-(6-(propylamino)pyridin-3-yl)-N-(3-methyl-4-(1,5,7-trimethyl-3,7-diazabicyclo[3.3.1]nonan-3-yl)phenyl)pyrimidin-2-amine;

4-(6-(3-dimethylamino)propylaminopyridin-3-yl)-N-(3-methyl-4-(1,5,7-trimethyl-3,7-diazabicyclo[3.3.1]nonan-3-yl)phenyl)pyrimidin-2-amine;

4-(6-(2-oxa-5-azabicyclo[2.2.1]heptan-5-yl)pyridin-3-yl)-N-(3-methyl-4-(5-methyl-2,5-diazabicyclo[2.2.1]heptan-2-yl)phenyl)pyrimidin-2-amine;

4-(6-(5-oxa-2-azabicyclo[2.2.1]heptan-2-yl)pyridin-3-yl)-N-(3-methyl-4-(5-oxa-2-azabicyclo[2.2.1]heptan-2-yl)phenyl)pyrimidin-2-amine;

4-(6-(3-methylbutyl)aminopyridin-3-yl)-N-(3-methyl-4-(5-methyl-2,5-diazabicyclo[2.2.1]heptan-2-yl)phenyl)pyrimidin-2-amine;

4-(6-(3,3-dimethylbutyl)aminopyridin-3-yl)-N-(3-methyl-4-(5-methyl-2,5-diazabicyclo[2.2.1]heptan-2-yl)phenyl)pyrimidin-2-amine;

4-(6-(2-methoxyethyl)(methyl)aminopyridin-3-yl)-N-(3-methyl-4-(5-methyl-2,5-diazabicyclo[2.2.1]heptan-2-yl)phenyl)pyrimidin-2-amine;

4-(6-(2-methoxyethyl)(methyl)aminopyridin-3-yl)-N-(3-methyl-4-(5-oxa-2-azabicyclo[2.2.1]heptan-2-yl)phenyl)pyrimidin-2-amine;

4-(6-(2-methoxyethyl)(methyl)aminopyridin-3-yl)-N-(3-methyl-4-(1,5,7-trimethyl-3,7-diazabicyclo[3.3.1]nonan-3-yl)phenyl)pyrimidin-2-amine;

4-(6-(morpholin-4-yl)pyridin-3-yl)-N-(3-methyl-4-(2-azabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(2-azabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(2-methylsulfonyl-2-azabicyclo[2.2.1]heptan-5-yl)phenyl)pyrimidin-2-amine and 4-(2,2-dimethyl-3-oxo-3,4-dihydro-2H-pyrido[3,2-b][1,4]oxazin-7-yl)-N-(3-methyl-4-(2-methylsulfonyl-2-azabicyclo[2.2.1]heptan-6-yl)phenyl)pyrimidin-2-amine (68:31);

4-(6-(morpholin-4-yl)pyridin-3-yl)-N-(3-methyl-4-(2-methylsulfonyl-2-azabicyclo[2.2.1]heptan-5-yl)phenyl)pyrimidin-2-amine and 4-(6-(morpholin-4-yl)pyridin-3-yl)-N-(3-methyl-4-(2-methylsulfonyl-2-azabicyclo[2.2.1]heptan-6-yl)phenyl)pyrimidin-2-amine (85:15);

4-(2,2-dimethyl-3-oxo-3,4-dihydro-2H-pyrido[3,2-b][1,4]oxazin-7-yl)-N-(4-(2-methylsulfonyl-2-azabicyclo[2.2.1]heptan-5-yl)phenyl)pyrimidin-2-amine;

4-(6-(morpholin-4-yl)pyridin-3-yl)-N-(4-(2-methylsulfonyl-2-azabicyclo[2.2.1]heptan-5-yl)phenyl)pyrimidin-2-amine;

4-(2,2-dimethyl-3-oxo-3,4-dihydro-2H-pyrido[3,2-b][1,4]oxazin-7-yl)-N-(4-(2-methylsulfonyl-2-azabicyclo[2.2.1]heptan-6-yl)phenyl)pyrimidin-2-amine;

4-(6-(morpholin-4-yl)pyridin-3-yl)-N-(4-(2-methylsulfonyl-2-azabicyclo[2.2.1]heptan-6-yl)phenyl)pyrimidin-2-amine;

4-(6-(thiamorpholin-4-yl)pyridin-3-yl)-N-(3-methyl-4-(5-methyl-2,5-diazabicyclo[2.2.1]heptan-2-yl)phenyl)pyrimidin-2-amine;

4-(6-(morpholin-4-yl)pyridin-3-yl)-N-(3-methyl-4-(5-methyl-2,5-diazabicyclo[2.2.1]heptan-2-yl)phenyl)pyrimidin-2-amine;

4-(1-(pyridin-4-yl)-1H-indol-5-yl)-N-(3-methyl-4-(5-methyl-2,5-diazabicyclo[2.2.1]heptan-2-yl)phenyl)pyrimidin-2-amine;

4-(1-(pyridin-4-yl)-1H-indol-5-yl)-N-(3-fluoro-4-(5-methyl-2,5-diazabicyclo[2.2.1]heptan-2-yl)phenyl)pyrimidin-2-amine;

4-(1-(pyridin-4-yl)-1H-indol-5-yl)-N-(3-methyl-4-(5-ethyl-2,5-diazabicyclo[2.2.1]heptan-2-yl)phenyl)pyrimidin-2-amine;

4-(1-(pyridin-4-yl)-1H-indol-5-yl)-N-(3-methyl-4-(5-isobutyl-2,5-diazabicyclo[2.2.1]heptan-2-yl)phenyl)pyrimidin-2-amine;

4-(7-oxo-5,6,7,8-tetrahydro-1,8-naphthyridin-3-yl)-N-(3-methyl-4-(5-methylsulfonyl-2,5-diazabicyclo[2.2.1]heptan-2-yl)phenyl)pyrimidin-2-amine;

4-(6-(propylamino)pyridin-3-yl)-N-(3-methyl-4-(5-methylsulfonyl-2,5-diazabicyclo[2.2.1]heptan-2-yl)phenyl)pyrimidin-2-amine;

4-(3-oxo-3,4-dihydro-2H-benzo[b][1,4]thiazin-7-yl)-N-(4-(5-methyl-2,5-diazabicyclo[2.2.1]heptan-2-yl)phenyl)pyrimidin-2-amine;

4-(2,2-dimethyl-3-oxo-3,4-dihydro-2H-benzo[b][1,4]oxazin-7-yl)-N-(3-methyl-4-(5-methyl-2,5-diazabicyclo[2.2.1]heptan-2-yl)phenyl)pyrimidin-2-amine;

4-(2,2-dimethyl-3-oxo-3,4-dihydro-2H-benzo[b][1,4]oxazin-7-yl)-N-(3-methyl-4-(5-methylsulfonyl-2,5-diazabicyclo[2.2.1]heptan-2-yl)phenyl)pyrimidin-2-amine;

4-(2-oxo-2,3,4,5-tetrahydro-1H-benzo[b]azepin-7-yl)-N-(3-methyl-4-(5-methyl-2,5-diazabicyclo[2.2.1]heptan-2-yl)phenyl)pyrimidin-2-amine;

4-(2-oxo-2,3,4,5-tetrahydro-1H-benzo[b]azepin-7-yl)-N-(3-methyl-4-(5-methylsulfonyl-2,5-diazabicyclo[2.2.1]heptan-2-yl)phenyl)pyrimidin-2-amine;

4-(2,2-dimethyl-3-oxo-3,4-dihydro-2H-benzo[b][1,4]oxazin-7-yl)-N-(3-methyl-4-(6,9-methanooctahydro-1H-pyrido[1,2-a]pyrazin-2-yl)phenyl)pyrimidin-2-amine;

4-(6-(morpholin-4-yl)pyridin-3-yl)-N-(3-methyl-4-(6,9-methanooctahydro-1H-pyrido[1,2-a]pyrazin-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-(1-methylethyl)-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-cyclopropyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-chloro-4-(5-methyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-chloro-4-(5-(methylsulfonyl)-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-cyclopentyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(5-acetyl-2,5-diazabicyclo[2.2.1]heptan-2-yl)phenyl)pyrimidin-2-amine;

4-(2,2-dimethyl-3-oxo-3,4-dihydro-2H-pyrido[3,2-b][1,4]oxazin-7-yl)-N-(3-methyl-4-(1,4-diazabicyclo[3.2.1]octan-4-yl)phenyl)pyrimidin-2-amine;

4-(5-(1-methylethoxy)carbonylpropyl-6-aminopyridin-3-yl)-N-(3-methyl-4-(5-methyl-2,5-diazabicyclo[2.2.1]heptan-2-yl)phenyl)pyrimidin-2-amine;

4-(6-(morpholin-4-yl)pyridin-3-yl)-N-(3-methyl-4-(5-cyclopropyl-2,5-diazabicyclo[2.2.1]heptan-2-yl)phenyl)pyrimidin-2-amine;

4-(6-(morpholin-4-yl)pyridin-3-yl)-N-(3-chloro-4-(5-methyl-2,5-diazabicyclo[2.2.1]heptan-2-yl)phenyl)pyrimidin-2-amine;

4-(2-(trifluoromethyl)pyridin-4-yl)-N-(3-methyl-4-(5-methyl-2,5-diazabicyclo[2.2.1]heptan-2-yl)phenyl)pyrimidin-2-amine;

4-(6-(morpholin-4-yl)pyridin-3-yl)-N-(3-chloro-4-(5-(methylsulfonyl)-2,5-diazabicyclo[2.2.1]heptan-2-yl)phenyl)pyrimidin-2-amine;

4-(6-(tetrahydropyran-4-yloxy)pyridin-3-yl)-N-(3-chloro-4-(5-(methylsulfonyl)-2,5-diazabicyclo[2.2.1]heptan-2-yl)phenyl)pyrimidin-2-amine;

4-(6-(morpholin-4-yl)pyridin-3-yl)-N-(3-chloro-4-(5-acetyl-2,5-diazabicyclo[2.2.1]heptan-2-yl)phenyl)pyrimidin-2-amine;

4-(6-(tetrahydropyran-4-yloxy)pyridin-3-yl)-N-(3-chloro-4-(5-acetyl-2,5-diazabicyclo[2.2.1]heptan-2-yl)phenyl)pyrimidin-2-amine;

4-(6-(tetrahydropyran-4-yloxy)pyridin-3-yl)-N-(3-methyl-4-(5-methyl-2,5-diazabicyclo[2.2.1]heptan-2-yl)phenyl)pyrimidin-2-amine;

4-(6-(tetrahydropyran-4-yloxy)pyridin-3-yl)-N-(3-methyl-4-(5-cyclopentyl-2,5-diazabicyclo[2.2.1]heptan-2-yl)phenyl)pyrimidin-2-amine;

4-(6-(morpholin-4-yl)pyridin-3-yl)-N-(3-chloro-4-(5-(1-methylethyl)-2,5-diazabicyclo[2.2.1]heptan-2-yl)phenyl)pyrimidin-2-amine;

4-(6-(2-oxa-5-azabicyclo[2.2.1]heptan-5-yl)pyridin-3-yl)-N-(3-methyl-4-(5-(methylsulfonyl)-2,5-diazabicyclo[2.2.1]heptan-2-yl)phenyl)pyrimidin-2-amine;

4-(6,7,8,9-tetrahydro-5H-pyrido[2,3-b]indol-3-yl)-N-(3-methyl-4-(5-methyl-2,5-diazabicyclo[2.2.1]heptan-2-yl)phenyl)pyrimidin-2-amine;

4-(6,7,8,9-tetrahydro-5H-pyrido[2,3-b]indol-3-yl)-N-(3-methyl-4-(5-(methylsulfonyl)-2,5-diazabicyclo[2.2.1]heptan-2-yl)phenyl)pyrimidin-2-amine;

4-(4-(trifluoromethyl)phenyl)-N-(3-methyl-4-(5-methyl-2,5-diazabicyclo[2.2.1]heptan-2-yl)phenyl)pyrimidin-2-amine;

4-(7,8,9,9a-tetrahydro-5H-pyrido[2,3-e]pyrrolo[1,2-b][1,4]diazepin-10(11H)-on-3-yl)-N-(3-methyl-4-(5-methyl-2,5-diazabicyclo[2.2.1]heptan-2-yl)phenyl)pyrimidin-2-amine;

4-(2,2-dimethyl-3-oxo-3,4-dihydro-2H-benzo[b][1,4]oxazin-7-yl)-N-(3-cyano-4-(5-methyl-2,5-diazabicyclo[2.2.1]heptan-2-yl)phenyl)pyrimidin-2-amine;

4-(2-oxo-2,3,4,5-tetrahydro-1H-benzo[b]azepin-7-yl)-N-(3-cyano-4-(5-methyl-2,5-diazabicyclo[2.2.1]heptan-2-yl)phenyl)pyrimidin-2-amine;

4-(3-oxo-3,4-dihydro-2H-benzo[b][1,4]thiazin-7-yl)-N-(3-cyano-4-(5-methyl-2,5-diazabicyclo[2.2.1]heptan-2-yl)phenyl)pyrimidin-2-amine;

4-(3-oxo-3,4-dihydro-2H-benzo[b][1,4]thiazin-7-yl)-N-(3-methyl-4-(5-methyl-2,5-diazabicyclo[2.2.1]heptan-2-yl)phenyl)pyrimidin-2-amine;

4-(6-(tetrahydropyran-4-yloxy)pyridin-3-yl)-N-(3-methyl-4-(1,4-diazabicyclo[3.2.1]octan-4-yl)phenyl)pyrimidin-2-amine;

4-(6-(morpholin-4-yl)pyridin-3-yl)-N-(3-methyl-4-(1,4-diazabicyclo[3.2.1]octan-4-yl)phenyl)pyrimidin-2-amine;

4-(2-oxo-2,3,4,5-tetrahydro-1H-benzo[b]azepin-7-yl)-N-(3-methyl-4-(6,9-methanooctahydro-1H-pyrido[1,2-a]pyrazin-2-yl)phenyl)pyrimidin-2-amine;

4-(3-oxo-3,4-dihydro-2H-benzo[b][1,4]thiazin-7-yl)-N-(3-methyl-4-(6,9-methanooctahydro-1H-pyrido[1,2-a]pyrazin-2-yl)phenyl)pyrimidin-2-amine;

4-(6-(2-oxa-5-azabicyclo[2.2.1]heptan-5-yl)pyridin-3-yl)-N-(3-methyl-4-(1,4-diazabicyclo[3.2.2]nonan-4-yl)phenyl)pyrimidin-2-amine;

4-(6-(morpholin-4-yl)pyridin-3-yl)-N-(3-cyano-4-(3,9-diazabicyclo[3.3.2]decan-10-on-3-yl)phenyl)pyrimidin-2-amine;

4-(2,2-dimethyl-3-oxo-3,4-dihydro-2H-pyrido[3,2-b][1,4]oxazin-7-yl)-N-(3-cyano-4-(3,9-diazabicyclo[3.3.2]decan-10-on-3-yl)phenyl)pyrimidin-2-amine;

4-(6-(tetrahydropyran-4-yloxy)pyridin-3-yl)-N-(3-methyl-4-(3-(dimethylamino)-8-azabicyclo[3.2.1]octan-8-yl)phenyl)pyrimidin-2-amine;

4-(6-(morpholin-4-yl)pyridin-3-yl)-N-(3-methyl-4-(3-(morpholin-4-yl)-8-azabicyclo[3.2.1]octan-8-yl)phenyl)pyrimidin-2-amine;

4-(6-(tetrahydropyran-4-yloxy)pyridin-3-yl)-N-(3-methyl-4-(3-(morpholin-4-yl)-8-azabicyclo[3.2.1]octan-8-yl)phenyl)pyrimidin-2-amine;

4-(6-(morpholin-4-yl)pyridin-3-yl)-N-(3-methyl-4-(3-(dimethylamino)-8-azabicyclo[3.2.1]octan-8-yl)phenyl)pyrimidin-2-amine;

4-(6-(dimethylamino)pyridin-3-yl)-N-(6-(5-methyl-2,5-diazabicyclo[2.2.1]heptan-2-yl)pyridin-3-yl)pyrimidin-2-amine;

4-(6-(methylcarbonylamino)pyridin-3-yl)-N-(4-(5-methyl-2,5-diazabicyclo[2.2.1]heptan-2-yl)pyridin-3-yl)pyrimidin-2-amine;

4-(4-(dimethylamino)phenyl)-N-(6-(5-methyl-2,5-diazabicyclo[2.2.1]heptan-2-yl)pyridin-3-yl)pyrimidin-2-amine;

4-(6-(4-acetylpiperazin-1-yl)pyridin-3-yl)-N-(6-(5-methyl-2,5-diazabicyclo[2.2.1]heptan-2-yl)pyridin-3-yl)pyrimidin-2-amine;

4-(5-methyl-6-(morpholin-4-yl)pyridin-3-yl)-N-(6-(5-methyl-2,5-diazabicyclo[2.2.1]heptan-2-yl)pyridin-3-yl)pyrimidin-2-amine;

4-(6-(dimethylamino)pyridin-3-yl)-N-(5-methyl-6-(5-methyl-2,5-diazabicyclo[2.2.1]heptan-2-yl)pyridin-3-yl)pyrimidin-2-amine;

4-(4-(dimethylamino)phenyl)-N-(5-methyl-6-((5-methyl-2,5-diazabicyclo[2.2.1]heptan-2-yl)pyridin-3-yl)pyrimidin-2-amine;

4-(6-(4-acetylpiperazin-1-yl)pyridin-3-yl)-N-(5-methyl-6-(5-methyl-2,5-diazabicyclo[2.2.1]heptan-2-yl)pyridin-3-yl)pyrimidin-2-amine;

4-(5-methyl-6-(morpholin-4-yl)pyridin-3-yl)-N-(5-methyl-6-(5-methyl-2,5-diazabicyclo[2.2.1]heptan-2-yl)pyridin-3-yl)pyrimidin-2-amine;

4-(4-methyl-3,4-dihydro-2H-pyrido[3,2-b][1,4]oxazin-7-yl)-N-(5-methyl-6-(5-methyl-2,5-diazabicyclo[2.2.1]heptan-2-yl)pyridin-3-yl)pyrimidin-2-amine;

4-(6-(morpholin-4-yl)pyridin-3-yl)-N-(5-methyl-6-(5-methyl-2,5-diazabicyclo[2.2.1]heptan-2-yl)pyridin-3-yl)pyrimidin-2-amine;

4-(4-(t-butylcarbonylamino)phenyl)-N-(5-methyl-6-(5-methyl-2,5-diazabicyclo[2.2.1]heptan-2-yl)pyridin-3-yl)pyrimidin-2-amine;

4-(2,2-dimethyl-3-oxo-3,4-dihydro-2H-pyrido[3,2-b][1,4]oxazin-7-yl)-N-(5-methyl-6-(5-methyl-2,5-diazabicyclo[2.2.1]heptan-2-yl)pyridin-3-yl)pyrimidin-2-amine;

4-(4-(3-cyclopropylureido)phenyl)-N-(5-methyl-6-(5-methyl-2,5-diazabicyclo[2.2.1]heptan-2-yl)pyridin-3-yl)pyrimidin-2-amine;

4-(6-(2-(morpholin-4-yl)acetamido)pyridin-3-yl)-N-(5-methyl-6-(5-methyl-2,5-diazabicyclo[2.2.1]heptan-2-yl)pyridin-3-yl)pyrimidin-2-amine;

4-(6-aminopyridin-3-yl)-N-(5-methyl-6-(5-methyl-2,5-diazabicyclo[2.2.1]heptan-2-yl)pyridin-3-yl)pyrimidin-2-amine;

4-(6-(acetamido)pyridin-3-yl)-N-(5-methyl-6-(5-methyl-2,5-diazabicyclo[2.2.1]heptan-2-yl)pyridin-3-yl)pyrimidin-2-amine;

4-(6-(methylsulfonylamino)pyridin-3-yl)-N-(5-methyl-6-(5-methyl-2,5-diazabicyclo[2.2.1]heptan-2-yl)pyridin-3-yl)pyrimidin-2-amine;

4-(2-(dimethylamino)thiazol-4-yl)-N-(6-(5-methyl-2,5-diazabicyclo[2.2.1]heptan-2-yl)pyridin-3-yl)pyrimidin-2-amine;

4-(5-(morpholin-4-yl)pyrazin-2-yl)-N-(6-(5-methyl-2,5-diazabicyclo[2.2.1]heptan-2-yl)pyridin-3-yl)pyrimidin-2-amine;

4-(1-(pyridin-4-yl)-1H-indol-5-yl)-N-(5-methyl-6-(5-methyl-2,5-diazabicyclo[2.2.1]heptan-2-yl)pyridin-3-yl)pyrimidin-2-amine; and 4-(6-(2-oxa-5-azabicyclo[2.2.1]heptan-5-yl)pyridin-3-yl)-N-(5-methyl-6-(5-methyl-2,5-diazabicyclo[2.2.1]heptan-2-yl)pyridin-3-yl)pyrimidin-2-amine.

It is understood that the various embodiments of the compounds of the invention, as set forth above, do not encompass compounds which are specifically disclosed in prior publications, including scientific journals, patents and published patent applications.

Another aspect of the invention are pharmaceutical compositions comprising a pharmaceutically acceptable excipient and a therapeutically effective amount of a compound of the invention, as set forth above in the Summary of the Invention, as an isolated stereoisomer or a mixture thereof, or as a pharmaceutically acceptable salt thereof. In particular, some embodiments of the pharmaceutical compositions of the invention comprise a pharmaceutically acceptable excipient and a therapeutically effective amount of an embodiment of a compound of formula (I), as set forth above. More specific embodiments are pharmaceutical compositions comprising a pharmaceutically acceptable excipient and a therapeutically effective amount of a compound of formula (Ia), as set forth above.

Another aspect of the invention are methods of treating diseases or conditions associated with JAK2 activity in a mammal utilizing the compounds and the pharmaceutical compositions of the invention. One embodiment of the methods of the invention disclosed herein is the administration of a therapeutically effective amount of a compound of formula (Ia), as set forth above, to a mammal, preferably a human, in need thereof. Another embodiment of the methods of the invention disclosed herein are methods of treating the diseases or conditions associated with JAK2 activity in a mammal wherein the disease or conditions is leukemia, lymphoma, multiple myeloma, transplant rejection, bone marrow transplant applications, autoimmune diseases, inflammation, myeloproliferative disorders, polycythemia vera disorder, essential thrombocythemia disorder and primary myelofibrosis.

It is understood that any embodiment of the compounds of the invention, as set forth above, and any specific substituent set forth herein for a particular n, m, $R^1$, $R^2$, $R^3$, $R^4$, $R^5$ or Y in the compounds of the invention, as set forth above, may be independently combined with other embodiments and/or substituents of compounds of the invention to form embodiments of the inventions not specifically set forth above. In addition, in the event that a list of substituents is listed for any particular R group or Y in a particular embodiment and/or claim, it is understood that each individual substituent may be deleted from the particular embodiment and/or claim and that the remaining list of substituents will be considered to be within the scope of the invention.

Specific embodiments of the invention are described in more detail below in the following sections.

UTILITY AND TESTING OF THE COMPOUNDS OF THE INVENTION

The present invention provides pyrimidine-2-amine compounds or pharmaceutically acceptable salts thereof, as described above in the Summary of the Invention, for use in treating the diseases or conditions as described herein. The present invention further provides use of the compounds of the present invention in the manufacture of a medicament for the treatment of diseases or conditions in which targeting of the JAK pathway or inhibition of JAK kinases, particularly JAK2, can be therapeutically useful. These include diseases or conditions where the function of lymphocytes, macrophages, or mast cells is involved. Accordingly, diseases or conditions associated with JAK2 activity, in particular, are diseases or conditions in which targeting of the JAK pathway or inhibition of the JAK kinases, particularly JAK2, can be therapeutically useful include, but are not limited to, leukemia, lymphoma, multiple myeloma, transplant rejection (e.g. pancreas islet transplant rejection), bone marrow transplant conditions (e.g., graft-versus-host disease), autoimmune diseases (e.g., rheumatoid arthritis), inflammation (e.g., asthma, etc.), myeloproliferative disorders (MPD) (e.g., polycythemia vera (PV), essential thrombocythemia (ET) and primary myelofibrosis (PMF)), and other diseases or conditions as described in greater detail herein or which are known to one skilled in the art as being associated with JAK2 activity.

As noted previously, numerous diseases or conditions can be treated using the compounds of the invention, or pharmaceutically acceptable salts thereof, and pharmaceutically compositions comprising the compounds or pharmaceutically acceptable salts thereof. As well understood in the art, "treatment" is an approach for obtaining beneficial or desired results, including clinical results. For the purposes of this invention, beneficial or desired results can include one or more, but are not limited to: alleviation or amelioration of one or more symptoms; diminishment of extent of a condition, including a disease; stabilization (i.e., not worsening) of the state of a condition, including diseases; preventing spread of disease; delay or slowing of a condition, including disease progression; amelioration or palliation of the condition, including disease state; and remission (whether partial or total); in each case whether detectable or undetectable. Preferred are compounds that are potent and can be administered locally at very low doses, thus minimizing systemic adverse effects.

The compounds of the invention, or pharmaceutically acceptable salts thereof, described herein are potent and selective inhibitors of JAK kinases, and particularly selective for cytokine signaling pathways containing JAK2. As a consequence of this activity, the compounds can be used in a variety of in vitro, in vivo and ex vivo contexts to regulate or inhibit JAK kinase activity, signaling cascades in which JAK kinases play a role, and the biological responses effected by such signaling cascades. For example, in one embodiment, the compounds can be used to inhibit JAK kinase, either in vitro or in vivo, in virtually any cell type expressing the JAK kinase.

In hematopoietic cells in which a JAK kinase is expressed, the compounds of the invention may be used to regulate signal transduction cascades in which the JAK kinase, particularly JAK2, plays a role. Such JAK-dependent signal transduction cascades include, but are not limited to, the signaling cascades of a wide range of cytokine receptors, including those activated by growth hormone, erythropoietin, prolactin, granulocyte colony stimulating factor (G-CSF), macrophage colony-stimulating factor, ciliary neurotrophic factor, leukemia inhibitory factor, oncostatin M, interferon-γ, thrombopoietin, leptin, IL-3, IL-5, IL-6, IL-11, IL-12 and some G-protein-coupled (GPCR) receptor signaling cascades (angiotensin II, bradykinin, endothelin, platelet activating factor, α-melanocyte stimulating hormone, isoproterenol, and phenylephrine). The compounds may also be used in vitro or in vivo to regulate, and in particular inhibit, cellular or biological responses affected by such JAK-dependent signal transduction cascades. Such cellular or biological responses include, but are not limited to, MAPK and AKT pathway activation, IL-3 mediated cell proliferation, etc.

Importantly, the compounds can be used to inhibit JAK kinases in vivo as a therapeutic approach towards the treatment or prevention of diseases or conditions mediated, either wholly or in part, by a JAK kinase activity (referred to herein as "JAK kinase mediated diseases or conditions"). Non-limiting examples of JAK kinase mediated diseases or conditions that can be treated or prevented with the compounds of the invention, or pharmaceutically acceptable salts thereof, include, but are not limited to: allergies; asthma; autoimmune diseases such as transplant rejection (e.g., kidney, heart, lung, liver, pancreas, skin; host versus graft reaction (HVGR), graft versus host reaction (GVHR) etc.), rheumatoid arthritis, and amyotrophic lateral sclerosis; T-cell mediated autoimmune diseases such as multiple sclerosis, psoriasis and Sjogren's syndrome; Type II inflammatory diseases such as vascular inflammation (including vasculitis, arteritis, atherosclerosis and coronary artery disease); diseases of the central nervous system such as stroke; pulmonary diseases such as bronchitis obliteraus, primary pulmonary hypertension and pulmonary arterial hypertension, and solid, delayed Type IV hypersensitivity reactions; and hematologic malignancies such as leukemia and lymphomas. The compounds of the invention may also be used for treatment of obesity, since in obese animals, JAK2/STAT and MAP kinase pathways are hyperactivated in response to insulin.

This invention also provides a method of inhibiting an activity of a JAK kinase, comprising contacting the JAK kinase with an amount of a compound effective to inhibit an activity of the JAK kinase wherein the compound is selected from the compounds of this invention or pharmaceutically acceptable salts thereof. In certain embodiments of the methods described herein, the method is carried out in vivo. In certain embodiments of the methods described herein, the method is carried out in vitro.

In certain embodiments of the methods, the compound is administered to a subject suffering from a T-cell mediated autoimmune disease. In some other embodiments, the subject is a transplant recipient suffering from or predisposed to an allograft transplant rejection. In some other embodiments, the compound is administered to a subject suffering from or predisposed to develop a Type IV hypersensitivity reaction.

This invention also provides a method of inhibiting an activity of a JAK kinase, comprising contacting in vitro a JAK2 kinase with an amount of a compound effective to inhibit an activity of the JAK kinase wherein the compound is selected from the compounds of this invention, or pharmaceutically acceptable salts thereof.

In a specific embodiment, the compounds of the invention, or pharmaceutically acceptable salts thereof, can be used to treat and/or prevent rejection in organ and/or tissue transplant recipients (i.e., treat and/or prevent allograft rejection). Allografts can be rejected through either a cell-mediated or humoral immune reaction of the recipient against transplant (histocompatibility) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relatively uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process, and that the antigen is presented by donor and host dendritic cells. The CD4+ helper T-cells help recruit other effector cells, such as macrophages and eosinophils, to the graft. Accessing T-cell activation signal transduction cascades (for example, CD28, CD40L and CD2 cascades) are also involved.

The cell-mediated acute rejection can be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial endothelium is primarily involved, with extensive proliferation that may gradually occlude the vessel lumen, leading to ischemia, fibrosis, a thickened intima and atherosclerotic changes. Chronic rejection is mainly due to a progressive obliteration of graft vasculature, and resembles a slow, vasculitic process.

In Type IV hypersensitivity, CD8 cytotoxic T-cells and CD4 helper T cells recognize either intracellular or extracellular-synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAK kinases play a critical role in the activation of T-cells, the pyrimidine-2-amine compounds or pharmaceutically acceptable salts thereof described herein can be used to treat and/or prevent many aspects of transplant rejection, and are particularly useful in the treatment and/or prevention of rejection reactions that are mediated, at least in part, by T-cells, such as HVGR or GVHR. The pyrimidine-2-amine compounds can also be used to treat and/or prevent chronic rejection in transplant recipients, and in particular in renal transplant recipients.

This invention also provides a method of treating a T-cell mediated autoimmune disease, comprising administering to a patient suffering from such an autoimmune disease an amount of a compound effective to treat the autoimmune disease wherein the compound is selected from the compounds of the invention or pharmaceutically acceptable salts thereof. In certain embodiments of the methods the autoimmune disease is multiple sclerosis (MS), psoriasis, or Sjogren's syndrome.

Therapy using the pyrimidine-2-amine compounds, or pharmaceutically acceptable salts thereof, described herein can be applied alone, or they can be applied in combination with or adjunctive to other common immunosuppressive therapies, such as, for example, mercaptopurine, corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also, the prescribing information in the 2006 Edition of *The Physician's Desk Reference*), the disclosures of which are incorporated herein by reference. Azathioprine is currently available from Salix Pharmaceuticals, Inc. under the brand name AZASAN; mercaptopurine is currently available from Gate Pharmaceuticals, Inc. under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and Abbott under the brand name GENGRAF; IMPDH inhibitors such as mycophenolate mofetil and mycophenolic acid are currently available from Roche under the brand name CELLCEPT and Novartis under the brand name MYFORTIC; azathioprine is currently available from Glaxo Smith Kline under the brand name IMURAN; and antibodies are currently available from Ortho Biotech under the brand name ORTHOCLONE, Novartis under the brand name SIMULECT (basiliximab) and Roche under the brand name ZENAPAX (daclizumab).

In addition, the pyrimidine-2-amine compounds of the invention could be administered either in combination or adjunctively with an inhibitor of a Syk kinase. Syk kinase is a tyrosine kinase known to play a critical role in Fcγ receptor signaling, as well as in other signaling cascades, such as those involving B-Cell receptor signaling (Tumer et al., (2000), *Immunology Today* 21:148-154) and integrins beta (1), beta (2) and beta (3) in neutrophils (Mocsavi et al., (2002), *Immunity* 16:547-558). For example, Syk kinase plays a pivotal role in high affinity IgE receptor signaling in mast cells that leads to activation and subsequent release of multiple chemical mediators that trigger allergic attacks. However, unlike the JAK kinases, which help regulate the pathways involved in delayed, or cell-mediated Type IV hypersensitivity reactions, Syk kinase helps regulate the pathways involved in immediate IgE-mediated, Type I hypersensitivity reactions. Certain compounds that affect the Syk pathway may or may not also affect the JAK pathways.

Suitable Syk inhibitory compounds are described, for example, in U.S. patent application Ser. No. 10/355,543, filed Jan. 31, 2003 (publication no. 2004/0029902); PCT Published Patent Application No. WO 03/063794; U.S. patent application Ser. No. 10/631,029, filed Jul. 29, 2003; PCT Published Patent Application No. WO 2004/014382; U.S. patent application Ser. No. 10/903,263, filed Jul. 30, 2004; PCT Published Patent Application No. WO 2005/016893; U.S. patent application Ser. No. 10/903,870, filed Jul. 30, 2004; PCT Patent Application No. PCT/US2004/24920, filed Jul. 30, 2004; U.S. Patent Application Ser. No. 60/630,808, filed Nov. 24, 2004; U.S. Patent Application Ser. No. 60/645,424, filed Jan. 19, 2005; and U.S. Patent Application Ser. No. 60/654,620, filed Feb. 18, 2005, the disclosures of which are incorporated herein by reference in their entireties. The pyrimidine-2-amine described herein and Syk inhibitory compounds could be used alone, or in combination with one or more conventional transplant rejection treatments, as described above.

In addition, the pyrimidine-2-amine compounds of the invention, or pharmaceutically acceptable salts thereof, can be used to treat or prevent these diseases or conditions in patients that are either initially non-responsive (resistant) to, or that become non-responsive to treatment with a Syk inhibitory compound, or one of the other current treatments for the particular disease. The pyrimidine-2-amine compounds of the invention, or pharmaceutically acceptable salts thereof, could also be used in combination with Syk inhibitory compounds in patients that are Syk-compound resistant or non-responsive. Suitable Syk-inhibitory compounds with which the pyrimidine-2-amine compounds of the invention, or pharmaceutically acceptable salts thereof, can be administered are provided supra.

This invention also provides a method of treating a T-cell mediated autoimmune disease, comprising administering to a patient suffering from such an autoimmune disease an amount of a compound effective to treat the autoimmune disease wherein the compound is selected from the compounds of the invention, as described herein, or pharmaceutically acceptable salts thereof, and the compound or pharmaceutically acceptable salt thereof is administered in combination with, or adjunctively to, a compound that inhibits Syk kinase with an $IC_{50}$ in the range of at least 10 μM.

This invention also provides a method of treating or preventing allograft transplant rejection in a transplant recipient, comprising administering to the transplant recipient an amount of a compound effective to treat or prevent the rejection wherein the compound is selected from the compounds of the invention, or pharmaceutically acceptable salts thereof, as described herein. In a further embodiment, the compound or pharmaceutically acceptable salt, is administered to a tissue or an organ prior to transplanting the tissue or organ in the transplant recipient.

This invention also provides a method of treating or preventing allograft transplant rejection in a transplant recipient, in which the rejection is acute rejection, comprising administering to the transplant recipient an amount of a compound effective to treat or prevent the rejection wherein the compound is selected from the compounds of the invention, or pharmaceutically acceptable salts thereof.

This invention also provides a method of treating or preventing allograft transplant rejection in a transplant recipient, in which the rejection is chronic rejection, comprising administering to the transplant recipient an amount of a compound effective to treat or prevent the rejection wherein the compound is selected from the compounds of the invention, or pharmaceutically acceptable salts thereof, as described herein.

This invention also provides a method of treating or preventing allograft transplant rejection in a transplant recipient, in which the rejection is mediated by HVGR or GVHR, comprising administering to the transplant recipient an amount of a compound effective to treat or prevent the rejection wherein the compound is selected from the compounds of this invention, or pharmaceutically acceptable salts thereof, as described herein.

This invention also provides a method of treating or preventing allograft transplant rejection in a transplant recipient, in which the allograft transplant is selected from a kidney, a heart, a liver and a lung, comprising administering to the transplant recipient an amount of a compound effective to treat or prevent the rejection wherein the compound is selected from the compounds of this invention, or pharmaceutically acceptable salts thereof, as described herein.

This invention also provides a method of treating or preventing allograft transplant rejection in a transplant recipient, in which the allograft transplant is selected from a kidney, a heart, a liver and a lung, comprising administering to the transplant recipient an amount of a compound effective to treat or prevent the rejection wherein the compound is selected from the compounds of the invention, or pharmaceutically acceptable salts thereof, as described herein, in which the compound or pharmaceutically acceptable salt is administered in combination with, or adjunctively to, another immunosuppressant.

This invention also provides a method of treating or preventing allograft transplant rejection in a transplant recipient, in which the allograft transplant is selected from a kidney, a heart, a liver and a lung, comprising administering to the transplant recipient an amount of a compound effective to treat or prevent the rejection wherein the compound is selected from the compounds of the invention, or pharmaceutically acceptable salts thereof, as described herein, in which the compound or pharmaceutically acceptable salts is administered in combination with, or adjunctively to, another immunosuppressant, in which the immunosuppressant is selected from cyclosporine, tacrolimus, sirolimus, an inhibitor of IMPDH, mycophenolate, mycophanolate mofetil, an anti-T-Cell antibody and OKT3.

The pyrimidine-2-amine compounds of the invention, or pharmaceutically acceptable salts thereof, described herein are cytokine moderators of IL-4 signaling. As a consequence, the pyrimidine-2-amine compounds of the invention, or pharmaceutically acceptable salts thereof, could slow the response of Type I hypersensitivity reactions. Thus, in a specific embodiment, the pyrimidine-2-amine compounds of the invention, or pharmaceutically acceptable salts thereof, could be used to treat such reactions, and therefore the diseases associated with, mediated by or caused by such hypersensitivity reactions (for example, allergies), prophylactically. For example, an allergy sufferer could take one or more of the JAK selective compounds described herein prior to expected exposure to allergens to delay the onset or progress, or eliminate altogether, an allergic response.

When used to treat or prevent such diseases, the pyrimidine-2-amine compounds of the invention, or pharmaceutically acceptable salts thereof, can be administered singly, as mixtures of one or more pyrimidine-2-amine compounds, or pharmaceutically acceptable salts thereof, or in mixture or combination with other agents useful for treating such diseases and/or the symptoms associated with such diseases. The pyrimidine-2-amine compounds, or pharmaceutically acceptable salts thereof, may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, β-agonists, tryptase inhibitors, aspirin, cyclooxygenase (COX) inhibitors, methotrexate, anti-TNF drugs, retuxin, PD4 inhibitors, p38 inhibitors, PDE4 inhibitors, and antihistamines, to name a few. The pyrimidine-2-amine compounds, or pharmaceutically acceptable salts thereof, can be administered per se, or in the form of prodrugs or as pharmaceutical compositions comprising an active compound.

This invention also provides a method of treating or preventing a Type IV hypersensitivity reaction, comprising administering to a subject an amount of a compound of effective to treat or prevent the hypersensitivity reaction wherein the compound is selected from the compounds of this invention, or pharmaceutically acceptable salts thereof, as described herein.

This invention also provides a method of treating or preventing a Type IV hypersensitivity reaction, which is practical prophylactically, comprising administering to a subject an amount of a compound of effective to treat or prevent the hypersensitivity reaction wherein the compound is selected from the compounds of this invention, or pharmaceutically acceptable salts thereof, as described herein, and is administered prior to exposure to an allergen.

This invention also provides a method of inhibiting a signal transduction cascade in which JAK2 kinase plays a role, comprising contacting a cell expressing a receptor involved in such a signaling cascade with a compound wherein the compound is selected from the compounds of this invention, or pharmaceutically acceptable salts thereof, as described herein.

In another embodiment, this invention provides a method of treating or preventing a JAK kinase-mediated disease, comprising administering to a subject an amount of compound effective to treat or prevent the JAK kinase-mediated disease wherein the compound is selected from the compounds of this invention, or pharmaceutically acceptable salts thereof, as described herein.

This invention also provides a method of treating or preventing a JAK kinase-mediated disease, in which the JAK-mediated disease is HVGR or GVHR, comprising administering to a subject an amount of compound effective to treat or prevent the JAK kinase-mediated disease wherein the compound is selected from the compounds of the invention, or pharmaceutically acceptable salts thereof, as described herein.

This invention also provides a method of treating or preventing a JAK kinase-mediated disease, in which the JAK-mediated disease is acute allograft rejection, comprising administering to a subject an amount of compound effective to treat or prevent the JAK kinase-mediated disease wherein the compound is selected from the compounds of the invention, or pharmaceutically acceptable salts thereof, as described herein.

This invention also provides a method of treating or preventing a JAK kinase-mediated disease, in which the JAK-mediated disease is chronic allograft rejection, comprising administering to a subject an amount of compound effective to treat or prevent the JAK kinase-mediated disease wherein the compound is selected from the compounds of the invention, or pharmaceutically acceptable salts thereof, as described herein.

Active compounds of the invention, or pharmaceutically acceptable salts thereof, typically inhibit the JAK/Stat pathway. The activity of a specified compound as an inhibitor of a JAK kinase can be assessed in vitro or in vivo. In some embodiments, the activity of a specified compound can be tested in a cellular assay. Suitable assays include assays that determine inhibition of either the phosphorylation activity or ATPase activity of a JAK kinase. Thus, a compound is said to inhibit an activity of a JAK kinase if it inhibits the phosphorylation or ATPase activity of a JAK kinase with an $IC_{50}$ of about 20 µM or less.

One means of assaying for such inhibition is detection of the effect of the pyrimidine-2-amine compounds on the upregulation of downstream gene products. In the Ramos/IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (e.g., the pyrimidine-2-amine compounds described herein) on the JAK1 and JAK3 kinases, human Ramos B cells are stimulated with human IL-4. Twenty to 24 hours post stimulation, cells are stained for upregulation of CD23 and analyzed using flow cytometry (FACS). A reduction of the amount of CD23 present compared to control conditions indicates the test compound actively inhibits the JAK kinase pathway. An exemplary assay of this type is described in greater detail in the Biological Examples described below.

The biological activity of the compounds of the invention may further be characterized by assaying the effect of the pyrimidine-2-amine compounds described herein on the proliferative response of primary human T-cells. In this assay, primary human T-cells derived from peripheral blood and pre-activated through stimulation of the T-cell receptor and CD28, proliferate in culture in response to the cytokine Interleukin-2 (IL-2). This proliferative response is dependent on the activation of JAK1 and JAK3 tyrosine kinases, which phosphorylate and activate the transcription factor Stat-5. The primary human T-cells are incubated with the pyrimidine-2-amine compounds in the presence of IL-2 for 72 hours and at the assay endpoint intracellular ATP concentrations are measured to assess cell viability. A reduction in cell proliferation compared to control conditions is indicative of inhibition of the JAK kinase pathway. An exemplary assay of this type is described in greater detail in the Biological Examples described below.

The biological activity of the compounds of the invention may additionally be characterized by assaying the effect of the pyrimidine-2-amine compounds described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1β receptor activates the TRAF6/NFκB pathway resulting in up-regulation of ICAM-1. IFNγ induces ICAM-1 up-regulation through activation of the JAK1/JAK2 pathway. The up-regulation of ICAM-1 can be quantified by flow cytometry across a compound dose curve and $EC_{50}$ values are calculated. An exemplary assay of this type is described in greater detail in the Biological Examples described below.

Biologically active compounds of the invention, or pharmaceutically acceptable salts thereof, generally inhibit the JAK kinase pathway with an $IC_{50}$ in the range of about 1 mM or less, as measured in the assays described herein. Of course, skilled artisans will appreciate that compounds which exhibit lower $IC_{50}$s, for example on the order of 100 µM, 75 µM, 50 µM, 40 µM, 30 µM, 20 µM, 15 µM, 10 µM, 5 µM, 1 µM, 500 nM, 100 nM, 10 nM, 1 nM, or even lower, can be particularly useful in therapeutic applications. In instances where activity specific to a particular cell type is desired, the compound can be assayed for activity with the desired cell type and counter-screened for a lack of activity against other cell types. The desired degree of "inactivity" in such counter screens, or the desired ratio of activity vs. inactivity may vary for different situations, and can be selected by the user.

The pyrimidine-2-amine active compounds of the invention, or pharmaceutically acceptable salts thereof, also typically inhibit IL-4 stimulated expression of CD23 in B-cells with an $IC_{50}$ in the range of about 20 µM or less, typically in the range of about 10 µM, 1 µM, 500 nM, 100 nM, 10 nM, 1 nM, or even lower. A suitable assay that can be used is the assay described in the Biological Example 1 described below, entitled "Assay for Ramos B-Cell Line Stimulated with IL-4." In certain embodiments, the active pyrimidine-2-amine compounds of the invention have an $IC_{50}$ of less than or equal to 5 µM, greater than 5 µM but less than 20 µM, greater than 20 µM, or greater than 20 µM but less than 50 µM in the assay described in Biological Example 1.

Additionally, the pyrimidine-2-amine active compounds of the invention, or pharmaceutically acceptable salts thereof, also typically inhibit an activity of an human primary T-cells with an $IC_{50}$ in the range of about 20 µM or less, typically in the range of about 10 µM, 1 µM, 500 nM, 100 nM, 10 nM, 1 nM, or even lower. The $IC_{50}$ against human primary T-cells can be determined in a standard in vitro assay with isolated human primary T-cells. A suitable assay that can be used is the assay described in the Biological Example 2 below, entitled "Primary Human T-cell Proliferation Assay Stimulated with IL-2." In certain embodiments, the active pyrimidine-2-amine compounds have an $IC_{50}$ of less than or equal to 5 µM, greater than 5 µM but less than 20 µM, greater than 20 µM, or greater than 20 µM but less than 50 µM in the assay described in Biological Example 2.

The pyrimidine-2-amine active compounds of the invention, or pharmaceutically acceptable salts thereof, also typically inhibit expression of ICAM1 (CD54) induced by IFNγ exposure in U937 or A549 cells with an $IC_{50}$ in the range of about 20 µM or less, typically in the range of about 10 µM, 1 µM, 500 nM, 100 nM, 10 nM, 1 nM, or even lower. The $IC_{50}$ against expression of ICAM (CD54) in IFNγ stimulated cells can be determined in a functional cellular assay with an isolated A549 or U937 cell line. Suitable assays that can be used are the assays described in Biological Examples 5 and 6 below, entitled "A549 Epithelial Line Stimulated with IFNγ," and "U937 IFNγ ICAM1 FACS Assay," respectively. In certain embodiments, the active pyrimidine-2-amine compounds have an $IC_{50}$ of less than or equal to 20 µM, greater than 20 µM, or greater than 20 µM but less than 50 µM in the assays described in Biological Example 5 or Biological Example 6.

For purposes of this invention, the phrase "cell proliferative disorder" refers to a disorder characterized by abnormal proliferation of cells. A cell proliferative disorder does not imply any limitation with respect to the rate of cell growth, but merely indicates loss of normal controls that affect growth and cell division. Thus, in some embodiments, cells of a cell proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

Accordingly, cell proliferative disorders treatable with the compounds of the invention, or pharmaceutically acceptable salts thereof, relate to any disorder characterized by aberrant cell proliferation. These include various tumors and cancers, benign or malignant, metastatic or non-metastatic. Cell proliferative disorders include a variety of cancers, including, among others, cancer of the tongue, mouth, pharynx, esophagus, stomach, small intestine, colon, rectum, anus, liver, gallbladder, pancreas, larynx, lung and bronchus, bones and joints including synovial sarcoma and osteosarcoma, melanomas including basal cell carcinoma, squamous carcinoma, breast, cervix, endometrium, ovary, vulva, vagina, prostate, testis, penis, urinary bladder, kidney and renal pelvis, ureter, eye, brain including glioma, glioblastoma, astrocytoma, neuroblastoma, medulloblastoma, and thyroid. For example, cell proliferative disorders treatable with the compounds of the invention, or pharmaceutically acceptable salts thereof, include, but are not limited to, the following:

a) proliferative disorders of the breast, which include, but are not limited to, invasive ductal carcinoma, invasive lobular carcinoma, ductal carcinoma, lobular carcinoma in situ and metastatic breast cancer;

b) proliferative disorders of the skin, which include, but are not limited to, basal cell carcinoma, squamous cell carcinoma, malignant melanoma and Karposi's sarcoma;

c) proliferative disorders of the respiratory tract, which include, but are not limited to, small cell and non-small cell lung carcinoma, bronchial adema, pleuropulmonary blastoma and malignant mesothelioma;

d) proliferative disorders of the brain, which include, but are not limited to, brain stem and hyptothalamic glioma, cerebellar and cerebral astrocytoma, medullablastoma, ependymal tumors, oligodendroglial, meningiomas and neuroectodermal and pineal tumors;

e) proliferative disorders of the male reproductive organs, which include, but are not limited to, prostate cancer, testicular cancer and penile cancer;

f) proliferative disorders of the female reproductive organs, which include, but are not limited to, uterine cancer (endometrial), cervical, ovarian, vaginal, vulval cancers, uterine sarcoma and ovarian germ cell tumor;

g) proliferative disorders of the digestive tract, which include, but are not limited to, anal, colon, colorectal, esophageal, gallbladder, stomach (gastric), pancreatic cancer, pancreatic cancer-Islet cell, rectal, small-intestine and salivary gland cancers;

h) proliferative disorders of the liver, which include, but are not limited to, hepatocellular carcinoma, cholangiocarcinoma, mixed hepatocellular cholangiocarcinoma, primary liver cancer and metastatic liver cancer;

i) proliferative disorders of the eye, which include, but are not limited to, intraocular melanoma, retinoblastoma, and rhabdomyosarcoma;

j) proliferative disorders of the head and neck, which include, but are not limited to, laryngeal, hypopharyngeal, nasopharyngeal, oropharyngeal cancers, and lip and oral cancer, squamous neck cancer, metastatic paranasal sinus cancer;

k) proliferative disorders of lymphocytic cells, which include, but are not limited to, various T cell and B cell lymphomas, non-Hodgkins lymphoma, cutaneous T cell lymphoma, Hodgkins disease, and lymphoma of the central nervous system;

l) leukemias, which include, but are not limited to, acute myeloid leukemia, acute lymphoblastic leukemia, chronic lymphocytic leukemia, chronic myelogenous leukemia, and hairy cell leukemia, m) proliferative disorders of the thyroid, which include, but are not limited to, thyroid cancer, thymoma, malignant thymoma, medullary thyroid carcinomas, papillary thyroid carcinomas, multiple endocrine neoplasia type 2A (MEN2A), pheochromocytoma, parathyroid adenomas, multiple endocrine neoplasia type 2B (MEN2B), familial medullary thyroid carcinoma (FMTC) and carcinoids;

n) proliferative disorders of the urinary tract, which include, but are not limited to, bladder cancer;

o) sarcomas, which include, but are not limited to, sarcoma of the soft tissue, osteosarcoma, malignant fibrous histiocytoma, lymphosarcoma, and rhabdomyosarcoma;

p) proliferative disorders of the kidneys, which include, but are not limited to, renal cell carcinoma, clear cell carcinoma of the kidney; and renal cell adenocarcinoma;

q) precursor B-lymphoblastic leukemia/lymphoma (precursor B-cell acute lymphoblastic leukemia), B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma and Burkitt's lymphoma/Burkitt cell leukemia (r) precursor T-lymphoblastic lymphoma/leukemia (precursor T-cell acute lymphoblastic leukemia), T-cell prolymphocytic leukemia, T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, mycosis fungoides/Sezary syndrome, anaplastic large-cell lymphoma, T/null cell, primary cutaneous type, peripheral T-cell lymphoma, not otherwise characterized, angioimmunoblastic T-cell lymphoma, anaplastic large-cell lymphoma, T/null cell, and primary systemic type;

(s) nodular lymphocyte-predominant Hodgkin's lymphoma, nodular sclerosis Hodgkin's lymphoma (grades 1 and 2), lymphocyte-rich classical Hodgkin's lymphoma, mixed cellularity Hodgkin's lymphoma, and lymphocyte depletion Hodgkin's lymphoma;

(t) myelogenous leukemia (e.g., Philadelphia chromosome positive (t(9;22)(qq34;q11)), multiple myeloma, chronic neutrophilic leukemia, chronic eosinophilic leukemia/hypereosinophilic syndrome, chronic idiopathic myelofibrosis, polycythemia vera, essential thrombocythemia, chronic myelomonocytic leukemia, atypical chronic myelogenous leukemia, juvenile myelomonocytic leukemia, refractory anemia with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9;12)(q22;p12);

(u) AML with t(8;21)(q22;q22), AML1(CBF-alpha)/ETO, acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities, AML minimally differentiated, AML without maturation, AML with maturation, acute myelomonocytic leukemia, acute monocytic leukemia, acute erythroid leukemia, acute megakaryocytic leukemia, acute basophilic leukemia, and acute panmyelosis with myelofibrosis.

The antiproliferative effect of a combination therapy of the invention may be assessed by administering the compound of the invention to a cultured tumor cell line. In the context of an in vitro assay, administration of a compound of the invention may be simply achieved by contacting the cells in culture with the compound in amounts effective to inhibit cell proliferation. Alternatively, the antiproliferative effect of a compound of the invention may be assessed by administering the compound to an animal in an approved in vivo model for cell proliferation.

Examples of tumor cell lines derived from human tumors and available for use in the in vivo studies include, but are not limited to, leukemia cell lines (e.g., CCRF-CEM, HL-60 (TB), K-562, MOLT-4, RPM1-8226, SR, P388 and P388/ADR); non-small cell lung cancer cell lines (e.g., A549/ATCC, EKVX, HOP-62, HOP-92, NCI-H226, NCI-H23, NCI-H322M, NCI-H460, NCI-H522 and LXFL 529); small cell lung cancer cell lines (e.g., DMS 114 and SHP-77); colon cancer cell lines (e.g., COLO 205, HCC-2998, HCT-116, HCT-15, HT29, KM12, SW-620, DLD-1 and KM20L2); central nervous system (CNS) cancer cell lines (e.g., SF-268, SF-295, SF-539, SNB-19, SNB-75, U251, SNB-78 and XF 498); melanoma cell lines (e.g., LOX I MVI, MALME-3M, M14, SK-MEL-2, SK-MEL-28, SK-MEL-5, UACC-257, UACC-62, RPMI-7951 and M19-MEL); ovarian cancer cell lines (e.g., IGROV1, OVCAR-3, OVCAR-4, OVCAR-5, OVCAR-8 and SK-OV-3); renal cancer cell lines (e.g., 786-0, A498, ACHN, CAKI-1, RXF 393, SN12C, TK-10, UO-31, RXF-631 and SN12K1); prostate cancer cell lines (e.g., PC-3 and DU-145); breast cancer cell lines (e.g., MCF7, NCI/ADR-RES, MDA-MB-231/ATCC, HS 578T, MDA-MB-435, BT-549, T-47D and MDA-MB-468); and thyroid cancer cell lines (e.g., SK-N-SH).

In some embodiments of the invention, the cell proliferative disorder treated by the compounds of the invention, or pharmaceutically acceptable salts thereof, is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, *Blood* 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, *Blood* 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., *Proc. Natl. Acad. Sci. USA*, 2003, 100:11842-9).

In some embodiments of the invention, the hematopoietic neoplasm treated by the compounds of the invention, or pharmaceutically acceptable salts thereof, is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/

Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds of the invention, include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant JAK activity can be treated with the JAK inhibitory compounds.

In some embodiments of the invention, the hematopoietic neoplasm treated by the compounds of the invention, or pharmaceutically acceptable salts thereof, is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant JAK activity can be treated with the JAK inhibitory compounds.

In some embodiments of the invention, the JAK inhibitory compounds of the invention, or pharmaceutically acceptable salts thereof, can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1(CBF-alpha)/ETO, Acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

Animal models useful for testing the efficacy of compounds to treat or prevent the various diseases or conditions described above are well-known in the art. Suitable animal models of hypersensitivity or allergic reactions are described in Foster, (1995) *Allergy* 50(21 Suppl):6-9, discussion 34-38 and Tumas et al., (2001), *J. Allergy Clin. Immunol.* 107(6): 1025-1033. Suitable animal models of allergic rhinitis are described in Szelenyi et al., (2000), *Arzneimittelforschung* 50(11):1037-42; Kawaguchi et al., (1994), *Clin. Exp. Allergy* 24(3):238-244 and Sugimoto et al., (2000), *Immunopharmacology* 48(1):1-7. Suitable animal models of allergic conjunctivitis are described in Carreras et al., (1993), *Br. J. Ophthalmol.* 77(8):509-514; Saiga et al., (1992), *Ophthalmic Res.* 24(1):45-50; and Kunert et al., (2001), *Invest. Ophthalmol. Vis. Sci.* 42(11):2483-2489. Suitable animal models of systemic mastocytosis are described in O'Keefe et al., (1987), *J. Vet. Intern. Med.* 1(2):75-80 and Bean-Knudsen et al., (1989), *Vet. Pathol.* 26(1):90-92. Suitable animal models of hyper IgE syndrome are described in Claman et al., (1990), *Clin. Immunol. Immunopathol.* 56(1):46-53. Suitable animal models of B-cell lymphoma are described in Hough et al., (1998), *Proc. Natl. Acad. Sci. USA* 95:13853-13858 and Hakim et al., (1996), *J. Immunol.* 157(12):5503-5511. Suitable animal models of atopic disorders such as atopic dermatitis, atopic eczema and atopic asthma are described in Chan et al., (2001), *J. Invest. Dermatol.* 117(4):977-983 and Suto et al., (1999), *Int. Arch. Allergy Immunol.* 120(Suppl 1):70-75. Suitable animal models of transplant rejection, such as models of HVGR are described in O'Shea et al., (2004), *Nature Reviews Drug Discovery* 3:555-564; Cetkovic-Curlje & Tibbles, (2004), *Current Pharmaceutical Design* 10:1767-1784; and Chengelian et al., (2003), *Science* 302:875-878. Suitable animal models of polycythemia vera, essential thrombocythemia and primary myelofibrosis are described in Shimoda, (2008) *Leukemia* 22(1):87-95; Lacout, (2006) *Blood* 108(5):1652-60; and Wernig, (2006) *Blood* 107(11):4274-81.

Pharmaceutical Compositions of the Invention and Administration

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral, as used herein, includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units where, for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 75% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.70 mg) to about 100 mg/kg (i.e., 7.0 gm); preferably a therapeutically effective dose is (for a 70 kg mammal) from about 0.01 mg/kg (i.e., 0.7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

Compounds of the invention, or pharmaceutically acceptable salts thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Preparation of the Compounds of the Invention

The following Reaction Schemes illustrate methods to make compounds of formula (I), as isolated stereoisomers or mixtures thereof, or as pharmaceutically acceptable salts thereof. In particular, the following Reaction Scheme illustrates a method to make certain compounds of formula (I), i.e., the compounds of formula (Ia):

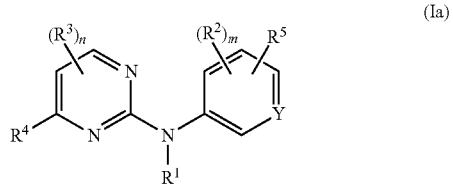

(Ia)

where n, m, Y, $R^1$, $R^2$, $R^3$, $R^4$ and $R^5$ are as described above in the Embodiments section for compounds of formula (Ia), as isolated stereoisomers or mixtures thereof, or as pharmaceutically acceptable salts thereof. It is understood that in the following Reaction Schemes, combinations of substituents and/or variables of the depicted formulae are permissible only if such contributions result in stable compounds. It is also understood that other compounds of formula (I), particularly, compounds of formulae (Ia-1), (Ia-1a), (Ia-1b), (Ia-1c), (Ia-1d), (Ia-1e), (Ia-1f), (Ia-1g), (Ia-1h), (Ia-1i), (Ia-1j), (Ia-1k), (Ia-1l), (Ia-2), (Ia-2a), (Ia-2b), (Ia-2c), (Ia-2d), (Ia-2e), (Ia-2f), (Ia-2g), (Ia-2h), (Ia-2i), (Ia-2j), (Ia-2k) and (Ia-2l), and other compounds of the formula (I) not specifically disclosed herein, may be prepared by one skilled in the organic chemistry field by the methods disclosed herein (by utilizing the appropriately substituted starting materials and modifying the parameters of the synthesis as needed utilizing methods known to one skilled in the art) or by known methods.

Skilled artisans will recognize that in some instances, starting materials and intermediates in the preparation of the compounds of the invention may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts, *Greene's Protective Groups in Organic Synthesis*, 3d Edition, John Wiley & Sons, Inc., New York (1999) and the references cited therein (hereinafter "Greene & Wuts").

Thus, protecting group refers to a group of atoms that, when attached to a reactive functional group in a molecule, mask, reduce or prevent the reactivity of the functional group. Typically, a protecting group can be selectively removed as desired during the course of a synthesis. Examples of protecting groups can be found in Greene and Wuts, as mentioned above, and additionally, in Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated to form acetate and benzoate esters or alkylated to form benzyl and trityl ethers, as well as alkyl ethers, tetrahydropyranyl ethers, trialkylsilyl ethers (e.g., TMS or TIPPS groups) and allyl ethers.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein. $^1$H NMR spectra are recorded in CDCl$_3$, DMSO-d$_6$, CD$_3$OD, or Acetone-d$_6$ with trimethylsilane (TMS) as internal reference using Gemini 300 MHz instrument. Reagents and solvents were purchased from commercial sources and used without further purification. Flash column chromatography was conducted using silica gel (230-400 mesh) under a positive pressure of nitrogen. LCMS spectra for purity and mass were recorded using Waters LCMS instruments. Deionized water was used to dilute the reactions and wash the products. Brine used was prepared by dissolving sodium chloride into deionized water to saturation point.

A. Preparation of Compounds of Formula (Ia1)

Compounds of formula (Ia1) are compounds of formula (Ia), as described above in the Embodiments, where R$^4$ in the compounds of formula (Ia) has the following formula:

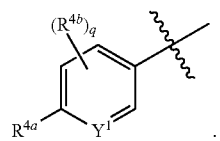

Compounds of formula (Ia1) can be prepared as described below in Reaction Scheme 1 wherein n, m, Y, R$^1$, R$^2$ and R$^3$ are as described above in the Embodiments for compounds of formula (Ia); q is 0, 1 or 2; Y$^1$ is =C(R$^6$) (where R$^6$ is as described above for R$^6$ in the compounds of formula (I), as described above in the Summary of the Invention) or =N—; each Z is chloro or bromo; R$^{4a}$ is —N(R$^6$)R$^7$ (where R$^6$ and R$^7$ are each as described above in the compounds of formula (I), as described above in the Summary of the Invention); and each R$^{4b}$, if present, is independently selected from the group consisting of alkyl, halo and haloalkyl. Preferably, for compounds of formula (Ia1), q is 0.

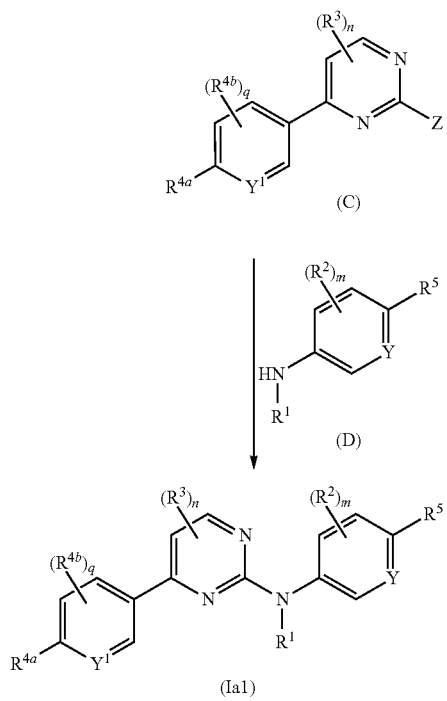

Compounds of formula (A), formula (B) and formula (D) are commercially available, or can be prepared according to methods known to one skilled in the art, or by the methods disclosed herein.

In general, compounds of formula (Ia1) can be prepared by methods known to one skilled in the art and/or by the methods depicted above in Reaction Scheme 1 wherein a compound of formula (B) is coupled with a compound of formula (A) under suitable aromatic coupling conditions, such as, but not limited to, Suzuki coupling conditions known to one skilled in the art to provide a compound of formula (C). Compounds (C) are then treated with a compound of formula (D) under SNAr (Substitution Nucleophilic Aromatic) conditions known to one skill in the art to provide a compound of formula (Ia1).

A specific example of the preparation of a compound of the invention by the method disclosed above in Reaction Scheme 1 is the preparation of the compound (1), which is a compound of formula (Ia1), as shown below in Reaction Scheme 1A.

REACTION SCHEME 1

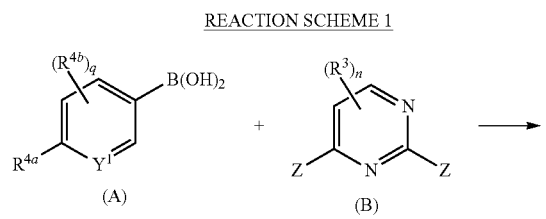

REACTION SCHEME 1A

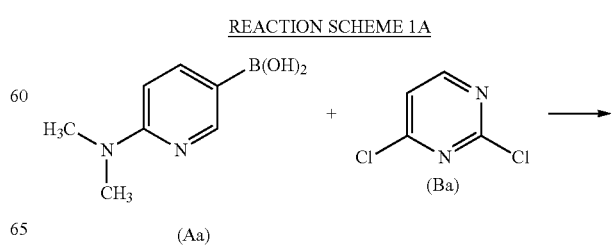

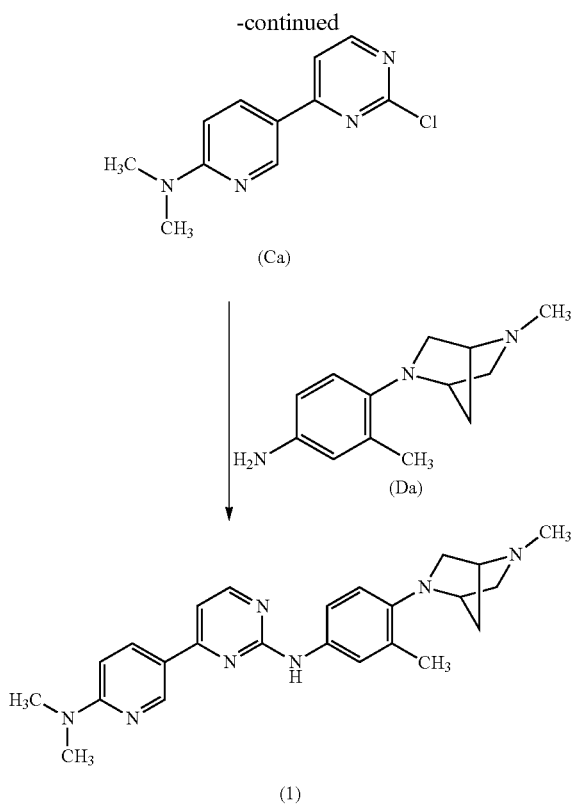

Details of the preparation of compound (1) are provided below in the appropriate Synthetic Preparation and/or Synthetic Example below.

Alternatively, compounds of formula (Ia1) (where n is 0) can be prepared, for example, using a convergent synthesis as described below in Reaction Scheme 2. In particular, compounds of formula (Ia1-1), which are compounds of formula (Ia1) where n is 0 and $R^{4a}$ is $-N(R^{6b})R^{7b}$ (where $R^{6b}$ and $R^{7b}$ are independently selected from hydrogen or alkyl, or together with the common nitrogen to which they are attached, form an optionally substituted N-heterocyclyl), can be prepared as described below in Reaction Scheme 2 wherein m, Y, $R^1$, and $R^2$ are as described above in the Embodiments for compounds of formula (Ia); q is 0, 1 or 2; $Y^1$ is $=C(R^6)$ (where $R^6$ is as described above for $R^6$ in compounds of formula (Ia)) or $=N-$; Z is chloro or bromo; each $R^{4b}$, if present, is independently selected from the group consisting of alkyl, halo and haloalkyl. Preferably, for compounds of formula (Ia1), q is 0, and $R^{6b}$ and $R^{7b}$ are independently selected from hydrogen or alkyl, or together with the common nitrogen to which they are attached, form an optionally substituted N-heterocyclyl.

Compounds of formula (D), formula (E), formula (F), formula (H) and formula (M) are commercially available, or can be prepared according to methods known to one skilled in the art or by the methods disclosed herein.

REACTION SCHEME 2

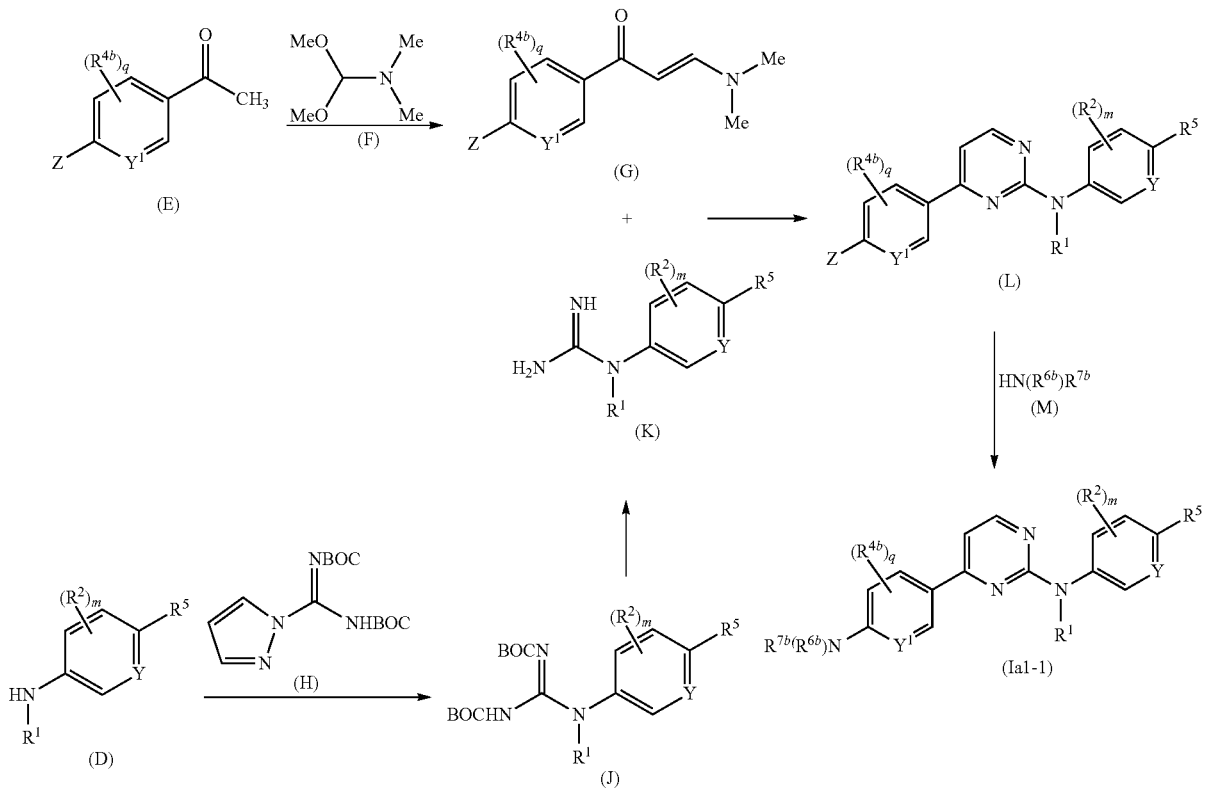

In general, compounds of formula (Ia1-1) can be prepared by methods known to one of ordinary skill in the art and/or by the methods depicted above in the Reaction Scheme 2 wherein, for example, α,β-unsaturated enamines of formula (G) are formed from the corresponding ketones of formula (E), for example, via Wittig-type homologation using compound (F). Guanidines of formula (K) are prepared, for example, via conversion of anilines of formula (D) to the corresponding BOC-protected guanidines of formula (J), followed by deprotection. Guanidines of formula (K) and α,β-unsaturated enamines of formula (G) are then reacted to form the pyrimidine-2-amines of formula (L), which can be further converted to the pyrimidine-2-amines of formula (Ia1-1) via, for example, standard SNAr reaction conditions using, for example, an nucleophilic amine of formula (M).

A specific example of the preparation of a compound of the invention by the method disclosed above in Reaction Scheme 2 is the preparation of compound (1), as shown below in Reaction Scheme 2A.

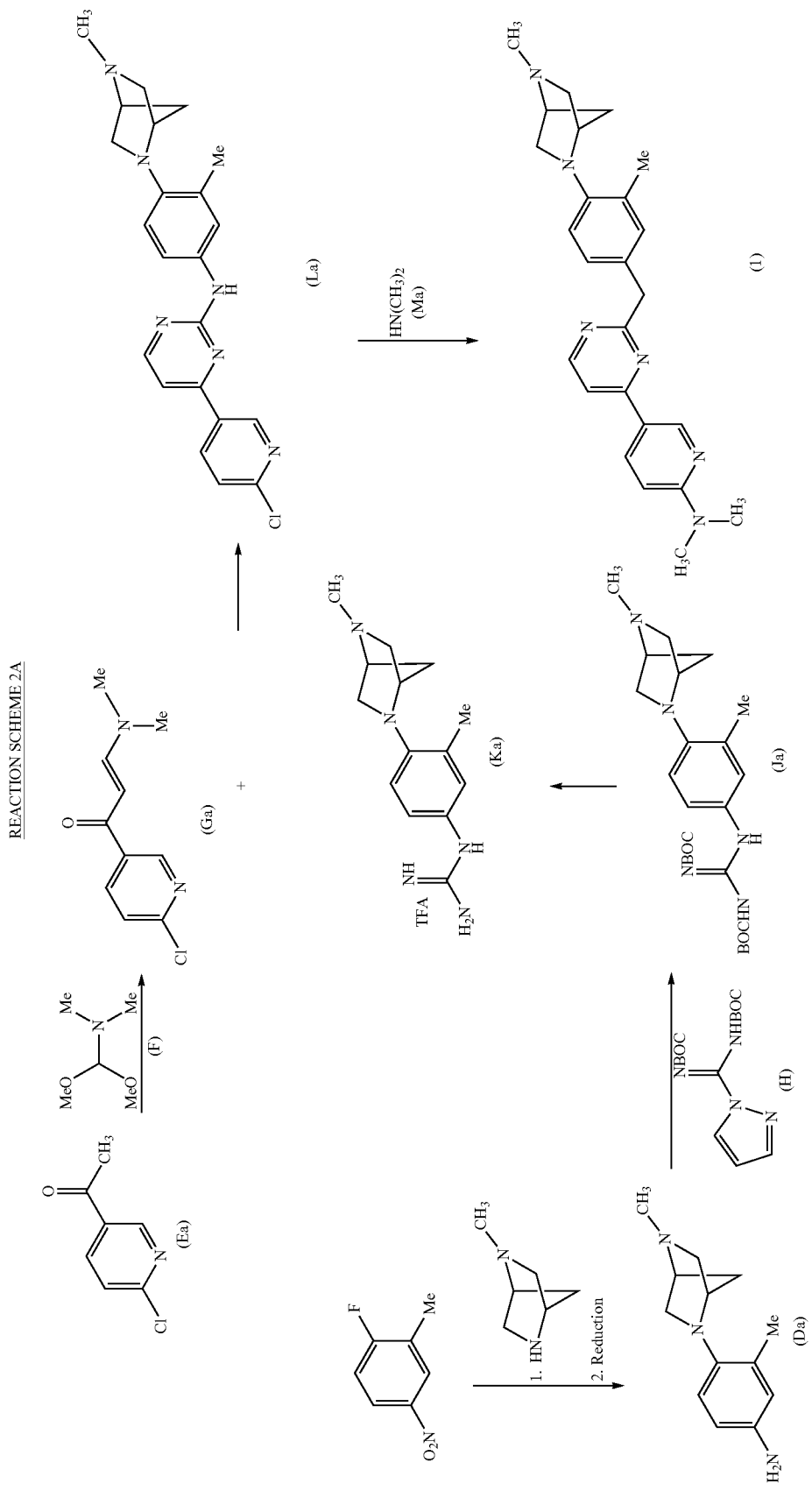

Details of the preparation of compound (I) by this method are provided below in the appropriate Synthetic Preparations and Synthetic Examples.

Another specific example of the preparation of a compound of the invention by the method disclosed above in Reaction Scheme 2 is the preparation of compound (10), as shown below in Reaction Scheme 2B.

REACTION SCHEME 2B
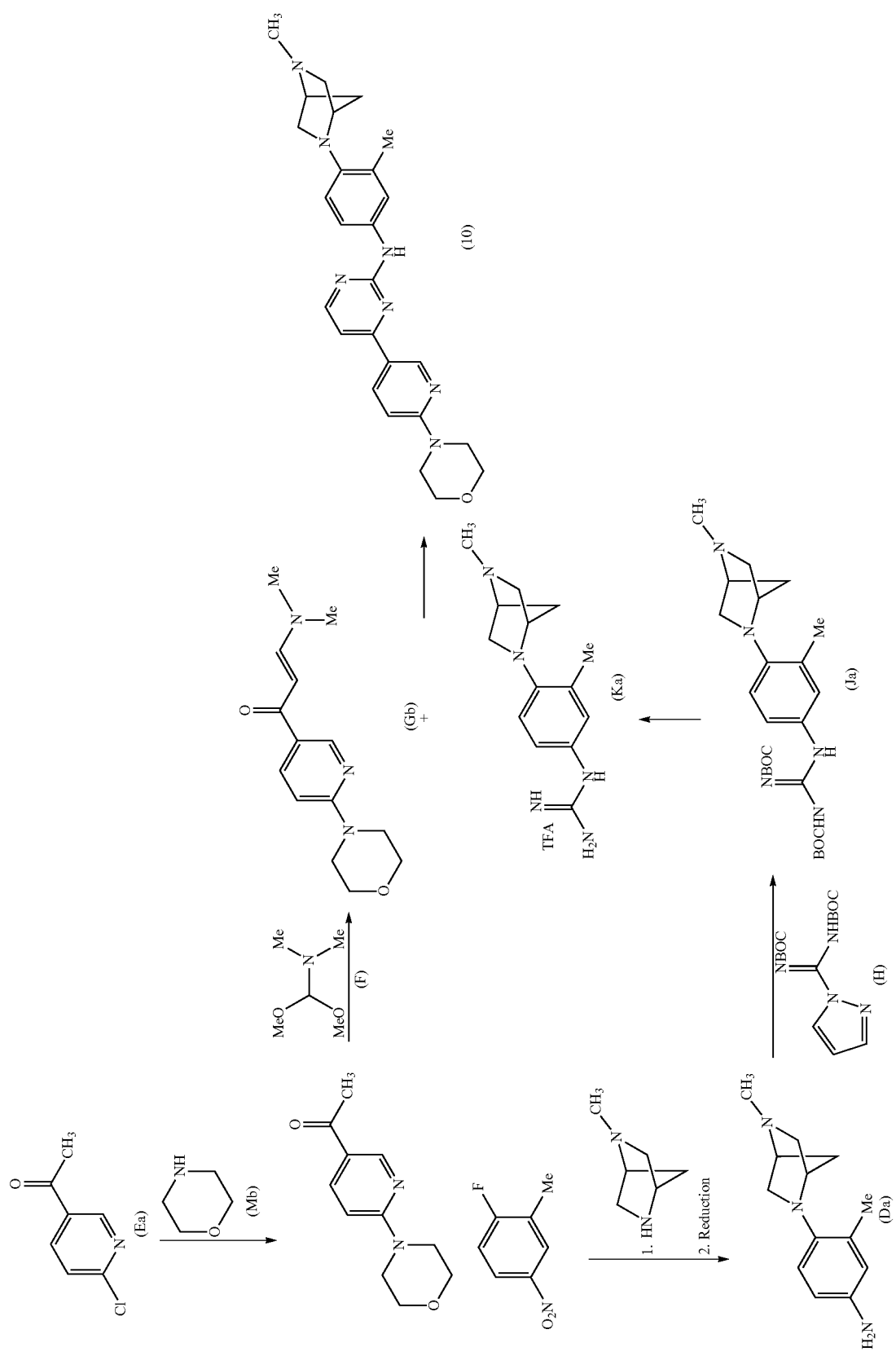

In this example, nucleophilic amine (Mb) was added to pyridine (Ea) prior to formation of the enamine, pyrimidine, etc. Consistent with the prior example, ketone (Eb) is homologated to enamine (Gb). Enamine (Gb) is reacted with guanidine (Ka) to form pyrimidine-2-amine (10). Details of the preparation of compound (10) by this method are provided below in the appropriate Synthetic Preparations and Synthetic Examples.

The pharmaceutically acceptable salts of the compounds of the invention can be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The following specific Synthetic Preparations (for starting materials and intermediates) and Synthetic Examples (for compounds of the invention) are provided as a guide to assist in the practice of the invention, and are not intended as a limitation on the scope of the invention. The number following each compound below refers to its number in Table 2 or Table 3, as discussed in more detail below.

Synthetic Preparation 1

Compounds of Formula (Ca)

2-Chloro-4-(6-dimethylaminopyridin-3-yl)pyrimidine

A flask containing 2,4-dichloropyrimidine (0.5 g, 3.35 mmol), [6-(dimethylamino)pyridin-3-yl]boronic acid (0.61 g, 3.67 mmol) and DME (10 mL) was purged with $N_2$ for 10 min. Dichloro[1,1'-bis(diphenylphosphino)]ferrocene-palladium $CH_2Cl_2$ adduct (0.37 g, 0.50 mmol) and triethylamine (0.85 g, 1.17 mL, 8.33 mmol) were added successively to the flask with continuous bubbling of $N_2$ including 5 min. post addition of the reagents. The reaction mixture was stirred and heated at 90° C. for 5 h. Reaction progress was monitored by TLC (silica gel). The reaction mixture was concentrated and diluted with water, wherein a tan solid formed. The solid was filtered, dried and purified by silica gel column chromatography using 50% EtOAc/hexanes as eluent to provide 2-chloro-4-(6-dimethylaminopyridin-3-yl)pyrimidine as a white solid (0.56 g, 71%); $^1$H NMR (DMSO-d6): δ 8.91 (s, 1H), 8.60 (d, 1H, J=5.3 Hz), 8.20 (dd, 1H, J=2.3 and 9.1 Hz), 7.95 (d, 1H, J=5.3 Hz), 6.74 (d, 1H, J=9.1 Hz), 3.11 (s, 3H). LCMS: purity: 98%; MS (m/e): 235 (MH$^+$).

Synthetic Preparation 2

Compounds of Formula (Da)

3-Methyl-4-[(1S,4S)-5-methyl-2,5-diazabicyclo [2.2.1]heptan-2-yl]aniline

A. (1S,4S)-2-Methyl-2,5-diazabicyclo[2.2.1] heptane.2HBr (6 g, 21.89 mmol) (which can be prepared by similar methods as described in Braish, T. F et al., *J. Org. Chem.* (1990), Vol. 55, pp. 1684-1687), 2-fluoro-5-nitrotoluene (2.61 g, 16.82 mmol) and $K_2CO_3$ (10.57 g, 76.46 mmol) in 30 mL NMP were heated at 110° C. for 14 h while stirring. The reaction mixture was cooled to ambient temperature, poured onto ice-water and stirred until precipitate formation. The yellow solid formed was collected by filtration and washed with 15% EtOAc/hexanes to provide 2-[(1S,4S)-5-methyl-2,5-diazabicyclo[2.2.1]heptan-2-yl]-5-nitrotoluene (3.4 g, 79%) in 98% purity; $^1$H NMR (DMSO-d$_6$): δ 7.88-7.55 (m, 2H), 6.69 (d, 1H, J=8.8 Hz), 4.37 (s, 1H), 3.64 (dd, 1H, J=2.0 and 9.9 Hz), 3.38-3.55 (m, 2H), 2.81 (d, 1H, J=9.9 Hz), 2.65 (d, 1H, J=9.9 Hz), 2.33 (s, 3H), 2.23 (s, 3H), 1.87 (d, 1H, J=9.3 Hz), 1.75 (d, 1H, J=9.3 Hz); LCMS: purity: 98%; MS (m/e): 248 (MH$^+$).

B. 2-[(1S,4S)-5-Methyl-2,5-diazabicyclo[2.2.1]hept-2-yl]-5-nitrotoluene (3.3 g) was dissolved in EtOH (50 mL) and transferred to Parr hydrogenation flask. Catalyst, Pd/C (450 mg), was added and the mixture subjected to hydrogenation at 30 PSI for 2 h. The reaction mixture was filtered through Celite and the Celite filter cake washed with EtOH. Concentration of the combined filtrate provided 3-methyl-4-[(1S,4S)-5-methyl-2,5-diazabicyclo[2.2.1]heptan-2-yl] aniline, as a tan solid (2.52 g, 86%). $^1$H NMR (DMSO-d$_6$): δ 6.58 (d, 1H, J=8.8 Hz), 6.34 (s, 1H), 6.27 (d, 1H, J=8.8 Hz), 4.46 (s, 2H), 3.61 (s, 1H), 3.24 (s, 1H), 3.16 (d, 1H, J=9.3 Hz), 2.93 (dd, 1H, J=1.8 and 9.3 Hz), 2.61 (qt, 2H, J=9.3 Hz), 2.26 (s, 3H), 2.05 (s, 3H), 1.70 (d, 1H, J=9.1 Hz), 1.63 (d, 1H, J=9.1 Hz). LCMS: purity: 97%; MS (m/e): 218 (MH$^+$).

C. Alternatively, a heterogeneous mixture of (1S,4S)-2-methyl-2,5-diazabicyclo[2.2.1]heptane 2HBr salt (0.544 g, 2 mmol), 2-fluoro-5-nitrotoluene (0.310 g, 2 mmol) and DIPEA (0.387 g, 6 mmol) in NMP was refluxed for 2 days. The resulting residue was purified by column chromatography (silica gel, hexanes then 5-10% EtOAc in hexanes to afford 2-[(1S,4S)-5-methyl-2,5-diazabicyclo[2.2.1]heptan-2-yl]-5-nitrotoluene, which was reduced by hydrogenation ($H_2$, 10% Pd/C, MeOH, 40 PSI) to afford 3-methyl-4-[(1S, 4S)-5-methyl-2,5-diazabicyclo[2.2.1]heptan-2-yl]aniline; LCMS: purity: 91%; MS (m/e): 218 (MH$^+$).

D. Alternatively, (1S,4S)-2-Methyl-2,5-diazabicyclo [2.2.1]heptane.2HBr (24.8 g, 90.5 mmol), 2-fluoro-5-nitrotoluene (12.0 g, 77.3 mmol) and $K_2CO_3$ (43.7 g, 316.9 mmol) in 90 mL NMP were heated at 110° C. for 14 h by stirring. The reaction mixture was allowed to cool and quenched by pouring into water (500 mL). The contents were then stirred until precipitation was observed (3-4 h). The yellow solid formed was collected by filtration. The resulting filter cake washed with water (700 mL) and dried under vacuum suction. The filter cake was re-suspended in 10% EtOAc/hexanes (100 mL) as a slurry and then filtered to provide the desired material 2-[(1S,4S)-5-methyl-2,5-diazabicyclo[2.2.1]hept-2-yl]-5-nitrotoluene (14.2 g, 74% based on nitrotoluene; 63% based on diazabicycloheptane) after drying; $^1$H NMR (DMSO-d$_6$): δ 7.88-7.55 (m, 2H), 6.69 (d, 1H, J=8.8 Hz), 4.37 (s, 1H), 3.64 (dd, 1H, J=2.0 and 9.9 Hz), 3.38-3.55 (m, 2H), 2.81 (d, 1H, J=9.9 Hz), 2.65 (d, 1H, J=9.9 Hz), 2.33 (s, 3H), 2.23 (s, 3H), 1.87 (d, 1H, J=9.3 Hz), 1.75 (d, 1H, J=9.3 Hz). LCMS: purity: 98%; MS (m/e): 248 (MH$^+$).

E. 2-[(1S,4S)-5-Methyl-2,5-diazabicyclo[2.2.1]hept-2-yl]-5-nitrotoluene (14.2 g), as prepared above in Paragraph D, was dissolved in EtOH (50 mL), transferred to a Parr hydrogenation flask. Pd/C (1.5 g) was introduced to above flask and subjected to hydrogenation at 30 psi for 2 h. The reaction mixture was filtered through Celite and the filter cake was washed further with EtOH (300 mL). Concentration of the filtrate provided 3-Methyl-4-[(1S,4S)-5-methyl-2,5-diazabicyclo[2.2.1]hept-2-yl]aniline as a white-tan solid (11.7 g, 86%); $^1$H NMR (DMSO-d$_6$): δ 6.58 (d, 1H, J=8.8 Hz), 6.34 (s, 1H), 6.27 (d, 1H, J=8.8 Hz), 4.46 (s, 2H), 3.61 (s, 1H), 3.24 (s, 1H), 3.16 (d, 1H, J=9.3 Hz), 2.93 (dd, 1H, J=1.8 and 9.3 Hz), 2.61 (qt, 2H, J=9.3 Hz), 2.26 (s, 3H), 2.05

(s, 3H), 1.70 (d, 1H, J=9.1 Hz), 1.63 (d, 1H, J=9.1 Hz). LCMS: purity: 97%; MS (m/e): 218 (MH$^+$).

Synthetic Preparation 3

Compounds of Formula (D)

4-(1,4-Diazabicyclo[3.2.2.]nonan-4-yl)-3-methylaniline

A. A mixture of 2-fluoro-5-nitrotoluene (1.08 g, 6.98 mmol), 1,4-diazabicyclo[3.2.2]nonane (0.8 g, 6.34 mmol) and K$_2$CO$_3$ (2.2 g, 15.86 mmol) in 8 mL of DMF was stirred at 100° C. for 16 h. After cooling to ambient temperature, water (40 mL) was slowly added to the mixture. The resulting (yellow) solid was filtered and washed three times with water. Thin layer chromatography showed trace amount of starting aryl fluoride. The solid 4-(2-methyl-4-nitrophenyl)-1,4-diazabicyclo[3.2.2]nonane was suspended in 25 mL of Et$_2$O, sonicated for 10 min, collected by filtration and washed with Et$_2$O; 950 mg; Purity (LC-MS): >97%; MS (m/e): 262.4 (MH$^+$).

B. 4-(2-Methyl-4-nitrophenyl)-1,4-diazabicyclo[3.2.2]nonane (950 m) was dissolved in 30 mL of MeOH. Catalyst, 10% Pd—C (300 mg), was then added, and the mixture was hydrogenated at the atmosphere of H$_2$ (50 psi) for 1 h. The reaction mixture was filtered through Celite and washed with MeOH. 4-(1,4-Diazabicyclo[3.2.2.]nonan-4-yl)-3-methylaniline was obtained as a dark oil in quantitative yield; Purity (LC-MS): 97.48%; MS (m/e): 231.1 (MH$^+$).

Synthetic Preparation 4

Compounds of Formula (Eb)

1-[6-(Morpholin-4-yl)pyridin-3-yl)]ethanone 1-(6-chloro-3-pyridinyl)ethanone (20 g, 128.55 mmol) and morpholine (43 mL, 43 g, 493 mmol) in ethanol (100 mL) were heated to reflux at 95° C. Upon consumption of 1-(6-chloro-3-pyridinyl)ethanone (18 h), the reaction mixture was cooled and concentrated to dryness. An ice-cold solution of water (65 mL) was transferred to the above material, then sonicated for 10 min and stirred at 0° C. for a period of 2 h. The solid formed was collected by filtration and suction dried. Further workup of the solid by reslurrying in ice-cold solution of water (250 mL) and filtration of the slurry provided 18.8 g (70%) of 1-[6-(morpholin-4-yl)pyridin-3-yl)]ethanone as off-white tan solid after vacuum drying; $^1$H NMR (DMSO-d$_6$): δ 8.71 (d, 1H, J=2.4 Hz), 8.00 (dd, 1H, J=1.4 and 9.0 Hz), 6.86 (d, 1H, J=9.0 Hz), 2.44 (s, 3H). LCMS: purity: 96%; MS (m/e): 207 (MH$^+$).

Synthetic Preparation 5

Compounds of Formula (Ga)

3-(3-(Dimethylamino)prop-2-en-1-onyl)-6-chloropyridine

A homogeneous mixture of 3-acetyl-6-chloropyridine (5 mL) (which can be prepared in a similar manner by the methods disclosed in Lee, C-H. et al., *J. Med. Chem.* (2001), Vol. 44, pp. 2133-2138) in N,N-dimethylformamide dimethylacetal (15 mL) was refluxed for 4 h. After cooling the reaction mixture to ambient temperature, it was diluted with hexanes (100 mL), sonicated for 30 seconds and the solid formed was isolated by filtration. The resulting solid was then washed with hexanes (3×25 mL), dried and analyzed to afford 3-(3-(dimethylamino)prop-2-en-1-onyl)-6-chloropyridine; LCMS: purity: 92%; MS (m/e): 212 (MH$^+$).

Synthetic Preparation 6

Compounds of Formula (Gb)

3-[3-(Dimethylamino-2-propen-1-one)-6-(morpholin-4-yl)pyridine

1-[6-(morpholin-4-yl)pyridin-3-yl)]ethanone (18 g, 87.3 mmol) in N,N-dimethylformamide dimethylacetal (100 mL) was heated to reflux (110° C.) till complete consumption of 1-[6-(morpholin-4-yl)pyridin-3-yl)]ethanone as determined by silica gel TLC and LC/MS. After 45 h, the heterogeneous reaction mixture was cooled to ambient temperature and the crude product collected by filtration. The filter cake was washed with Et$_2$O (75 mL) and dried under vacuum to provide 18.0 g (78%) of 3-[3-(dimethylamino-2-propen-1-one)-6-(morpholin-4-yl)pyridine; $^1$H NMR (DMSO-d$_6$): δ 8.69 (d, 1H, J=2.4 Hz), 8.00 (dd, 1H, J=2.4 and 9.0 Hz), 7.62 (d, 1H, J=12.3 Hz), 6.80 (d, 1H, J=9.0 Hz), 5.76 (d, 1H, J=12.3 Hz), 3.68-3.65 (m 4H), 3.61-3.59 (m, 4H), 3.30 (s, 3H), 2.87 (s, 3H). LCMS: purity: 99%; MS (m/e): 262 (MH$^+$)

Synthetic Preparation 7

Compounds of Formula (Ja)

[3-methyl-4-((1S,4S)-2-methyl-2,5-diazabicyclo[2.2.1]heptan-5-yl)phenyl][N,N-bis(tert-butoxycarbonyl)]guanidine A. Compound (Da), 3-methyl-4-[(1S,4S)-5-methyl-2,5-diazabicyclo[2.2.1]heptan-2-yl]aniline, (0.105 g, 0.6 mmol) and 1-(tert-butoxycarbonylamino(tert-butoxycarbonylimino)methyl)pyrazole (H) (0.186 g, 0.6 mmol) were combined in DMF (2 mL) and stirred at ambient temperature for 3 days. The reaction was monitored by LCMS. The homogenous reaction mixture was then diluted with water (20 mL), the solid precipitate formed was isolated by filtration, and purified by column chromatography (silica gel, CH$_2$Cl$_2$ then 2-5% MeOH in CH$_2$Cl$_2$) to give [3-methyl-4-((1S,4S)-2-methyl-2,5-diazabicyclo[2.2.1]heptan-5-yl)phenyl][N,N-bis(tert-butoxycarbonyl)]guanidine; LCMS: purity: 99%; MS (m/e): 460 (MH$^+$).

B. On a larger scale, 3-methyl-4-[(1S,4S)-5-methyl-2,5-diazabicyclo[2.2.1]hept-2-yl]aniline (10.0 g, 45.8 mmol) and 1-(tert-butoxycarbonylamino(tert-butoxycarbonylimino)methyl)pyrazole (15.0 g, 48.2 mmol) were combined in DMF (25 mL) and stirred at ambient temperature. The progress of homogenous reaction was monitored by LC/MS. After 36 h, the reaction mixture was added slowly to water (300 mL) in a beaker with vigorous stirring, whereupon a precipitate formed. The reaction flask was rinsed with DMF (2×5 mL) and transferred to the beaker. Suction filtration of the suspension, further washing of the resulting filter cake with water (200 mL) and air drying under suction provided 20.5 g (97%) of [3-methyl-4-((1S, 4S)-2-methyl-2,5-diazabicyclo[2.2.1]heptan-5-yl)phenyl] [N,N-bis(tert-butoxycarbonyl)]guanidine (Ja) as a off-white purple solid; LCMS: purity: 96%; MS (m/e): 449 (MH$^+$).

Synthetic Preparation 8

Compounds of Formula (Ka)

[3-methyl-4-((1S,4S)-2-methyl-2,5-diazabicyclo[2.2.1]heptan-5-yl)phenyl]guanidine A. A solution of [3-methyl-4-((1S,4S)-2-methyl-2,5-diazabicyclo[2.2.1]heptan-5-yl)phenyl][N,N-bis(tert-butoxycarbonyl)]guanidine (0.100 g) in $CH_2Cl_2$ (20 mL) with TFA (5 mL) was stirred at ambient temperature for 4 h. The reaction progress was monitored by TLC (silica gel). The resulting mixture was concentrated and the lyophilized to afford [3-methyl-4-((1S,4S)-2-methyl-2,5-diazabicyclo[2.2.1]heptan-5-yl)phenyl]guanidine, as a TFA salt; LCMS: purity: 89%; MS (m/e): 260 (MH$^+$).

B. Alternatively, TFA (80 mL) was added to a stirred solution of [3-methyl-4-((1S,4S)-2-methyl-2,5-diazabicyclo[2.2.1]heptan-5-yl)phenyl][N,N-bis(tert-butoxycarbonyl)]guanidine (20.2 g) in $CH_2Cl_2$ (80 mL) at 0° C. over a period of 30 min. The ice-bath was removed after 1 h and the reaction contents allowed to stir. Progress of the reaction mixture was monitored by LC/MS. The reaction mixture was concentrated after complete conversion of the starting material to [3-methyl-4-((1S,4S)-2-methyl-2,5-diazabicyclo[2.2.1]heptan-5-yl)phenyl]guanidine, dried overnight under high vacuum and used in the next step without further purification. LCMS: purity: 96%; Crude weight: 45.4 g, back calculation provided approximately 34 g of total amount of TFA present in the crude.

Synthetic Example 1

4-(6-(N,N-dimethylamino)pyridin-3-yl)-N-(3-methyl-4-((1S,4S)-5-methyl-2,5-diazabicyclo[2.2.1]heptan-2-yl)phenyl)pyrimidin-2-amine

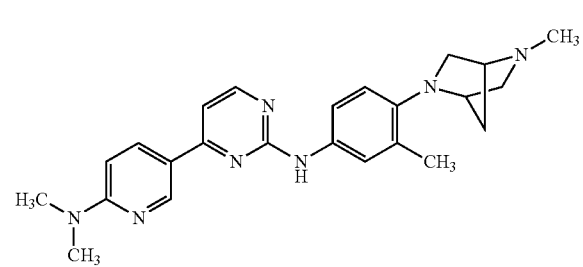

A. 2-Chloro-4-(6-dimethylaminopyridin-3-yl)pyrimidine (35 mg, 0.15 mmol) and 3-methyl-4-[(1S,4S)-5-methyl-2,5-diazabicyclo[2.2.1]heptan-2-yl]phenylamine (55 mg, 0.25 mmol) in 1.5 mL 2-propanol with TFA (4 drops) were heated at 100° C. for 12 h in a sealed tube. Reaction progress was monitored by LC/MS. Upon completion, the reaction mixture was concentrated and purified by preparative HPLC. The pure concentrate, obtained after purification, was exposed to aq. $K_2CO_3$ solution to neutralize any acid remaining. The solid formed upon exposure to aq. $K_2CO_3$ solution was collected by filtration, washed with water and dried to provide 4-(6-(N,N-dimethylamino)pyridin-3-yl)-N-(3-methyl-4-((1S,4S)-5-methyl-2,5-diazabicyclo[2.2.1]heptan-2-yl)phenyl)pyrimidin-2-amine, compound #1, as an off-white solid (35 mg, 56%). $^1$H NMR (DMSO-d$_6$): δ 9.13 (s, 1H), 8.81 (s, 1H), 8.31 (d, 1H, J=5.3 Hz), 8.20 (dd, 1H, J=2.3 and 8.8 Hz), 7.49 (dd, 1H, J=2.3 and 8.8 Hz), 7.43 (s, 1H), 7.17 (d, 1H, J=5.3 Hz), 6.74 (d, 2H, J=8.8 Hz), 3.88 (s, 1H), 3.20 (app qt, 2H, J=9.0 Hz), 3.09 (s, 6H), 2.71 (app qt, 2H, J=9.0 Hz), 2.27 (s, 3H), 2.19 (s, 3H), 1.77 (d, 1H, J=9.0 Hz), 1.69 (d, 1H, J=9.0 Hz); LCMS: purity: 98%; MS (m/e): 416 (MH$^+$).

B. Alternatively, a heterogeneous mixture of 3-(3-(dimethylamino)prop-2-en-1-onyl)-6-chloropyridine (0.063 g, 0.75 mmol) and [3-methyl-4-((1S,4S)-2-methyl-2,5-diazabicyclo[2.2.1]heptan-5-yl)phenyl]guanidine TFA salt (0.110 g, 0.75 mmol) with $K_2CO_3$ (0.051 g, 2.25 mmol) in isopropanol (1 mL) was shaken in a sealed tube at 100° C. in for 24 h. The formation of 4-(6-(chloro)pyridin-3-yl)-N-(3-methyl-4-((1S,4S)-5-methyl-2,5-diazabicyclo[2.2.1]heptan-2-yl)phenyl)pyrimidin-2-amine was confirmed by LCMS. To this reaction vial 40% of aqueous solution of $Me_2NH.HCl$ solution (1 mL) was added and then heated in a sealed tube for 3 h at 100° C. The resulting reaction mixture was purified by column chromatography (silica gel; $CH_2Cl_2$ then 1% 2N $NH_3$/MeOH in $CH_2Cl_2$) to afford 4-(6-(N,N-dimethylamino)pyridin-3-yl)-N-(3-methyl-4-((1S,4S)-5-methyl-2,5-diazabicyclo[2.2.1]heptan-2-yl)phenyl)pyrimidin-2-amine, compound #1; LCMS: purity: 99%; MS (m/e): 416 (MH$^+$).

Synthetic Example 2

4-(6-(N,N-dimethylamino)pyridin-3-yl)-5-methyl-N-(3-methyl-4-((1S,4S)-5-methyl-2,5-diazabicyclo[2.2.1]heptan-2-yl)phenyl)pyrimidin-2-amine

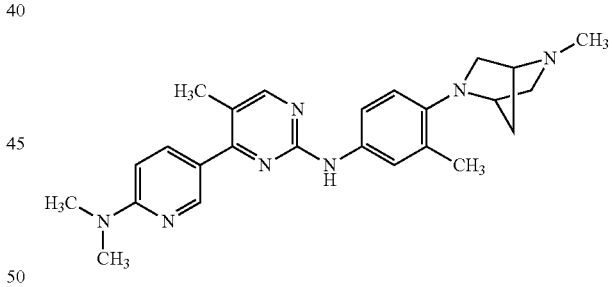

Following substantially one of the procedures as described in SYNTHETIC EXAMPLE 1 and making non-critical variations in the experimental parameters and using the appropriately substituted starting materials and reagents, 4-(6-(N,N-dimethylamino)pyridin-3-yl)-5-methyl-N-(3-methyl-4-((1S,4S)-5-methyl-2,5-diazabicyclo[2.2.1]heptan-2-yl)phenyl)pyrimidin-2-amine, compound #2, was obtained; $^1$H NMR (DMSO-d$_6$): δ 9.04 (s, 1H), 8.48 (d, 1H, J=1.8 Hz), 8.22 (s, 1H), 7.89 (dd, 1H, J=2.0 and 8.8 Hz), 7.45 (app d, 1H, J=8.8 Hz), 7.40 (s, 1H), 6.71 (t, 2H, J=8.8 Hz), 3.84 (s, 1H), 3.18 (d, 1H, J=9.0 Hz), 3.11 (d, 1H, J=9.0 Hz), 3.08 (s, 6H), 2.72 (d, 1H, J=9.0 Hz), 2.64 (d, 1H, J=9.0 Hz), 2.25 (s, 3H), 2.23 (s, 3H), 2.16 (s, 3H), 1.75 (d, 1H, J=9.0 Hz), 1.67 (d, 1H, J=9.0 Hz); LCMS: purity: 99%; MS (m/e): 430 (MH$^+$).

Synthetic Example 3

4-(6-(N,N-dimethylamino)pyridin-3-yl)-5-trifluoromethyl-N-(3-methyl-4-((1S,4S)-5-methyl-2,5-diazabicyclo[2.2.1]heptan-2-yl)phenyl)pyrimidin-2-amine

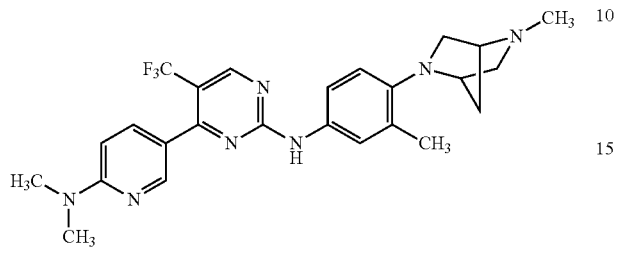

Following substantially one of the procedures as described in SYNTHETIC EXAMPLE 1 and making non-critical variations in the experimental parameters and using the appropriately substituted starting materials and reagents, 4-(6-(N,N-dimethylamino)pyridin-3-yl)-5-trifluoromethyl-N-(3-methyl-4-((1S,4S)-5-methyl-2,5-diazabicyclo[2.2.1]heptan-2-yl)phenyl)pyrimidin-2-amine, compound #3, was obtained; $^1$H NMR (DMSO-d$_6$): δ 9.91 (s, 1H), 8.68 (s, 1H), 8.34 (s, 1H), 7.74 (app d, 1H, J=8.8 Hz), 7.40-7.37 (m, 2H), 6.73 (d, 1H, J=8.8 Hz), 6.71 (d, 1H, J=8.8 Hz), 3.90 (s, 1H), 3.18 (s, 2H), 3.08 (s, 6H), 2.72 (d, 1H, J=9.0 Hz), 2.65 (d, 1H, J=9.0 Hz), 2.25 (s, 3H), 2.17 (s, 3H), 1.77 (d, 1H, J=9.0 Hz), 1.67 (d, 1H, J=9.0 Hz); LCMS: purity: 99%; MS (m/e): 484 (MH$^+$).

Synthetic Example 4

4-(6-(N,N-dimethylamino)pyridin-3-yl)-5-fluoro-N-(3-methyl-4-((1S,4S)-5-methyl-2,5-diazabicyclo[2.2.1]heptan-2-yl)phenyl)pyrimidin-2-amine

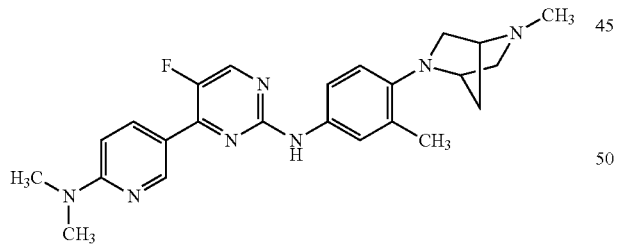

Following substantially one of the procedures as described in SYNTHETIC EXAMPLE 1 and making non-critical variations in the experimental parameters and using the appropriately substituted starting materials and reagents, 4-(6-(N,N-dimethylamino)pyridin-3-yl)-5-fluoro-N-(3-methyl-4-((1S,4S)-5-methyl-2,5-diazabicyclo[2.2.1]heptan-2-yl)phenyl)pyrimidin-2-amine, compound #4, was obtained; $^1$H NMR (DMSO-d$_6$): δ 9.23 (s, 1H), 8.80 (s, 1H), 8.40 (d, 1H, J=4.1 Hz), 8.15 (app d, 1H, J=9.1 Hz), 7.43-7.38 (m, 2H), 6.79 (d, 1H, J=9.1 Hz), 6.73 (d, 1H, J=8.8 Hz), 3.87 (s, 1H), 3.21 (d, 1H, J=9.0 Hz), 3.17 (d, 1H, J=9.0 Hz), 3.10 (s, 6H), 2.72 (d, 1H, J=9.0 Hz), 2.66 (d, 1H, J=9.0 Hz), 2.26 (s, 3H), 2.18 (s, 3H), 1.76 (d, 1H, J=9.0 Hz), 1.67 (d, 1H, J=9.0 Hz); LCMS: purity: 99%; MS (m/e): 434 (MH$^+$).

Synthetic Example 5

4-(6-(N,N-dimethylamino)pyridin-3-yl)-5-fluoro-N-(3-fluoro-4-((1S,4S)-5-methyl-2,5-diazabicyclo[2.2.1]heptan-2-yl)phenyl)pyrimidin-2-amine

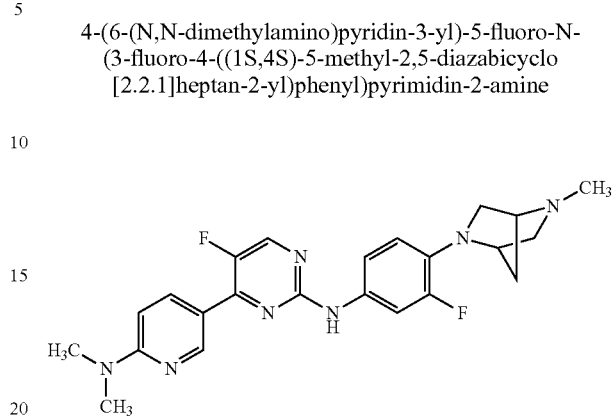

Following substantially one of the procedures as described in SYNTHETIC EXAMPLE 1 and making non-critical variations in the experimental parameters and using the appropriately substituted starting materials and reagents, 4-(6-(N,N-dimethylamino)pyridin-3-yl)-5-fluoro-N-(3-fluoro-4-((1S,4S)-5-methyl-2,5-diazabicyclo[2.2.1]heptan-2-yl)phenyl)pyrimidin-2-amine, compound #5, was obtained; $^1$H NMR (DMSO-d$_6$): δ 9.45 (s, 1H), 8.80 (s, 1H), 8.44 (d, 1H, J=1.4 and 9.0 hz), 7.58 (dd, 1H, J=9.1 and 16 Hz), 7.29 (d, 1H, J=8.8 hz), 6.80 (d, 1H, J=9.1H), 6.68 (app t, 1H, J=9.3 Hz), 4.15 (s, 1H), 3.39 (d, 1H, J=9.0 Hz), 3.16 (d, 1H, J=9.0 Hz), 3.11 (s, 6H), 2.72 (d, 1H, J=9.1 Hz), 2.59 (d, 1H, J=9.0 Hz), 2.23 (s, 3H), 1.80 (d, 1H, J=9.0 Hz), 1.69 (d, 1H, J=9.0 Hz); LCMS: purity: 98%; MS (m/e): 438 (MH$^+$).

Synthetic Example 6

4-(6-(N,N-dimethylamino)pyridin-3-yl)-5-methyl-N-(3-fluoro-4-((1S,4S)-5-methyl-2,5-diazabicyclo[2.2.1]heptan-2-yl)phenyl)pyrimidin-2-amine

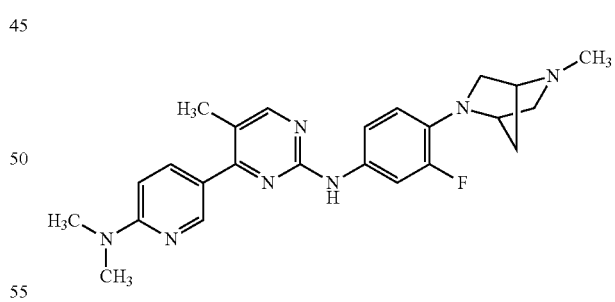

Following substantially one of the procedures as described in SYNTHETIC EXAMPLE 1 and making non-critical variations in the experimental parameters and using the appropriately substituted starting materials and reagents, 4-(6-(N,N-dimethylamino)pyridin-3-yl)-5-methyl-N-(3-fluoro-4-((1S,4S)-5-methyl-2,5-diazabicyclo[2.2.1]heptan-2-yl)phenyl)pyrimidin-2-amine, compound #6, was obtained; $^1$H NMR (DMSO-d$_6$): δ 9.27 (s, 1H), 8.49 (d, 1H, J=2.3 Hz), 8.26 (s, H), 7.88 (d, 1H, J=2.3 and 8.8 Hz), 7.66 (d, 1H, J=2.3 and 16.8 Hz), 7.31 (d, 1H, J=8.8 Hz), 6.73 (d, 1H, J=8.8 Hz), 6.65 (app t, 1H, J=10.0 Hz), 4.13 (s, 1H), 3.37 (app d, 1H, J=9.0 Hz), 3.15 (dd, 1H, J=2.6 and 9.0 Hz), 3.08 (s, 6H), 2.70 (d, 1H, J=9.0 Hz), 2.59 (d, 1H, J=9.0 Hz), 2.24 (s, 3H), 2.23 (s, 3H), 1.79 (d, 1H, J=9.0 Hz), 1.69 (d, 1H, J=9.0 Hz); LCMS: purity: 98%; MS (m/e): 434 (MH⁺).

Synthetic Example 7

4-(6-(N,N-dimethylamino)pyridin-3-yl)-N-(3-fluoro-4-((1S,4S)-5-methyl-2,5-diazabicyclo[2.2.1]heptan-2-yl)phenyl)pyrimidin-2-amine

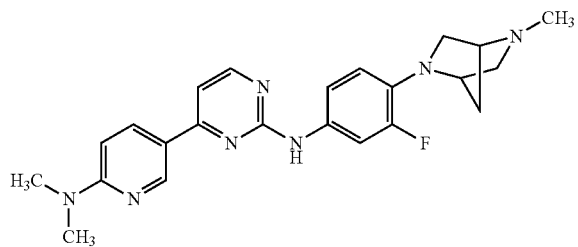

Following substantially one of the procedures as described in SYNTHETIC EXAMPLE 1 and making non-critical variations in the experimental parameters and using the appropriately substituted starting materials and reagents, 4-(6-(N,N-dimethylamino)pyridin-3-yl)-N-(3-fluoro-4-((1S,4S)-5-methyl-2,5-diazabicyclo[2.2.1]heptan-2-yl)phenyl)pyrimidin-2-amine, compound #7, was obtained; ¹H NMR (DMSO-d₆): δ 9.36 (s, 1H), 8.88 (s, 1H), 8.35 (d, 1H, J=5.3 Hz), 8.19 (dd, 1H, J=2.3 and 8.8 Hz), 7.64 (d, 1H, J=2.3 and 16.8 Hz), 7.35 (d, 1H, J=8.2 Hz), 7.22 (d, 1H, J=5.3 Hz), 6.75 (d, 1H, J=9.1 Hz), 6.65 (app t, 1H, J=9.0 Hz), 4.16 (s, 1H), 3.39 (app d, 1H, J=9.0 Hz), 3.18 (app d, 1H, J=9.0 Hz), 3.10 (s, 6H), 2.72 (d, 1H, J=9.1 Hz), 2.59 (d, 1H, J=9.0 Hz), 2.23 (s, 3H), 1.79 (d, 1H, J=9.0 Hz), 1.69 (d, 1H, J=9.0 Hz); LCMS: purity: 98%; MS (m/e): 420 (MH⁺).

Synthetic Example 8

4-(4-methyl-3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine

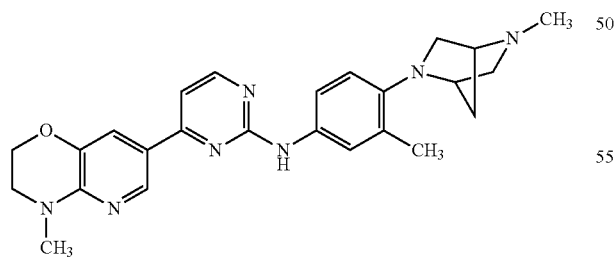

Following substantially one of the procedures as described in SYNTHETIC EXAMPLE 1 and making non-critical variations in the experimental parameters and using the appropriately substituted starting materials and reagents, 4-(4-methyl-3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine, compound #8, was obtained; ¹H NMR (DMSO-d₆): δ 9.13 (s, 1H), 8.49 (app s, 1H), 8.31 (d, 1H, J=5.3 Hz), 7.70 (app s, 1H), 7.45 (app s, 2H), 7.16 (d, 1H, J=5.3 Hz), 6.73 (d, 1H, J=8.4 Hz), 4.22 (m, 2H), 3.88 (s, 1H), 3.51 (s, 2H), 3.19 (d, 1H, J=9.5 Hz), 3.14 (app d, 1H, J=9.5 Hz), 3.10 (s, 6H), 2.72 (d, 1H, J=9.5 Hz), 2.65 (d, 1H, J=9.5 Hz), 2.26 (s, 3H), 2.18 (s, 3H), 1.76 (d, 1H, J=9.0 Hz), 1.69 (d, 1H, J=9.0 Hz); LCMS: purity: 98%; MS (m/e): 444 (MH⁺).

Synthetic Example 9

4-(4-methyl-3,4-dihydro-2H-pyrido[3,2-b][1,4]oxazin-7-yl)-N-(3-fluoro-4-((1S,4S)-5-methyl-2,5-diazabicyclo[2.2.1]heptan-2-yl)phenyl)pyrimidin-2-amine

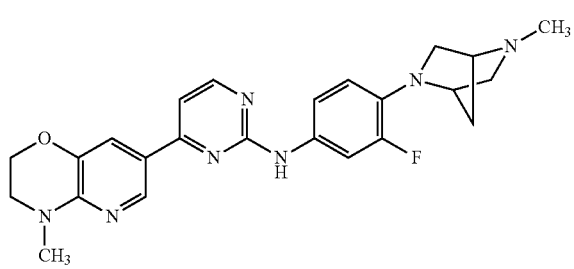 [SMILES: CN1CCOc2cc(-c3ccnc(Nc4ccc(N5CC6CC5CN6C)c(F)c4)n3)cnc21]

Following substantially one of the procedures as described in SYNTHETIC EXAMPLE 1 and making non-critical variations in the experimental parameters and using the appropriately substituted starting materials and reagents, 4-(4-methyl-3,4-dihydro-2H-pyrido[3,2-b][1,4]oxazin-7-yl)-N-(3-fluoro-4-((1S,4S)-5-methyl-2,5-diazabicyclo[2.2.1]heptan-2-yl)phenyl)pyrimidin-2-amine, compound #9, was obtained; ¹H NMR (DMSO-d₆): δ 9.34 (s, 1H), 8.51 (d, 1H, J=0.9 Hz), 8.35 (d, 1H, J=5.3 Hz), 7.67 (d, 1H, J=17.4 Hz), 7.60 (d, 1H, J=0.9 Hz), 7.31 (d, 1H, J=8.2 Hz), 7.20 (d, 1H, J=5.3 Hz), 6.68 (app t, 1H, J=9.5 Hz), 4.23-4.21 (m, 2H), 4.16 (s, 1H), 3.53-3.50 (m, 2H), 3.39 (d, 1H, J=9.6 Hz), 3.17 (d, 1H, J=9.6 Hz), 3.11 (s, 3H), 2.72 (d, 1H, J=9.6 Hz), 2.59 (d, 1H, J=9.6 Hz), 2.23 (s, 3H), 1.77 (d, 1H, J=9.4 Hz), 1.69 (d, 1H, J=9.4 Hz); LCMS: purity: 98%; MS (m/e): 448 (MH⁺).

Synthetic Example 10

4-(6-(morpholin-4-yl)pyridin-3-yl)-N-(3-methyl-4-((1S,4S)-5-methyl-2,5-diazabicyclo[2.2.1]heptan-2-yl)phenyl)pyrimidin-2-amine

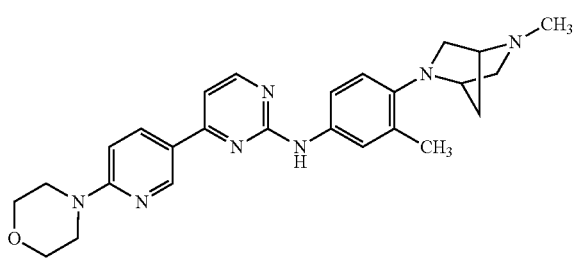 [SMILES: Cc1cc(Nc2nccc(-c3ccc(N4CCOCC4)nc3)n2)ccc1N1CC2CC1CN2C]

A. Following substantially one of the procedures as described in SYNTHETIC EXAMPLE 1 and making non-critical variations in the experimental parameters and using the appropriately substituted starting materials and reagents, 4-(6-1S,4S)-5-methyl-2,5-diazabicyclo[2.2.1]heptan-2-yl)phenyl)pyrimidin-2-amine, compound #10, was obtained; $^1$H NMR (DMSO-d$_6$): δ 9.19 (s, 1H), 8.91 (d, 1H, J=0.9 Hz), 8.35 (d, 1H, J=5.3 Hz), 8.26 (d, 1H, J=9.1 Hz), 7.48-7.44 (m, 2H), 7.20 (d, 1H, J=5.3 Hz), 6.95 (d, 1H, J=9.1 Hz), 3.66-3.63 (m, 4H), 3.55-3.53 (m, 4H), 3.19 (d, 1H, J=8.8 Hz), 3.17 (d, 1H, J=8.8 Hz), 2.70 (d, 1H, J=9.1 Hz), 2.68 (d, 1H, J=9.1 Hz), 2.27 (s, 3H), 2.18 (s, 3H), 1.77 (d, 1H, J=9.1 Hz), 1.69 (d, 1H, J=9.1 Hz); LCMS: purity: 98%; MS (m/e): 459 (MH$^+$).

B. Alternatively, [3-methyl-4-((1S,4S)-2-methyl-2,5-diazabicyclo[2.2.1]heptan-5-yl)phenyl]guanidine TFA salt (45.4 g) was dissolved in 2-propanol (200 mL) and basified with 40 g of solid K$_2$CO$_3$ in portions. The pH was measured by diluting the respective aliquots with water drawn upon base addition [20 g (pH 5), 25 g (pH 7), 33 g (pH 9) and 40 g (pH 10)]. 3-[3-(Dimethylamino-2-propen-1-one)-6-(morpholin-4-yl)pyridine (10.5 g, 40.1 mmol) and additional 2-propanol (100 mL) were transferred to the above off-white basified guanidine heterogeneous mixture and heated to reflux at 120° C. Progress of the reaction was monitored by LC/MS. Analysis of the reaction after 96 h provided 23%, 6% and 67% of the guanidine, the enamine and the desired product, respectively. The resulting pale yellow heterogeneous mixture was cooled to ambient temperature and diluted with water (200 mL). The pale yellow solid formed upon stirring was filtered to provide 10.2 g of crude product. The collected solid was suspended in water and filtered to provide 8.8 g (47%) of 4-(6-(morpholin-4-yl)pyridin-3-yl)-N-(3-methyl-4-((1S,4S)-5-methyl-2,5-diazabicyclo[2.2.1]heptan-2-yl)phenyl)pyrimidin-2-amine as a pale yellow powder upon drying, compound #10, $^1$H NMR (DMSO-d$_6$): δ 9.19 (s, 1H), 8.91 (d, 1H, J=0.9 Hz), 8.35 (d, 1H, J=5.3 Hz), 8.26 (d, 1H, J=9.1 Hz), 7.48-7.44 (m, 2H), 7.20 (d, 1H, J=5.3 Hz), 6.95 (d, 1H, J=9.1 Hz), 3.66-3.63 (m, 4H), 3.55-3.53 (m, 4H), 3.19 (d, 1H, J=8.8 Hz), 3.17 (d, 1H, J=8.8 Hz), 2.70 (d, 1H, J=9.1 Hz), 2.68 (d, 1H, J=9.1 Hz), 2.27 (s, 3H), 2.18 (s, 3H), 1.77 (d, 1H, J=9.1 Hz), 1.69 (d, 1H, J=9.1 Hz); LCMS: purity: 98%; MS (m/e): 458 (MH$^+$).

Synthetic Example 11

4-(6-(morpholin-4-yl)pyridin-3-yl)-N-(3-fluoro-4-((1S,4S)-5-methyl-2,5-diazabicyclo[2.2.1]heptan-2-yl)phenyl)pyrimidin-2-amine

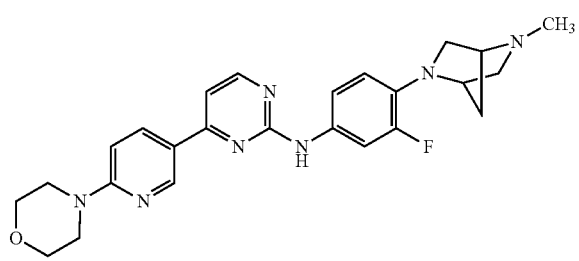 [SMILES: CN1CC2CC1CN2c1ccc(Nc2nccc(-c3ccc(N4CCOCC4)nc3)n2)cc1F]

Following substantially one of the procedures as described in SYNTHETIC EXAMPLE 1 and making non-critical variations in the experimental parameters and using the appropriately substituted starting materials and reagents, 4-(6-(morpholin-4-yl)pyridin-3-yl)-N-(3-fluoro-4-((1S,4S)-5-methyl-2,5-diazabicyclo[2.2.1]heptan-2-yl)phenyl)pyrimidin-2-amine, compound #11, was obtained; $^1$H NMR (DMSO-d$_6$): δ 9.40 (s, 1H), 8.91 (s, 1H), 8.38 (d, 1H, J=5.3 Hz), 8.24 (d, 1H, J=8.8 Hz), 7.67 (d, 1H, J=16.4 Hz), 7.34 (d, 1H, J=8.2 Hz), 7.25 (d, 1H, J=5.3 Hz), 6.96 (d, 1H, J=9.1 Hz), 6.68 (app t, 1H, J=9.9 Hz), 4.16 (s, 1H), 3.69-3.67 (m, 4H), 3.58-3.57 (m, 4H), 3.41 (d, 1H, J=9.1 Hz), 3.17 (d, 1H, J=9.1 Hz), 2.72 (d, 1H, J=9.1 Hz), 2.59 (d, 1H, J=9.1 Hz), 2.23 (s, 3H), 1.79 (d, 1H, J=8.8 Hz), 1.69 (d, 1H, J=8.8 Hz); LCMS: purity: 99%; MS (m/e): 462 (MH$^+$).

Synthetic Example 12

In a similar manner as described above utilizing the appropriately substituted starting materials and reagents, the following compounds of formula (Ia) were prepared:

4-(4-(N,N-dimethylamino)phenyl)-N-(3-methyl-4-((1S,4S)-5-methyl-2,5-diazabicyclo[2.2.1]heptan-2-yl)phenyl)pyrimidin-2-amine, compound #14, $^1$H NMR (DMSO-d$_6$): δ 9.09 (s, 1H), 8.28 (d, 1H, J=5.4 Hz), 8.00 (d, 2H, J=8.4 Hz), 7.48 (bs, 2H), 7.13 (d, 1H, J=5.4 Hz), 6.78 (d, 2H, J=8.7 Hz), 6.73 (d, 1H, J=9.6 Hz), 3.87 (s, 1H), 3.17 (m, 2H), 2.98 (s, 6H), 2.69 (m, 2H), 2.26 (s, 3H), 2.19 (s, 3H), 1.76 (d, 1H, J=9.3 Hz), 1.68 (d, 1H, J=9.3 Hz); LCMS: purity: 99%; MS (m/e): 415 (MH$^+$);

4-(4-(N,N-dimethylamino)phenyl)-N-(3-fluoro-4-((1S,4S)-5-methyl-2,5-diazabicyclo[2.2.1]heptan-2-yl)phenyl)pyrimidin-2-amine, compound #15, $^1$H NMR (DMSO-d$_6$): δ 9.33 (s, 1H), 8.32 (d, 1H, J=5.1 Hz), 7.99 (d, 2H, J=9.0 Hz), 7.72 (d, 1H, J=16.5 Hz), 7.36 (d, 1H, J=8.7 Hz), 7.18 (d, 1H, J=5.1 Hz), 6.74 (m, 3H), 4.21 (s, 1H), 3.47 (m, 2H), 3.21 (m, 1H), 2.99 (s, 6H), 2.80 (bs, 2H), 2.34 (s, 3H), 1.87 (d, 1H, J=8.7 Hz), 1.77 (d, 1H, J=8.7 Hz); LCMS: purity: 99%; MS (m/e): 419 (MH$^+$);

4-(6-(4-acetylpiperazin-1-yl)pyridin-3-yl)-N-(3-fluoro-4-((1S,4S)-5-methyl-2,5-diazabicyclo[2.2.1]heptan-2-yl)phenyl)pyrimidin-2-amine, compound #16, $^1$H NMR (DMSO-d$_6$): δ 9.40 (s, 1H), 8.91 (s, 1H), 8.37 (d, 1H, J=5.4 Hz), 8.24 (d, 1H, J=8.7 Hz), 7.66 (d, 1H, J=16.2 Hz), 7.34 (d, 1H, J=9.3 Hz), 7.25 (d, 1H, J=5.1 Hz), 6.97 (d, 1H, J=9.0 Hz), 6.68 (t, 1H, J=9.6 Hz, J=9.8 Hz), 4.16 (s, 1H), 3.59 (m, 8H), 3.40 (m, 1H), 3.16 (m, 1H), 2.72 (d, 1H, J=9.6 Hz), 2.58 (d, 1H, J=9.6 Hz), 2.23 (s, 3H), 2.03 (s, 3H), 1.79 (d, 1H, J=9.3 Hz), 1.69 (d, 1H, J=9.3 Hz); LCMS: purity: 99%; MS (m/e): 503 (MH$^+$);

4-(2,2-dimethyl-3-oxo-3,4-dihydro-2H-pyrido[3,2-b][1,4]oxazin-7-yl)-N-(3-fluoro-4-((1S,4S)-5-methyl-2,5-diazabicyclo[2.2.1]heptan-2-yl)phenyl)pyrimidin-2-amine, compound #19, $^1$H NMR (CD$_3$OD, 300 MHz) 8.68 (m, 1H), 8.41 (m, 2H), 7.99 (m, 1H), 7.68 (m, 1H), 7.25 (m, 2H), 6.80 (m, 1H), 4.57 (s, 1H), 4.27 (s, 1H), 3.80 (m, 2H), 4.46 (m, 1H), 3.24 (s, 1H), 2.93 (s, 3H), 2.66 (m, 3H), 2.30 (m, 2H), 1.55 (s, 6H); MS (ES) 476.19 (M+H);

4-(2,2-dimethyl-3-oxo-3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine, compound #20, $^1$H NMR (CD$_3$OD, 300 MHz) 8.68 (m, 1H), 8.48 (s, 1H), 8.38 (m, 1H), 8.00 (m, 1H), 7.49 (m, 2H), 7.21 (m, 1H), 6.96 (m, 1H), 4.23 (m, 2H), 3.74 (m, 1H), 3.50 (m, 2H), 3.24 (d, 1H), 2.94 (s, 3H), 2.65 (m, 1H), 2.32 (s, 3H), 2.89 (m, 2H), 1.54 (s, 6H); MS (ES) 472.22 (M+H);

4-(1H-indol-6-yl)-N-(3-methyl-4-((1S,4S)-5-methyl-2,5-diazabicyclo[2.2.1]heptan-2-yl)phenyl)pyrimidin-2-amine, compound #21, $^1$H NMR (300 MHz, CDCl$_3$): δ 10.26 (b, 1H), 8.36-8.34 (m, 1H), 8.20 (b, 1H), 7.79-7.76 (d, J=8.8 Hz, 1H), 7.67-7.64 (d, J=8.8 Hz, 1H), 7.79-7.41 (m, 3H), 7.31 (b, 1H), 7.13-7.12 (m, 1H), 6.81-6.79 (d, J=9 Hz, 1H), 6.51 (b, 1H), 3.93 (s, 1H), 3.42-3.39 (m, 1H), 3.20-3.17 (d, J=9.9 Hz, 1H), 2.91-2.82 (m, 1H), 2.69 (s, 4H), 2.41 (s, 3H), 2.31 (s, 3H); LCMS: purity: 99%; MS (m/z); 411 (M+H)⁺;

4-(1H-pyrrolo[2,3-b]pyridin-5-yl)-N-(3-methyl-4-((1S,4S)-5-methyl-2,5-diazabicyclo[2.2.1]heptan-2-yl)phenyl)pyrimidin-2-amine, compound #22, ¹H NMR (300 MHz, CDCl₃): δ 9.10-9.03 (m, 2H), 8.61 (s, 1H), 8.41-8.40 (d, J=5.2 Hz, 1H), 7.45-7.35 (m, 3H), 7.14-7.13 (d, J=4.1 Hz, 1H), 7.01 (s, 1H), 6.83-6.81 (d, J=8.8 Hz, 1H), 6.60 (b, 1H), 3.95 (b, 1H), 3.46-3.43 (m, 2H), 3.22-3.19 (d, J=9.6 Hz, 1H), 2.96-2.84 (m, 2H), 2.44 (s, 3H), 2.33 (s, 3H), 1.96-1.86 (m, 2H); LCMS: purity: 100%; MS (m/z); 412 (M+H)⁺;

4-(1H-pyrrolo[2,3-b]pyridin-5-yl)-N-(3-fluoro-4-((1S,4S)-5-methyl-2,5-diazabicyclo[2.2.1]heptan-2-yl)phenyl)pyrimidin-2-amine, compound #23, ¹H NMR (300 MHz, d₆-DMSO): δ 11.86 (b, 1H), 9.55-9.46 (b, 2H), 8.97 (s, 1H), 8.64 (s, 1H), 8.44-8.42 (d, J=5.2 Hz, 1H), 7.52-7.39 (m, 3H), 6.85 (t, J=18.7 Hz, 1H), 6.52 (s, 1H), 4.5 (b, 1H), 4.23 (b, 1H), 3.70-3.58 (m, 2H), 3.33-3.29 (b, 1H), 3.06-3.03 (b, 1H), 2.82 (b, 3H), 2.33-2.29 (m, 1H), 2.09-2.05 (m, 1H); LCMS; purity: 100%; MS (m/z); 416 (M+H)⁺;

4-(6-(dimethylamino)pyridin-3-yl)-N-(3-methyl-4-((1S,4S)-5-ethyl-2,5-diazabicyclo[2.2.1]heptan-2-yl)phenyl)pyrimidin-2-amine, compound #24, ¹H NMR (300 MHz, CDCl₃): δ 8.86 (s, 1H), 8.30 (dd, J=1.3 and 1.6 Hz, 1H), 8.16-8.13 (d, J=9.0 Hz, 1H), 7.47-7.44 (d, J=9.0 Hz, 1H), 6.96-6.94 (m, 1H), 6.87 (s, 1H), 6.80-6.78 (d, J=7.9 Hz, 1H), 6.58-6.55 (d, J=8.8 Hz, 1H), 3.95 (s, 1H), 3.53 (s, 1H), 3.42-3.39 (m, 1H), 3.17 (s, 6H), 3.00-2.97 (d, J=9.6 Hz, 1H), 2.79-2.76 (d, J=9.4 Hz, 1H), 2.63-2.51 (m, 1H), 2.30 (s, 3H), 1.93-1.85 (m, 2H), 1.59 (b, 2H), 1.11-1.06 (m, 3H); LCMS: purity: 100%; MS (m/z); 430 (M+H)⁺;

4-(6-(morpholin-4-yl)pyridin-3-yl)-N-(3-methyl-4-((1S,4S)-5-ethyl-2,5-diazabicyclo[2.2.1]heptan-2-yl)phenyl)pyrimidin-2-amine, compound #25, ¹H NMR (300 MHz, CDCl₃): δ 8.86 (s, 1H), 8.33-8.31 (d, J=5.2 Hz, 1H), 8.19-8.17 (d, J=8.8 Hz, 1H), 7.44-7.41 (d, J=8.8 Hz, 1H), 7.23 (s, 1H), 6.97-6.90 (m, 2H), 6.80-6.77 (d, J=8.5 Hz, 1H), 6.69-6.66 (d, J=8.5 Hz, 1H), 3.95 (s, 1H), 3.82-3.81 (m, 4H), 3.64-3.61 (m, 5H), 3.43-3.40 (d, J=9.1 Hz, 1H), 3.21-3.17 (d, J=9.1 Hz, 1H), 3.01-2.98 (d, J=8.8 Hz, 1H), 2.80-2.78 (d, J=8.5 Hz, 1H), 2.64-2.57 (m, 2H), 2.30 (s, 3H), 1.91-1.89 (m, 2H), 1.12-1.07 (m, 3H); LCMS: purity: 98%; MS (m/z); 472 (M+H)⁺;

4-(6-(morpholin-4-yl)pyridin-3-yl)-N-(3-methyl-4-((1S,4S)-5-((ethylamino)carbonyl)-2,5-diazabicyclo[2.2.1]heptan-2-yl)phenyl)pyrimidin-2-amine, compound #26, ¹H NMR (300 MHz, CDCl₃): δ 8.86 (s, 1H), 8.33 (dd, J=1.3 and 1.3 Hz, 1H), 8.19 (d, J=9.4 Hz, 1H), 7.47 (d, J=8.5 Hz, 1H), 7.29, (s, 1H), 6.98 (d, J=6.6 Hz, 1H), 6.91-6.79 (m, 2H), 6.69 (d, J=9.1 Hz, 1H), 4.64 (s, 1H), 4.15 (s, 1H), 4.04 (s, 1H), 3.82 (d, J=3.5 Hz, 4H), 3.64-3.61 (m, 4H), 3.52 (d, J=7.9 Hz, 1H), 3.44-3.24 (m, 3H), 2.28 (s, 3H), 2.03 (d, J=9.9 Hz, 1H), 1.88 (d, J=8.8 Hz, 1H), 1.56 (b, 2H), 1.16-1.11 (m, 3H); LCMS: purity: 96%; MS (m/z); 515 (M+H)⁺;

4-(2,2-dimethyl-3-oxo-3,4-dihydro-2H-pyrido[3,2-b][1,4]oxazin-7-yl)-N-(3-methyl-4-((1S,4S)-5-oxa-2-azabicyclo[2.2.1]heptan-2-yl)phenyl)pyrimidin-2-amine, compound #27, ¹H NMR (300 MHz, d₆-DMSO): δ 9.22 (s, 1H), 8.64-8.62 (m, 1H), 8.36 (d, J=5.2 Hz, 1H), 7.77 (s, 1H), 7.48-7.41 (m, 3H), 7.23 (d, J=4.9 Hz, 1H), 6.82-6.77 (m, 1H), 4.52 (s, 1H), 4.12 (s, 1H), 3.90-3.87 (d, J=7.1 Hz, 2H), 3.71 (d, J=5.7 Hz, 2H), 3.07-3.02 (m, 1H), 2.18 (s, 3H), 1.88-1.73 (m, 1H), 1.38-1.35 (m, 8H); LCMS: purity; 99%: MS (m/z); 459 (M+H)⁺;

4-(2,2-dimethyl-3-oxo-3,4-dihydro-2H-pyrido[3,2-b][1,4]oxazin-7-yl)-N-(3-methyl-4-((1S,4S)-5-(ethylcarbonyl)-2,5-diazabicyclo[2.2.1]heptan-2-yl)phenyl)pyrimidin-2-amine, compound #28, ¹H NMR (300 MHz, d₆-DMSO): δ 9.31 (s, 1H), 8.68 (s, 1H), 8.41-8.39 (m, 1H), 7.92 (s, 1H), 7.49-7.40 (m, 2H), 7.30 (d, J=5.2 Hz, 1H), 6.83 (t, J=15.9 Hz, 1H), 4.68 (b, 1H), 4.18 (d, J=19.5 Hz, 1H), 3.51-3.38 (m, 2H), 3.14-3.05 (m, 1H), 2.19 (s, 6H) 1.93-1.77 (m, 2H), 1.42 (s, 6H), 0.99-0.92 (m, 3H); LCMS: purity: 99%; MS (m/z); 514 (M+H)⁺;

4-(2,2-dimethyl-3-oxo-3,4-dihydro-2H-pyrido[3,2-b][1,4]oxazin-7-yl)-N-(3-methyl-4-((1S,4S)-5-(methylsulfonyl)-2,5-diazabicyclo[2.2.1]heptan-2-yl)phenyl)pyrimidin-2-amine, compound #29, ¹H NMR (300 MHz, d₆-DMSO): δ 11.47 (s, 1H), 9.36 (s, 1H), 8.73 (t, J=3.3 Hz, 1H), 8.45 (m, 1H), 8.01 (s, 1H), 7.51 (s, 1H), 7.45 (d, J=8.5 Hz, 1H), 7.34-7.32 (m, 1H), 6.88 (d, J=6.8 Hz, 1H), 4.33 (s, 1H), 4.15 (s, 1H), 3.41-3.22 (m, 4H), 2.96 (d, J=1.6 Hz, 3H), 2.21 (d, J=1.9 Hz, 3H), 1.92-1.80 (m, 2H), 1.45 (s, 6H); LCMS: purity; 99%; MS (m/z); 536 (M+H)⁺;

4-(2,2-dimethyl-3-oxo-3,4-dihydro-2H-pyrido[3,2-b][1,4]oxazin-7-yl)-N-(3-methyl-4-((1S,4S)-5-ethyl-2,5-diazabicyclo[2.2.1]heptan-2-yl)phenyl)pyrimidin-2-amine, compound #30, ¹H NMR (300 MHz, CDCl₃): δ 8.64 (s, 1H), 8.39 (d, J=3.8 Hz, 1H), 8.06 (s, 1H), 7.87 (s, 1H), 7.46-7.38 (m, 2H), 7.00 (d, J=4.1 Hz, 1H), 6.79 (d, J=8.26 Hz, 1H), 3.94 (b, 1H), 3.53 (b, 1H), 3.39 (d, J=9.3 Hz, 1H), 3.22 (d, J=9.0 Hz, 1H), 2.94 (b, 4H), 2.29 (s, 3H), 1.89 (d, J=6.6 Hz, 2H), 1.54 (s, 6H), 1.09 (m, 3H); LCMS: purity: 98%; MS (m/z); 486 (M+H)⁺;

4-(3'-oxo-3,4'-dihydrospiro[cyclobutane-1,2'-pyrido[3,2-b][1,4]oxazine]-7-yl)-N-(3-methyl-4-((1S,4S)-5-methyl-2,5-diazabicyclo[2.2.1]heptan-2-yl)phenyl)pyrimidin-2-amine, compound #31, ¹H NMR (300 MHz, CDCl₃): δ 8.63 (s, 1H), 8.39 (d, J=5.2 Hz, 1H), 7.92 (s, 1H), 7.72 (s, 1H), 7.45-7.36 (m, 3H), 7.00 (d, J=4.9 Hz, 1H), 6.81 (d, J=8.2 Hz, 1H), 3.94 (s, 1H), 3.41 (d, J=4.9 Hz, 2H), 3.22 (d, J=8.5 Hz, 1H), 2.93-2.82 (m, 3H), 2.67 (b, 4H), 2.41-2.26 (m, 6H), 2.01-1.84 (m, 3H); LCMS: purity: 95%; MS (m/z); 484 (M+H)⁺;

4-(3'-oxo-3',4'-dihydrospiro[cyclobutane-1,2'-pyrido[3,2-b][1,4]oxazine]-7'-yl)-N-(3-methyl-4-((1S,4S)-5-ethyl-2,5-diazabicyclo[2.2.1]heptan-2-yl)phenyl)pyrimidin-2-amine, compound #32, ¹H NMR (300 MHz, CDCl₃): δ 8.63 (s, 1H), 8.39 (d, J=4.9 Hz, 1H), 7.96 (d, J=13.7 Hz, 2H), 7.49-7.37 (m, 2H), 7.00 (d, J=5.2 Hz, 1H) 6.79 (d, J=8.2 Hz, 1H), 3.94 (s, 1H), 3.53 (s, 1H), 3.39 (d, J=9.0 Hz, 1H), 3.22 (d, J=9.0 Hz, 1H), 2.98 (d, J=9.3 Hz, 2H), 2.80 (d, J=9.3 Hz, 1H), 2.66-2.51 (m, 5H), 2.37-2.25 (m, 5H), 2.03-1.84 (m, 3H), 1.09 (t, J=13.7 Hz, 3H); LCMS; purity: 97%; MS (m/z); 498 (M+H)⁺;

4-(1H-pyrrolo[2,3-b]pyridin-5-yl)-N-(3-methyl-4-((1S,4S)-5-oxa-2-azabicyclo[2.2.1]heptan-2-yl)phenyl)pyrimidin-2-amine, compound #33, ¹H NMR (300 MHz, d₆-DMSO): δ 9.30 (s, 1H), 9.01 (d, J=1.6 Hz, 1H), 8.67 (s, 1H), 8.43 (d, J=5.2 Hz, 1H), 7.55-7.50 (m, 2H), 6.84 (d, J=8.5 Hz, 1H), 6.56 (d, J=3.3 Hz, 1H), 4.52 (s, 1H), 4.14 (s, 1H), 3.92 (d, J=7.1 Hz, 2H), 3.73 (d, J=5.7 Hz, 2H), 3.08 (d, J=9.3 Hz, 1H), 2.21 (s, 3H), 1.90-1.78 (m, 2H); LCMS: purity 95%; MS (m/z); 399 (M+H)⁺;

4-(1H-pyrrolo[2,3-b]pyridin-5-yl)-N-(3-methyl-4-((1S,4S)-5-(2,2,2-trifluoroethyl)-2,5-diazabicyclo[2.2.1]heptan-2-yl)phenyl)pyrimidin-2-amine, compound #34, ¹H NMR (300 MHz, d₆-DMSO): δ 9.30 (s, 1H), 9.02 (t, J=9.6 Hz, 1H), 8.68 (t, J=9.9 Hz, 1H), 8.43 (t, J=5.2 Hz, 1H), 7.55 (m, 4H), 7.38 (m, 1H), 6.80 (d, J=8.8 Hz, 1H), 6.57-6.52 (m, 1H), 3.96-2.85 (m, 7H), 2.22-2.19 (m, 4H), 1.77 (b, 2H); LCMS: purity; 96%; MS (m/z); 480 (M+H)⁺;

4-(1H-pyrrolo[2,3-b]pyridin-5-yl)-N-(3-methyl-4-((1S,4S)-5-(cyclopropyl)methyl-2,5-diazabicyclo[2.2.1]heptan-2-yl)phenyl)pyrimidin-2-amine, compound #35, ¹H NMR (300 MHz, d₆-DMSO): δ 9.18 (b, 1H), 8.95 (t, J=8.2 Hz, 1H), 8.59 (d, J=1.9 Hz, 1H), 8.33 (d, J=5.2 Hz, 1H), 7.46-7.37 (m, 4H), 7.28 (d, J=5.5 Hz, 1H), 6.68 (d, J=8.5 Hz, 1H), 6.47 (d, J=3.5 Hz, 1H), 3.82 (b, 1H), 2.81 (d, J=7.4 Hz, 1H), 2.62 (d, J=8.8 Hz, 1H), 2.41 (b, 2H), 2.27 (d, J=6.3 Hz, 2H), 2.13 (s, 3H), 1.65-1.63 (m, 3H), 0.71 (b, 1H), 0.33-0.30 (m, 2H), 0.00-01 (m, 2H); LCMS: purity; 95%; MS (m/z); 452 (M+H)⁺;

4-(6-(morpholin-4-yl)pyridin-3-yl)-N-(3-methyl-4-((1S,4S)-5-(2,2,2-trifluoroethyl)-2,5-diazabicyclo[2.2.1]heptan-2-yl)phenyl)pyrimidin-2-amine, compound #36, ¹H NMR (300 MHz, d₆-DMSO): δ 9.21 (b, 1H), 8.90 (b, 1H), 8.37-8.34 (m, 1H), 8.25 (d, J=6.6 Hz, 1H), 7.46 (b, 2H), 7.24-7.20 (m, 1H), 6.98-6.93 (m, 1H), 6.79-6.74 (m, 1H), 3.95 (b, 1H), 3.70 (b, 4H), 3.57 (b, 4H), 2.97 (b, 2H), 2.87-2.84 (m, 2H), 2.21-2.20 (m, 5H), 1.77 (b, 3H); LCMS: purity; 99%; MS (m/z); 526 (M+H)⁺;

4-(6-(morpholin-4-yl)pyridin-3-yl)-N-(3-methyl-4-((1S,4S)-5-(cyclopropyl)methyl-2,5-diazabicyclo[2.2.1]heptan-2-yl)phenyl)pyrimidin-2-amine, compound #37, ¹H NMR (300 MHz, d₆-DMSO): δ 9.18 (b, 1H), 8.89 (b, 1H), 8.35-8.22 (m, 2H), 7.46-7.42 (d, J=12.1 Hz, 2H), 7.21-7.19 (m, 1H), 6.95 (d, J=9.0 Hz, 1H), 6.72 (d, J=7.9 Hz, 1H), 3.88 (b, 1H), 3.68 (b, 4H), 3.57 (b, 4H), 3.15 (s, 2H), 2.87 (d, J=8.8 Hz, 1H), 2.69 (d, J=9.3 Hz, 1H), 2.48 (b, 1H), 2.34 (d, J=5.7 Hz, 2H), 2.18 (s, 3H), 1.71 (d, J=6.3 Hz, 2H), 0.78 (b, 1H), 0.40 (t, J=7.7 Hz, 2H), 0.06 (b, 2H); LCMS: purity; 98%; MS (m/z); 498 (M+H)⁺;

4-(2,2-dimethyl-3-oxo-3,4-dihydro-2H-pyrido[3,2-b][1,4]oxazin-7-yl)-N-(3-methyl-4-((1S,4S)-5-(aminosulfonyl)-2,5-diazabicyclo[2.2.1]heptan-2-yl)phenyl)pyrimidin-2-amine, compound #38, ¹H NMR (300 MHz, d₆-DMSO): δ 11.50 (d, J=7.7 Hz, 1H), 9.47 (b, 1H), 8.73 (d, J=6.33 Hz, 1H), 8.46 (t, J=13.2 Hz, 1H), 8.02 (d, J=7.1 Hz, 1H), 7.53-7.33 (m, 4H), 6.94 (b, 3H), 4.23 (d, J=7.7 Hz, 2H), 3.37 (m, 4H), 1.92-1.85 (m, 2H), 1.47-1.38 (m, 8H); LCMS; purity; 100%; MS (m/z); 537 (M+H)⁺;

4-(3-fluoro-2-(morpholin-4-yl)pyridin-4-yl)-N-(3-fluoro-4-((1S,4S)-5-methyl-2,5-diazabicyclo[2.2.1]heptan-2-yl)phenyl)pyrimidin-2-amine, compound #39, ¹H NMR (DMSO-d₆): δ 9.68 (s, 1H), 8.55 (dd, 1H, J=1.4 and 4.9 Hz), 8.15 (d, 1H, J=4.9 Hz), 7.62 (d, 1H, J=15.4 Hz), 7.31-7.28 (m, 2H), 7.15-7.14 (m, 1H), 6.67 (t, 1H, J=9.1 Hz), 4.15 (s, 1H), 3.73-3.71 (m, 4H), 3.39-3.37 (m, 5H), 3.15 (app d, 1H, J=6.1 Hz), 2.70 (d, 1H, J=9.0 Hz), 2.57 (d, 1H, J=9.0 Hz), 2.22 (s, 3H), 1.79 (d, 1H, J=9.0 Hz), 1.68 (d, 1H, J=9.0 Hz); LCMS: purity: 99%; MS (m/e): 480 (MH⁺);

4-(2-(morpholin-4-yl)pyrimidin-5-yl)-N-(4-((1S,4S)-5-methyl-2,5-diazabicyclo[2.2.1]heptan-2-yl)phenyl)pyrimidin-2-amine, compound #40, ¹H NMR (CD₃OD, 300 MHz): δ 9.02 (s, 2H), 8.26 (d, 1H), 7.45 (d, 2H), 7.08 (d, 1H), 6.63 (d, 2H), 4.31 (s, 1H), 3.89 (m, 4H), 3.75 (m, 4H), 3.45 (m, 2H), 2.81 (m, 2H), 2.65 (m, 2H), 2.39 (m, 2H), 2.37 (s, 3H), 1.98 (m, 2H); LCMS (m/z): 445.54 (MH⁺);

4-(2-(morpholin-4-yl)pyrimidin-5-yl)-N-(3-methyl-4-((1S,4S)-5-methyl-2,5-diazabicyclo[2.2.1]heptan-2-yl)phenyl)pyrimidin-2-amine, compound #41, ¹H NMR (CD₃OD, 300 MHz): δ 9.02 (s, 2H), 8.54 (s, 1H), 8.29 (d, 1H), 7.38 (m, 1H), 7.08 (d, 1H), 6.87 (d, 1H), 4.00 (s, 1H), 3.89 (m, 4H), 3.75 (m, 4H), 3.56 (m, 1H), 3.42 (m, 1H), 3.25 (m, 1H), 3.04 (m, 1H), 2.86 (m, 1H), 2.65 (m, 1H), 2.49 (s, 3H), 2.29 (m, 3H), 1.96 (m, 2H); LCMS (m/z): 459.57 (MH⁺);

4-(2-(morpholin-4-yl)pyrimidin-5-yl)-N-(3-methyl-4-((1S,4S)-5-oxa-2-azabicyclo[2.2.1]heptan-2-yl)phenyl)pyrimidin-2-amine, compound #42, ¹H NMR (CD₃OD, 300 MHz): δ 9.02 (s, 2H), 8.32 (m, 1H), 7.96 (m, 1H), 7.38 (m, 1H), 7.12 (m, 1H), 6.80 (m, 1H), 4.58 (s, 1H), 4.07 (m, 1H), 3.85 (m, 2H), 3.81 (m, 1H), 3.76 (m, 2H), 3.36 (m, 1H), 3.34 (s, 3H), 3.00 (m, 1H), 2.86 (m, 1H), 2.66 (m, 1H), 2.29 (m, 2H), 2.20 (m, 2H), 2.01 (m, 1H), 1.89 (m, 1H); LCMS (m/z): 446.39 (MH⁺);

4-(2-(morpholin-4-yl)pyrimidin-5-yl)-N-(3-fluoro-4-((1S,4S)-5-methyl-2,5-diazabicyclo[2.2.1]heptan-2-yl)phenyl)pyrimidin-2-amine, compound #43, ¹H NMR (CD₃OD, 300 MHz): δ 9.03 (s, 2H), 8.53 (s, 1H), 8.33 (d, 1H), 7.57 (m, 1H), 7.23 (d, 1H), 7.13 (d, 1H), 6.74 (m, 1H), 4.46 (s, 1H), 3.90 (m, 4H), 3.76 (m, 4H), 3.66 (m, 1H), 3.40 (m, 1H), 3.36 (m, 1H), 3.14 (m, 1H), 2.96 (m, 1H), 2.57 (m, 1H), 2.52 (s, 3H), 2.04 (m, 2H); LCMS (m/z): 463 (MH⁺);

4-(2-((cyclopropyl)carbonylamino)-pyrimidin-5-yl)-N-(3-methyl-4-((1S,4S)-5-methyl-2,5-diazabicyclo[2.2.1]heptan-2-yl)phenyl)pyrimidin-2-amine, compound #44, ¹H NMR (CD₃OD, 300 MHz): δ 9.17 (s, 2H), 8.36 (s, 1H), 7.41 (d, 1H), 7.18 (m, 1H), 7.08 (d, 1H), 6.80 (d, 1H), 4.30 (s, 1H), 4.16 (m, 1H), 4.05 (m, 1H), 3.78 (m, 1H), 3.58 (m, 1H), 3.32 (m, 1H), 2.89 (s, 3H), 2.47 (m, 1H), 2.65 (m, 1H), 2.26 (m, 3H), 2.21 (m, 1H), 1.13 (m, 2H), 0.92 (m, 2H); LCMS (m/z): 457 (MH⁺);

4-(4-(4,5-dihydrothiazol-2-ylcarbamoyl)phenyl)-N-(3-methyl-4-((1S,4S)-5-methyl-2,5-diazabicyclo[2.2.1]heptan-2-yl)phenyl)pyrimidin-2-amine, compound #45, LCMS (m/z): 500 (MH⁺);

4-(4-(1,1-dimethylethyl)phenyl)-N-(3-methyl-4-((1S,4S)-5-methyl-2,5-diazabicyclo[2.2.1]heptan-2-yl)phenyl)pyrimidin-2-amine, compound #46, ¹H NMR (CD₃OD, 300 MHz): δ 8.34 (m, 2H), 8.04 (m, 2H), 7.56 (m, 1H), 7.53 (m, 2H), 7.20 (m, 1H), 6.97 (m, 1H), 4.25 (d, 2H), 3.80 (m, 1H), 3.5 (m, 2H), 2.97 (m, 3H), 2.30 (m, 6H), 1.36 (m, 9H); LCMS (m/z): 428 (MH⁺);

4-(4-(morpholin-4-yl)phenyl)-N-(3-fluoro-4-((1S,4S)-5-methyl-2,5-diazabicyclo[2.2.1]heptan-2-yl)phenyl)pyrimidin-2-amine.TFA salt, compound #47, ¹H NMR (DMSO-d₆): δ 9.54-9.42 (2H, m), 8.39 (1H, d, J=5.5 Hz), 8.04 (2H, d, J=8.8 Hz), 7.80 (1H, dd, J=16.4, 2.3 Hz), 7.41 (1H, dd, J=8.7, 2.1 Hz), 7.27 (1H, d, J=5.2 Hz), 7.05 (2H, d, J=9.1 Hz), 6.84 (1H, t, J=9.6 Hz), 4.48 (1H, s), 4.27 (1H, s), 3.79-3.67 (6H, m), 3.34 (1H, d, J=10.7 Hz), 3.26 (4H, app. t, J=4.7 Hz), 3.09 (1H, d, J=11.6 Hz), 2.87 (2H, d, J=5.0 Hz), 2.82 (1H, d, J=5.0 Hz), 2.35 (1H, d, J=11.0 Hz), 2.11 (1H, d, J=11.0 Hz); MS: 461 (M+H)⁺;

4-(4-((methyl)aminocarbonylmethyl)-phenyl)-N-(3-methyl-4-((1S,4S)-5-methyl-2,5-diazabicyclo[2.2.1]heptan-2-yl)phenyl)pyrimidin-2-amine.TFA salt, compound #48, ¹H NMR (CD₃OD): δ 8.32 (1H, d, J=6.1 Hz), 8.15 (2H, d, J=8.5 Hz), 7.46 (3H, d, J=8.5 Hz), 7.42 (2H, d, J=6.1 Hz), 7.02 (1H, d, J=8.3 Hz), 4.32 (2H, br s), 3.98 (1H, d, J=11.3 Hz), 3.60 (2H, s), 3.52 (2H, d, J=9.4 Hz), 3.18 (1H, d, J=11.6 Hz), 3.00 (3H, s), 2.75 (3H, s), 2.40-2.28 (5H, m); MS: 443 (M+H)-TFA⁺;

4-(4-((cyclopropyl)aminocarbonyl-methyl)phenyl)-N-(3-methyl-4-((1S,4S)-5-methyl-2,5-diazabicyclo[2.2.1]heptan-2-yl)phenyl)pyrimidin-2-amine, compound #49, ¹H NMR (CD₃OD): δ 8.31 (1H, d, J=6.1 Hz), 8.15 (2H, d, J=8.5 Hz), 7.47-7.43 (5H, m), 7.03 (1H, d, J=8.3 Hz), 4.33

(2H, d, J=7.2 Hz), 3.99 (1H, d, J=11.0 Hz), 3.60-3.47 (4H, m), 3.18 (1H, d, J=11.8 Hz), 3.00 (3H, s), 2.71-2.66 (1H, m), 2.40-2.28 (5H, m), 0.77-0.71 (2H, m), 0.53-0.48 (2H, m); MS: 469 (M+H)$^+$;

4-(6-(methylaminocarbonyl)pyridin-3-yl)-N-(3-methyl-4-((1S,4S)-5-methyl-2,5-diazabicyclo[2.2.1]heptan-2-yl)phenyl)pyrimidin-2-amine, compound #50, $^1$H NMR (CD$_3$OD): δ 9.31-9.30 (1H, m), 8.60 (1H, dd, J=8.3, 2.2 Hz), 8.51-8.44 (2H, m), 8.16 (1H, d, J=8.3 Hz), 7.54 (1H, dd, J=8.7, 2.6 Hz), 7.49 (1H, d, J=2.2 Hz), 7.33 (1H, d, J=5.0 Hz), 6.96 (1H, d, J=8.5 Hz), 4.26 (2H, d, J=11.6 Hz), 3.77 (1H, d, J=11.3 Hz), 3.54 (1H, d, J=11.3 Hz), 3.45 (1H, dd, J=11.4, 2.6 Hz), 3.26 (1H, dd, J=11.3, 2.2 Hz), 3.00 (3H, s), 2.97 (3H, s), 2.32 (3H, s), 2.30 (2H, d, J=2.8 Hz); MS: 430 (M+H)$^+$;

4-(7-oxo-5,6,7,8-tetrahydro-1,8-naphthyridin-3-yl)-N-(3-methyl-4-((1S,4S)-5-methyl-2,5-diazabicyclo[2.2.1]heptan-2-yl)phenyl)pyrimidin-2-amine.TFA salt, compound #51x, $^1$H NMR (DMSO-d$_6$): δ 10.75 (1H, s), 9.44 (1H, s), 8.90 (1H, d, J=1.9 Hz), 8.46 (1H, d, J=5.2 Hz), 8.29 (1H, s), 7.59-7.51 (2H, m), 7.34 (1H, d, J=5.2 Hz), 6.93 (1H, d, J=8.8 Hz), 4.28-4.22 (2H, m), 3.43-3.38 (2H, m), 3.06-2.87 (7H, m), 2.61-2.53 (4H, m), 2.34-2.08 (3H, m), MS: 442 (M+H)$^+$-TFA$^+$;

4-(5-((morpholin-4-yl)carbonyl)pyridin-3-yl)-N-(3-methyl-4-((1S,4S)-5-methyl-2,5-diazabicyclo[2.2.1]heptan-2-yl)phenyl)pyrimidin-2-amine. Bis TFA salt, compound #52, $^1$H NMR (CD$_3$OD): δ 9.36 (1H, d, J=2.2 Hz), 8.74 (1H, d, J=1.9 Hz), 8.59 (1H, dd, J=2.2, 1.9 Hz), 8.49 (1H, d, J=5.2 Hz), 8.47 (1H, s), 7.53-7.50 (2H, m), 7.37 (1H, d, J=5.2 Hz), 6.97 (1H, d, J=9.4 Hz), 4.27 (2H, d, J=11.0 Hz), 3.80-3.66 (8H, m), 3.54 (2H, d, J=11.6 Hz), 3.47 (2H, dd, J=11.6, 2.5 Hz), 2.97 (3H, s), 2.33 (3H, s), 2.30 (2H, br s); MS: 486 (M+H)$^+$;

4-(2,2-dimethyl-3-oxo-3,4-dihydro-2H-pyrido[3,2-b][1,4]oxazin-7-yl)-N-(3-cyano-4-((1S,4S)-5-methyl-2,5-diazabicyclo[2.2.1]heptan-2-yl)phenyl)pyrimidin-2-amine, compound #53, $^1$H NMR (DMSO-d$_6$): δ 11.50 (1H, s), 9.69 (1H, s), 8.73 (1H, s), 8.52 (1H, d, J=5.2 Hz), 8.13 (1H, d, J=1.9 Hz), 8.03 (1H, s), 7.78 (1H, d, J=9.4 Hz), 7.43 (1H, d, J=5.0 Hz), 7.01 (1H, d, J=9.1 Hz), 4.71 (1H, s), 4.36 (1H, s), 3.98 (1H, d, J=9.1 Hz), 3.72 (2H, d, J=10.7 Hz), 3.12 (1H, d, J=10.7 Hz), 2.86 (2H, d, J=4.4 Hz), 2.80 (1H, br s), 2.41 (1H, d, J=11.8 Hz), 2.18 (1H, d, J=10.7 Hz), 1.47 (6H, s); MS: 483 (M+H)$^+$;

4-(5-methyl-6-(morpholin-4-yl)pyridin-3-yl)-N-(3-fluoro-4-((1S,4S)-5-methyl-2,5-diazabicyclo[2.2.1]heptan-2-yl)phenyl)pyrimidin-2-amine, compound #59, LCMS: purity: 99%; MS (m/e): 476 (MH$^+$);

4-(5-methyl-6-(morpholin-4-yl)pyridin-3-yl)-N-(3-methyl-4-((1S,4S)-5-methyl-2,5-diazabicyclo[2.2.1]heptan-2-yl)phenyl)pyrimidin-2-amine, compound #60, LCMS: purity: 99%; MS (m/e): 472 (MH$^+$);

5-methyl-4-(6-(morpholin-4-yl)pyridin-3-yl)-N-(3-methyl-4-((1S,4S)-5-methyl-2,5-diazabicyclo[2.2.1]heptan-2-yl)phenyl)pyrimidin-2-amine, compound #67, LCMS: purity: 99%; MS (m/e): 472 (MH$^+$);

5-methyl-4-(6-(morpholin-4-yl)pyridin-3-yl)-N-(3-fluoro-4-((1S,4S)-5-methyl-2,5-diazabicyclo[2.2.1]heptan-2-yl)phenyl)pyrimidin-2-amine, compound #68, LCMS: purity: 99%; MS (m/e): 476 (MH$^+$);

4-(6-(2-(morpholin-4-yl)ethyl)aminopyridin-3-yl)-N-(4-((1S,4S)-5-methyl-2,5-diazabicyclo[2.2.1]heptan-2-yl)phenyl)pyrimidin-2-amine, compound #69, LCMS: purity: 99%; MS (m/e): 487 (MH$^+$);

4-(6-(2-(morpholin-4-yl)ethyl)aminopyridin-3-yl)-N-(3-fluoro-4-((1S,4S)-5-methyl-2,5-diazabicyclo[2.2.1]heptan-2-yl)phenyl)pyrimidin-2-amine, compound #70, LCMS: purity: 99%; MS (m/e): 505 (MH$^+$);

4-(2,2-dimethyl-3-oxo-3,4-dihydro-2H-pyrido[3,2-b][1,4]oxazin-7-yl)-N-(3-methyl-4-((1R,4R)-5-methyl-2,5-diazabicyclo[2.2.1]heptan-2-yl)phenyl)pyrimidin-2-amine, compound #71, $^1$H NMR (DMSO-d6): δ 9.81 (s, 1H), 9.23 (s, 1H), 8.95 (m, 1H), 8.52 (s, 1H), 7.88 (m, 3H), 7.24 (d, 1H, J=3.6 Hz), 4.29 (s, 1H), 3.82 (s, 2H), 3.69 (s, 2H), 3.20 (m, 2H), 2.98 (s, 4H), 2.77 (s, 2H), 2.70 (s, 2H), 1.95 (s, 6H); LCMS: purity: 99%; MS (m/e): 476 (MH$^+$);

4-(6-(morpholin-4-yl)pyridin-3-yl)-N-(3-methyl-4-((1R,4R)-5-methyl-2,5-diazabicyclo[2.2.1]heptan-2-yl)phenyl)pyrimidin-2-amine, compound #72, $^1$H NMR (DMSO-d6): δ 9.29 (s, 1H), 8.92 (d, 1H, J=2.4 Hz), 8.37 (d, 1H, J=5.4 Hz), 8.25 (m, 1H), 7.54 (m, 2H), 7.24 (d, 1H, J=5.4 Hz), 6.95 (d, 1H, J=9.3 Hz), 6.85 (d, 1H J=9.3 Hz), 4.07 (s, 1H), 3.69 (m, 4H), 3.58 (m, 4H), 3.32 (m, 4H), 2.65 (s, 3H), 2.19 (s, 3H), 1.95 (m, 2H); LCMS: purity: 99%; MS (m/e): 458 (MH$^+$);

4-(2,2-dimethyl-3-oxo-3,4-dihydro-2H-pyrido[3,2-b][1,4]oxazin-7-yl)-N-(3-fluoro-4-((1R,4R)-5-methyl-2,5-diazabicyclo[2.2.1]heptan-2-yl)phenyl)pyrimidin-2-amine, compound #73, LCMS: purity: 99%; MS (m/e): 476 (MH$^+$);

4-(6-(morpholin-4-yl)pyridin-3-yl)-N-(3-fluoro-4-((1R,4R)-5-methyl-2,5-diazabicyclo[2.2.1]heptan-2-yl)phenyl)pyrimidin-2-amine, compound #74, LCMS: purity: 99%; MS (m/e): 462 (MH$^+$);

4-(6-(morpholin-4-yl)pyridin-3-yl)-N-(3-methyl-4-(1,5,7-trimethyl-3,7-diazabicyclo[3.3.1]nonan-3-yl)phenyl)pyrimidin-2-amine, compound #75, $^1$H NMR (DMSO-d6): δ 8.92 (d, 1H, J=2.1 Hz), 8.38 (d, 1H, J=5.1 Hz), 8.25 (m, 1H), 7.56 (m, 3H), 7.25 (d, 1H, J=4.8 Hz), 6.95 (d, 1H, J=9.3 Hz), 3.68 (m, 4H), 3.58 (m, 4H), 3.31 (m, 8H), 2.91 (s, 2H), 2.31 (s, 3H), 0.87 (s, 6H); LCMS: purity: 99%; MS (m/e): 514 (MH$^+$);

4-(6-(dimethylamino)pyridin-3-yl)-N-(3-methyl-4-(1,5,7-trimethyl-3,7-diazabicyclo[3.3.1]nonan-3-yl)phenyl)pyrimidin-2-amine, compound #76, LCMS: purity: 99%; MS (m/e): 472 (MH$^+$);

4-(6-(cyclohexylamino)pyridin-3-yl)-N-(3-methyl-4-(1,5,7-trimethyl-3,7-diazabicyclo[3.3.1]nonan-3-yl)phenyl)pyrimidin-2-amine, compound #77, LCMS: purity: 99%; MS (m/e): 526 (MH$^+$);

4-(6-(cyclohexylamino)pyridin-3-yl)-N-(3-methyl-4-((1S,4S)-5-methyl-2,5-diazabicyclo[2.2.1]heptan-2-yl)phenyl)pyrimidin-2-amine, compound #78, LCMS: purity: 99%; MS (m/e): 470 (MH$^+$);

4-(6-(cyclohexylamino)pyridin-3-yl)-N-(3-fluoro-4-((1S,4S)-5-methyl-2,5-diazabicyclo[2.2.1]heptan-2-yl)phenyl)pyrimidin-2-amine, compound #79, LCMS: purity: 99%; MS (m/e): 474 (MH$^+$);

4-(6-(benzylamino)pyridin-3-yl)-N-(3-methyl-4-((1S,4S)-5-methyl-2,5-diazabicyclo[2.2.1]heptan-2-yl)phenyl)pyrimidin-2-amine, compound #80, LCMS: purity: 99%; MS (m/e): 478 (MH$^+$);

4-(6-(benzylamino)pyridin-3-yl)-N-(3-fluoro-4-((1S,4S)-5-methyl-2,5-diazabicyclo[2.2.1]heptan-2-yl)phenyl)pyrimidin-2-amine, compound #81, LCMS: purity: 99%; MS (m/e): 482 (MH$^+$);

4-(5-methyl-6-(morpholin-4-yl)pyridin-3-yl)-N-(3-fluoro-4-(1,5,7-trimethyl-3,7-diazabicyclo[3.3.1]nonan-3-yl)phenyl)pyrimidin-2-amine, compound #82, LCMS: purity: 99%; MS (m/e): 532 (MH$^+$);

4-(6-(dimethylamino)pyridin-3-yl)-N-(3-fluoro-4-(1,5,7-trimethyl-3,7-diazabicyclo[3.3.1]nonan-3-yl)phenyl)pyrimidin-2-amine, compound #83, LCMS: purity: 99%; MS (m/e): 476 (MH$^+$);

4-(4-(dimethylamino)phenyl)-N-(3-fluoro-4-(1,5,7-trimethyl-3,7-diazabicyclo[3.3.1]nonan-3-yl)phenyl)pyrimidin-2-amine, compound #84, LCMS: purity: 99%; MS (m/e): 475 (MH$^+$);

4-(6-(morpholin-4-yl)pyridin-3-yl)-N-(3-fluoro-4-(1,5,7-trimethyl-3,7-diazabicyclo[3.3.1]nonan-3-yl)phenyl)pyrimidin-2-amine, compound #85, LCMS: purity: 99%; MS (m/e): 518 (MH$^+$);

4-(3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine, compound #86, LCMS: purity: 99%; MS (m/e): 430 (MH$^+$);

4-(3,4-dihydro-2H-pyrido[3,2-b][1,4]oxazin-7-yl)-N-(3-fluoro-4-((1S,4S)-5-methyl-2,5-diazabicyclo[2.2.1]heptan-2-yl)phenyl)pyrimidin-2-amine, compound #87, LCMS: purity: 99%; MS (m/e): 434 (MH$^+$);

4-(3,4-dihydro-2H-pyrido[3,2-b][1,4]oxazin-7-yl)-N-(3-methyl-4-(1,5,7-trimethyl-3,7-diazabicyclo[3.3.1]nonan-3-yl)phenyl)pyrimidin-2-amine, compound #88, LCMS: purity: 99%; MS (m/e): 486 (MH$^+$);

4-(3,4-dihydro-2H-pyrido[3,2-b][1,4]oxazin-7-yl)-N-(3-fluoro-4-(1,5,7-trimethyl-3,7-diazabicyclo[3.3.1]nonan-3-yl)phenyl)pyrimidin-2-amine, compound #89, LCMS: purity: 99%; MS (m/e): 490 (MH$^+$);

4-(6-(benzyl)pyridin-3-yl)-N-(3-methyl-4-(1,5,7-trimethyl-3,7-diazabicyclo[3.3.1]nonan-3-yl)phenyl)pyrimidin-2-amine, compound #90, LCMS: purity: 99%; MS (m/e): 534 (MH$^+$);

4-(6-(benzyl)pyridin-3-yl)-N-(3-fluoro-4-(1,5,7-trimethyl-3,7-diazabicyclo[3.3.1]nonan-3-yl)phenyl)pyrimidin-2-amine, compound #91, LCMS: purity: 99%; MS (m/e): 538 (MH$^+$);

4-(2-(propyl)aminopyrimidin-5-yl)-N-(3-methyl-4-((1S,4S)-5-methyl-2,5-diazabicyclo[2.2.1]heptan-2-yl)phenyl)pyrimidin-2-amine, compound #92, LCMS: purity: 99%; MS (m/e): 431 (MH$^+$);

4-(2-(propyl)aminopyrimidin-5-yl)-N-(3-fluoro-4-((1S,4S)-5-methyl-2,5-diazabicyclo[2.2.1]heptan-2-yl)phenyl)pyrimidin-2-amine, compound #93, LCMS: purity: 99%; MS (m/e): 435 (MH$^+$);

4-(6-(cyclohexylamino)pyridin-3-yl)-N-(3-trifluoromethyl-4-((1S,4S)-5-methyl-2,5-diazabicyclo[2.2.1]heptan-2-yl)phenyl)pyrimidin-2-amine, compound #94, LCMS: purity: 99%; MS (m/e): 524 (MH$^+$);

4-(5-(methyl)sulfonylpyridin-3-yl)-N-(3-methyl-4-((1S,4S)-5-methyl-2,5-diazabicyclo[2.2.1]heptan-2-yl)phenyl)pyrimidin-2-amine, compound #95, LCMS: purity: 99%; MS (m/e): 451 (MH$^+$);

4-(6-(dimethylamino)pyridin-3-yl)-N-(3-trifluoromethyl-4-((1S,4S)-5-methyl-2,5-diazabicyclo[2.2.1]heptan-2-yl)phenyl)pyrimidin-2-amine, compound #96, LCMS: purity: 99%; MS (m/e): 470 (MH$^+$);

4-(6-(morpholin-4-yl)pyridin-3-yl)-N-(3-trifluoromethyl-4-((1S,4S)-5-methyl-2,5-diazabicyclo[2.2.1]heptan-2-yl)phenyl)pyrimidin-2-amine, compound #97, LCMS: purity: 99%; MS (m/e): 512 (MH$^+$);

4-(3,4-dihydro-2H-pyrido[3,2-b][1,4]oxazin-7-yl)-N-(3-trifluoromethyl-4-((1S,4S)-5-methyl-2,5-diazabicyclo[2.2.1]heptan-2-yl)phenyl)pyrimidin-2-amine, compound #98, LCMS: purity: 99%; MS (m/e): 484 (MH$^+$);

4-(6-((2-(cyclopropylsulfonyl)aminoethyl)-amino)pyridin-3-yl)-N-(3-methyl-4-((1S,4S)-5-methyl-2,5-diazabicyclo[2.2.1]heptan-2-yl)phenyl)pyrimidin-2-amine, compound #99, LCMS: purity: 99%; MS (m/e): 535 (MH$^+$);

4-(6-((2-(cyclopropylsulfonyl)aminoethyl)-amino)pyridin-3-yl)-N-(3-methyl-4-((1S,4S)-5-oxa-2-azabicyclo[2.2.1]heptan-2-yl)phenyl)pyrimidin-2-amine, compound #100, LCMS: purity: 99%; MS (m/e): 522 (MH$^+$);

4-(5-(methyl)sulfonylpyridin-3-yl)-N-(3-fluoro-4-((1S,4S)-5-methyl-2,5-diazabicyclo[2.2.1]heptan-2-yl)phenyl)pyrimidin-2-amine, compound #101, LCMS: purity: 99%; MS (m/e): 455 (MH$^+$);

4-(5-(methyl)sulfonylpyridin-3-yl)-N-(3-trifluoromethyl-4-((1S,4S)-5-methyl-2,5-diazabicyclo[2.2.1]heptan-2-yl)phenyl)pyrimidin-2-amine, compound #102, LCMS: purity: 99%; MS (m/e): 505 (MH$^+$);

4-(imidazo[1,2-a]pyridin-6-yl)-N-(3-methyl-4-((1S,4S)-5-methyl-2,5-diazabicyclo[2.2.1]heptan-2-yl)phenyl)pyrimidin-2-amine, compound #103, $^1$H NMR (CD$_3$OD, 300 MHz): δ 9.29 (s, 1H), 8.42 (m, 1H), 8.06 (m, 1H), 7.96 (s, 1H), 7.64 (m, 2H), 7.55 (m, 1H), 7.49 (m, 1H), 7.27 (m, 1H), 6.99 (m, 1H), 4.29 (m, 2H), 3.79 (m, 1H), 3.52 (m, 3H), 2.99 (s, 3H), 2.32 (m, 5H); MS (ES) 412.0 (M+H);

4-(4-(5-(4-dimethylaminophenyl)oxazol-2-yl)phenyl)-N-(3-methyl-4-((1S,4S)-5-methyl-2,5-diazabicyclo[2.2.1]heptan-2-yl)phenyl)pyrimidin-2-amine, compound #104, $^1$H NMR (CD$_3$OD, 300 MHz): δ 8.32 (m, 1H), 8.22 (m, 2H), 8.06 (m, 2H), 7.61 (m, 2H), 7.43 (m, 4H), 6.98 (m, 3H), 4.31 (m, 2H), 3.98 (m, 1H), 3.52 (m, 2H), 3.17 (m, 1H), 3.05 (m, 9H), 2.33 (m, 5H); MS (ES) 558.1 (M+H);

4-(6-methoxy-1H-indol-2-yl)-N-(3-methyl-4-((1S,4S)-5-methyl-2,5-diazabicyclo[2.2.1]heptan-2-yl)phenyl)pyrimidin-2-amine, compound #105, $^1$H NMR (CD$_3$OD, 300 MHz): δ 7.98 (m, 1H), 7.51 (m, 1H), 7.44 (s, 1H), 7.37 (m, 1H), 7.28 (m, 2H), 7.03 (m, 1H), 6.93 (m, 1H), 6.76 (m, 1H), 4.34 (m, 2H), 3.98 (m, 1H), 3.85 (s, 3H), 3.54 (m, 3H), 2.99 (s, 3H), 2.32 (m, 5H); MS (ES) 441.1 (M+H);

4-(1-(3-chlorophenyl)-1H-pyrazol-4-yl)-N-(3-methyl-4-((1S,4S)-5-methyl-2,5-diazabicyclo[2.2.1]heptan-2-yl)phenyl)pyrimidin-2-amine, compound #106, $^1$H NMR (CD$_3$OD, 300 MHz): δ 9.10 (m, 1H), 8.35 (m, 1H), 8.20 (m, 1H), 7.92 (m, 1H), 7.79 (m, 1H), 7.50 (m, 1H), 7.40 (m, 3H), 7.27 (m, 1H), 7.03 (m, 1H), 4.34 (m, 2H), 3.98 (m, 1H), 3.54 (m, 2H), 3.18 (m, 1H), 2.99 (s, 3H), 2.32 (m, 5H); MS (ES) 472.0 (M+H);

4-(1-methylbenzimidazol-6-yl)-N-(3-methyl-4-((1S,4S)-5-methyl-2,5-diazabicyclo[2.2.1]heptan-2-yl)phenyl)pyrimidin-2-amine, compound #107, $^1$H NMR (CD$_3$OD, 300 MHz): δ 9.41 (s, 1H), 8.73 (s, 1H), 8.47 (m, 2H), 7.96 (m, 1H), 7.53 (m, 3H), 7.02 (m, 1H), 4.31 (m, 2H), 4.21 (s, 3H), 3.97 (m, 1H), 3.51 (m, 2H), 3.19 (m, 1H), 2.99 (s, 3H), 2.34 (m, 5H); MS (ES) 426.1 (M+H);

4-(5-cyano-1H-indol-2-yl)-N-(3-methyl-4-((1S,4S)-5-methyl-2,5-diazabicyclo[2.2.1]heptan-2-yl)phenyl)pyrimidin-2-amine, compound #108, $^1$H NMR (CD$_3$OD, 300 MHz): δ 8.17 (m, 1H), 8.01 (m, 1H), 7.56 (m, 1H), 7.39 (m, 5H), 7.01 (m, 1H), 4.32 (m, 2H), 3.97 (m, 1H), 3.53 (m, 2H), 3.16 (m, 1H), 2.99 (s, 3H), 2.31 (m, 5H); MS (ES) 436.1 (M+H);

4-(1-(4-fluorophenyl)-1H-pyrazol-4-yl)-N-(3-methyl-4-((1S,4S)-5-methyl-2,5-diazabicyclo[2.2.1]heptan-2-yl)phenyl)pyrimidin-2-amine, compound #109, $^1$H NMR (CD$_3$OD, 300 MHz): δ 8.75 (s, 1H), 8.26 (m, 2H), 7.79 (m, 2H), 7.46 (m, 2H), 7.23 (m, 2H), 7.00 (m, 1H), 6.93 (m, 1H), 4.22 (m, 2H), 3.73 (m, 1H), 3.53 (m, 1H), 3.33 (m, 1H), 3.22 (m, 1H), 2.94 (s, 3H), 2.28 (m, 5H); MS (ES) 456.0 (M+H);

4-(6-(morpholin-4-yl)pyridin-3-yl)-N-(3-methyl-4-(7-azabicyclo[2.2.1]heptan-7-yl)phenyl)pyrimidin-2-amine, compound #110, $^1$H NMR (CD$_3$OD, 300 MHz): δ 8.87 (m, 1H), 8.58 (m, 1H), 8.50 (m, 1H), 7.81 (m, 2H), 7.60 (m, 1H), 7.36 (m, 2H), 4.80 (m, 2H), 3.85 (m, 4H), 3.76 (m, 4H), 2.57 (s, 3H), 2.22 (m, 4H), 1.98 (m, 4H); MS (ES) 443.1 (M+H);

4-(6-cyanopyridin-3-yl)-N-(3-methyl-4-((1S,4S)-5-methyl-2,5-diazabicyclo[2.2.1]heptan-2-yl)phenyl)pyrimidin-2-amine, compound #111, $^1$H NMR (CD$_3$OD, 300 MHz): δ 9.48 (m, 1H), 8.64 (m, 2H), 8.05 (m, 1H), 7.90 (m, 2H), 7.64 (m, 1H), 7.46 (m, 1H), 4.31 (m, 2H), 3.97 (m, 1H), 3.50 (m, 2H), 3.18 (m, 1H), 2.99 (s, 3H), 2.30 (m, 5H); MS (ES) 398.1 (M+H);

4-(6-cyanopyridin-3-yl)-N-(3-methyl-4-(7-azabicyclo[2.2.1]heptan-7-yl)phenyl)pyrimidin-2-amine, compound #112, $^1$H NMR (CD$_3$OD, 300 MHz): δ 9.47 (m, 1H), 8.66 (m, 2H), 8.03 (m, 1H), 7.87 (m, 2H), 7.60 (m, 1H), 7.51 (m, 1H), 4.81 (m, 1H), 2.57 (s, 3H), 2.22 (m, 4H), 1.98 (m, 4H); MS (ES) 383.0 (M+H);

4-(2-oxoindolin-5-yl)-N-(3-methyl-4-((1S,4S)-5-methyl-2,5-diazabicyclo[2.2.1]heptan-2-yl)phenyl)pyrimidin-2-amine, compound #113, $^1$H NMR (CD$_3$OD, 300 MHz): δ 8.25 (m, 3H), 7.41 (m, 3H), 7.02 (m, 2H), 4.32 (m, 2H), 3.98 (m, 1H), 3.54 (m, 2H), 3.18 (m, 1H), 2.99 (m, 5H), 2.33 (m, 5H); MS (ES) 427.0 (M+H);

4-(5-cyanopyridin-3-yl)-N-(3-methyl-4-((1S,4S)-5-methyl-2,5-diazabicyclo[2.2.1]heptan-2-yl)phenyl)pyrimidin-2-amine, compound #114, $^1$H NMR (CD$_3$OD, 300 MHz): δ 8.82 (m, 2H), 7.42 (m, 4H), 6.97 (m, 2H), 4.30 (m, 2H), 3.97 (m, 1H), 3.49 (m, 2H), 3.17 (m, 1H), 2.98 (s, 3H), 2.30 (m, 5H); MS (ES) 398.1 (M+H);

4-(6-(1H-tetrazol-5-yl)pyridin-3-yl)-N-(3-methyl-4-((1S,4S)-5-methyl-2,5-diazabicyclo[2.2.1]heptan-2-yl)phenyl)pyrimidin-2-amine, compound #115, $^1$H NMR (CD$_3$OD, 300 MHz): δ 9.49 (m, 1H), 8.72 (m, 1H), 8.51 (m, 1H), 8.36 (m, 1H), 7.53 (m, 2H), 7.40 (m, 1H), 6.98 (m, 1H), 4.29 (m, 2H), 3.96 (m, 1H), 3.49 (m, 2H), 3.16 (m, 1H), 2.65 (s, 3H), 2.32 (m, 5H); MS (ES) 441.1 (M+H);

4-(6-(morpholin-4-yl)pyridin-3-yl)-N-(3-cyano-4-((1S,4S)-5-acetyl-2,5-diazabicyclo[2.2.1]heptan-2-yl)phenyl)pyrimidin-2-amine, compound #116, $^1$H NMR (CD$_3$OD, 300 MHz): δ 8.79 (m, 1H), 8.39 (m, 1H), 8.31 (m, 1H), 7.86 (m, 1H), 7.59 (m, 1H), 7.29 (m, 1H), 7.12 (m, 1H), 6.87 (m, 1H), 4.04 (m, 2H), 3.80 (m, 4H), 3.58 (m, 8H), 2.07 (m, 5H); MS (ES) 497.1 (M+H);

4-(6-(morpholin-4-yl)pyridin-3-yl)-N-(3-cyano-4-((1S,4S)-5-methylsulfonyl-2,5-diazabicyclo[2.2.1]heptan-2-yl)phenyl)pyrimidin-2-amine, compound #117, $^1$H NMR (CD$_3$OD, 300 MHz): δ 8.83 (m, 1H), 8.41 (m, 1H), 8.32 (m, 1H), 7.88 (m, 1H), 7.60 (m, 1H), 7.34 (m, 1H), 7.17 (m, 1H), 6.93 (m, 1H), 4.55 (m, 2H), 4.04 (m, 3H), 3.82 (m, 5H), 3.73 (m, 4H), 2.96 (s, 3H), 2.01 (m, 2H); MS (ES) 533.1 (M+H);

4-(6-(morpholin-4-yl)pyridin-3-yl)-N-(3-cyano-4-((1S,4S)-5-methyl-2,5-diazabicyclo[2.2.1]heptan-2-yl)phenyl)pyrimidin-2-amine, compound #118, $^1$H NMR (CD$_3$OD, 300 MHz): δ 8.83 (m, 1H), 8.49 (m, 1H), 8.39 (m, 1H), 8.00 (m, 1H), 7.74 (m, 1H), 7.33 (m, 1H), 7.22 (m, 1H), 6.98 (m, 1H), 4.83 (m, 1H), 4.41 (m, 1H), 4.05 (m, 3H), 3.85 (m, 4H), 3.74 (m, 4H), 3.65 (m, 1H), 3.00 (s, 3H), 2.39 (m, 2H); MS (ES) 469.1 (M+H);

4-(6-(morpholin-4-yl)pyridin-3-yl)-N-(3-cyano-4-((1S,4S)-5-cyclopentyl-2,5-diazabicyclo[2.2.1]heptan-2-yl)phenyl)pyrimidin-2-amine, compound #119, $^1$H NMR (CD$_3$OD, 300 MHz): δ 8.83 (m, 1H), 8.49 (m, 1H), 8.40 (m, 1H), 8.01 (m, 1H), 7.75 (m, 1H), 7.34 (m, 1H), 7.23 (m, 1H), 6.99 (m, 1H), 4.57 (m, 1H), 4.08 (m, 1H), 3.81 (m, 11H), 3.46 (m, 1H), 2.33 (m, 2H), 1.76 (m, 8H); MS (ES) 523.1 (M+H);

4-(6-(morpholin-4-yl)pyridin-3-yl)-N-(3-methyl-4-(1,4-diazabicyclo[3.2.1]octan-4-yl)phenyl)pyrimidin-2-amine, compound #120, $^1$H NMR (CD$_3$OD, 300 MHz): δ 8.93 (m, 1H), 8.40 (m, 1H), 8.29 (m, 1H), 7.74 (m, 1H), 7.52 (m, 2H), 7.29 (m, 1H), 7.19 (m, 1H), 7.05 (m, 1H), 3.97 (m, 1H), 3.82 (m, 4H), 3.69 (m, 9H), 3.37 (m, 1H), 3.14 (m, 2H), 2.37 (s, 3H), 2.16 (m, 2H); MS (ES) 458.1 (M+H);

4-(2-oxoindolin-5-yl)-N-(3-methyl-4-(1,4-diazabicyclo[3.2.1]octan-4-yl)phenyl)pyrimidin-2-amine, compound #121, $^1$H NMR (CD$_3$OD, 300 MHz): δ 8.20 (m, 3H), 7.44 (m, 3H), 7.12 (m, 2H), 3.95 (m, 1H), 3.60 (m, 5H), 3.36 (m, 1H), 3.10 (m, 4H), 2.37 (s, 3H), 2.16 (m, 2H); MS (ES) 427.0 (M+H);

(1-methylbenzimidazol-6-yl)-N-(3-methyl-4-(1,4-diazabicyclo[3.2.1]octan-4-yl)phenyl)pyrimidin-2-amine, compound #122, $^1$H NMR (CD$_3$OD, 300 MHz): δ 8.40 (m, 2H), 8.24 (m, 1H), 8.14 (m, 1H), 7.76 (m, 1H), 7.67 (m, 1H), 7.60 (m, 1H), 7.39 (m, 1H), 7.14 (m, 1H), 3.99 (s, 3H), 3.94 (m, 1H), 3.60 (m, 5H), 3.36 (m, 1H), 3.14 (m, 2H), 2.38 (s, 3H), 2.16 (m, 2H); MS (ES) 426.1 (M+H);

4-(imidazo[1,2-a]pyridin-6-yl)-N-(3-methyl-4-(1,4-diazabicyclo[3.2.1]octan-4-yl)phenyl)pyrimidin-2-amine, compound #123, $^1$H NMR (CD$_3$OD, 300 MHz): δ 9.30 (m, 1H), 8.45 (m, 1H), 8.39 (m, 1H), 8.07 (m, 1H), 7.96 (m, 1H), 7.60 (m, 3H), 7.30 (m, 1H), 7.15 (m, 1H), 3.95 (m, 1H), 3.60 (m, 5H), 3.36 (m, 1H), 3.14 (m, 2H), 2.37 (s, 3H), 2.16 (m, 2H); MS (ES) 412.1 (M+H);

4-(2H-benzo[b][1,4]oxazin-3(4H)-on-6-yl)-N-(3-fluoro-4-((1S,4S)-5-methyl-2,5-diazabicyclo[2.2.1]heptan-2-yl)phenyl)pyrimidin-2-amine, compound #124, $^1$H NMR (CD$_3$OD, 300 MHz): δ 8.36 (m, 1H), 7.75 (m, 3H), 7.33-6.77 (m, 4H), 4.63 (s, 2H), 4.59 (s, 1H), 4.31 (s, 1H), 3.92 (m, 2H), 3.41 (m, 1H), 3.15 (m, 1H), 2.97 (s, 3H), 2.33 (m, 2H); MS (ES) 447.09 (M+H);

4-(2,2,4-trimethyl-3-oxo-3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine, compound #125, $^1$H NMR (CD$_3$OD, 300 MHz) 8.80 (m, 1H), 8.39 (m, 1H), 8.01 (m, 2H), 7.55 (m, 2H), 7.26 (m, 1H), 6.98 (m, 1H), 4.63 (s, 1H), 4.31 (s, 1H), 4.25 (s, 1H), 3.50 (m, 4H), 3.28 (m, 2H), 2.99 (s, 3H), 2.32 (m, 5H), 1.54 (m, 6H); MS (ES) 486.21 (M+H);

4-(2,2,4-trimethyl-3-oxo-3,4-dihydro-2H-pyrido[3,2-b][1,4]oxazin-7-yl)-N-(3-fluoro-4-((1S,4S)-5-methyl-2,5-diazabicyclo[2.2.1]heptan-2-yl)phenyl)pyrimidin-2-amine, compound #126, $^1$H NMR (CD$_3$OD, 300 MHz): δ 8.75 (m, 1H), 8.39 (m, 2H), 7.96 (m, 1H), 7.65 (m, 1H), 7.25 (m, 2H), 6.79 (m, 1H), 4.57 (s, 1H), 4.29 (s, 1H), 3.84 (m, 2H), 3.48 (m, 5H), 3.30 (m, 6H), 2.94 (m, 3H), 2.30 (m, 2H); MS (ES) 490.19 (M+H);

4-(5-(3-methylpiperidin-1-yl)pyrazin-2-yl)-N-(3-fluoro-4-((1S,4S)-5-methyl-2,5-diazabicyclo[2.2.1]heptan-2-yl)phenyl)pyrimidin-2-amine, compound #127, $^1$H NMR (CD$_3$OD, 300 MHz): δ 9.00 (m, 1H), 8.31 (m, 2H), 7.57 (m, 2H), 7.31 (m, 1H), 6.85 (m, 1H), 4.64 (s, 1H), 4.45 (m, 2H), 4.33 (s, 1H), 4.29 (s, 1H), 3.96 (m, 2H), 3.45 (m, 1H), 3.19 (m, 1H), 3.07 (m, 1H), 2.98 (s, 3H), 2.74 (m, 2H), 2.35 (m, 2H), 1.19-1.26 (m, 4H), 1.00 (d, J=5.4 Hz, 3H); MS (ES) 475.48 (M+H);

4-(4-(t-butylcarbonylamino)phenyl)-N-(3-fluoro-4-((1S,4S)-5-methyl-2,5-diazabicyclo[2.2.1]heptan-2-yl)phenyl)pyrimidin-2-amine, compound #128, $^1$H NMR (CD$_3$OD, 300 MHz): δ 8.42 (m, 2H), 8.10 (m, 2H), 7.75 (m, 3H), 7.25 (m, 2H), 4.57 (s, 1H), 4.26 (s, 1H), 3.81 (m, 2H), 3.46 (m, 2H), 2.93 (s, 3H), 2.29 (m, 2H), 1.34 (s, 9H); MS (ES) 475.12 (M+H);

4-(4-(t-butylcarbonylamino)phenyl)-N-(3-methyl-4-((1S,4S)-5-methyl-2,5-diazabicyclo[2.2.1]heptan-2-yl)phenyl) pyrimidin-2-amine, compound #129, $^1$H NMR (CD$_3$OD, 300 MHz): δ 8.34 (m, 2H), 8.10 (m, 2H), 7.72 (m, 2H), 7.51 (m, 2H), 7.22 (m, 1H), 6.95 (m, 1H), 4.29 (s, 1H), 4.22 (s, 1H), 3.76 (m, 2H), 3.47 (m, 2H), 2.97 (m, 3H), 2.31 (m, 5H), 1.32 (s, 9H); MS (ES) 471.15 (M+H);

4-(2,2-dimethyl-3-oxo-3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine, compound #130, $^1$H NMR (CD$_3$OD, 300 MHz): δ 8.68 (m, 1H), 8.48 (m, 1H), 8.39 (m, 1H), 7.49 (m, 2H), 7.27 (m, 1H), 6.96 (m, 1H), 4.23 (m, 2H), 3.72 (m, 1H), 3.50 (m, 2H), 3.26 (m, 1H), 2.95 (s, 3H), 2.66 (m, 1H), 2.32 (s, 3H), 2.30 (m, 2H), 1.54 (s, 6H); MS (ES) 472.22 (M+H);

4-(6-(acetamido)pyridin-3-yl)-N-(3-methyl-4-((1S,4S)-5-methyl-2,5-diazabicyclo[2.2.1]heptan-2-yl)phenyl)pyrimidin-2-amine, compound #132, $^1$H NMR (CD$_3$OD, 300 MHz): δ 9.02 (m, 1H), 8.42 (m, 2H), 8.21 (m, 2H), 7.52 (m, 2H), 7.23 (m, 1H), 6.97 (m, 1H), 4.29 (s, 1H), 4.30 (s, 1H), 4.24 (s, 1H), 3.77 (m, 1H), 3.52 (m, 1H), 2.97 (s, 3H), 2.31 (m, 5H), 2.21 (s, 3H); MS (ES) 430.07 (M+H);

4-(4-((pyridin-2-yl)aminocarbonyl)phenyl)-N-(3-fluoro-4-((1S,4S)-5-methyl-2,5-diazabicyclo[2.2.1]heptan-2-yl)phenyl)pyrimidin-2-amine, compound #133, $^1$H NMR (CD$_3$OD, 300 MHz): δ 8.50-8.15 (m, 6H), 8.00 (m, 1H), 7.73 (m, 1H), 7.39 (m, 4H), 6.83 (m, 1H), 4.61 (s, 1H), 4.32 (s, 1H), 3.92 (m, 3H), 3.44 (m, 1H), 3.18 (m, 1H), 2.97 (s, 3H), 2.37 (m, 2H); MS (ES) 496.05 (M+H);

4-(4-((pyridin-2-yl)aminocarbonyl)phenyl)-N-(3-methyl-4-((1S,4S)-5-methyl-2,5-diazabicyclo[2.2.1]heptan-2-yl)phenyl)pyrimidin-2-amine, compound #134, $^1$H NMR (CD$_3$OD, 300 MHz): δ 8.45-7.96 (m, 8H), 7.50 (m, 4H), 6.99 (m, 1H), 4.61 (s, 1H), 4.30 (m, 2H), 3.98 (m, 1H), 3.50 (m, 2H), 3.15 (m, 1H), 2.99 (s, 3H), 2.33 (m, 5H); MS (ES) 492.08 (M+H);

4-(4-(methylsulfonylamino)phenyl)-N-(3-fluoro-4-((1S,4S)-5-methyl-2,5-diazabicyclo[2.2.1]heptan-2-yl)phenyl)pyrimidin-2-amine, compound #135, $^1$H NMR (CD$_3$OD, 300 MHz): δ 8.36 (m, 1H), 8.13 (m, 2H), 7.65 (m, 1H), 7.32 (m, 3H), 6.83 (m, 1H), 4.62 (s, 1H), 4.32 (s, 1H), 3.92 (m, 3H), 3.39 (m, 1H), 3.20 (m, 1H), 3.05 (m, 3H), 2.97 (s, 3H), 2.34 (m, 2H); MS (ES) 469.03 (M+H);

4-(4-(methylsulfonylamino)phenyl)-N-(3-methyl-4-((1S,4S)-5-methyl-2,5-diazabicyclo[2.2.1]heptan-2-yl)phenyl)pyrimidin-2-amine, compound #136, $^1$H NMR (CD$_3$OD, 300 MHz): δ 8.21 (m, 3H), 7.39 (m, 5H), 7.01 (m, 1H), 4.34 (m, 2H), 3.99 (m, 1H), 3.77 (m, 1H), 3.53 (m, 2H), 3.20 (m, 1H), 3.07 (s, 3H), 2.99 (s, 3H), 2.66 (m, 1H), 2.33 (m, 5H); MS (ES) 465.05 (M+H);

4-(2,2-dimethyl-3-oxo-3,4-dihydro-2H-pyrido[3,2-b][1,4]oxazin-7-yl)-N-(4-((1S,4S)-5-methyl-2,5-diazabicyclo[2.2.1]heptan-2-yl)phenyl)pyrimidin-2-amine, compound #137, $^1$H NMR (CD$_3$OD, 300 MHz): δ 8.67 (m, 1H), 8.48 (m, 1H), 8.39 (m, 2H), 7.98 (m, 1H), 7.54 (m, 2H), 7.20 (m, 1H), 6.69 (m, 2H), 4.63 (s, 1H), 4.33 (s, 1H), 3.72 (m, 2H), 3.37 (m, 2H), 3.24 (m, 1H), 2.93 (s, 3H), 2.34 (s, 2H), 1.54 (s, 6H); MS (ES) 458.21 (M+H);

4-(4-(3-cyclopropylureido)phenyl)-N-(4-((1S,4S)-5-methyl-2,5-diazabicyclo[2.2.1]heptan-2-yl)phenyl)pyrimidin-2-amine, compound #139, $^1$H NMR (CD$_3$OD, 300 MHz): δ 8.28 (m, 2H), 8.18 (m, 1H), 8.03 (m, 1H), 7.55 (m, 3H), 7.13 (m, 2H), 6.69 (m, 2H), 4.64 (s, 1H), 4.35 (s, 1H), 3.77 (m, 2H), 3.36 (m, 2H), 2.95 (s, 3H), 2.61 (m, 1H), 2.35 (m, 3H), 0.76 (m, 1H), 0.53 (m, 3H); MS (ES) 456.52 (M+H);

4-(6-(2-(morpholin-4-yl)acetamido)pyridin-3-yl)-N-(3-methyl-4-((1S,4S)-5-methyl-2,5-diazabicyclo[2.2.1]heptan-2-yl)phenyl)pyrimidin-2-amine, compound #141, $^1$H NMR (CD$_3$OD, 300 MHz): δ 9.10 (m, 1H), 8.51 (m, 2H), 8.39 (m, 1H), 7.49 (m, 2H), 7.31 (m, 1H), 6.99 (m, 1H), 4.28 (m, 4H), 3.97 (m, 6H), 3.48 (m, 4H), 3.34 (m, 1H), 3.21 (m, 1H), 2.99 (s, 3H), 2.32 (m, 6H); MS (ES) 515.72 (M+H);

4-(6-(2-(morpholin-4-yl)acetamido)pyridin-3-yl)-N-(4-((1S,4S)-5-methyl-2,5-diazabicyclo[2.2.1]heptan-2-yl)phenyl)pyrimidin-2-amine, compound #142, $^1$H NMR (CD$_3$OD, 300 MHz): δ 9.10 (m, 1H), 8.51 (m, 1H), 8.36 (m, 2H), 7.52 (m, 2H), 7.32 (m, 1H), 6.73 (m, 1H), 4.66 (s, 1H), 4.36 (s, 1H), 4.26 (s, 1H), 4.12-3.78 (m, 6H), 3.46 (m, 4H), 3.21 (m, 2H), 2.97 (s, 3H), 2.33 (m, 3H); MS (ES) 501.06 (M+H);

4-(6-(2-(morpholin-4-yl)acetamido)pyridin-3-yl)-N-(3-fluoro-4-((1S,4S)-5-methyl-2,5-diazabicyclo[2.2.1]heptan-2-yl)phenyl)pyrimidin-2-amine, compound #143, $^1$H NMR (CD$_3$OD, 300 MHz): δ 9.05 (m, 1H), 8.51 (m, 1H), 8.24 (m, 2H), 7.66 (m, 1H), 7.29 (m, 2H), 6.80 (m, 1H), 4.66 (s, 1H), 4.59 (m, 1H), 4.31 (s, 1H), 3.80 (m, 6H), 3.50 (m, 1H), 3.26 (m, 2H), 2.96 (s, 3H), 2.64 (m, 4H), 2.32 (m, 3H); MS (ES) 519.06 (M+H);

4-(6-(acetamido)pyridin-3-yl)-N-(3-methyl-4-((1S,4S)-5-oxa-2-azabicyclo[2.2.1]heptan-2-yl)phenyl)pyrimidin-2-amine, compound #147, $^1$H NMR (CD$_3$OD, 300 MHz): δ 9.03 (m, 1H), 8.42 (m, 2H), 8.22 (m, 2H), 7.41 (m, 2H), 7.20 (m, 1H), 6.88 (m, 1H), 4.58 (s, 1H), 4.17 (s, 1H), 4.05 (m, 1H), 3.82 (m, 1H), 3.23 (m, 2H), 2.28 (m, 3H), 2.21 (s, 3H), 2.03 (m, 1H), 1.91 (m, 1H); MS (ES) 416.97 (M+H);

4-(6-aminopyridin-3-yl)-N-(3-methyl-4-((1S,4S)-5-ethylcarbonyl-2,5-diazabicyclo[2.2.1]heptan-2-yl)phenyl)pyrimidin-2-amine, compound #148, $^1$H NMR (CD$_3$OD, 300 MHz): δ 8.65 (m, 1H), 8.38 (m, 2H), 8.06 (m, 1H), 7.40 (m, 2H), 7.14 (m, 1H), 6.89 (m, 1H), 4.65 (s, 1H), 4.23 (s, 1H), 4.19 (m, 1H), 3.70-3.36 (m, 3H), 2.65 (s, 3H), 2.44 (m, 2H), 2.37 (s, 3H), 2.14-1.89 (m, 2H), 1.14 (m, 2H); MS (ES) 430.02 (M+H);

4-(6-(acetamido)pyridin-3-yl)-N-(3-methyl-4-((1S,4S)-5-ethylcarbonyl-2,5-diazabicyclo[2.2.1]heptan-2-yl)phenyl)pyrimidin-2-amine, compound #149, $^1$H NMR (CD$_3$OD, 300 MHz): δ 9.03 (m, 1H), 8.39 (m, 2H), 8.22 (m, 2H), 7.42 (m, 2H), 7.21 (m, 1H), 6.91 (m, 1H), 4.65 (s, 1H), 4.25 (s, 1H), 3.68-3.32 (m, 5H), 2.66-2.32 (m, 2H), 2.29 (s, 3H), 2.21 (s, 3H), 2.08-1.82 (m, 2H), 1.14 (m, 2H); MS (ES) 472.06 (M+H);

4-(6-aminopyridin-3-yl)-N-(3-methyl-4-((1S,4S)-5-methylsulfonyl-2,5-diazabicyclo[2.2.1]heptan-2-yl)phenyl)pyrimidin-2-amine, compound #150, $^1$H NMR (CD$_3$OD, 300 MHz): δ 8.68 (m, 1H), 8.28 (m, 2H), 8.09 (m, 1H), 7.41 (m, 2H), 7.09 (m, 1H), 6.75 (m, 1H), 4.65 (s, 1H), 4.20 (m, 1H), 4.19 (m, 1H), 3.71-3.39 (m, 3H), 2.66-2.39 (m, 2H), 2.29 (s, 3H), 2.21 (s, 3H), 2.13-1.88 (m, 2H), 1.14 (m, 2H); MS (ES) 451.99 (M+H);

4-(6-(methylsulfonylamino)pyridin-3-yl)-N-(3-methyl-4-((1S,4S)-5-methyl-2,5-diazabicyclo[2.2.1]heptan-2-yl)phenyl)pyrimidin-2-amine, compound #151, $^1$H NMR (CD$_3$OD, 300 MHz): δ 8.96 (m, 1H), 8.43 (m, 1H), 8.30 (m, 1H), 7.54 (m, 1H), 7.23 (m, 1H), 7.15 (m, 1H), 6.97 (m, 1H), 4.30 (s, 1H), 4.25 (s, 1H), 3.80-3.37 (m, 3H), 3.23 (m, 2H), 2.98 (s, 3H), 2.66 (m, 2H), 2.32 (brs, 6H); MS (ES) 466.03 (M+H);

4-(6-(2-(dimethylamino)acetamido)-pyridin-3-yl)-N-(3-methyl-4-((1S,4S)-5-methyl-2,5-diazabicyclo[2.2.1]heptan-2-yl)phenyl)pyrimidin-2-amine, compound #152, $^1$H NMR (CD$_3$OD, 300 MHz): δ 8.52 (m, 1H), 8.31 (m, 1H), 8.20 (m, 1H), 7.52 (m, 2H), 7.21 (m, 2H), 6.96 (m, 1H), 4.31 (s, 1H), 4.24 (s, 1H), 3.91-3.48 (m, 5H), 2.99 (s, 3H), 2.83 (s, 3H), 2.65 (s, 3H), 2.32 (m, 6H); MS (ES) 473.04 (M+H);

4-(6-(methylsulfonylamino)pyridin-3-yl)-N-(3-fluoro-4-((1S,4S)-5-methyl-2,5-diazabicyclo[2.2.1]heptan-2-yl)phenyl)pyrimidin-2-amine, compound #153, $^1$H NMR (CD$_3$OD, 300 MHz): δ 8.94 (m, 1H), 8.39 (m, 3H), 7.62 (m, 1H), 7.22 (m, 3H), 6.78 (m, 1H), 4.56 (s, 1H), 4.29 (s, 1H), 3.79-3.43 (m, 5H), 2.93 (m, 2H), 2.66 (m, 1H), 2.30 (m, 3H); MS (ES) 469.99 (M+H);

4-(6-(morpholin-4-yl)pyridin-3-yl)-N-(4-(8-methyl-3,8-diazabicyclo[3.2.1]octan-3-yl)phenyl)pyrimidin-2-amine, compound #155, $^1$H NMR (CD$_3$OD, 300 MHz): δ 8.90 (m, 1H), 8.49 (m, 1H), 8.25 (m, 2H), 7.59 (m, 2H), 7.13 (m, 1H), 6.94 (m, 1H), 6.87 (m, 1H), 3.93 (m, 2H), 3.78 (m, 4H), 3.61 (m, 6H), 3.13 (m, 2H), 2.81 (s, 3H), 2.19 (m, 4H); MS (ES) 458.03 (M+H);

4-(6-(methylsulfonylamino)pyridin-3-yl)-N-(4-(8-methyl-3,8-diazabicyclo[3.2.1]octan-3-yl)phenyl)pyrimidin-2-amine, compound #156, $^1$H NMR (CD$_3$OD, 300 MHz): δ 8.90 (m, 1H), 8.36 (m, 3H), 7.75 (m, 1H), 7.56 (m, 2H), 7.13 (m, 2H), 6.91 (m, 2H), 3.97 (m, 2H), 3.72 (m, 2H), 3.19 (m, 2H), 2.83 (s, 3H), 2.25 (m, 5H); MS (ES) 466.03 (M+H);

4-(2,2-dimethyl-3-oxo-3,4-dihydro-2H-pyrido[3,2-b][1,4]oxazin-7-yl)-N-(4-(8-methyl-3,8-diazabicyclo[3.2.1]octan-3-yl)phenyl)pyrimidin-2-amine, compound #157, $^1$H NMR (CD$_3$OD, 300 MHz): δ 8.67 (m, 1H), 8.38 (m, 1H), 7.99 (m, 1H), 7.59 (m, 2H), 7.21 (m, 1H), 6.95 (m, 2H), 3.97 (m, 2H), 3.68 (m, 2H), 3.17 (m, 3H), 2.85 (s, 3H), 2.65 (m, 1H), 2.22 (m, 4H), 1.55 (s, 6H); MS (ES) 472.09 (M+H);

4-(6-aminopyridin-3-yl)-N-(4-(8-methyl-3,8-diazabicyclo[3.2.1]octan-3-yl)phenyl)pyrimidin-2-amine, compound #158, $^1$H NMR (CD$_3$OD, 300 MHz): δ 8.87 (m, 1H), 8.28 (m, 2H), 8.15 (m, 1H), 7.58 (m, 2H), 7.09 (m, 1H), 6.93 (m, 2H), 6.65 (m, 1H), 4.03 (m, 2H), 3.68 (m, 2H), 3.25 (m, 3H), 2.89 (s, 3H), 2.64 (m, 1H), 2.23 (m, 4H); MS (ES) 388.04 (M+H);

4-(6-(morpholin-4-yl)pyridin-3-yl)-N-(3-methyl-4-(1,4-diazabicyclo[3.2.2]nonan-4-yl)phenyl)pyrimidin-2-amine, compound #159, $^1$H NMR (CD$_3$OD, 300 MHz): δ 8.27 (m, 3H), 7.51 (m, 2H), 7.15 (m, 2H), 6.86 (m, 1H), 3.80 (m, 4H), 3.60 (m, 7H), 3.46 (m, 4H), 3.30 (m, 2H), 2.41 (m, 2H), 2.35 (m, 3H), 2.07 (m, 2H); MS (ES) 472.12 (M+H);

4-(2,2-dimethyl-3-oxo-3,4-dihydro-2H-pyrido[3,2-b][1,4]oxazin-7-yl)-N-(3-methyl-4-(1,4-diazabicyclo[3.2.2]nonan-4-yl)phenyl)pyrimidin-2-amine, compound #160, $^1$H NMR (CD$_3$OD, 300 MHz): δ 8.64 (m, 1H), 8.47 (m, 1H), 8.38 (m, 1H), 7.95 (m, 1H), 7.51 (m, 2H), 7.14 (m, 2H), 3.51-3.43 (m, 9H), 2.40 (m, 2H), 2.34 (s, 3H), 2.34 (m, 2H), 1.54 (s, 6H); MS (ES) 486.11 (M+H);

4-(4-((pyridin-2-yl)aminocarbonyl)phenyl)-N-(3-methyl-4-(1,4-diazabicyclo[3.2.2]nonan-4-yl)phenyl)pyrimidin-2-amine, compound #161, $^1$H NMR (CD$_3$OD, 300 MHz): δ 8.47-8.22 (m, 4H), 8.10 (m, 3H), 7.84 (m, 1H), 7.60 (m, 2H), 7.35-7.15 (m, 3H), 3.61-3.48 (m, 9H), 2.44 (m, 2H), 2.37 (s, 3H), 2.12 (m, 2H); MS (ES) 506.06 (M+H);

4-(4-(acetamido)phenyl)-N-(4-(8-methyl-3,8-diazabicyclo[3.2.1]octan-3-yl)phenyl)pyrimidin-2-amine, compound #162, $^1$H NMR (CD$_3$OD, 300 MHz): δ 8.34 (m, 1H), 8.10 (m, 2H), 7.66 (m, 4H), 7.19 (m, 1H), 6.95 (m, 2H), 3.99 (m, 2H), 3.68 (m, 2H), 3.13 (m, 2H), 2.86 (s, 3H), 2.23 (m, 4H), 2.16 (s, 3H); MS (ES) 429.32 (M+H);

4-(2-(diethylamino)thiazol-4-yl)-N-(3-methyl-4-((1S,4S)-5-methyl-2,5-diazabicyclo[2.2.1]heptan-2-yl)phenyl)pyrimidin-2-amine, compound #163, $^1$H NMR (CD$_3$OD, 300 MHz): δ 8.37 (m, 1H), 7.53 (m, 1H), 7.46 (m, 2H), 7.29 (m, 1H), 6.95 (m, 1H), 4.31 (s, 1H), 4.23 (s, 1H), 3.56 (m, 6H), 2.99 (s, 3H), 2.31 (brs, 5H), 1.27 (m, 8H); MS (ES) 450.30 (M+H);

4-(2-(diethylamino)thiazol-4-yl)-N-(3-fluoro-4-((1S,4S)-5-methyl-2,5-diazabicyclo[2.2.1]heptan-2-yl)phenyl)pyrimidin-2-amine, compound #164, $^1$H NMR (CD$_3$OD, 300 MHz): δ 8.47 (m, 1H), 8.38 (m, 1H), 7.70 (m, 1H), 7.45 (m, 1H), 7.29 (m, 2H), 6.77 (m, 1H), 4.54 (s, 1H), 4.23 (s, 1H), 3.60 (m, 5H), 3.03 (m, 1H), 2.91 (s, 3H), 2.29 (m, 2H), 1.27 (m, 8H); MS (ES) 454.00 (M+H);

4-(2,2-dimethyl-3-oxo-3,4-dihydro-2H-pyrido[3,2-b][1,4]oxazin-7-yl)-N-(3-methyl-4-(8-methyl-3,8-diazabicyclo[3.2.1]octan-3-yl)phenyl)pyrimidin-2-amine, compound #165, $^1$H NMR (CD$_3$OD, 300 MHz): δ 8.70 (m, 1H), 8.42 (m, 1H), 8.01 (m, 1H), 7.56 (m, 2H), 7.27 (m, 3H), 4.01 (brs, 2H), 3.25-3.10 (m, 3H), 2.89 (s, 3H), 2.41 (s, 3H), 2.31 (m, 5H), 1.55 (s, 6H); MS (ES) 486.08 (M+H);

4-(6-(morpholin-4-yl)pyridin-3-yl)-N-(3-methyl-4-(8-methyl-3,8-diazabicyclo[3.2.1]octan-3-yl)phenyl)pyrimidin-2-amine, compound #166, $^1$H NMR (CD$_3$OD, 300 MHz): δ 8.88 (m, 1H), 8.42 (m, 1H), 8.31 (m, 1H), 7.48 (m, 2H), 7.35 (m, 1H), 7.21 (m, 2H), 4.03 (brs, 2H), 3.85-3.74 (m, 7H), 3.34 (m, 1H), 3.12 (m, 2H), 2.89 (s, 3H), 2.67 (s, 3H), 2.40 (m, 6H); MS (ES) 472.13 (M+H);

4-(6-(methylsulfonylamino)pyridin-3-yl)-N-(3-methyl-4-(8-methyl-3,8-diazabicyclo[3.2.1]octan-3-yl)phenyl)pyrimidin-2-amine, compound #167, $^1$H NMR (CD$_3$OD, 300 MHz): δ 8.39 (m, 1H), 8.15 (m, 2H), 7.56 (m, 2H), 7.34 (m, 2H), 7.26 (m, 2H), 7.16 (m, 2H), 4.01 (brs, 2H), 3.44-3.10 (m, 3H), 3.24 (m, 1H), 3.05 (s, 3H), 2.89 (s, 3H), 2.28 (m, 6H); MS (ES) 479.08 (M+H);

4-(4-(t-butylcarbonylamino)phenyl)-N-(3-methyl-4-(8-methyl-3,8-diazabicyclo[3.2.1]octan-3-yl)phenyl)pyrimidin-2-amine, compound #168, $^1$H NMR (CD$_3$OD, 300 MHz): δ 8.33 (m, 1H), 8.15 (m, 2H), 7.78 (m, 2H), 7.54 (m, 2H), 7.41 (m, 1H), 7.20 (m, 1H), 4.02 (brs, 2H), 3.30-3.08 (m, 3H), 3.08 (m, 3H), 2.66 (s, 3H), 2.40 (m, 5H), 1.32 (s, 9H); MS (ES) 485.62 (M+H);

4-(1H-pyrrol-3-yl)-N-(3-methyl-4-((1S,4S)-5-methyl-2,5-diazabicyclo[2.2.1]heptan-2-yl)phenyl)pyrimidin-2-amine, compound #169, $^1$H NMR (CD$_3$OD, 300 MHz): δ 8.27 (m, 1H), 8.17 (m, 1H), 7.51 (m, 3H), 6.94 (m, 2H), 4.30 (s, 1H), 4.22 (s, 1H), 3.76 (m, 1H), 3.46 (m, 2H), 3.29 (s, 3H), 2.97 (s, 3H), 2.31 (m, 4H); MS (ES) 361.07 (M+H);

4-(1H-pyrrol-3-yl)-N-(4-((1S,4S)-5-methyl-2,5-diazabicyclo[2.2.1]heptan-2-yl)phenyl)pyrimidin-2-amine, compound #170, e$^1$H NMR (CD$_3$OD, 300 MHz): δ 8.10 (m, 1H), 7.52 (m, 3H), 6.93 (m, 2H), 6.80 (m, 1H), 6.70 (m, 2H), 4.63 (s, 1H), 4.35 (s, 1H), 3.75 (m, 2H), 3.34 (m, 2H), 2.95 (s, 3H), 2.34 (m, 2H); MS (ES) 347.04 (M+H);

4-(1H-pyrrol-3-yl)-N-(3-trifluoromethyl-4-((1S,4S)-5-methyl-2,5-diazabicyclo[2.2.1]heptan-2-yl)phenyl)pyrimidin-2-amine, compound #171, $^1$H NMR (CD$_3$OD, 300 MHz): δ 8.41 (m, 2H), 8.23 (m, 1H), 7.82 (m, 1H), 7.55 (s, 1H), 7.38 (m, 1H), 6.99 (m, 1H), 6.81 (m, 1H), 6.73 (m, 1H), 4.33 (s, 1H), 4.03 (s, 1H), 3.70 (m, 3H), 3.24 (m, 2H), 2.97 (s, 3H), 2.34 (m, 2H); MS (ES) 415.04 (M+H);

4-(2,2-dimethyl-3-oxo-3,4-dihydro-2H-pyrido[3,2-b][1,4]oxazin-7-yl)-N-(3-trifluoromethyl-4-((1S,4S)-2,5-diazabicyclo[2.2.1]heptan-2-yl)phenyl)pyrimidin-2-amine, compound #172, $^1$H NMR (CD$_3$OD, 300 MHz): δ 8.69 (m, 1H), 8.48 (m, 2H), 8.31 (m, 1H), 8.03 (m, 1H), 7.86 (m, 1H), 7.33 (m, 2H), 4.33 (s, 1H), 4.08 (s, 1H), 3.65-3.55 (m, 3H), 3.22 (m, 1H), 2.97 (s, 3H), 2.34 (m, 2H), 1.55 (s, 6H); MS (ES) 526.11 (M+H);

4-(6-ethoxypyridin-3-yl)-N-(3-methyl-4-((1S,4S)-5-methyl-2,5-diazabicyclo[2.2.1]heptan-2-yl)phenyl)pyrimidin-2-amine, compound #173, $^1$H NMR (DMSO-d$_6$): δ 9.30 (s, 1H), 8.92 (s, 1H), 8.42 (d, 1H, J=4.3 Hz), 8.37 (dd, 1H, J=2.3 and 8.8 Hz), 7.47 (d, 1H, J=8.8 Hz), 7.42 (s, 1H), 7.28 (d, 1H, J=4.9 Hz), 6.93 (d, 1H, J=8.5 Hz), 6.74 (d, 1H, J=8.5 Hz), 4.36 (qt, 2H, J=7.0 Hz), 3.88 (s, 1H), 3.17 (app qt, 2H, J=9.1 Hz), 2.73 (d, 1H, J=9.0 Hz), 2.66 (d, 1H, J=9.0 Hz), 2.25 (s, 3H), 2.18 (s, 3H), 1.77 (d, 1H, J=9.0 Hz), 1.68 (d, 1H, J=9.0 Hz), 1.32 (t, 3H, J=7.0 Hz); LCMS: purity: 99%; MS (m/e): 417 (MH$^+$);

4-(6-ethoxypyridin-3-yl)-N-(3-fluoro-4-((1S,4S)-5-methyl-2,5-diazabicyclo[2.2.1]heptan-2-yl)phenyl)pyrimidin-2-amine, compound #174, LCMS: purity: 99%; MS (m/e): 421 (MH$^+$);

4-(2-(dimethylamino)thiazol-4-yl)-N-(3-methyl-4-((1S,4S)-5-methyl-2,5-diazabicyclo[2.2.1]heptan-2-yl)phenyl)pyrimidin-2-amine, compound #175, $^1$H NMR (DMSO-d$_6$): δ 9.24 (s, 1H), 8.43 (d, 1H, J=4.9 Hz), 7.53 (d, 1H, J=16.7 Hz), 7.51 (m, 1H), 7.44 (s, 1H), 7.19 (d, 1H, J=4.9 Hz), 6.76 (d, 1H, J=8.5 Hz), 3.90 (s, 1H), 3.42 (s, 1H), 3.19 (app qt, 2H, J=9.1 Hz), 3.08 (s, 6H), 2.78 (s, 2H), 2.34 (s, 3H), 2.18 (s, 3H), 1.83 (d, 1H, J=9.0 Hz), 1.73 (d, 1H, J=9.0 Hz); LCMS: purity: 99%; MS (m/e): 422 (MH$^+$);

4-(2-(dimethylamino)thiazol-4-yl)-N-(3-fluoro-4-((1S,4S)-5-methyl-2,5-diazabicyclo[2.2.1]heptan-2-yl)phenyl)pyrimidin-2-amine, compound #176, $^1$H NMR (DMSO-d$_6$): δ 9.43 (s, 1H), 8.45 (d, 1H, J=4.9 Hz), 7.53 (d, 1H, J=16.7 Hz), 7.51 (m, 1H), 7.38 (d, 1H, J=7.3 Hz), 7.21 (d, 1H, J=4.9 Hz), 6.68 (t, 1H, J=9.1 Hz), 4.14 (s, 1H), 3.39 (d, 1H, J=9.3 Hz), 3.16 (d, 1H, J=9.3 Hz), 3.08 (s, 6H), 2.72 (d, 1H, J=9.0 Hz), 2.59 (d, 1H, J=9.0 Hz), 2.23 (s, 3H), 1.79 (d, 1H, J=9.0 Hz), 1.69 (d, 1H, J=9.0 Hz); LCMS: purity: 99%; MS (m/e): 426 (MH$^+$);

4-(5-(morpholin-4-yl)pyrazin-2-yl)-N-(3-methyl-4-((1S,4S)-5-methyl-2,5-diazabicyclo[2.2.1]heptan-2-yl)phenyl)pyrimidin-2-amine, compound #178, $^1$H NMR (DMSO-d$_6$): δ 9.27 (s, 1H), 8.98 (s, 1H), 8.43 (d, 1H, J=4.9 Hz), 8.40 (s, 1H), 7.49 (d, 1H, J=8.8 Hz), 7.42 (s, 1H), 7.36 (d, 1H, J=4.9 Hz), 6.75 (d, 1H, J=8.8 Hz), 3.88 (s, 1H), 3.69-3.67 (m, 8H), 3.17 (app qt, 2H, J=9.1 Hz), 2.73 (d, 1H, J=9.1 Hz), 2.66 (d, 1H, J=9.1 Hz), 2.25 (s, 3H), 2.19 (s, 3H), 1.76 (d, 1H, J=8.8 Hz), 1.69 (d, 1H, J=8.8 Hz); LCMS: purity: 90%; MS (m/e): 459 (MH$^+$);

4-(5-(morpholin-4-yl)pyrazin-2-yl)-N-(3-fluoro-4-((1S,4S)-5-methyl-2,5-diazabicyclo[2.2.1]heptan-2-yl)phenyl)pyrimidin-2-amine, compound #179, $^1$H NMR (DMSO-d$_6$): δ 9.48 (s, 1H), 8.98 (s, 1H), 8.47 (d, 1H, J=4.9 Hz), 8.42 (s, 1H), 7.64 (d, 1H, J=16.7 Hz), 7.40-7.34 (m, 2H), 6.71 (d, 1H, J=9.1 Hz), 4.16 (s, 1H), 3.69-3.68 (m, 8H), 3.39 (d, 1H, J=9.6 Hz), 3.17 (d, 1H, J=9.6 Hz), 2.72 (d, 1H, J=9.1 Hz), 2.59 (d, 1H, J=9.1 Hz), 2.22 (s, 3H), 1.79 (d, 1H, J=8.8 Hz), 1.69 (d, 1H, J=8.8 Hz); LCMS: purity: 99%; MS (m/e): 463 (MH$^+$);

4-(4-(1-ethoxyethyl)phenyl)-N-(3-methyl-4-((1S,4S)-5-methyl-2,5-diazabicyclo[2.2.1]heptan-2-yl)phenyl)pyrimidin-2-amine, compound #181, LCMS: purity: 99%; MS (m/e): 444 (MH$^+$);

4-(4-(1-ethoxyethyl)phenyl)-N-(3-fluoro-4-((1S,4S)-5-methyl-2,5-diazabicyclo[2.2.1]heptan-2-yl)phenyl)pyrimidin-2-amine, compound #182, LCMS: purity: 99%; MS (m/e): 447 (MH$^+$);

4-(6-(dimethylamino)pyridin-3-yl)-N-(4-((1S,4S)-5-methyl-2,5-diazabicyclo[2.2.1]heptan-2-yl)phenyl)pyrimidin-2-amine, compound #183, $^1$H NMR (DMSO-d$_6$): δ 9.09 (s, 1H), 8.87 (s, 1H), 8.29 (d, 1H, J=4.9 Hz), 8.19 (d, 1H, J=8.8 Hz), 7.53 (d, 2H, J=8.5 Hz), 7.14 (d, 1H, J=5.3 Hz), 6.73 (d, 1H, J=9.1 Hz), 6.53 (d, 2H, J=8.5 Hz), 4.21 (s, 1H), 3.35 (s, 1H), 3.26 (s, 1H), 3.09-3.04 (m, 7H), 2.73 (d, 1H, J=9.6 Hz), 2.21 (s, 3H), 1.82 (d, 1H, J=8.8 Hz), 1.73 (d, 1H, J=8.8 Hz); LCMS: purity: 99%; MS (m/e): 402 (MH$^+$);

4-(6-(morpholin-4-yl)pyridin-3-yl)-N-(4-((1S,4S)-5-methyl-2,5-diazabicyclo[2.2.1]heptan-2-yl)phenyl)pyrimidin-2-amine, compound #184, $^1$H NMR (DMSO-d$_6$): δ 9.13 (s, 1H), 8.90 (d, 1H, J=2.0 Hz), 8.33 (d, 1H, J=4.7 Hz), 8.24 (dd, 1H, J=2.0 and 8.8 Hz), 7.52 (d, 2H, J=8.8 Hz), 7.18 (d, 1H, J=4.7 Hz), 6.94 (d, 1H, J=8.8 Hz), 6.53 (d, 2H, J=8.8 Hz), 4.20 (s, 1H), 3.69-3.67 (m, 4H), 3.56 (br s, 4H), 3.35 (s, 1H), 3.27 (s, 1H), 3.09 (d, 1H, J=8.8 Hz), 2.73 (d, 1H, J=8.8 Hz), 2.21 (s, 3H), 1.82 (d, 1H, J=8.8 Hz), 1.73 (d, 1H, J=8.8 Hz); LCMS: purity: 99%; MS (m/e): 444 (MH$^+$);

4-(4-methyl-3,4-dihydro-2H-pyrido[3,2-b][1,4]oxazin-7-yl)-N-(4-((1S,4S)-5-methyl-2,5-diazabicyclo[2.2.1]heptan-2-yl)phenyl)pyrimidin-2-amine, compound #185, $^1$H NMR (DMSO-d$_6$): δ 9.08 (s, 1H), 8.49 (d, 1H, J=1.8 Hz), 8.28 (d, 1H, J=4.9 Hz), 7.58 (d, 1H, J=1.8 Hz), 7.49 (d, 2H, J=8.8 Hz), 7.14 (d, 1H, J=4.9 Hz), 6.53 (d, 2H, J=8.8 Hz), 4.21 (s, 3H), 3.51-3.50 (m, 2H), 3.35 (s, 1H), 3.26 (s, 1H), 3.10 (s, 3H), 3.06 (d, 1H, J=8.8 Hz), 2.73 (d, 1H, J=8.8 Hz), 2.21 (s, 3H), 1.82 (d, 1H, J=9.1 Hz), 1.72 (d, 1H, J=9.1 Hz); LCMS: purity: 99%; MS (m/e): 430 (MH$^+$);

4-(6-(3-ethoxypropyl)aminopyridin-3-yl)-N-(3-methyl-4-((1S,4S)-5-methyl-2,5-diazabicyclo[2.2.1]heptan-2-yl)phenyl)pyrimidin-2-amine, compound #186, LCMS: purity: 99%; MS (m/e): 474 (MH$^+$);

4-(6-(cis-2,6-dimethylmorpholin-4-yl)pyridin-3-yl)-N-(3-methyl-4-((1S,4S)-5-methyl-2,5-diazabicyclo[2.2.1]heptan-2-yl)phenyl)pyrimidin-2-amine, compound #187, $^1$H NMR (DMSO-d$_6$): δ 9.20 (s, 1H), 8.89 (d, 1H, J=2.3 Hz), 8.34 (d, 1H, J=5.3 Hz), 8.24 (dd, 1H, J=2.3 and 9.1 Hz), 7.48 (d, 1H, J=9.1 Hz), 7.44 (s, 1H), 7.21 (d, 1H, J=5.3 Hz), 6.97 (d, 1H, J=9.1 Hz), 6.74 (d, 1H, J=9.1 Hz), 4.30-4.26 (m, 2H), 3.88 (s, 1H), 3.61-3.56 (m, 2H), 3.21-3.13 (m, 2H), 2.73 (app qt, 2H, J=9.1 Hz), 2.27 (s, 3H), 2.18 (s, 3H), 1.77 (d, 1H, J=9.0 Hz), 1.68 (d, 1H, J=9.0 Hz), 1.15 (d, 6H, J=6.2 Hz); LCMS: purity: 99%; MS (m/e): 486 (MH$^+$);

4-(6-(propylamino)pyridin-3-yl)-N-(3-methyl-4-((1S,4S)-5-methyl-2,5-diazabicyclo[2.2.1]heptan-2-yl)phenyl)pyrimidin-2-amine, compound #188, $^1$H NMR (DMSO-d$_6$): δ 9.14 (s, 1H), 8.78 (s, 1H), 8.30 (d, 1H, J=5.3 Hz), 8.06 (d, 1H, J=8.8 Hz), 7.49 (d, 1H, J=8.5 Hz), 7.43 (s, 1H), 7.13-7.12 (m, 2H), 6.75 (d, 1H, J=8.8 Hz), 6.54 (d, 1H, J=8.8 Hz), 3.89 (s, 1H), 3.28-3.14 (m, 5H), 2.76-2.79 (m, 2H), 2.29 (s, 3H), 2.18 (s, 3H), 1.79 (d, 1H, J=9.1 Hz), 1.69 (d, 1H, J=9.1 Hz), 1.60-1.48 (m, 2H), 0.90 (t, 3H, J=7.3 Hz); LCMS: purity: 99%; MS (m/e): 430 (MH$^+$);

4-(6-(2-(dimethylamino)methylmorpholin-4-yl)pyridin-3-yl)-N-(3-methyl-4-((1S,4S)-5-methyl-2,5-diazabicyclo[2.2.1]heptan-2-yl)phenyl)pyrimidin-2-amine, compound #189, $^1$H NMR (DMSO-d$_6$): δ 9.20 (s, 1H), 8.90 (s, 1H), 8.35 (d, 1H, J=4.9 Hz), 8.25 (app d, 1H, J=8.8 Hz), 7.48

(d, 1H, J=8.5 Hz), 7.43 (s, 1H), 7.21 (d, 1H, J=4.9 Hz), 6.94 (d, 1H, J=8.5 Hz), 6.74 (d, 1H, J=8.8 Hz), 4.34 (d, 1H, J=12.4 Hz), 4.14 (d, 1H, J=12.4 Hz), 3.94-2.88 (m, 2H), 3.57-3.49 (m, 2H), 3.21-3.10 (m, 3H), 2.96-2.92 (m, 1H), 2.74-2.58 (m, 3H), 2.41-2.30 (m, 2H), 2.30 (s, 3H), 2.18 (overlap s, 9H), 1.77 (d, 1H, J=9.1 Hz), 1.68 (d, 1H, J=9.1 Hz); LCMS: purity: 99%; MS (m/e): 515 (MH$^+$);

4-(6-(piperidin-1-yl)pyridin-3-yl)-N-(3-methyl-4-((1S,4S)-5-methyl-2,5-diazabicyclo[2.2.1]heptan-2-yl)phenyl)pyrimidin-2-amine, compound #190, $^1$H NMR (DMSO-d$_6$): δ 9.17 (s, 1H), 8.86 (s, 1H), 8.33 (d, 1H, J=5.3 Hz), 8.20-8.17 (d, 1H, J=9.1 Hz), 7.49 (d, 1H, J=8.8 Hz), 7.43 (s, 1H), 7.17 (d, 1H, J=5.3Hz), 6.91 (d, 1H, J=8.8 Hz), 6.73 (d, 1H, J=8.8 Hz), 3.87 (s, 1H), 3.62 (br s, 4H), 3.29 (s, 1H), 3.21-3.12 (m, 2H), 2.72 (d, 1H, J=9.1 Hz), 2.66 (d, 1H, J=9.1 Hz), 2.26 (s, 3H), 2.18 (s, 3H), 1.77-1.52 (m, 8H); LCMS: purity: 99%; MS (m/e): 456 (MH$^+$);

4-(6-(3-(aminocarbonyl)piperidin-1-yl)pyridin-3-yl)-N-(3-methyl-4-((1S,4S)-5-methyl-2,5-diazabicyclo[2.2.1]heptan-2-yl)phenyl)pyrimidin-2-amine, compound #191, LCMS: purity: 99%; MS (m/e): 499 (MH$^+$);

4-(6-(morpholin-4-yl)pyridin-3-yl)-N-(3-methyl-4-((1S,4S)-5-methylsulfonyl-2,5-diazabicyclo[2.2.1]heptan-2-yl)phenyl)pyrimidin-2-amine, compound #192, $^1$H NMR (DMSO-d$_6$): δ 9.48 (s, 1H), 8.92 (s, 1H), 8.35 (s, 1H), 8.29 (d, 1H, J=8.8 Hz), 7.47 (app s, 2H), 7.28 (s, 1H), 7.01 (d, 1H, J=8.8 Hz), 6.91 (d, 1H, J=8.8 Hz), 4.35 (s, 1H), 4.18 (s, 1H), 3.68 (br s, 4H), 3.60 (br s, 4H), 3.40-3.37 (m, 4H), 2.96 (s, 3H), 2.21 (s, 3H), 1.90-1.85 (m, 2H); LCMS: purity: 99%; MS (m/e): 522 (MH$^+$);

4-(4-methyl-3,4-dihydro-2H-pyrido[3,2-b][1,4]oxazin-7-yl)-N-(3-methyl-4-((1S,4S)-5-methylsulfonyl-2,5-diazabicyclo[2.2.1]heptan-2-yl)phenyl)pyrimidin-2-amine, compound #193, $^1$H NMR (DMSO-d$_6$): δ 9.37 (s, 1H), 8.51 (s, 1H), 8.32 (d, 1H, J=4.3 Hz), 7.64 (s, 1H), 7.48 (s, 2H), 7.23 (d, 1H, J=4.3 Hz), 6.89 (d, 1H, J=8.8 Hz), 4.34 (s, 1H), 4.23-4.17 (m, 3H), 3.53 (s, 2H), 3.42-3.23 (m, 4H), 3.12 (s, 3H), 2.95 (s, 3H), 2.21 (s, 3H), 1.91 (d, 1H, J=9.1 Hz), 1.82 (d, 1H, J=9.1 Hz); LCMS: purity: 99%; MS (m/e): 508 (MH$^+$);

4-(6-(morpholin-4-yl)pyridin-3-yl)-N-(3-methyl-4-((1S,4S)-5-oxa-2-azabicyclo[2.2.1]heptan-2-yl)phenyl)pyrimidin-2-amine, compound #194, $^1$H NMR (DMSO-d$_6$): δ 9.24 (s, 1H), 8.91 (s, 1H), 8.36 (d, 1H, J=5.3 Hz), 8.25 (d, 1H, J=9.1 Hz), 7.52-7.47 (m, 2H), 7.22 (d, 1H, J=5.2 Hz), 6.95 (d, 1H, J=9.1 Hz), 6.80 (d, 1H, J=8.5 Hz), 4.50 (s, 1H), 4.12 (s, 1H), 3.89 (d, 1H, J=7.3 Hz), 3.69-3.67 (br m, 5H), 3.57 (br m, 5H), 3.04 (d, 1H, J=9.6 Hz), 2.18 (s, 3H), 1.87 (d, 1H, J=8.5 Hz), 1.75 (d, 1H, J=8.5 Hz); LCMS: purity: 99%; MS (m/e): 445 (MH$^+$);

4-(4-methyl-3,4-dihydro-2H-pyrido[3,2-b][1,4]oxazin-7-yl)-N-(3-methyl-4-((1S,4S)-5-oxa-2-azabicyclo[2.2.1]heptan-2-yl)phenyl)pyrimidin-2-amine, compound #195, $^1$H NMR (DMSO-d$_6$): δ 9.23 (s, 1H), 8.51 (d, 1H, J=1.8 Hz), 8.32 (d, 1H, J=5.3 Hz), 7.62 (d, 1H, J=1.8 Hz), 7.47 (s, 2H), 7.19 (d, 1H, J=5.3 Hz), 6.81 (d, 1H, J=9.1 Hz), 4.51 (s, 1H), 4.24-4.21 (m, 2H), 4.14 (s, 1H), 3.89 (d, 1H, J=7.3 Hz), 3.70 (d, 1H, J=7.3 Hz), 3.53-3.50 (m, 2H), 3.33 (d, 1H, J=9.1 Hz), 3.11 (s, 3H), 3.06 (d, 1H, J=8.2 Hz), 2.18 (s, 3H), 1.87 (d, 1H, J=9.1 Hz), 1.76 (d, 1H, J=9.1 Hz); LCMS: purity: 99%; MS (m/e): 431 (MH$^+$);

4-(6-(morpholin-4-yl)pyridin-3-yl)-N-(3-methyl-4-((1S,4S)-5-ethylcarbonyl-2,5-diazabicyclo[2.2.1]heptan-2-yl)phenyl)pyrimidin-2-amine, compound #196, $^1$H NMR (DMSO-d$_6$): δ 9.24 (s, 1H), 8.92 (s, 1H), 8.36 (d, 1H, J=2.0 Hz), 8.25 (dd, 1H, J=2.3 and 9.1 Hz), 7.52-7.47 (m, 2H), 7.22 (d, 1H, J=5.3 Hz), 6.95 (d, 1H, J=8.8 Hz), 6.81 (app t, 1H, J=8.8 Hz), 4.68 (s, 0.5H), 4.55 (s, 0.5 Hz), 4.17 (s, 0.5H), 4.11 (s, 0.5 Hz), 3.69-3.59 (m, 4H), 3.56-3.55 (m, 4H), 3.51-3.43 (m, 3H), 3.37-3.30 (m, 4H), 3.13-3.03 (m, 1H), 2.36-2.25 (m, 1H), 2.18 (s, 3H), 2.13-2.10 (m, 1H), 1.96-1.73 (m, 2H), 0.97 (t, 3H, J=7.6 Hz); LCMS: purity: 99%; MS (m/e): 500 (MH$^+$);

4-(6-(2-(morpholin-4-yl)ethyl)aminopyridin-3-yl)-N-(3-methyl-4-((1S,4S)-5-ethylcarbonyl-2,5-diazabicyclo[2.2.1]heptan-2-yl)phenyl)pyrimidin-2-amine, compound #197, LCMS: purity: 99%; MS (m/e): 543 (MH$^+$);

4-(6-(3-dimethylamino)propylaminopyridin-3-yl)-N-(3-methyl-4-((1S,4S)-5-methyl-2,5-diazabicyclo[2.2.1]heptan-2-yl)phenyl)pyrimidin-2-amine, compound #198, $^1$H NMR (DMSO-d$_6$) δ 9.11 (s, 1H), 8.79 (d, 1H, J=2.0 Hz), 8.30 (d, 1H, J=5.3 Hz), 8.06 (dd, 1H, J=2.3 and 9.1 Hz), 7.48-7.45 (m, 2H), 7.13-7.09 (m, 2H), 6.75 (d, 1H, J=8.8 Hz), 6.54 (d, 1H, J=8.8 Hz), 3.88 (s, 1H), 3.30 (m, 3H), 3.22-3.14 (m, 2H), 2.75-2.66 (m, 2H), 2.27-2.24 (m, 5H), 2.18 (s, 3H), 2.12 (s, 6H), 1.79-1.62 (m, 4H); LCMS: purity: 99%; MS (m/e): 473 (MH$^+$);

4-(6-(morpholin-4-yl)pyridin-3-yl)-N-(3-methyl-4-((1S,4S)-5-amidino-2,5-diazabicyclo[2.2.1]heptan-2-yl)phenyl)pyrimidin-2-amine, compound #199, $^1$H NMR (DMSO-d$_6$): δ 9.32 (s, 1H), 8.92 (s, 1H), 8.37 (d, 1H, J=5.3 Hz), 8.25 (d, 1H, J=9.1 Hz), 7.55 (d, 1H, J=9.1 Hz), 7.51 (s, 1H), 7.31 (s, 2H), 7.24 (d, 1H, J=5.3 Hz), 7.17 (br s, 1H), 6.96 (d, 1H, J=8.8 Hz), 6.83 (d, 1H, J=8.8 Hz), 4.70 (s, 1H), 4.28 (s, 1H), 3.69-3.68 (br m, 4H), 3.57-3.56 (br m, 4H), 3.51-3.40 (m, 3H), 3.17 (d, 1H, J=9.3 Hz), 2.20 (s, 3H), 2.06-1.93 (m, 2H); LCMS: purity: 92%; MS (m/e): 486 (MH$^+$-TFA);

4-(6-(3-ethoxypropyl)aminopyridin-3-yl)-N-(3-methyl-4-((1S,4S)-5-oxa-2-azabicyclo[2.2.1]heptan-2-yl)phenyl)pyrimidin-2-amine, compound #200, $^1$H NMR (DMSO-d$_6$): δ 9.17 (s, 1H), 8.80 (d, 1H, J=2.3 Hz), 8.31 (d, 1H, J=5.3 Hz), 8.07 (dd, 1H, J=2.3 and 8.8 Hz), 7.51 (d, 1H, J=8.8 Hz), 7.46 (d, 1H, J=2.0 Hz), 7.14-7.09 (m, 2H), 6.80 (d, 1H, J=8.8 Hz), 6.54 (d, 1H, J=8.8 Hz), 4.50 (s, 1H), 4.11 (s, 1H), 3.89 (d, 1H, J=7.3 Hz), 3.70 (d, 1H, J=7.3 Hz), 3.41-3.29 (m, 7H), 3.04 (d, 1H, J=9.3 Hz), 2.17 (s, 3H), 1.86 (d, 1H, J=7.3 Hz), 1.78-1.73 (m, 3H), 1.09 (t, 3H, J=7.3 Hz); LCMS: purity: 99%; MS (m/e): 461 (MH$^+$);

4-(6-cis-2,6-dimethylmorpholin-4-yl)pyridin-3-yl)-N-(3-methyl-4-((1S,4S)-5-oxa-2-azabicyclo[2.2.1]heptan-2-yl)phenyl)pyrimidin-2-amine, compound #201, LCMS: purity: 99%; MS (m/e): 473 (MH$^+$);

4-(6-(propylamino)pyridin-3-yl)-N-(3-methyl-4-((1S,4S)-5-oxa-2-azabicyclo[2.2.1]heptan-2-yl)phenyl)pyrimidin-2-amine, compound #202, $^1$H NMR (DMSO-d$_6$): δ 9.20 (s, 1H), 8.76 (s, 1H), 8.32 (d, 1H, J=4.7 Hz), 8.11 (d, 1H, J=8.8 Hz), 7.51-7.49 (m, 1H), 7.45 (s, 1H), 7.32 (m, 1H), 7.15 (s, 1H), 6.80 (d, 1H, J=8.8 Hz), 6.60 (d, 1H, J=8.8 Hz), 4.50 (s, 1H), 4.12 (s, 1H), 3.89 (d, 1H, J=7.3 Hz), 3.70 (d, 1H, J=7.3 Hz), 3.32-3.24 (m, 3H), 3.04 (d, 1H, J=8.8 Hz), 2.17 (s, 3H), 1.86 (d, 1H, J=7.3 Hz), 1.76 (d, 1H, J=8.8 Hz), 1.55-1.49 (m, 2H), 0.91 (t, 3H, J=7.3 Hz); LCMS: purity: 99%; MS (m/e): 417 (MH$^+$);

4-(6-(3-dimethylamino)propylaminopyridin-3-yl)-N-(3-methyl-4-((1S,4S)-5-oxa-2-azabicyclo[2.2.1]heptan-2-yl)phenyl)pyrimidin-2-amine, compound #203, $^1$H NMR (DMSO-d$_6$): δ 9.17 (s, 1H), 8.80 (s, 1H), 8.31 (d, 1H, J=5.3 Hz), 8.07 (dd, 1H, J=2.3 and 9.1 Hz), 7.51 (d, 1H, J=8.8 Hz), 7.46 (d, 1H, J=2.0 Hz), 7.14-7.13 (m, 2H), 6.80 (d, 1H, J=8.5 Hz), 6.53 (d, 1H, J=8.8 Hz), 4.50 (s, 1H), 4.12 (s, 1H), 3.89 (d, 1H, J=7.3 Hz), 3.70 (d, 1H, J=7.3 Hz), 3.30-3.26 (m, 4H), 3.03 (d, 1H, J=8.8 Hz), 2.27 (t, 2H, J=7.0 Hz), 2.17 (s, 3H), 2.11 (s, 6H), 1.87 (d, 1H, J=7.3 Hz), 1.76 (d, 1H, J=8.5 Hz), 1.65 (q, 2H, J=7.0 Hz); LCMS: purity: 99%; MS (m/e): 460 (MH⁺);

4-(6-(1,4-oxazepan-4-yl)pyridin-3-yl)-N-(3-methyl-4-((1S,4S)-5-oxa-2-azabicyclo[2.2.1]heptan-2-yl)phenyl)pyrimidin-2-amine, compound #204, ¹H NMR (DMSO-d₆): δ 9.20 (s, 1H), 8.87 (d, 1H, J=2.0 Hz), 8.33 (d, 1H, J=5.3 Hz), 8.21 (d, 1H, J=2.0 and 8.8 Hz), 7.53 (app d, 1H, J=8.8 Hz), 7.45 (d, 1H, J=2.0 Hz), 7.19 (d, 1H, J=5.3 Hz), 6.82 (d, 1H, J=8.8 Hz), 6.80 (d, 1H, J=8.8 Hz), 4.50 (s, 1H), 4.12 (s, 1H), 3.90-3.65 (m, 7H), 3.59 (t, 2H, J=5.8 Hz), 3.05-2.97 (m, 2H), 2.18 (s, 3H), 1.87-1.73 (m, 2H), 1.14 (t, 2H, J=7.3 Hz); LCMS: purity: 99%; MS (m/e): 459 (MH⁺);

4-(6-(morpholin-4-yl)pyridin-3-yl)-N-(3-methyl-4-((1S,4S)-5-isobutyl-2,5-diazabicyclo[2.2.1]heptan-2-yl)phenyl)pyrimidin-2-amine, compound #205, ¹H NMR (DMSO-d₆): δ 9.19 (s, 1H), 8.91 (s, 1H), 8.35 (d, 1H, J=5.3 Hz), 8.25 (dd, 1H, J=2.3 and 8.8 Hz), 7.47-7.44 (app m, 2H), 7.20 (d, 1H, J=5.3 Hz), 6.95 (d, 1H, J=8.8 Hz), 6.72 (d, 1H, J=8.8 Hz), 3.89 (s, 1H), 3.70-3.68 (m, 4H), 3.59-3.57 (m, 4H), 3.36 (s, 1H), 3.21-3.14 (m, 2H), 2.80 (d, 1H, J=9.1 Hz), 2.66 (d, 1H, J=8.5 Hz), 2.31-2.22 (m, 2H), 2.18 (s, 3H), 1.70 (d, 1H, J=8.5 Hz), 1.66 (d, 1H, J=9.1 Hz), 1.56-1.52 (m, 1H), 0.83 (d, 6H, J=6.4 Hz), LCMS: purity: 99%; MS (m/e): 500 (MH⁺);

4-(6-(1,4-oxazepan-4-yl)pyridin-3-yl)-N-(3-methyl-4-((1S,4S)-5-methyl-2,5-diazabicyclo[2.2.1]heptan-2-yl)phenyl)pyrimidin-2-amine, compound #206, ¹H NMR (DMSO-d₆): δ 9.16 (s, 1H), 8.87 (d, 1H, J=2.0 Hz), 8.33 (d, 1H, J=5.3 Hz), 8.22 (dd, 1H, J=2.3 and 9.1 Hz), 7.50 (d, 1H, J=8.8 Hz), 7.42 (d, 1H, J=2.3 Hz), 7.18 (d, 1H, J=5.3 Hz), 6.82 (d, 1H, J=8.8 Hz), 6.74 (d, 1H, J=8.8 Hz), 3.87 (s, 1H), 3.82-3.71 (m, 6H), 3.61-3.57 (m, 2H), 3.21-3.12 (m, 2H), 2.73 (d, 1H, J=9.1 Hz), 2.66 (d, 1H, J=9.1 Hz), 2.62 (s, 3H), 2.18 (s, 3H), 1.91-1.83 (m, 2H), 1.76 (d, 1H, J=9.1 Hz), 1.68 (d, 1H, J=9.1 Hz); LCMS: purity: 99%; MS (m/e): 472 (MH⁺);

4-(2,2-dimethyl-3-oxo-3,4-dihydro-2H-pyrido[3,2-b][1,4]oxazin-7-yl)-N-(3-methyl-4-(1,5,7-trimethyl-3,7-diazabicyclo[3.3.1]nonan-3-yl)phenyl)pyrimidin-2-amine, compound #207, ¹H NMR (DMSO-d₆): δ 11.51 (s, 1H), 9.57 (s, 1H), 8.75 (d, 1H, J=2.0 Hz), 8.50 (d, 1H, J=5.3 Hz), 8.04 (d, 1H, J=2.0 Hz), 7.66 (d, 1H, J=2.0 Hz), 7.59 (dd, 1H, J=2.0 and 8.8 Hz), 7.41 (d, 1H, J=5.3 Hz), 7.11 (d, 1H, J=8.8 Hz), 3.53 (d, 2H, J=10.8 Hz), 3.03 (d, 2H, J=10.8 Hz), 2.94-2.85 (app t, 2H, J=9.9 Hz), 2.75 (s, 3H), 2.67 (d, 2H, J=10.8 Hz), 2.31 (s, 3H), 1.54-1.46 (m, 2H), 1.45 (s, 6H), 0.92 (s, 6H); LCMS: purity: 99%; MS (m/e): 528 (MH⁺);

4-(2,2-dimethyl-3-oxo-3,4-dihydro-2H-pyrido[3,2-b][1,4]oxazin-7-yl)-N-(3-fluoro-4-(1,5,7-trimethyl-3,7-diazabicyclo[3.3.1]nonan-3-yl)phenyl)pyrimidin-2-amine, compound #208, ¹H NMR (DMSO-d₆): δ 11.53 (s, 1H), 9.79 (s, 1H), 8.75 (d, 1H, J=2.0 Hz), 8.53 (d, 1H, J=5.3 Hz), 8.04 (d, 1H, J=1.7 Hz), 7.85 (dd, 1H, J=2.3 and 17.0 Hz), 7.46-7.41 (m, 2H), 7.09 (t, 1H, J=9.1 Hz), 3.44 (d, 2H, J=11.4 Hz), 3.15 (d, 2H, J=10.8 Hz), 2.94-2.87 (t, 2H, J=9.9 Hz), 2.75 (s, 3H), 2.67 (d, 2H, J=10.8 Hz), 1.54-1.39 (m, 2H), 1.46 (s, 6H), 0.92 (s, 6H); LCMS: purity: 99%; MS (m/e): 532 (MH⁺);

4-(3-oxo-3,4-dihydro-2H-pyrido[3,2-b][1,4]oxazin-7-yl)-N-(3-methyl-4-((1S,4S)-5-methyl-2,5-diazabicyclo[2.2.1]heptan-2-yl)phenyl)pyrimidin-2-amine, compound #209, ¹H NMR (DMSO-d₆): δ 11.53 (s, 1H), 9.16 (s, 1H), 8.55 (d, 1H, J=2.0 Hz), 8.31 (d, 1H, J=5.3 Hz), 7.62 (s, 1H), 7.47-7.42 (m, 2H), 7.18 (d, 1H, J=5.3 Hz), 6.73 (d, 1H, J=8.5 Hz), 4.29 (s, 2H), 3.81 (s, 1H), 3.21-3.14 (m, 3H), 2.72 (d, 1H, J=9.1 Hz), 2.66 (d, 1H, J=9.1 Hz), 2.26 (s, 3H), 2.19 (s, 3H), 1.76 (d, 1H, J=9.1 Hz), 1.68 (d, 1H, J=9.1 Hz); LCMS: purity: 99%; MS (m/e): 444 (MH⁺);

4-(3-oxo-3,4-dihydro-2H-pyrido[3,2-b][1,4]oxazin-7-yl)-N-(3-methyl-4-((1S,4S)-5-oxa-2-azabicyclo[2.2.1]heptan-2-yl)phenyl)pyrimidin-2-amine, compound #210, ¹H NMR (DMSO-d₆): δ 11.53 (s, 1H), 9.35 (s, 1H), 8.70 (d, 1H, J=1.8 Hz), 8.45 (d, 1H, J=5.3 Hz), 7.99 (d, 1H, J=1.8 Hz), 7.49 (s, 1H), 7.45 (d, 1H, J=8.8 Hz), 7.33 (d, 1H, J=5.3 Hz), 6.80 (d, 1H, J=8.8 Hz), 4.72 (s, 2H), 4.50 (s, 1H), 4.13 (s, 1H), 3.89 (d, 1H, J=7.3 Hz), 3.71 (d, 1H, J=7.3 Hz), 3.04 (d, 1H, J=9.3 Hz), 2.18 (s, 3H), 1.86 (d, 1H, J=9.3 Hz), 1.75 (d, 1H, J=9.3 Hz), LCMS: purity: 99%; MS (m/e): 431 (MH⁺);

4-(6-(3-ethoxypropyl)aminopyridin-3-yl)-N-(3-methyl-4-(1,5,7-trimethyl-3,7-diazabicyclo[3.3.1]nonan-3-yl)phenyl)pyrimidin-2-amine, compound #211, ¹H NMR (DMSO-d₆): δ 9.19 (s, 1H), 8.79 (s, 1H), 8.32 (d, 1H, J=4.9 Hz), 8.08 (d, 1H, J=2.6 and 9.1 Hz), 7.52 (d, 1H, J=9.1 Hz), 7.48 (s, 1H), 7.16-7.11 (m, 2H), 6.86 (d, 1H, J=8.8 Hz), 6.54 (d, 1H, J=8.8 Hz), 3.44-3.32 (m, 6H), 3.15-3.13 (m, 2H), 2.85 (d, 2H, J=9.6 Hz), 2.71 (d, 2H, J=9.6 Hz), 2.30 (s, 3H), 2.13-2.11 (m, 1H), 2.08 (s, 3H), 1.80-1.73 (m, 5H), 1.10 (t, 3H, J=7.3 Hz), 0.82 (s, 6H); LCMS: purity: 99%; MS (m/e): 530 (MH⁺);

4-(6-((2S,6R)-2,6-dimethylmorpholin-4-yl)pyridin-3-yl)-N-(3-methyl-4-(1,5,7-trimethyl-3,7-diazabicyclo[3.3.1]nonan-3-yl)phenyl)pyrimidin-2-amine, compound #212, LCMS: purity: 99%; MS (m/e): 542 (MH⁺);

4-(6-(propylamino)pyridin-3-yl)-N-(3-methyl-4-(1,5,7-trimethyl-3,7-diazabicyclo[3.3.1]nonan-3-yl)phenyl)pyrimidin-2-amine, compound #213, ¹H NMR (DMSO-d₆): δ 9.18 (s, 1H), 8.78 (s, 1H), 8.32 (d, 1H, J=5.3 Hz), 8.07 (dd, 1H, J=2.6 and 9.1 Hz), 7.54 (d, 1H, J=8.2 Hz), 7.48 (s, 1H), 7.16-7.11 (m, 2H), 6.86 (d, 1H, J=8.2 Hz), 6.54 (d, 1H, J=9.1 Hz), 3.26-3.24 (m, 2H), 2.85 (d, 2H, J=10.2 Hz), 2.70 (d, 2H, J=12.5 Hz), 2.30 (s, 3H), 2.08 (s, 3H), 1.76 (d, 2H, J=9.6 Hz), 1.54 (q, 2H, J=7.3 Hz), 1.19-1.03 (m, 2H), 0.09 (t, 3H, J=7.3 Hz), 0.82 (s, 6H); LCMS: purity: 99%; MS (m/e): 486 (MH⁺);

4-(6-(3-dimethylamino)propylaminopyridin-3-yl)-N-(3-methyl-4-(1,5,7-trimethyl-3,7-diazabicyclo[3.3.1]nonan-3-yl)phenyl)pyrimidin-2-amine, compound #214, ¹H NMR (DMSO-d₆): δ 9.18 (s, 1H), 8.78 (d, 1H, J=2.3 Hz), 8.32 (d, 1H, J=5.3 Hz), 8.07 (dd, 1H, J=2.3 and 8.8 Hz), 7.52 (d, 1H, J=8.5 Hz), 7.49 (d, 1H, J=2.3 Hz), 7.15-7.09 (m, 2H), 6.85 (d, 1H, J=8.5 Hz), 6.54 (d, 1H, J=8.8 Hz), 2.86 (d, 2H, J=10.8 Hz), 2.71 (d, 2H, J=10.8 Hz), 2.30 (s, 3H), 2.25-2.23 (m, 3H), 2.11 (s, 6H), 2.08 (s, 3H), 1.78 (d, 2H, J=9.5 Hz), 1.68 (q, 2H, J=7.3 Hz), 1.19 (d, 1H, J=12.0 Hz), 1.07 (d, 1H, J=12.0 Hz), 0.82 (s, 6H); LCMS: purity: 99%; MS (m/e): 529 (MH⁺);

4-(6-((1S,4S)-2-oxa-5-azabicyclo[2.2.1]heptan-5-yl)pyridin-3-yl)-N-(3-methyl-4-((1S,4S)-5-methyl-2,5-diazabicyclo[2.2.1]heptan-2-yl)phenyl)pyrimidin-2-amine, compound #215, ¹H NMR (DMSO-d₆): δ 9.16 (s, 1H), 8.87 (d, 1H, J=2.3 Hz), 8.33 (d, 1H, J=5.3 Hz), 8.21 (dd, 1H, J=2.0 and 8.8 Hz), 7.49 (d, 1H, J=9.1 Hz), 7.43 (d, 1H, J=5.3 Hz), 7.18 (d, 1H, J=5.3 Hz), 7.74 (d, 1H, J=8.8 Hz), 6.64 (d, 1H, J=8.8 Hz), 4.95 (s, 1H), 4.67 (s, 1H), 3.88 (s, 1H), 3.79 (d, 1H, J=6.7 Hz), 3.65 (d, 1H, J=7.6 Hz), 3.50 (d, 1H, J=10.3 Hz), 3.21-3.12 (m, 2H), 2.73 (d, 1H, J=9.4 Hz), 2.67 (d, 1H, J=9.4 Hz), 2.27 (s, 3H), 2.19 (s, 3H), 1.93 (d, 1H, J=9.4 Hz), 1.87 (d, 1H, J=9.4 Hz), 1.77 (d, 1H, J=9.1 Hz), 1.68 (d, 1H, J=9.1 Hz); LCMS: purity: 99%; MS (m/e): 470 (MH⁺);

4-(6-((1S,4S)-5-oxa-2-azabicyclo[2.2.1]heptan-2-yl)pyridin-3-yl)-N-(3-methyl-4-((1S,4S)-5-oxa-2-azabicyclo[2.2.1]heptan-2-yl)phenyl)pyrimidin-2-amine, compound #216, $^1$H NMR (DMSO-d$_6$): δ 9.19 (s, 1H), 8.86 (s, 1H), 8.33 (d, 1H, J=5.3 Hz), 8.21 (dd, 1H, J=2.0 and 8.8 Hz), 7.52 (d, 1H, J=8.5 Hz), 7.45 (s, 1H), 7.18 (d, 1H, J=5.3 Hz), 6.81 (d, 1H, J=8.5 Hz), 6.62 (d, 1H, J=8.8 Hz), 4.95 (s, 1H), 4.68 (s, 1H), 4.50 (s, 1H), 4.12 (s, 1H), 3.89 (d, 1H, J=7.3 Hz), 3.79 (d, 1H, J=7.3 Hz), 3.70 (d, 1H, J=7.0 Hz), 3.49 (d, 1H, J=9.9 Hz), 3.2 (d, 1H, J=9.9 Hz), 3.04 (d, 1H, J=9.6 Hz), 2.18 (s, 3H), 1.94-1.85 (m, 3H), 1.75 (d, 1H, J=9.1 Hz); LCMS: purity: 99%; MS (m/e): 457 (MH$^+$);

4-(6-(3-methylbutyl)aminopyridin-3-yl)-N-(3-methyl-4-((1S,4S)-5-methyl-2,5-diazabicyclo[2.2.1]heptan-2-yl)phenyl)pyrimidin-2-amine, compound #217, $^1$H NMR (DMSO-d$_6$): δ 9.12 (s, 1H), 8.79 (d, 1H, J=2.3 Hz), 8.29 (d, 1H, J=4.7 Hz), 8.06 (dd, 1H, J=2.3 and 8.8 Hz), 7.47 (d, 1H, J=8.8 Hz), 7.43 (d, 1H, J=2.3 Hz), 7.12 (d, 1H, J=4.7 Hz), 7.06 (t, 1H, J=5.3 Hz), 6.74 (d, 1H, J=8.8 Hz), 6.53 (d, 1H, J=8.8 Hz), 3.87 (s, 1H), 3.21-3.12 (m, 2H), 2.72 (d, 1H, J=9.3 Hz), 2.66 (d, 1H, J=9.3 Hz), 2.26 (s, 3H), 2.18 (s, 3H), 1.73 (d, 1H, J=8.5 Hz), 1.69-1.63 (m, 2H), 1.46-1.39 (app qt, 2H, J=7.3 Hz), 0.89 (d, 6H, J=6.7 Hz); LCMS: Purity: 99%; MS (m/e): 458 (MH$^+$);

4-(6-(3,3-dimethylbutyl)aminopyridin-3-yl)-N-(3-methyl-4-((1S,4S)-5-methyl-2,5-diazabicyclo[2.2.1]heptan-2-yl)phenyl)pyrimidin-2-amine, compound #218, $^1$H NMR (DMSO-d$_6$): δ 9.12 (s, 1H), 8.79 (d, 1H, J=2.3 Hz), 8.30 (d, 1H, J=5.3 Hz), 8.06 (dd, 1H, J=2.3 and 8.8 Hz), 7.48 (d, 1H, J=8.8 Hz), 7.43 (d, 1H, J=2.3 Hz), 7.13 (d, 1H, J=5.3 Hz), 7.01 (t, 1H, J=5.3 Hz), 6.74 (d, 1H, J=8.5 Hz), 6.51 (d, 1H, J=9.1 Hz), 3.88 (s, 1H), 3.16-3.12 (m, 2H), 2.73 (d, 1H, J=9.3 Hz), 2.68 (d, 1H, J=9.3 Hz), 2.27 (s, 3H), 2.18 (s, 3H), 1.77 (d, 1H, J=9.3 Hz), 1.68 (d, 1H, J=9.3 Hz), 1.49-1.43 (m, 2H), 0.92 (s, 9H); LCMS: Purity: 99%; MS (m/e): 472 (MH$^+$);

4-(6-(2-methoxyethyl)(methyl)aminopyridin-3-yl)-N-(3-methyl-4-((1S,4S)-5-methyl-2,5-diazabicyclo[2.2.1]heptan-2-yl)phenyl)pyrimidin-2-amine, compound #219, $^1$H NMR (DMSO-d$_6$): δ 9.16 (s, 1H), 8.86 (d, 1H, J=2.3 Hz), 8.32 (d, 1H, J=5.3 Hz), 8.20 (dd, 1H, J=2.3 and 9.1 Hz), 7.49 (d, 1H, J=8.5 Hz), 7.43 (d, 1H, J=2.3 Hz), 7.18 (d, 1H, J=5.3 Hz), 6.77 (d, 1H, J=9.1 Hz), 6.74 (d, 1H, J=8.5 Hz), 3.88 (s, 1H), 3.75 (t, 2H, J=5.8 Hz), 3.51 (t, 2H, J=5.3 Hz), 3.23 (app s, 3H), 3.18-3.12 (m, 2H), 3.08 (s, 3H), 2.73 (d, 1H, J=9.1 Hz), 2.66 (d, 1H, J=9.1 Hz), 2.26 (s, 3H), 2.18 (s, 3H), 1.77 (d, 1H, J=9.4 Hz), 1.68 (d, 1H, J=9.3 Hz). LCMS: Purity: 99%; MS (m/e): 460 (MH$^+$);

4-(6-(2-methoxyethyl)(methyl)aminopyridin-3-yl)-N-(3-methyl-4-((1S,4S)-5-oxa-2-azabicyclo[2.2.1]heptan-2-yl)phenyl)pyrimidin-2-amine, compound #220, $^1$H NMR (DMSO-d$_6$): δ 9.19 (s, 1H), 8.87 (d, 1H, J=2.3 Hz), 8.33 (d, 1H, J=5.3 Hz), 8.20 (dd, 1H, J=2.3 and 9.1 Hz), 7.53 (d, 1H, J=9.1 Hz), 7.45 (d, 1H, J=2.3 Hz), 6.81 (d, 1H, J=9.1 Hz), 6.75 (d, 1H, J=9.1 Hz), 4.50 (s, 1H), 4.12 (s, 1H), 3.89 (d, 1H, J=7.3 Hz), 3.78-3.69 (m, 3H), 3.51 (t, 3H, J=5.3 Hz), 3.23 (s, 3H), 3.08 (s, 3H), 3.03 (d, 1H, J=9.6 Hz), 2.18 (s, 3H), 1.87 (d, 1H, J=9.1 Hz), 1.75 (d, 1H, J=9.1 Hz); LCMS: Purity: 99%; MS (m/e): 447 (MH$^+$);

4-(6-(2-methoxyethyl)(methyl)aminopyridin-3-yl)-N-(3-methyl-4-(1,5,7-trimethyl-3,7-diazabicyclo[3.3.1]nonan-3-yl)phenyl)pyrimidin-2-amine, compound #221, $^1$H NMR (DMSO-d$_6$): δ 9.23 (s, 1H), 8.87 (d, 1H, J=2.3 Hz), 8.34 (d, 1H, J=5.3 Hz), 8.20 (dd, 1H, J=2.3 and 9.1 Hz), 7.55 (d, 1H, J=8.5 Hz), 7.48 (d, 1H, J=2.3 Hz), 7.20 (d, 1H, J=5.3 Hz), 6.86 (d, 1H, J=8.8 Hz), 6.76 (d, 1H, J=9.1 Hz), 3.76 (t, 2H, J=5.3 Hz), 3.51 (t, 2H, J=5.3 Hz), 3.23 (s, 3H), 3.08 (s, 3H), 2.85 (d, 2H, J=10.8 Hz), 2.70 (d, 2H, J=10.8 Hz), 2.31 (s, 3H), 2.07 (s, 3H), 1.76 (d, 2H, J=11.4 Hz), 1.19-1.02 (m, 2H), 0.82 (s, 6H); LCMS: Purity: 99%; MS (m/e): 516 (MH$^+$);

4-(6-(morpholin-4-yl)pyridin-3-yl)-N-(3-methyl-4-((1S,4R)-2-azabicyclo[2.2.1]heptan-2-yl)phenyl)pyrimidin-2-amine, compound #222, $^1$H NMR (DMSO-d$_6$): δ 9.17 (s, 1H), 8.91 (d, 1H, J=2.3 Hz), 8.34 (d, 1H, J=5.3 Hz), 8.25 (d, 1H, J=2.3 and 8.8 Hz), 7.45 (d, 1H, J=8.5 Hz), 7.41 (d, 1H, J=2.0 Hz), 7.20 (d, 1H, J=5.3 Hz), 6.95 (d, 1H, J=8.8 Hz), 6.73 (d, 1H, J=8.8 Hz), 3.81 (s, 1H), 3.69-3.67 (m, 4H), 3.57-3.55 (m, 4H), 2.75 (d, 1H, J=8.5 Hz), 2.18 (s, 3H), 1.81-1.56 (m, 4H), 1.38-1.29 (m, 2H); LCMS: Purity: 99%; MS (m/e): 443 (MH$^+$);

4-(2,2-dimethyl-3-oxo-3,4-dihydro-2H-pyrido[3,2-b][1,4]oxazin-7-yl)-N-(3-methyl-4-((1S,4R)-2-azabicyclo[2.2.1]heptan-2-yl)phenyl)pyrimidin-2-amine, compound #223, LCMS: Purity: 99%; MS (m/e): 457 (MH$^+$);

4-(2,2-dimethyl-3-oxo-3,4-dihydro-2H-pyrido[3,2-b][1,4]oxazin-7-yl)-N-(3-methyl-4-(2-methylsulfonyl-2-azabicyclo[2.2.1]heptan-5-yl)phenyl)pyrimidin-2-amine and 4-(2,2-dimethyl-3-oxo-3,4-dihydro-2H-pyrido[3,2-b][1,4]oxazin-7-yl)-N-(3-methyl-4-(2-methylsulfonyl-2-azabicyclo[2.2.1]heptan-6-yl)phenyl)pyrimidin-2-amine (68:31), compound #224, Mixture: LCMS: Purity: 99% (68:31); MS (m/e): 521 (MH$^+$); 4-(2,2-dimethyl-3-oxo-3,4-dihydro-2H-pyrido[3,2-b][1,4]oxazin-7-yl)-N-(3-methyl-4-(2-methylsulfonyl-2-azabicyclo[2.2.1]heptan-5-yl)phenyl)pyrimidin-2-amine $^1$H NMR (DMSO-d$_6$): δ 11.50 (s, 1H), 9.52 (s, 1H), 8.75 (d, 1H, J=2.3 Hz), 8.49 (d, 1H, J=5.3 Hz), 8.04 (d, 1H, J=2.3 Hz), 7.62 (s, 1H), 7.55 (dd, 1H, J=2.3 and 8.5 Hz), 7.39 (d, 1H, J=5.3 Hz), 7.13 (d, 1H, J=8.5 Hz), 4.10 (s, 1H), 3.26-3.25 (m, 1H), 3.12-3.05 (m, 2H), 2.91 (s, 3H), 2.62 (s, 1H), 2.27 (s, 3H), 2.20-2.17 (m, 1H), 1.70-1.60 (m, 3H), 1.45 (s, 6H); LCMS: Purity: 95%; MS (m/e): 535 (MH$^+$);

4-(6-(morpholin-4-yl)pyridin-3-yl)-N-(3-methyl-4-(2-methylsulfonyl-2-azabicyclo[2.2.1]heptan-5-yl)phenyl)pyrimidin-2-amine and 4-(6-(morpholin-4-yl)pyridin-3-yl)-N-(3-methyl-4-(2-methylsulfonyl-2-azabicyclo[2.2.1]heptan-6-yl)phenyl)pyrimidin-2-amine (85:15), compound #225, Mixture: LCMS: Purity: 97% (85:15); MS (m/e): 521 (MH$^+$);

4-(2,2-dimethyl-3-oxo-3,4-dihydro-2H-pyrido[3,2-b][1,4]oxazin-7-yl)-N-(4-(2-methylsulfonyl-2-azabicyclo[2.2.1]heptan-5-yl)phenyl)pyrimidin-2-amine, compound #226, $^1$H NMR (DMSO-d$_6$): δ 11.51 (s, 1H), 9.61 (s, 1H), 8.74 (d, 1H, J=1.8 Hz), 8.50 (d, 1H, J=4.3 Hz), 8.03 (s, 1H), 7.70-7.69 (d, 2H, J=8.8 Hz), 7.40 (d, 1H, J=4.3 Hz), 7.20 (d, 1H, J=8.5 Hz), 4.10 (s, 1H), 3.26-3.23 (m, 1H), 3.09-2.99 (m, 2H), 2.90 (s, 3H), 2.58 (s, 1H), 2.20-2.13 (m, 1H), 1.79-1.53 (m, 3H), 1.45 (s, 6H); LCMS: Purity: 96%; MS (m/e): 521 (MH$^+$);

4-(6-(morpholin-4-yl)pyridin-3-yl)-N-(4-(2-methylsulfonyl-2-azabicyclo[2.2.1]heptan-5-yl)phenyl)pyrimidin-2-amine, compound #227, $^1$H NMR (DMSO-d$_6$): δ 9.62 (s, 1H), 8.90 (s, 1H), 8.43 (d, 1H, J=5.5 Hz), 8.32 (app d, 2H, J=9.1 Hz), 7.72-7.69 (m, 2H), 7.33 (d, 1H, J=5.5 Hz), 7.20 (d, 1H, J=8.8 Hz), 7.04 (d, 1H, J=9.1 Hz), 4.11 (s, 1H), 3.71-3.69 (m, 4H), 3.62-3.60 (m, 4H), 3.25-3.22 (m, 1H), 3.10-2.99 (m, 2H), 2.90 (s, 3H), 2.59 (s, 1H), 2.20-2.13 (m, 1H), 1.78-1.54 (m, 3H); LCMS: Purity: 96%; MS (m/e): 507 (MH$^+$);

4-(2,2-dimethyl-3-oxo-3,4-dihydro-2H-pyrido[3,2-b][1,4]oxazin-7-yl)-N-(4-(2-methylsulfonyl-2-azabicyclo[2.2.1]

heptan-6-yl)phenyl)pyrimidin-2-amine, compound #228, $^1$H NMR (DMSO-d$_6$): δ 11.51 (s, 1H), 9.64 (s, 1H), 8.74 (d, 1H, J=1.8 Hz), 8.50 (d, 1H, J=5.3 Hz), 8.03 (d, 1H, J=1.8 Hz), 7.72 (d, 2H, J=8.8 Hz), 7.41 (d, 1H, J=5.3 Hz), 7.17 (d, 2H, J=8.8 Hz), 4.01 (s, 1H), 3.22-3.17 (m, 2H), 2.98-2.95 (d, 1H, J=8.2 Hz), 2.91 (s, 3H), 2.67 (s, 1H), 1.92-1.86 (m, 2H), 1.60-1.50 (m, 2H), 1.45 (s, 6H); LCMS: Purity: 97%; MS (m/e): 521 (MH$^+$);

4-(6-(morpholin-4-yl)pyridin-3-yl)-N-(4-(2-methylsulfonyl-2-azabicyclo[2.2.1]heptan-6-yl)phenyl)pyrimidin-2-amine, compound #229, $^1$H NMR (DMSO-d$_6$): δ 9.59 (s, 1H), 8.92 (s, 1H), 8.42 (d, 1H, J=5.0 Hz), 8.31 (d, 1H, J=9.1 Hz), 7.73 (d, 2H, J=8.5 Hz), 7.32 (d, 1H, J=5.0 Hz), 7.16 (d, 2H, J=8.5 Hz), 7.02 (d, 1H, J=9.1 Hz), 4.01 (s, 1H), 3.70-3.68 (m, 4H), 3.61-3.59 (m, 4H), 3.23-3.16 (m, 2H), 2.98-2.95 (d, 1H, J=8.2 Hz), 2.91 (s, 3H), 2.67 (s, 1H), 1.92-1.89 (m, 2H), 1.60-1.47 (m, 2H); LCMS: Purity: 87%; MS (m/e): 507 (MH$^+$);

4-(6-(thiamorpholin-4-yl)pyridin-3-yl)-N-(3-methyl-4-((1S,4S)-5-methyl-2,5-diazabicyclo[2.2.1]heptan-2-yl)phenyl)pyrimidin-2-amine, compound #230, $^1$H NMR (DMSO-d$_6$): δ 9.19 (s, 1H), 8.88 (s, 1H), 8.34 (d, 1H, J=5.3 Hz), 8.22 (d, 1H, J=8.8 Hz), 7.49 (d, 1H, J=8.8 Hz), 7.44 (s, 1H), 7.20 (d, 1H, J=5.3 Hz), 6.96 (d, 1H, J=9.1 Hz), 6.74 (d, 1H, J=9.1 Hz), 3.99 (s, 4H), 3.88 (s, 1H), 3.19 (d, 1H, J=9.1 Hz), 3.15 (d, 1H, J=9.1 Hz), 2.73 (d, 1H, J=9.1 Hz), 2.67 (d, 1H, J=9.1 Hz), 2.61 (s, 4H), 2.26 (s, 3H), 2.18 (s, 3H), 1.77 (d, 1H, J=9.1 Hz), 1.68 (d, 1H, J=9.1 Hz); LCMS: Purity: 99%; MS (m/e): 474 (MH$^+$);

4-(6-(morpholin-4-yl)pyridin-3-yl)-N-(3-methyl-4-((1S,4S)-5-methyl-2,5-diazabicyclo[2.2.1]heptan-2-yl)phenyl)pyrimidin-2-amine as a hemi-succinate salt, compound #231;

4-(1-(pyridin-4-yl)-1H-indol-5-yl)-N-(3-methyl-4-((1S,4S)-5-methyl-2,5-diazabicyclo[2.2.1]heptan-2-yl)phenyl)pyrimidin-2-amine, compound #232, $^1$H NMR (DMSO-d$_6$, 300 MHz): δ 9.27 (s, 1H), 8.72 (m, 2H), 8.50 (s, 1H), 8.43 (d, 1H, J=5.4 Hz), 8.09 (d, 1H, J=8.7 Hz), 7.92 (m, 2H), 7.75 (dd, 2H, J=1.5 & 4.3 Hz), 7.51 (m, 2H), 7.35 (d, 1H, J=5.4 Hz), 6.92 (d, 1H, J=3.3 Hz), 6.76 (d, 1H, J=8.4 Hz), 3.90 (s, 1H), 3.19 (m, 3H), 2.72 (q, 2H, J=8.4 Hz), 2.28 (s, 3H), 2.22 (s, 3H), 1.79 (d, 1H, J=9.3 Hz), 1.70 (d, 1H, J=8.7 Hz); LCMS (m/z): 488 (MH$^+$);

4-(1-(pyridin-4-yl)-1H-indol-5-yl)-N-(3-fluoro-4-((1S,4S)-5-methyl-2,5-diazabicyclo[2.2.1]heptan-2-yl)phenyl)pyrimidin-2-amine, compound #233, 1H NMR ((DMSO-d$_6$, 300 MHz): δ 9.48 (s, 1H), 8.71 (d, 1H, J=5.1 Hz), 8.49 (s, 1H), 8.46 (d, 1H, J=5.4 Hz), 8.25 (s, 1H), 8.09 (d, 1H, J=8.7 Hz), 7.92 (m, 2H), 7.74 (m, 2H), 7.39 (d, 2H, J=4.8 Hz), 6.92 (d, 1H, J=3.3 Hz), 6.71 (t, 1H, J=9.9 Hz), 4.19 (s, 1H), 3.22 (m, 3H), 2.72 (q, 2H, J=8.4 Hz), 2.29 (s, 3H), 1.84 (d, 1H, J=9.6 Hz), 1.74 (d, 1H, J=9.3 Hz); LCMS (m/z): 492 (MH$^+$);

4-(1-(pyridin-4-yl)-1H-indol-5-yl)-N-(3-methyl-4-((1S,4S)-5-ethyl-2,5-diazabicyclo[2.2.1]heptan-2-yl)phenyl)pyrimidin-2-amine, compound #234, $^1$H NMR ((DMSO-d$_6$, 300 MHz): δ 9.28 (s, 1H), 8.72 (d, 2H, J=6.0 Hz), 8.50 (s, 1H), 8.42 (d, 1H, J=5.4 Hz), 8.09 (d, 1H, J=9.0 Hz), 7.92 (m, 2H), 7.75 (d, 2H, J=6.0 Hz), 7.50 (m, 2H), 7.35 (d, 1H, J=5.4 Hz), 6.92 (d, 1H, J=3.6 Hz), 6.76 (d, 1H, J=8.7 Hz), 3.93 (s, 1H), 3.49 (s, 1H), 3.19 (s, 3H), 2.80 (m, 2H), 2.22 (s, 3H), 1.74 (m, 3H), 0.98 (t, 3H, J=7.2 Hz); LCMS (m/z): 502 (MH$^+$);

4-(1-(pyridin-4-yl)-1H-indol-5-yl)-N-(3-methyl-4-((1S,4S)-5-isobutyl-2,5-diazabicyclo[2.2.1]heptan-2-yl)phenyl)pyrimidin-2-amine, compound #235, $^1$H NMR ((DMSO-d$_6$, 300 MHz): δ 9.27 (s, 1H), 8.72 (m, 2H), 8.50 (s, 1H), 8.42 (d, 1H, J=5.4 Hz), 8.09 (d, 1H, J=8.7 Hz), 7.92 (m, 2H), 7.75 (dd, 2H, J=1.5 & 4.3 Hz), 7.51 (m, 2H), 7.35 (d, 1H, J=5.4 Hz), 6.92 (d, 1H, J=3.6 Hz), 6.74 (d, 1H, J=8.7 Hz), 3.91 (s, 1H), 3.39 (m, 1H), 3.20 (s, 2H), 2.81 (s, 1H)), 2.69 (s, 1H), 2.25 (s, 2H), 2.20 (s, 3H), 1.73 (m, 2H), 1.56 (s, 1H), 0.85 (d, 6H, J=6.3 Hz); LCMS (m/z): 530 (MH$^+$);

4-(7-oxo-5,6,7,8-tetrahydro-1,8-naphthyridin-3-yl)-N-(3-methyl-4-((1S,4S)-5-methylsulfonyl-2,5-diazabicyclo[2.2.1]heptan-2-yl)phenyl)pyrimidin-2-amine, compound #237, $^1$H NMR (DMSO-d$_6$): δ 10.75 (1H, s), 9.38 (1H, s), 8.89 (1H, d, J=8.5 Hz), 8.45 (1H, d, J=5.2 Hz), 8.34-8.32 (m, 1H), 7.56 (1H, s), 7.48 (1H, d, J=8.5 Hz), 7.32 (1H, d, J=5.2 Hz), 6.89 (1H, d, J=8.8 Hz), 4.35 (1H, s), 4.17 (1H, s), 3.07-2.97 (7H, m), 2.58-2.57 (4H, m), 2.23 (3H, s), 1.88 (2H, dd, J=25.2, 9.2 Hz); MS: 506 (M+H);

4-(6-(propylamino)pyridin-3-yl)-N-(3-methyl-4-((1S,4S)-5-methylsulfonyl-2,5-diazabicyclo[2.2.1]heptan-2-yl)phenyl)pyrimidin-2-amine, compound #238, $^1$H NMR (DMSO-d$_6$): δ 9.23 (s, 1H), 8.77 (s, 1H), 8.33 (d, 1H, J=5.3 Hz), 8.11 (d, 1H, J=9.1 Hz), 7.53 (d, 1H, J=8.5 Hz), 7.48 (s, 1H), 7.31 (br s, 1H), 7.16 (d, 1H, J=5.3 Hz), 6.88 (d, 1H, J=8.5 Hz), 6.60 (d, 1H, J=9.1 Hz), 4.33 (s, 1H), 4.14 (s, 1H), 3.41-3.22 (m, 6H), 2.95 (s, 3H), 2.19 (s, 3H), 1.90 (d, 1H, J=9.1 Hz), 1.88 (d, 1H, J=9.1 HZ), 1.55 (m, 2H), 0.90 (t, 3H, J=7.4 Hz); LCMS: Purity: 99%; MS (m/e): 494 (MH$^+$);

4-(3-oxo-3,4-dihydro-2H-benzo[b][1,4]thiazin-7-yl)-N-(4-((1S,4S)-5-methyl-2,5-diazabicyclo[2.2.1]heptan-2-yl)phenyl)pyrimidin-2-amine, compound #239, $^1$H NMR (CD$_3$OD, 300 MHz): δ 8.33 (m, 2H), 8.12 (s, 1H), 7.91 (m, 1H), 7.56 (m, 3H), 7.08 (m, 2H), 6.69 (m, 1H), 4.62 (s, 1H), 4.33 (s, 1H), 3.81 (m, 1H), 3.70 (m, 3H), 2.93 (s, 3H), 2.34 (m, 2H), 2.31 (m, 2H); MS (ES) 445.03 (M+H);

4-(2,2-dimethyl-3-oxo-3,4-dihydro-2H-benzo[b][1,4]oxazin-7-yl)-N-(3-methyl-4-((1S,4S)-5-methyl-2,5-diazabicyclo[2.2.1]heptan-2-yl)phenyl)pyrimidin-2-amine, compound #240, $^1$H NMR (CD$_3$OD, 300 MHz): δ 8.35 (m, 1H), 7.75 (m, 2H), 7.52 (m, 2H), 7.20 (m, 1H), 6.96 (m, 2H), 4.25 (m, 2H), 3.95 (m, 1H), 3.48 (m, 2H), 3.16 (m, 1H), 2.97 (s, 3H), 2.32 (m, 5H), 1.50 (s, 6H); MS (ES) 471.06 (M+H);

4-(2,2-dimethyl-3-oxo-3,4-dihydro-2H-benzo[b][1,4]oxazin-7-yl)-N-(3-methyl-4-((1S,4S)-5-methylsulfonyl-2,5-diazabicyclo[2.2.1]heptan-2-yl)phenyl)pyrimidin-2-amine, compound #241, $^1$H NMR (CD$_3$OD, 300 MHz): δ 8.31 (m, 1H), 7.71 (m, 2H), 7.46 (m, 2H), 7.10 (m, 2H), 6.95 (m, 2H), 4.44 (s, 1H), 4.19 (s, 1H), 3.63-3.37 (m, 4H), 2.94 (s, 3H), 2.31 (s, 3H), 2.03 (m, 2H), 1.51 (s, 6H); MS (ES) 535.12 (M+H);

4-(2-oxo-2,3,4,5-tetrahydro-1H-benzo[b]azepin-7-yl)-N-(3-methyl-4-((1S,4S)-5-methyl-2,5-diazabicyclo[2.2.1]heptan-2-yl)phenyl)pyrimidin-2-amine, compound #242, $^1$H NMR (CD$_3$OD, 300 MHz): δ 8.38 (m, 1H), 8.04 (m, 2H), 7.52 (m, 2H), 7.20 (m, 2H), 7.25 (m, 1H), 7.10 (m, 1H), 6.96 (m, 1H), 4.30 (s, 1H), 4.24 (s, 1H), 3.79 (m, 1H), 3.48 (m, 2H), 3.24 (m, 1H), 2.97 (s, 3H), 2.88 (m, 2H), 2.33 (m, 9H); MS (ES) 455.14 (M+H);

4-(2-oxo-2,3,4,5-tetrahydro-1H-benzo[b]azepin-7-yl)-N-(3-methyl-4-((1S,4S)-5-methylsulfonyl-2,5-diazabicyclo[2.2.1]heptan-2-yl)phenyl)pyrimidin-2-amine, compound #243, $^1$H NMR (CD$_3$OD, 300 MHz): δ 8.23 (m, 1H), 8.16 (m, 2H), 7.52 (m, 3H), 7.15 (m, 2H), 4.50 (s, 1H), 4.42 (s, 1H), 3.65 (m, 4H), 2.97 (s, 3H), 2.88 (m, 2H), 2.36-2.11 (m, 9H); MS (ES) 519.13 (M+H);

4-(2,2-dimethyl-3-oxo-3,4-dihydro-2H-benzo[b][1,4]oxazin-7-yl)-N-(3-methyl-4-((6R,9S)-6,9-methanooctahydro-1H-pyrido[1,2-a]pyrazin-2-yl)phenyl)pyrimidin-2- amine, compound #244, ¹H NMR (CD₃OD, 300 MHz): δ 8.42 (s, 1H), 8.36 (m, 1H), 7.76 (m, 2H), 7.55 (m, 2H), 7.21-7.10 (m, 2H), 6.97 (m, 1H), 3.95 (m, 2H), 3.70-3.48 (m, 3H), 2.58 (m, 1H), 2.41 (m, 1H), 1.34 (s, 3H), 1.97-1.66 (m, 6H), 1.51 (s, 6H); MS (ES) 511.13 (M+H);

4-(6-(morpholin-4-yl)pyridin-3-yl)-N-(3-methyl-4-((6R,9S)-6,9-methanooctahydro-1H-pyrido[1,2-a]pyrazin-2-yl)phenyl)pyrimidin-2-amine, compound #245, ¹H NMR (CD₃OD, 300 MHz): δ 8.90 (m, 1H), 8.40 (s, 1H), 8.32-8.21 (m, 2H), 7.49 (m, 2H), 7.13 (m, 2H), 6.87 (m, 1H), 4.01-3.91 (m, 2H), 3.81-3.48 (m, 11H), 3.13 (m, 2H), 2.56 (m, 1H), 2.39 (m, 1H), 2.39 (m, 1H), 2.33 (s, 3H), 1.91-1.66 (m, 6H), 1.51 (s, 6H); MS (ES) 498.13 (M+H);

4-(6-(dimethylamino)pyridin-3-yl)-N-(6-((1S,4S)-5-methyl-2,5-diazabicyclo[2.2.1]heptan-2-yl)pyridin-3-yl)pyrimidin-2-amine, compound #54, LCMS: purity: 99%; MS (m/e): 403 (MH⁺);

4-(6-(methylcarbonylamino)pyridin-3-yl)-N-(6-((1S,4S)-5-methyl-2,5-diazabicyclo[2.2.1]heptan-2-yl)pyridin-3-yl)pyrimidin-2-amine, compound #55, LCMS: purity: 99%; MS (m/e): 417 (MH⁺);

4-(4-(dimethylamino)phenyl)-N-(6-((1S,4S)-5-methyl-2,5-diazabicyclo[2.2.1]heptan-2-yl)pyridin-3-yl)pyrimidin-2-amine, compound #56, ¹H NMR (DMSO-d₆): δ 9.15 (s, 1H), 8.44 (s, 1H), 8.28 (d, 1H, J=6 Hz), 7.91 (m, 3H), 7.15 (d, 1H, J=5.6 Hz), 6.78 (d, 2H, J=10 Hz), 6.57 (d, 1H, J=11.5 Hz), 4.65 (s, 1H), 3.51 (m, 2H), 2.98 (s, 6H), 2.69 (m, 2H), 2.57 (s, 3H), 2.08 (m, 1H), 1.93 (m, 1 Hz); LCMS: purity: 99%; MS (m/e): 402 (MH⁺);

4-(6-(4-acetylpiperazin-1-yl)pyridin-3-yl)-N-(6-((1S,4S)-5-methyl-2,5-diazabicyclo[2.2.1]heptan-2-yl)pyridin-3-yl)pyrimidin-2-amine, compound #57, ¹H NMR (DMSO-d₆): δ 9.21 (s, 1H), 8.88 (s, 1H), 8.41 (s, 1H), 8.34 (d, 1H, J=6 Hz), 8.20 (m, 1H), 7.83 (m, 1H), 7.22 (d, 1H, J=5.1 Hz), 6.95 (d, 1H, J=9.3 Hz), 6.53 (d, 1H, J=9.3 Hz), 4.60 (s, 1H), 3.59 (m, 12H), 2.92 (m, 1H), 2.44 (s, 3H), 2.01 (m, 4H), 1.79 (m, 1H); LCMS: purity: 99%; MS (m/e): 486 (MH⁺);

4-(5-methyl-6-(morpholin-4-yl)pyridin-3-yl)-N-(6-((1S,4S)-5-methyl-2,5-diazabicyclo[2.2.1]heptan-2-yl)pyridin-3-yl)pyrimidin-2-amine, compound #58, LCMS: purity: 99%; MS (m/e): 459 (MH⁺);

4-(6-(dimethylamino)pyridin-3-yl)-N-(5-methyl-6-((1S,4S)-5-methyl-2,5-diazabicyclo[2.2.1]heptan-2-yl)pyridin-3-yl)pyrimidin-2-amine, compound #61, LCMS: purity: 99%; MS (m/e): 417 (MH⁺);

4-(4-(dimethylamino)phenyl)-N-(5-methyl-6-((1S,4S)-(5-methyl-2,5-diazabicyclo[2.2.1]heptan-2-yl)pyridin-3-yl)pyrimidin-2-amine, compound #62, LCMS: purity: 99%; MS (m/e): 416 (MH⁺);

4-(6-(4-acetylpiperazin-1-yl)pyridin-3-yl)-N-(5-methyl-6-((1S,4S)-5-methyl-2,5-diazabicyclo[2.2.1]heptan-2-yl)pyridin-3-yl)pyrimidin-2-amine, compound #63, LCMS: purity: 99%; MS (m/e): 500 (MH⁺);

4-(5-methyl-6-(morpholin-4-yl)pyridin-3-yl)-N-(5-methyl-6-((1S,4S)-5-methyl-2,5-diazabicyclo[2.2.1]heptan-2-yl)pyridin-3-yl)pyrimidin-2-amine, compound #64, LCMS: purity: 99%; MS (m/e): 473 (MH⁺);

4-(4-methyl-3,4-dihydro-2H-pyrido[3,2-b][1,4]oxazin-7-yl)-N-(5-methyl-6-((1S,4S)-5-methyl-2,5-diazabicyclo[2.2.1]heptan-2-yl)pyridin-3-yl)pyrimidin-2-amine, compound #65, LCMS: purity: 99%; MS (m/e): 445 (MH⁺);

4-(6-(morpholin-4-yl)pyridin-3-yl)-N-(5-methyl-6-((1S,4S)-5-methyl-2,5-diazabicyclo[2.2.1]heptan-2-yl)pyridin-3-yl)pyrimidin-2-amine, compound #66, LCMS: purity: 99%; MS (m/e): 459 (MH⁺);

4-(4-(t-butylcarbonylamino)phenyl)-N-(5-methyl-6-((1S,4S)-5-methyl-2,5-diazabicyclo[2.2.1]heptan-2-yl)pyridin-3-yl)pyrimidin-2-amine, compound #131, ¹H NMR (CD₃OD, 300 MHz): δ 9.26 (m, 1H), 8.64 (m, 1H), 8.41 (m, 1H), 8.11 (m, 2H), 7.90 (m, 1H), 7.74 (m, 2H), 7.37 (m, 1H), 4.29 (s, 1H), 4.40 (m, 2H), 3.99 (m, 2H), 3.36 (m, 2H), 3.24 (m, 1H), 3.01 (s, 3H), 2.40 (m, 5H), 1.33 (s, 9H); MS (ES) 472.12 (M+H);

4-(2,2-dimethyl-3-oxo-3,4-dihydro-2H-pyrido[3,2-b][1,4]oxazin-7-yl)-N-(5-methyl-6-((1S,4S)-5-methyl-2,5-diazabicyclo[2.2.1]heptan-2-yl)pyridin-3-yl)pyrimidin-2-amine, compound #138, ¹H NMR (CD₃OD, 300 MHz): δ 8.69 (m, 1H), 8.56 (m, 1H), 8.45 (m, 1H), 8.00 (m, 2H), 7.90 (m, 1H), 7.31 (m, 1H), 4.78 (m, 1H), 4.38 (s, 1H), (m, 1H), 4.08 (m, 1H), 3.96 (m, 1H), 3.63 (m, 1H), 3.23 (m, 1H), 3.00 (s, 3H), 2.38 (m, 5H), 1.54 (s, 6H); MS (ES) 473.10 (M+H);

4-(4-(3-cyclopropylureido)phenyl)-N-(5-methyl-6-((1S,4S)-5-methyl-2,5-diazabicyclo[2.2.1]heptan-2-yl)pyridin-3-yl)pyrimidin-2-amine, compound #140, ¹H NMR (CD₃OD, 300 MHz): δ 8.46 (m, 1H), 8.33 (m, 1H), 8.15 (m, 1H), 8.03 (m, 2H), 7.85 (m, 1H), 7.53 (m, 2H), 7.20 (m, 1H), 4.65 (s, 1H), 4.31 (s, 1H), 3.92 (m, 2H), 3.58 (m, 1H), 2.96 (s, 3H), 2.61 (m, 1H), 2.30 (m, 5H), 0.76 (m, 2H), 0.53 (m, 3H); MS (ES) 471.57 (M+H);

4-(6-(2-(morpholin-4-yl)acetamido)pyridin-3-yl)-N-(5-methyl-6-((1S,4S)-5-methyl-2,5-diazabicyclo[2.2.1]heptan-2-yl)pyridin-3-yl)pyrimidin-2-amine, compound #144, ¹H NMR (CD₃OD, 300 MHz): δ 9.10 (m, 1H), 8.53 (m, 3H), 8.25 (m, 1H), 7.87 (m, 1H), 7.33 (m, 1H), 4.23 (m, 4H), 3.98 (m, 4H), 3.46 (m, 4H), 3.34 (m, 1H), 3.23 (m, 1H), 2.99 (s, 3H), 2.35 (m, 6H); MS (ES) 516.07 (M+H);

4-(6-aminopyridin-3-yl)-N-(5-methyl-6-((1S,4S)-5-methyl-2,5-diazabicyclo[2.2.1]heptan-2-yl)pyridin-3-yl)pyrimidin-2-amine, compound #145, ¹H NMR (CD₃OD, 300 MHz): δ 8.70 (m, 1H), 8.39 (m, 1H), 8.33 (m, 1H), 8.20 (m, 3H), 7.84 (m, 1H), 7.14 (m, 1H), 6.66 (m, 1H), 4.64 (s, 1H), 4.30 (s, 1H), 3.99 (m, 1H), 3.86 (m, 1H), 3.58 (m, 1H), 2.96 (s, 3H), 2.65 (m, 1H), 2.30 (m, 5H); MS (ES) 389.01 (M+H);

4-(6-(acetamido)pyridin-3-yl)-N-(5-methyl-6-((1S,4S)-5-methyl-2,5-diazabicyclo[2.2.1]heptan-2-yl)pyridin-3-yl)pyrimidin-2-amine, compound #146, ¹H NMR (CD₃OD, 300 MHz): δ 9.02 (m, 1H), 8.44 (m, 2H), 8.23 (m, 2H), 7.83 (m, 1H), 7.25 (m, 1H), 4.65 (s, 1H), 4.30 (s, 1H), 4.00 (m, 1H), 3.85 (m, 1H), 3.59 (m, 2H), 2.96 (s, 3H), 2.65 (m, 1H), 2.30 (s, 3H), 2.21 (m, 2H); MS (ES) 431.05 (M+H);

4-(6-(methylsulfonylamino)pyridin-3-yl)-N-(5-methyl-6-((1S,4S)-5-methyl-2,5-diazabicyclo[2.2.1]heptan-2-yl)pyridin-3-yl)pyrimidin-2-amine, compound #154, ¹H NMR (CD₃OD, 300 MHz): δ 8.96 (m, 1H), 8.41 (m, 2H), 8.20 (m, 2H), 7.83 (m, 1H), 7.20 (m, 2H), 4.65 (s, 1H), 4.30 (s, 1H), 4.02-3.57 (m, 3H), 2.97 (s, 3H), 2.30 (m, 6H); MS (ES) 467.02 (M+H);

4-(2-(dimethylamino)thiazol-4-yl)-N-(6-((1S,4S)-5-methyl-2,5-diazabicyclo[2.2.1]heptan-2-yl)pyridin-3-yl)pyrimidin-2-amine, compound #177, ¹H NMR (DMSO-d₆): δ 9.20 (s, 1H), 8.41 (d, 1H, J=4.7 Hz), 8.33 (s, 1H), 7.86 (d, 1H, J=8.5 Hz), 7.47 (s, 1H), 7.18 (d, 1H, J=4.7 Hz), 6.47 (d, 1H, J=9.1 Hz), 4.48 (s, 1H), 3.40-3.37 (m, 2H), 3.23 (d, 1H, J=9.7 Hz), 3.07 (d, 6H), 2.77 (d, 1H, J=9.1 Hz), 2.42 (d, 1H, J=9.7 Hz), 2.24 (s, 3H), 1.83 (d, 1H, J=9.1 Hz), 1.70 (d, 1H, J=9.1 Hz); LCMS: purity: 99%; MS (m/e): 409 (MH⁺);

4-(5-(morpholin-4-yl)pyrazin-2-yl)-N-(6-((1S,4S)-5-methyl-2,5-diazabicyclo[2.2.1]heptan-2-yl)pyridin-3-yl)pyrimidin-2-amine, compound #180, $^1$H NMR (DMSO-d$_6$): δ 9.25 (s, 1H), 8.94 (s, 1H), 8.42-8.36 (m, 3H), 7.83 (dd, 1H, J=2.0 and 9.1 Hz), 7.35 (d, 1H, J=4.9 Hz), 6.51 (d, 1H, J=9.1 Hz), 4.50 (s, 1H), 3.69-3.67 (m, 8H), 3.41-3.38 (m, 2H), 3.23 (d, 1H, J=9.4 Hz), 2.77 (d, 1H, J=9.4 Hz), 2.43 (d, 1H, J=9.4 Hz), 2.23 (s, 3H), 1.83 (d, 1H, J=9.7 Hz), 1.71 (d, 1H, J=9.7 Hz); LCMS: purity: 90%; MS (m/e): 446 (MH$^+$);

4-(1-(pyridin-4-yl)-1H-indol-5-yl)-N-(5-methyl-6-((1S,4S)-5-methyl-2,5-diazabicyclo[2.2.1]heptan-2-yl)pyridin-3-yl)pyrimidin-2-amine, compound #236, $^1$H NMR ((DMSO-d$_6$, 300 MHz): δ 9.33 (s, 1H), 8.72 (d, 2H, J=6.3 Hz), 8.50 (s, 1H), 8.48 (s, 1H), 8.43 (d, 1H, J=5.1 Hz), 8.32 (s, 1H), 8.07 (d, 1H, J=9.0 Hz), 7.92 (m, 2H), 7.79 (s, 1H), 7.75 (d, 2H, J=6.3 Hz), 7.38 (d, 1H, J=5.4 Hz), 6.91 (d, 1H, J=3.6 Hz), 4.36 (s, 1H), 3.38 (m, 2H), 2.79 (m, 2H), 2.27 (s, 3H), 2.23 (s, 3H), 1.77 (d, 1H, J=8.7 Hz), 1.64 (d, 1H, J=9.0 Hz); LCMS (m/z): 489 (MH$^+$);

4-(2,2-dimethyl-3-oxo-3,4-dihydro-2H-pyrido[3,2-b][1,4]oxazin-7-yl)-N-(3-methyl-4-((1S,4S)-5-(1-methylethyl)-2,5-diazabicyclo[2.2.1]heptan-2-yl)phenyl)pyrimidin-2-amine, compound #246, $^1$H NMR (DMSO-d$_6$, 300 MHz): δ 11.48 (b, 1H), 9.44 (d, J=4.96 Hz, 1H), 8.73 (b, 1H), 8.46 (d, J=4.95 Hz, 1H), 8.02 (b, 1H), 7.57 (tr, J=19.53 Hz, 2H), 7.37 (d, J=4.40 Hz, 1H), 6.94 (m, 1H), 2.25-2.08 (m, 8H), 1.47 (s, 6H), 1.36-1.23 (m, 9H); LCMS: purity; 95%; [M+H]=500;

4-(2,2-dimethyl-3-oxo-3,4-dihydro-2H-pyrido[3,2-b][1,4]oxazin-7-yl)-N-(3-methyl-4-((1S,4S)-5-cyclopropyl-2,5-diazabicyclo[2.2.1]heptan-2-yl)phenyl)pyrimidin-2-amine, compound #247, $^1$H NMR (DMSO-d$_6$, 300 MHz): δ 11.48 (b, 1H), 9.44 (d, J=4.96 Hz, 1H), 8.73 (b, 1H), 8.46 (d, J=4.95 Hz, 1H), 8.02 (b, 1H), 7.57 (tr, J=19.53 Hz, 2H), 7.37 (d, J=4.40 Hz 1H), 6.94 (m, 1H), 2.5 (b, 8H), 2.21 (b, 3H), 1.86 (b, 1H), 1.47 (s, 6H), 0.91-0.87 (b, 4H); LCMS: purity; 100%; [M+H]$^+$=498;

4-(2,2-dimethyl-3-oxo-3,4-dihydro-2H-pyrido[3,2-b][1,4]oxazin-7-yl)-N-(3-chloro-4-((1S,4S)-5-methyl-2,5-diazabicyclo[2.2.1]heptan-2-yl)phenyl)pyrimidin-2-amine, compound #248, $^1$H NMR (CD$_3$OD, 300 MHz): δ 8.68 (s, 1H), 8.42 (m, 1H), 8.31 (s, 1H), 7.98 (m, 2H), 7.53 (m, 1H), 7.27 (m, 1H), 7.08 (m, 1H), 4.40 (m, 2H), 3.81 (m, 2H), 3.61 (m, 1H), 2.97 (m, 3H), 2.66 (m, 4H), 2.29 (m, 2H), 1.55 (s, 6H); LCMS (m/z): 492.09 (MH$^+$);

4-(2,2-dimethyl-3-oxo-3,4-dihydro-2H-pyrido[3,2-b][1,4]oxazin-7-yl)-N-(3-chloro-4-((1S,4S)-5-(methylsulfonyl)-2,5-diazabicyclo[2.2.1]heptan-2-yl)phenyl)pyrimidin-2-amine, compound #249, LCMS (m/z): 556.00 (ELSD);

4-(2,2-dimethyl-3-oxo-3,4-dihydro-2H-pyrido[3,2-b][1,4]oxazin-7-yl)-N-(3-methyl-4-((1S,4S)-5-cyclopentyl-2,5-diazabicyclo[2.2.1]heptan-2-yl)phenyl)pyrimidin-2-amine, compound #250, $^1$H NMR (CD$_3$OD, 300 MHz): δ 8.44 (m, 2H), 8.09 (m, 1H), 8.00 (m, 1H), 7.77 (m, 1H), 7.27 (m, 1H), 6.95 (m, 1H), 4.78 (m, 1H), 4.50 (m, 1H), 4.05 (m, 1H), 3.71 (m, 3H), 3.51 (m, 1H), 2.31 (s, 3H), 2.27 (m, 4H), 1.74 (m, 4H), 1.54 (s, 6H) ppm; MS (ES) 526.2 (M+H);

4-(2,2-dimethyl-3-oxo-3,4-dihydro-2H-pyrido[3,2-b][1,4]oxazin-7-yl)-N-(3-methyl-4-((1S,4S)-5-acetyl-2,5-diazabicyclo[2.2.1]heptan-2-yl)phenyl)pyrimidin-2-amine, compound #251, $^1$H NMR (CD$_3$OD, 300 MHz): δ 8.67 (m, 1H), 8.42 (m, 1H), 8.00 (m, 2H), 7.71 (m, 1H), 7.24 (m, 1H), 6.88 (m, 1H), 3.63 (m, 3H), 3.38 (m, 3H), 2.15 (s, 3H), 2.01 (m, 2H), 1.54 (s, 6H) ppm; MS (ES) 500.2 (M+H);

4-(2,2-dimethyl-3-oxo-3,4-dihydro-2H-pyrido[3,2-b][1,4]oxazin-7-yl)-N-(3-methyl-4-(1,4-diazabicyclo[3.2.1]octan-4-yl)phenyl)pyrimidin-2-amine, compound #252, $^1$H NMR (CD$_3$OD, 300 MHz): δ 8.71 (m, 1H), 8.41 (m, 1H), 7.59 (m, 2H), 7.25 (m, 2H), 7.12 (m, 1H), 3.91 (m, 1H), 3.57 (m, 5H), 3.27 (m, 2H), 3.07 (m, 1H), 2.36 (s, 3H), 2.13 (m, 2H), 1.54 (s, 6H) ppm; MS (ES) 472.1 (M+H);

4-(5-(1-methylethoxy)carbonylpropyl-6-aminopyridin-3-yl)-N-(3-methyl-4-((1S,4S)-5-methyl-2,5-diazabicyclo[2.2.1]heptan-2-yl)phenyl)pyrimidin-2-amine, compound #253, $^1$H NMR (DMSO-d$_6$, 300 MHz): δ 9.16 (s, 1H), 8.62 (b, 1H), 8.30 (d, J=5.23 Hz, 1H), 7.94 (b, 1H), 7.53 (b, 1H), 7.43 (d, J=8.53 Hz, 1H), 7.16 (d, J=5.22 Hz, 1H), 6.78 (d, J=8.52 Hz, 1H), 6.37 (b, 2H), 4.88-4.84 (m, 1H), 2.82 (b, 1H), 2.49-2.48 (m, 5H), 2.39-2.30 (m, 3H), 2.20 (s, 3H), 1.85-1.76 (m, 5H), 1.16 (d, J=6.5 Hz, 9H); LCMS: purity; 96.5%; [M+H]$^+$=516;

4-(6-(morpholin-4-yl)pyridin-3-yl)-N-(3-methyl-4-((1S,4S)-5-cyclopropyl-2,5-diazabicyclo[2.2.1]heptan-2-yl)phenyl)pyrimidin-2-amine; compound #254, $^1$H NMR (DMSO-d$_6$, 300 MHz): δ 9.18 (s, 1H), 8.90 (b, 1H), 8.35 (d, J=5.22 Hz, 1H), 8.26 (d, J=9.08 Hz, 1H), 7.48 (b, 2H), 7.21 (d, J=5.23 Hz, 1H), 6.96 (d, J=9.36 Hz, 1H), 6.76 (d, J=8.80 Hz, 1H), 3.93 (b, 1H), 3.70 (d, J=4.4 Hz, 4H), 3.59 (d, J=4.67 Hz, 4H), 2.87 (b, 2H), 2.49 (b, 3H), 2.20 (s, 3H), 1.95 (b, 1H), 1.74 (d, J=4.68 Hz, 2H), 0.37 (d, J=23.39 Hz, 4H); LCMS: purity; 97%; [M+H]$^+$=484;

4-(6-(morpholin-4-yl)pyridin-3-yl)-N-(3-chloro-4-((1S,4S)-5-methyl-2,5-diazabicyclo[2.2.1]heptan-2-yl)phenyl)pyrimidin-2-amine, compound #255, $^1$H NMR (CD$_3$OD, 300 MHz): δ 8.94 (s, 1H), 8.34 (m, 1H), 8.32 (s, 1H), 8.22 (m, 1H), 7.82 (m, 1H), 7.53 (M, 1H), 7.19 (m, 1H), 7.08 (m, 1H), 6.82 (m, 1H), 4.36 (m, 2H), 3.79 (m, 6H), 3.61 (m, 6H), 2.97 (s, 3H), 2.29 (m, 2H); LCMS (m/z): 478.05 (MH$^+$);

4-(2-(trifluoromethyl)pyridin-4-yl)-N-(3-methyl-4-((1S,4S)-5-methyl-2,5-diazabicyclo[2.2.1]heptan-2-yl)phenyl)pyrimidin-2-amine, compound #256, LCMS (m/z): 441.05 (MH$^+$);

4-(6-(morpholin-4-yl)pyridin-3-yl)-N-(3-chloro-4-((1S,4S)-5-(methylsulfonyl)-2,5-diazabicyclo[2.2.1]heptan-2-yl)phenyl)pyrimidin-2-amine, compound #257, LCMS (m/z): 541.00 (ELSD);

4-(6-(tetrahydropyran-4-yloxy)pyridin-3-yl)-N-(3-chloro-4-((1S,4S)-5-(methylsulfonyl)-2,5-diazabicyclo[2.2.1]heptan-2-yl)phenyl)pyrimidin-2-amine, compound #258, LCMS (m/z): 557.02 (MH$^+$);

4-(6-(morpholin-4-yl)pyridin-3-yl)-N-(3-chloro-4-((1S,4S)-5-acetyl-2,5-diazabicyclo[2.2.1]heptan-2-yl)phenyl)pyrimidin-2-amine, compound #259, LCMS (m/z): 506.01 (MH$^+$);

4-(6-(tetrahydropyran-4-yloxy)pyridin-3-yl)-N-(3-chloro-4-((1S,4S)-5-acetyl-2,5-diazabicyclo[2.2.1]heptan-2-yl)phenyl)pyrimidin-2-amine, compound #260, LCMS (m/z): 521.08 (MH$^+$);

4-(6-(tetrahydropyran-4-yloxy)pyridin-3-yl)-N-(3-methyl-4-((1S,4S)-5-methyl-2,5-diazabicyclo[2.2.1]heptan-2-yl)phenyl)pyrimidin-2-amine, compound #261, $^1$H NMR (CD$_3$OD, 300 MHz): δ 8.89 (m, 1H), 8.36 (m, 2H), 7.55 (m, 1H), 7.45 (m, 1H), 7.18 (m, 1H), 6.99 (m, 1H), 6.88 (m, 1H), 5.28 (m, 1H), 4.25 (m, 2H), 3.94 (m, 2H), 3.76 (m, 1H), 3.55 (m, 5H), 2.97 (s, 3H), 2.30 (s, 3H), 2.06 (m, 3H), 1.76 (m, 3H) ppm; MS (ES) 473.2 (M+H);

4-(6-(tetrahydropyran-4-yloxy)pyridin-3-yl)-N-(3-methyl-4-((1S,4S)-5-cyclopentyl-2,5-diazabicyclo[2.2.1]heptan-2-yl)phenyl)pyrimidin-2-amine, compound #262, $^1$H NMR (CD$_3$OD, 300 MHz): δ 8.88 (m, 1H), 8.42 (m, 1H), 8.34 (m, 1H), 8.05 (m, 1H), 7.79 (m, 1H), 7.23 (m, 1H), 6.94 (m, 1H), 6.86 (m, 1H), 5.29 (m, 1H), 4.00 (m, 4H), 3.62 (m, 7H), 2.32 (m, 7H), 1.75 (m, 10H) ppm; MS (ES) 527.2 (M+H);

4-(6-(morpholin-4-yl)pyridin-3-yl)-N-(3-chloro-4-((1S,4S)-5-(1-methylethyl)-2,5-diazabicyclo[2.2.1]heptan-2-yl)phenyl)pyrimidin-2-amine, compound #263, $^1$H NMR (DMSO-d$_6$, 300 MHz): δ 9.18 (s, 1H), 8.90 (b, 1H), 8.35 (d, J=5.22 Hz, 1H), 8.26 (d, J=9.08 Hz, 1H), 7.48 (b, 2H), 7.21 (d, J=5.23 Hz, 1H), 6.96 (d, J=9.36 Hz, 1H), 6.76 (d, J=8.80 Hz, 1H), 3.93 (b, 1H), 3.70 (d, J=4.4 Hz, 4H), 3.59 (d, J=4.67 Hz, 4H), 3.23-2.96 (m, 3H), 2.49 (b, 3H), 2.20 (s, 3H), 1.72 (b, 2H), 0.97 (d, J=4.13 Hz, 6H); LCMS: purity; 99.7%; [M+H]$^+$=486; 4-(6-((1S,4S)-2-oxa-5-azabicyclo[2.2.1]heptan-5-yl)pyridin-3-yl)-N-(3-methyl-4-((1S,4S)-5-(methylsulfonyl)-2,5-diazabicyclo[2.2.1]heptan-2-yl)phenyl)pyrimidin-2-amine, compound #264, $^1$H NMR (DMSO-d$_6$): δ 9.30 (s, 1H), 8.84 (s, 1H), 8.35 (d, 1H, J=5.0 Hz), 8.25 (d, 1H, J=7.3 Hz), 7.53 (d, 1H, J=8.8 Hz), 7.47 (s, 1H), 7.22 (d, 1H, J=5.0 Hz), 6.88 (d, 1H, J=8.5 Hz), 6.72 (d, 1H, J=7.3 Hz), 4.98 (s, 1H), 4.69 (s, 1H), 4.33 (s, 1H), 4.15 (s, 1H), 3.79 (d, 1H, J=6.7 Hz), 3.66 (d, 1H, J=6.7 hz), 3.53-3.39 (m, 6H), 2.95 (s, 3H), 2.20 (s, 3H), 1.95-1.80 (m, 4H). LCMS: Purity: 99%; MS (m/e): 534 (MH$^+$);

4-(6-((1R,4R)-2-oxa-5-azabicyclo[2.2.1]heptan-5-yl)pyridin-3-yl)-N-(3-methyl-4-((1S,4S)-5-methyl-2,5-diazabicyclo[2.2.1]heptan-2-yl)phenyl)pyrimidin-2-amine, compound #265, $^1$H NMR (DMSO-d$_6$): δ 9.27 (s, 1H), 8.87 (d, 1H, J=2.3 Hz), 8.33 (d, 1H, J=5.3 Hz), 8.21 (dd, 1H, J=2.0 and 8.8 Hz), 7.56 (d, 1H, 9.1 Hz), 7.48 (d, 1H, J=5.3 Hz), 7.20 (d, 1H, J=5.3 Hz), 6.86 (d, 1H, J=8.8 Hz), 6.64 (d, 1H, J=8.8 Hz), 4.96 (s, 1H), 4.68 (s, 1H), 3.79 (d, 1H, J=6.7 Hz), 3.65 (d, 1H, J=7.6 Hz), 3.5 (d, 1H, J=10.2 Hz), 3.16 (m, 2H), 2.75 (d, 1H, J=9.3 Hz), 2.67 (d, 1H, J=9.3 Hz), 2.29 (s, 3H), 2.20 (s, 3H), 1.90 (m, 4H); LCMS: purity: 99%; MS (m/e): 470 (MH$^+$);

4-(6-((1S,4S)-2-oxa-5-azabicyclo[2.2.1]heptan-5-yl)pyridin-3-yl)-N-(5-methyl-6-((1S,4S)-5-methyl-2,5-diazabicyclo[2.2.1]heptan-2-yl)pyridin-3-yl)pyrimidin-2-amine, compound #266, $^1$H NMR (DMSO-d$_6$): δ 9.22 (s, 1H), 8.85 (s, 1H), 8.34-8.33 (m, 2H), 8.18 (d, 1H, J=6.7 Hz), 7.70 (s, 1H), 7.20 (d, 1H, J=5.3 Hz), 6.65 (d, 1H, J=8.8 Hz), 4.96 (s, 1H), 4.67 (s, 1H), 4.34 (s, 1H), 3.78 (d, 1H, J=7.0 Hz), 3.64 (d, 1H, J=7.0 Hz), 3.49 (d, 1H, J=9.5 Hz), 3.42-3.36 (m, 4H), 2.74 (s, 2H), 2.24 (s, 3H), 2.19 (s, 3H), 1.92 (d, 1H, J=9.1 Hz), 1.85 (d, 1H, J=9.1 Hz), 1.74 (d, 1H, J=9.1 Hz), 1.62 (d, 1H, J=9.1 Hz). LCMS: Purity: 99%; MS (m/e): 471 (MH+);

4-(6,7,8,9-tetrahydro-5H-pyrido[2,3-b]indol-3-yl)-N-(3-methyl-4-((1S,4S)-5-methyl-2,5-diazabicyclo[2.2.1]heptan-2-yl)phenyl)pyrimidin-2-amine, compound #267, $^1$H NMR (DMSO-d$_6$, 300 MHz): δ 9.24 (b, 1H), 8.47 (d, J=5.50 Hz, 1H), 8.20 (b, 1H), 7.88 (d, J=7.16 Hz, 1H), 7.55 (d, J=5.50 Hz, 1H), 7.38 (b, 1H), 7.24-7.17 (m, 2H), 6.74 (d, J=8.52 Hz, 1H), 3.91 (b, 1H), 3.20 (b, 4H), 3.05 (b, 3H), 8.30 (m, 3H), 2.32 (s, 3H), 2.18 (s, 3H), 1.81-1.71 (m, 5H); LCMS: purity: 98.1%; [M+H]$^+$=466;

4-(6,7,8,9-tetrahydro-5H-pyrido[2,3-b]indol-3-yl)-N-(3-methyl-4-((1S,4S)-5-(methylsulfonyl)-2,5-diazabicyclo[2.2.1]heptan-2-yl)phenyl)pyrimidin-2-amine, compound #268, $^1$H NMR (DMSO-d$_6$, 300 MHz): δ 9.24 (b, 1H), 8.47 (d, J=5.50 Hz, 1H), 8.20 (b, 1H), 7.88 (d, J=7.16 Hz, 1H), 7.55 (d, J=5.50 Hz, 1H), 7.38 (b, 1H), 7.29-7.17 (m, 2H), 6.86 (b, 1H), 4.34 (b, 1H), 4.17 (b, 2H), 3.37-3.25 (m, 5H), 3.04 (b, 1H), 2.96 (s, 3H), 2.67 (b, 2H), 2.20 (b, 3H), 1.89-1.81 (m, 5H); LCMS: purity; 98.7%; [M+H]$^+$=530;

4-(4-(trifluoromethyl)phenyl)-N-(3-methyl-4-((1S,4S)-5-methyl-2,5-diazabicyclo[2.2.1]heptan-2-yl)phenyl)pyrimidin-2-amine, compound #269, LCMS (m/z): 440.09 (MH$^+$);

4-(7,8,9,9a-tetrahydro-5H-pyrido[2,3-e]pyrrolo[1,2-a][1,4]diazepin-10(11H)-on-3-yl)-N-(3-methyl-4-((1S,4S)-5-methyl-2,5-diazabicyclo[2.2.1]heptan-2-yl)phenyl)pyrimidin-2-amine, compound #270, $^1$H NMR (CD$_3$OD, 300 MHz): δ 9.28 (m, 1H), 8.63 (m, 1H), 8.43 (m, 1H), 7.42 (m, 3H), 7.01 (m, 1H), 4.78 (m, 2H), 4.55 (m, 1H), 4.41 (m, 2H), 4.30 (s, 1H), 3.99 (m, 3H), 3.50-3.36 (m, 3H), 3.16 (m, 1H), 2.99 (s, 3H), 2.82 (m, 1H), 2.32 (m, 5H), 2.10 (m, 3H); MS (ES) 497.10 (M+H);

4-(2,2-dimethyl-3-oxo-3,4-dihydro-2H-benzo[b][1,4]oxazin-7-yl)-N-(3-cyano-4-((1S,4S)-5-methyl-2,5-diazabicyclo[2.2.1]heptan-2-yl)phenyl)pyrimidin-2-amine, compound #271, $^1$H NMR (CD$_3$OD, 300 MHz): δ 8.39 (m, 2H), 8.16 (m, 1H), 7.72 (m, 3H), 7.20 (m, 1H), 6.94 (m, 2H), 4.76 (s, 1H), 4.32 (s, 1H), 4.04 (m, 1H), 3.69 (m, 2H), 3.31 (m, 2H), 2.93 (s, 3H), 2.35 (m, 2H), 1.51 (s, 6H); MS (ES) 482.08 (M+H);

4-(2-oxo-2,3,4,5-tetrahydro-1H-benzo[b]azepin-7-yl)-N-(3-cyano-4-((1S,4S)-5-methyl-2,5-diazabicyclo[2.2.1]heptan-2-yl)phenyl)pyrimidin-2-amine, compound #272, $^1$H NMR (CD$_3$OD, 300 MHz): δ 8.41 (m, 3H), 8.08 (m, 1H), 7.99 (m, 1H), 7.66 (m, 1H), 7.28 (m, 1H), 7.11 (m, 1H), 6.93 (m, 1H), 4.77 (s, 1H), 4.34 (s, 1H), 4.07 (m, 1H), 3.69 (m, 2H), 3.35 (m, 2H), 2.95 (s, 3H), 2.89 (m, 2H), 2.32 (m, 6H); MS (ES) 466.08 (M+H);

4-(3-oxo-3,4-dihydro-2H-benzo[b][1,4]thiazin-7-yl)-N-(3-cyano-4-((1S,4S)-5-methyl-2,5-diazabicyclo[2.2.1]heptan-2-yl)phenyl)pyrimidin-2-amine, compound #273, $^1$H NMR (CD$_3$OD, 300 MHz): δ 8.39 (m, 2H), 8.12 (s, 1H), 7.93 (m, 1H), 7.71 (m, 1H), 7.23 (m, 1H), 7.05 (m, 1H), 6.92 (m, 1H), 4.77 (s, 1H), 4.30 (s, 1H), 4.07 (m, 1H), 3.69 (m, 2H), 3.48 (s, 2H), 3.30 (m, 3H), 2.93 (s, 3H), 2.33 (m, 2H); MS (ES) 470.06 (M+H);

4-(3-oxo-3,4-dihydro-2H-benzo[b][1,4]thiazin-7-yl)-N-(3-methyl-4-((1S,4S)-5-methyl-2,5-diazabicyclo[2.2.1]heptan-2-yl)phenyl)pyrimidin-2-amine, compound #274, $^1$H NMR (CD$_3$OD, 300 MHz): δ 8.36 (m, 2H), 8.17 (s, 1H), 7.91 (m, 1H), 7.48 (m, 2H), 7.19 (m, 1H), 7.04 (m, 1H), 6.96 (m, 1H), 4.29 (s, 1H), 4.24 (s, 1H), 3.81 (m, 1H), 3.52 (m, 4H), 2.97 (s, 3H), 2.33 (s, 3H), 2.31 (s, 2H); MS (ES) 459.07 (M+H);

4-(6-(tetrahydropyran-4-yloxy)pyridin-3-yl)-N-(3-methyl-4-(1,4-diazabicyclo[3.2.1]octan-4-yl)phenyl)pyrimidin-2-amine, compound #275, $^1$H NMR (CD$_3$OD, 300 MHz): δ 8.92 (m, 1H), 8.38 (m, 2H), 7.62 (m, 1H), 7.53 (m, 1H), 7.21 (m, 1H), 7.11 (m, 1H), 6.88 (m, 1H), 5.30 (m, 1H), 3.95 (m, 4H), 3.58 (m, 8H), 3.11 (m, 1H), 2.35 (s, 3H), 2.12 (m, 4H), 1.78 (m, 3H) ppm; MS (ES) 473.2 (M+H);

4-(6-(morpholin-4-yl)pyridin-3-yl)-N-(3-methyl-4-((R)-1,4-diazabicyclo[3.2.1]octan-4-yl)phenyl)pyrimidin-2-amine, compound #276, $^1$H NMR (CD$_3$OD, 300 MHz): δ 8.92 (m, 1H), 8.32 (m, 1H), 8.24 (m, 1H), 7.59 (m, 1H), 7.55 (m, 1H), 7.13 (m, 2H), 6.86 (m, 1H), 3.92 (m, 1H), 3.79 (m, 4H), 3.61 (m, 9H), 3.31 (m, 1H), 3.10 (m, 2H), 2.35 (s, 3H), 2.13 (m, 2H) ppm; MS (ES) 458.1 (M+H);

4-(6-(morpholin-4-yl)pyridin-3-yl)-N-(3-methyl-4-((S)-1,4-diazabicyclo[3.2.1]octan-4-yl)phenyl)pyrimidin-2-amine, compound #277, $^1$H NMR (CD$_3$OD, 300 MHz): δ 8.92 (m, 1H), 8.31 (m, 1H), 8.25 (m, 1H), 7.58 (m, 1H), 7.14 (m, 2H), 6.88 (m, 1H), 3.93 (m, 1H), 3.77 (m, 4H), 3.59 (m, 9H), 3.32 (m, 1H), 3.11 (m, 2H), 2.36 (s, 3H), 2.14 (m, 2H) ppm; MS (ES) 458.1 (M+H);

4-(2-oxo-2,3,4,5-tetrahydro-1H-benzo[b]azepin-7-yl)-N-(3-methyl-4-((6R,9S)-6,9-methanooctahydro-1H-pyrido[1,2-a]pyrazin-2-yl)phenyl)pyrimidin-2-amine, compound #278, $^1$H NMR (CD$_3$OD, 300 MHz): δ 8.37 (m, 2H), 8.05 (m, 2H), 7.58 (m, 1H), 7.25 (m, 1H), 7.10 (m, 2H), 4.01 (m, 3H), 3.55 (m, 5H), 3.14 (m, 2H), 2.88 (m, 2H), 2.57 (m, 1H), 2.34 (m, 7H), 1.80 (m, 6H); MS (ES) 495.14 (M+H);

4-(3-oxo-3,4-dihydro-2H-benzo[b][1,4]thiazin-7-yl)-N-(3-methyl-4-((6R,9S)-6,9-methanooctahydro-1H-pyrido[1,2-a]pyrazin-2-yl)phenyl)pyrimidin-2-amine, compound #279, $^1$H NMR (CD$_3$OD, 300 MHz): δ 8.34 (m, 1H), 8.21 (s, 1H), 7.98 (m, 1H), 7.53 (m, 2H), 7.32 (m, 1H), 7.08 (m, 2H), 4.03 (s, 1H), 3.96 (m, 2H), 3.63 (m, 5H), 3.12 (m, 3H), 2.59 (s, 2H), 2.37 (s, 3H), 1.92-1.63 (m, 6H); MS (ES) 499.04 (M+H);

4-(6-((1S,4S)-2-oxa-5-azabicyclo[2.2.1]heptan-5-yl)pyridin-3-yl)-N-(3-methyl-4-(1,4-diazabicyclo[3.2.2]nonan-4-yl)phenyl)pyrimidin-2-amine, compound #280, $^1$H NMR (CD$_3$OD, 300 MHz): δ 8.88 (m, 1H), 8.32 (m, 3H), 7.52 (m, 2H), 7.22 (m, 2H), 6.63 (m, 1H), 4.74 (s, 1H), 3.92-3.81 (m, 2H), 3.58 (m, 4H), 3.43 (m, 4H), 2.65 (m, 2H), 2.43 (m, 2H), 2.36 (s, 3H), 2.13-2.03 (m, 4H); MS (ES) 484.16 (M+H);

4-(6-(morpholin-4-yl)pyridin-3-yl)-N-(3-cyano-4-(3,9-diazabicyclo[3.3.2]decan-10-on-3-yl)phenyl)pyrimidin-2-amine, compound #281, $^1$H NMR (CD$_3$OD, 300 MHz): δ 8.88 (s, 1H), 8.37 (d, 1H), 8.25 (m, 1H), 8.17 (d, 1H), 7.82 (m, 1H), 7.24 (m, 2H), 6.87 (d, 1H), 3.80 (m, 4H), 3.62 (m, 4H), 3.41 (m, 2H), 3.14 (m, 2H), 2.85 (m, 1H), 2.25 (m, 4H), 2.01 (m, 2H), 1.55 (m, 1H); LCMS (m/z): 510.00 (ELSD);

4-(2,2-dimethyl-3-oxo-3,4-dihydro-2H-pyrido[3,2-b][1,4]oxazin-7-yl)-N-(3-cyano-4-(3,9-diazabicyclo[3.3.2]decan-10-on-3-yl)phenyl)pyrimidin-2-amine, compound #282, $^1$H NMR (DMSO, 300 MHz): δ 11.5 (s, 1H), 9.87 (s, 1H), 8.73 (s, 1H), 8.54 (d, 1H), 8.24 (s, 1H), 8.03 (d, 1H), 7.84 (m, 2H), 7.46 (d, 1H), 7.31 (d, 1H), 3.41 (m, 1H), 3.11 (m, 1H), 3.02 (m, 2H), 2.68 (m, 1H), 2.11 (m, 4H), 1.83 (m, 1H), 1.46 (s, 6H); LCMS (m/z): 525.01 (MH$^+$);

4-(6-(tetrahydropyran-4-yloxy)pyridin-3-yl)-N-(3-methyl-4-(3-(dimethylamino)-8-azabicyclo[3.2.1]octan-8-yl)phenyl)pyrimidin-2-amine, compound #283, $^1$H NMR (CD$_3$OD, 300 MHz): δ 8.90 (m, 1H), 8.36 (m, 2H), 7.46 (m, 2H), 7.17 (m, 1H), 6.86 (m, 2H), 5.28 (m, 1H), 3.94 (m, 4H), 3.60 (m, 3H), 2.86 (s, 6H), 2.37 (s, 3H), 2.02 (m, 9H), 1.79 (m, 3H) ppm; MS (ES) 515.2 (M+H);

4-(6-(morpholin-4-yl)pyridin-3-yl)-N-(3-methyl-4-(3-(morpholin-4-yl)-8-azabicyclo[3.2.1]octan-8-yl)phenyl)pyrimidin-2-amine, compound #284, $^1$H NMR (CD$_3$OD, 300 MHz): δ 8.92 (m, 1H), 8.26 (m, 2H), 7.46 (m, 2H), 7.12 (m, 1H), 6.87 (m, 2H), 3.82 (m, 11H), 3.55 (m, 6H), 2.37 (s, 3H), 2.06 (m, 8H), 1.78 (m, 2H) ppm; MS (ES) 542.3 (M+H);

4-(6-(tetrahydropyran-4-yloxy)pyridin-3-yl)-N-(3-methyl-4-(3-(morpholin-4-yl)-8-azabicyclo[3.2.1]octan-8-yl)phenyl)pyrimidin-2-amine, compound #285, $^1$H NMR (CD$_3$OD, 300 MHz): δ 8.93 (m, 1H), 8.25 (m, 2H), 7.47 (m, 2H), 7.13 (m, 1H), 6.88 (m, 2H), 5.28 (m, 1H), 3.84 (m, 11H), 3.54 (m, 6H), 2.37 (s, 3H), 2.08 (m, 8H), 1.79 (m, 2H) ppm; MS (ES) 557.3 (M+H); and 4-(6-(morpholin-4-yl)pyridin-3-yl)-N-(3-methyl-4-(3-(dimethylamino)-8-azabicyclo[3.2.1]octan-8-yl)phenyl)pyrimidin-2-amine, compound #286, $^1$H NMR (CD$_3$OD, 300 MHz): δ 8.89 (m, 1H), 8.27 (m, 1H), 8.21 (m, 1H), 7.45 (m, 2H), 7.08 (m, 1H), 6.84 (m, 2H), 3.87 (m, 2H), 3.77 (m, 2H), 3.54 (m, 3H), 2.84 (s, 6H), 2.37 (s, 3H), 2.02 (m, 9H), 1.77 (m, 3H) ppm; MS (ES) 500.3 (M+H).

Testing of the Compounds of the Invention

Exemplary compounds of the invention were tested in the following biological assays for their ability to inhibit JAK activity.

Biological Example 1

Assay for Ramos B-Cell Line Stimulated with IL-4

B-cells stimulated with cytokine Interleukin-4 (IL-4) activate the JAK/Stat pathway through phosphorylation of the JAK family kinases, JAK-1 and JAK-3, which in turn phosphorylate and activate the transcription factor Stat-6. One of the genes upregulated by activated Stat-6 is the low affinity IgE receptor, CD23. To study the effect of inhibitors on the JAK family kinases, human Ramos B cells are stimulated with human IL-4.

The Ramos B-cell line was acquired from ATCC (ATCC Catalog No. CRL-1596). The cells were cultured in RPMI 1640 (Cellgro, MediaTech, Inc., Herndon, Va., Cat No. 10-040-CM) with 10% fetal bovine serum (FBS), heat inactivated (JRH Biosciences, Inc, Lenexa, Kans., Cat No. 12106-500M) according to ATCC propagation protocol. Cells were maintained at a density of 3.5×10$^5$. The day before the experiment, Ramos B-cells were diluted to 3.5× 10$^5$ cells/mL to ensure that they were in a logarithmic growth phase.

Cells were spun down and suspended in RPMI with 5% serum. 5×10$^4$ cells were used per point in a 96-well tissue culture plate. Cells were pre-incubated with compound or DMSO (Sigma-Aldrich, St. Louis, Mo., Cat No. D2650) vehicle control for 1 hour in a 37° C. incubator.

Cells were then stimulated with IL-4 (Peprotech Inc., Rocky Hill, N.J., Cat No. 200-04) for a final concentration of 50 units/mL for 20-24 hours. Cells were then spun down and stained with anti-CD23-PE(BD Pharmingen, San Diego, Calif., Cat No. 555711) and analyzed by FACS (Fluorescence Activated Cell Sorting). Detection was performed using a BD LSR I System Flow Cytometer, purchased from Becton Dickinson Biosciences of San Jose, Calif.

Biological Example 2

Primary Human T-Cell Proliferation Assay Stimulated with IL-2

Primary human T-cells derived from peripheral blood and pre-activated through stimulation of the T-cell receptor and CD28, proliferate in vitro in response to the cytokine Interleukin-2 (IL-2). This proliferative response is dependent on the activation of JAK-1 and JAK-3 tyrosine kinases, which phosphorylate and activate the transcription factor Stat-5.

Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 min at 4° C. at 1750 rpm. The lymphocytes at the serum:ficoll interface were recovered and washed twice with 5 volumes of PBS. The cells were resuspended in Yssel's medium (Gemini Bio-products, Woodland, Calif., Catalog #400-103) containing 40 U/mL recombinant IL2 (R and D Systems, Minneapolis, Minn., Catalog #202-IL (20 μg)) and seeded into a flask pre-coated with 1 µg/mL anti-CD3 (BD Pharmingen, San Diego, Calif., Catalog #555336) and 5 µg/mL anti-CD28 (Immunotech, Beckman Coulter of Brea Calif., Catalog #IM1376). The primary T-cells were stimulated for 3-4 days, then transferred to a fresh flask and maintained in RPMI with % FBS and 40 U/mL IL-2.

Primary T-cells were washed twice with PBS to remove the IL-2 and resuspended in Yssel's medium at $2 \times 10^6$ cells/mL. Cell suspension, 50 µL, containing 80 U/mL IL-2 was added to each well of a flat bottom 96 well black plate. For the unstimulated control, IL-2 was omitted from the last column on the plate. Compounds were serially diluted in dimethyl sulfoxide (DMSO, 99.7% pure, cell culture tested, Sigma-Aldrich, St. Louis, Mo., Catalog No. D2650) from 5 mM in 3-fold dilutions, and then diluted 1:250 in Yssel's medium. Compound, 50 µL per well, was added (done in duplicate, two rows per dilution factor) and the cells were allowed to proliferate for 72 hours at 37° C.

Proliferation was measured using CellTiter-Glo® Luminescent Cell Viability Assay (Promega), which determines the number of viable cells in culture based on quantitation of the ATP present, as an indicator of metabolically active cells. The substrate was thawed and allowed to come to ambient temperature. After mixing the Cell Titer-Glo reagent and diluent together, 100 µL was added to each well. The plates were mixed on an orbital shaker for two minutes to induce lysis and incubated at ambient temperature for an additional ten minutes to allow the signal to equilibrate. Detection was performed using a Wallac Victor2 1420 multilabel counter purchased from Perkin Elmer, Shelton, Conn.

Biological Example 3

Stat5 Assay Using Primary Human T-Cells or Mouse T-Cell Leukaemia CTLL-2 Cells Stimulated with IL-2

Stimulation of pre-activated primary human T-cells or mouse CTLL-2 cells with Interleukin-2 (IL-2) signals to JAK-1 and JAK-3 tyrosine kinases to phosphorylate their immediate downstream target, transcription factor Stat5. The effects can then be quantified using FACS.

Pre-activated human primary T cells are prepared as described in Biological Example 2. CTLL-2 cells are grown in RPMI containing 10% FBS and 10% T-STIM with Con A (Becton Dickinson).

CTLL-2 cells or human primary T-cells, which have been washed twice with PBS to remove any residual IL-2, are resuspended in RPMI with 10% FBS medium at $2 \times 10^6$ cells/mL 40 µL of T cells and 50 µL of 2x test compound are added to each well of a 96-well round-bottom plate and mixed. After 1 hour incubation with the text compound at 37° C., the cells are stimulated by addition of 10 µL per well of 10xIL-2 (400 U/mL) so that the final concentration is 40 U/mL. Cells are incubated further at 37° C. for 15 min. Stimulation is stopped and cells are fixed by addition of 100 µL per well of 3.2% para-formaldehyde and incubation for 10 min at ambient temperature. Following a wash, cells are permeabilized by addition of 150 µL per well of ice-cold methanol and incubation at 4° C. for 30 min. Pelleted cells are washed once with 150 µL per well FACS buffer (PBS+2% FCS) and stained with 50 µL per well of anti-phospho-Stat5 AlexaFluor488 1:100 in FACS buffer. Following overnight incubation at ambient temperature, the samples are analyzed by FACS after initial wash with FACS buffer.

Biological Example 4

Stat5 Assay of Unstimulated Human Erythroleukaemia SET2 Cells and Mouse Pre-B Ba/F3 Cells Expressing Human V617F JAK2 Kinase Human erythroleukaemia SET2 cells and mouse pre-B Ba/F3 cells both express constitutively active form of JAK2 containing mutation V617F in a pseudokinase domain of the enzyme, leading to constitutive phosphorylation of Stat5 transcription factor in the absence of any stimulation.

40 µL of the corresponding cell suspension and 50 µL of 2x text compound are mixed together in each well of a 96-well round-bottom plate and incubated for 1 hr at 37° C. The reaction is stopped by addition of 100 µL per well of 3.2% para-formaldehyde for 10 min followed by permeabilization step with 150 mL of ice-cold methanol at 4° C. for 30 min. After a wash, the cells are stained with 50 µL per well of anti-phospho-Stat5 AlexaFluor488 1:100 in FACS buffer. Following overnight incubation at ambient temperature, the samples are analyzed by FACS.

Biological Example 5

A549 Epithelial Line Stimulated with IFNγ

A549 lung epithelial cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The A549 lung epithelial carcinoma cell line originated from the American Type Culture Collection. Routine culturing was with F12K media (Mediatech Inc., Lenexa, Kans., Cat. No. 10-025-CV) with 10% fetal bovine serum, 100 I.U. penicillin and 100 ng/mL streptomycin (complete F12k media). Cells were incubated in a humidified atmosphere of 5% $CO_2$ at 37° C. Prior to use in the assay, A549 cells were washed with PBS and trypsinized (Mediatech Inc., Cat. No. 25-052-CI) to lift the cells. The trypsin cell suspension was neutralized with complete F12K media and centrifuged to pellet the cells. The cell pellet was resuspended in complete F12K media at a concentration of $2.0 \times 10^5$/mL. Cells were seeded at 20,000 per well, 100 µL total volume, in a flat bottom tissue culture plate and allowed to adhere overnight.

On day two, A549 cells were pre-incubated with test compound or DMSO (control) (Sigma-Aldrich, St. Louis, Mo., Catalog No. D2650) for 1 hour. The cells were then stimulated with IFNγ (75 ng/mL) (Peprotech Inc., Rocky Hill, N.J., Cat. No. 300-02) and allowed to incubate for 24 hours. The final test compound dose range was 30 µM to 14 nM in 200 µL F12K media containing 5% FBS, 0.3% DMSO.

On day three, the cell media was removed and the cells were washed with 200 µL PBS (phosphate buffered saline). Each well was trypsinized to dissociate the cells, then neutralized by addition of 200 µL complete F12K media. Cells were pelleted and stained with an APC conjugated mouse anti-human ICAM-1 (CD54) (BD Pharmingen, San Diego, Calif., Catalog #559771) antibody for 20 minutes at 4° C. Cells were washed with ice cold FACS buffer (PBS+2% FBS) and surface ICAM-1 expression was analyzed by flow cytometry. Detection was performed using a BD LSR I System Flow Cytometer, purchased from BD Biosciences of San Jose, Calif. Events were gated for live scatter and the geometric mean was calculated (Becton-Dickinson CellQuest software version 3.3, Franklin Lakes, N.J.). Geometric means were plotted against the compound concentration to generate a dose response curve.

Biological Example 6

U937 IFNγ ICAM1 FACS Assay

Human U937 monocytic cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The U937 human monocytic cell line was obtained from ATCC of Rockville Md., catalog number CRL-1593.2, and cultured in RPM1-1640 medium containing 10% (v/v) FCS. U937 cells were grown in 10% RPMI. The cells were then plated at a concentration of 100,000 cells per 160 μL in 96 well flat bottom plates. The test compounds were then diluted as follows: 10 mM test compound was diluted 1:5 in DMSO (3 μL 10 mM test compound in 12 μL DMSO), followed by a 1:3 serial dilution of test compound in DMSO (6 μL test compound serially diluted into 12 μL DMSO to give 3-fold dilutions). Then 4 μL of test compound was transferred to 76 μL of 10% RPMI resulting in a 10× solution (100 μM test compound, 5% DMSO). For control wells, 4 μL of DMSO was diluted into 76 μL 10% RPMI.

The assay was performed in duplicate with 8 points (8 3-fold dilution concentrations from 10 μL) and with 4 wells of DMSO only (control wells) under stimulated conditions and 4 wells of DMSO only under unstimulated conditions. The diluted compound plate was mixed 2× using a multimek (Beckman Coulter of Brea, Calif.) and then 20 μL of the diluted compounds was transferred to the 96 well plate containing 160 μL of cells, which were then mixed again twice at low speeds. The cells and compounds were then pre-incubated for 30 minutes at 37° C. with 5% $CO_2$.

The 10× stimulation mix was made by preparing a 100 ng/mL solution of human IFNγ in 10% RPMI. The cells and compound were then stimulated with 20 μL of IFNγ stimulation mix to give a final concentration of 10 ng/mL IFNγ, 10 μM test compound, and 0.5% DMSO. The cells were kept under conditions for stimulation for 18-24 hours at 37° C. with 5% $CO_2$.

The cells were transferred to a 96 well round bottom plate for staining and then kept on ice for the duration of the staining procedure. Cells were spun down at 1000 rpm for 5 minutes at 4° C., following which the supernatant was removed. Following removal of the supernatant, 1 μL APC conjugated mouse anti-human ICAM-1 antibody was added per 100 μL FACS buffer. The cells were then incubated on ice in the dark for 30 minutes. Following incubation, 150 μL of FACS buffer was added and the cells were centrifuged at 1000 rpm for 5 minutes at 4° C., following which the supernatant was removed. After removal of the supernatant, 200 μL of FACS buffer was added and the cells were resuspended. After suspension, the cells were centrifuged at 1000 rpm for 5 min at 4° C. Supernatant was then removed prior to resuspension of the cells in 150 μL FACS buffer.

Detection was performed using a BD LSR I System Flow Cytometer, purchased from BD Biosciences of San Jose, Calif. The live cells were gated for live scatter and the geometric mean of ICAM-APC was measured (Becton-Dickinson CellQuest software version 3.3, Franklin Lakes, N.J.). Both % live cells and ICAM-1 expression was analyzed. The assays for the test compounds were carried out in parallel with a control compound of known activity. The $EC_{50}$ for the control compound is typically 40-100 nM.

Biological Example 7

Fluorescence Polarization Kinase Assay

This assay may be utilized to determine the potency of a compound of the invention against certain JAK kinases and the selectivity of a compound of the invention in inhibiting certain JAK kinase activity in vitro.

Reagents and Buffers
Tyrosine Kinase Kit Green (Invitrogen, Cat #P2837)
Acetylated Bovine Gamma Globulin (BGG) (Invitrogen, Cat #P2255)
Active JAK1 (Carna Biosciences)
Active JAK2 (Carna Biosciences)
Active JAK3 (Carna Biosciences)
TK2 Peptide (Biotin-EGPWLEEEEEAYGWMDF-$CONH_2$) (SynPep Custom Synthesis)

Methods

Test compounds were serially diluted in DMSO starting from 500× the desired final concentration and then diluted to 1% DMSO in kinase buffer (20 mM HEPES, pH 7.4, 5 mM $MgCl_2$, 2 mM $MnCl_2$, 1 mM DTT, 0.1 mg/mL acetylated BGG). Test compound in 1% DMSO (0.2% DMSO final) was mixed with ATP and substrate in kinase buffer at ambient temperature.

The kinase reactions were performed in a final volume of 20 μL containing peptide substrate and ATP and started by addition of kinase in kinase buffer. The reactions were allowed to proceed at ambient temperature. Final substrate, ATP and enzyme concentrations and reaction times for the different kinase assays are listed in Table 1.

TABLE 1

FINAL SUBSTRATE, ATP, ENZYME CONCENTRATIONS AND REACTION TIMES

| Enzyme | Enzyme Amount per Reaction | Substrate | Substrate Concentration | ATP Concentration | Assay Time |
|---|---|---|---|---|---|
| JAK1 | 20 ng | TK2 | 10 μM | 5 μM | 20 min |
| JAK2 | 0.3 ng | TK2 | 10 μM | 5 μM | 20 min |
| JAK3 | 2 ng | TK2 | 10 μM | 5 μM | 20 min |

The reactions were stopped by adding 20 μL of PTK quench mix containing EDTA/anti-phosphotyrosine antibody (1× final)/fluorescent phosphopeptide tracer (0.5× final) diluted in FP Dilution Buffer according to manufacturer's instructions (Invitrogen). The plates were incubated for 30 minutes in the dark at ambient temperature and then read on a Polarion fluorescence polarization plate reader (Tecan).

Data were converted to amount of phosphopeptide present using a calibration curve generated by competition with the phosphopeptide competitor provided in the Tyrosine Kinase Assay Kit, Green (Invitrogen). For $IC_{50}$ determination, the compounds were tested at eleven concentrations in duplicate and curve-fitting was performed by non-linear regression analysis using Matlab version 6.5 (MathWorks, Inc., Natick, Mass., USA).

Biological Example 8

Proliferation Assay

Reagents and Buffers
Dimethyl Sulfoxide (DMSO) (Sigma-Aldrich, Cat No. D2650) (Control)
Iscove's DMEM, ATCC Catalog #30-2005
1 M HEPES, Cellgro Catalog #25-060-CI (100 mL)
100 mM Sodium Pyruvate, Cellgro Catalog #25-000-CI (100 mL)
Pennicillin/Streptomycin, 10000 U/mL each, Cellgro Catalog #30-002-CI (100 mL)
RPMI 1640 (Cellgro, Cat No. 10-040-CM)
Fetal Bovine Serum (JRH, Cat No. 12106-500M)
Donor Equine Serum, Hyclone Catalog #SH30074.02 (100 mL)
50 μM hydrocortisone solution, Sigma Catalog #H6909-10 ml (10 mL)
Culture Conditions
Ba/F3 V617F cells are maintained and plated in RPMI with 10% FBS. Plating density for these cells is $1 \times 10^5$ cells/mL.

UKE-1 are maintained and plated in Iscove's DMEM containing 10% FBS, 10% equine serum, 1% penicillin/streptomycin and 1 uM hydrocortisone. Plating density for these cells is $0.4 \times 10^6$ cells/mL.

SET2 cells are maintained and plated in RPMI with 20% FBS. Plating density for these cells is $2 \times 10^5$ cells/mL.

CTLL-2 cells are maintained and plated in RPMI containing 10% FBS and 10% T-STIM with Con A (Becton Dickinson). Plating density for these cells is $0.4 \times 10^5$ cells/mL Methods The cells were resuspended in a corresponding medium at a required cell density (see above). 100μ of cell suspension was added to each well of a flat bottom 96 well white plate. The compound was serially diluted in DMSO from 5 mM in 3-fold dilutions, and then diluted 1:250 in the RPMI 1640 medium containing 5% FBS and pen/strep. 100 μL of resulting 2× compound solution was added per well in duplicate and the cells were allowed to proliferate for 72 hours at 37° C.

Proliferation was measured using Cell Titer-Glo. The substrate was thawed and allowed to come to ambient temperature. After removal of top 100 μL of medium from each well, 100 μL of the premixed Cell Titer-Glo reagent was added to each well. The plates were mixed on an orbital shaker for three minutes to induce lysis and incubated at ambient temperature for an additional five minutes to allow the signal to equilibrate. The Luminescence was read on the Wallac Plate Reader.

The results of the ability of the compounds of the invention to inhibit JAK2 activity, when tested in the above assay utilizing Ba/F3 V617F cells, are shown in the following Tables 2-3 wherein the level of activity (i.e., the $IC_{50}$) for each compound is indicated in Tables 2-3. The compound numbers in Tables 2-3 refers to the compounds disclosed herein as being prepared by the methods disclosed herein:

TABLE 2

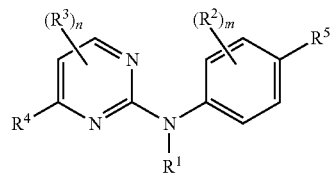

(Ia-1)

$IC_{50}$ activity: A = <1 μM
B = 1 to 10 μM
C = >10 to 20 μM
D = >20 μM

| Cpd # | Compound Name | n | m | R¹ | R² | R³ | R⁴ | R⁵ | IC₅₀ |
|---|---|---|---|---|---|---|---|---|---|
| 1 | 4-(6-(N,N-dimethylamino)-pyridin-3-yl)-N-(3-methyl-4-((1S,4S)-5-methyl-2,5-diazabicyclo-[2.2.1]heptan-2-yl)phenyl)-pyrimidin-2-amine | 0 | 1 | H | —CH₃ | — | H₃C—N(CH₃)—pyridinyl | N-methyl-diazabicycloheptyl | A |

TABLE 2-continued

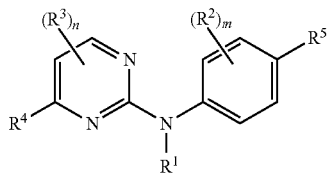

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 2 | 4-(6-(N,N-dimethylamino)-pyridin-3-yl)-5-methyl-N-(3-methyl-4-((1S,4S)-5-methyl-2,5-diazabicyclo-[2.2.1]-heptan-2-yl)phenyl)-pyrimidin-2-amine | 1 | 1 | H | —CH$_3$ | —CH$_3$ | 6-(N(CH$_3$)$_2$)-pyridin-3-yl | (1S,4S)-5-methyl-2,5-diazabicyclo[2.2.1]heptan-2-yl | A |
| 3 | 4-(6-(N,N-dimethylamino)-pyridin-3-yl)-5-trifluoromethyl-N-(3-methyl-4-((1S,4S)-5-methyl-2,5-diazabicyclo-[2.2.1]-heptan-2-yl)phenyl)-pyrimidin-2-amine | 1 | 1 | H | —CH$_3$ | —CF$_3$ | 6-(N(CH$_3$)$_2$)-pyridin-3-yl | (1S,4S)-5-methyl-2,5-diazabicyclo[2.2.1]heptan-2-yl | B |
| 4 | 4-(6-(N,N-dimethylamino)-pyridin-3-yl)-5-fluoro-N-(3-methyl-4-((1S,4S)-5-methyl-2,5-diazabicyclo-[2.2.1]-heptan-2-yl)phenyl)-pyrimidin-2-amine | 1 | 1 | H | —CH$_3$ | —F | 6-(N(CH$_3$)$_2$)-pyridin-3-yl | (1S,4S)-5-methyl-2,5-diazabicyclo[2.2.1]heptan-2-yl | A |
| 5 | 4-(6-(N,N-dimethylamino)-pyridin-3-yl)-5-fluoro-N-(3-fluoro-4-((1S,4S)-5-methyl-2,5-diazabicyclo-[2.2.1]-heptan-2-yl)phenyl)-pyrimidin-2-amine | 1 | 1 | H | —F | —F | 6-(N(CH$_3$)$_2$)-pyridin-3-yl | (1S,4S)-5-methyl-2,5-diazabicyclo[2.2.1]heptan-2-yl | B |

TABLE 2-continued

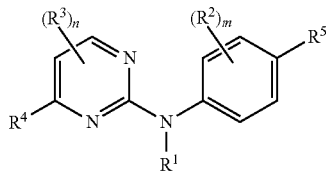

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 6 | 4-(6-(N,N-dimethylamino)-pyridin-3-yl)-5-methyl-N-(3-fluoro-4-((1S,4S)-5-methyl-2,5-diazabicyclo-[2.2.1]-heptan-2-yl)phenyl)-pyrimidin-2-amine | 1 | 1 | H | —F | —CH$_3$ | 6-(N,N-dimethylamino)pyridin-3-yl | (1S,4S)-5-methyl-2,5-diazabicyclo[2.2.1]heptan-2-yl | A |
| 7 | 4-(6-(N,N-dimethylamino)-pyridin-3-yl)-N-(3-fluoro-4-((1S,4S)-5-methyl-2,5-diazabicyclo-[2.2.1]heptan-2-yl)phenyl)-pyrimidin-2-amine | 0 | 1 | H | —F | — | 6-(N,N-dimethylamino)pyridin-3-yl | (1S,4S)-5-methyl-2,5-diazabicyclo[2.2.1]heptan-2-yl | A |
| 8 | 4-(4-methyl-3,4-dihydro-2H-pyrido-[3,2-b]-[1,4]-oxazin-7-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 4-methyl-3,4-dihydro-2H-pyrido[3,2-b][1,4]oxazin-7-yl | (1S,4S)-5-methyl-2,5-diazabicyclo[2.2.1]heptan-2-yl | A |
| 9 | 4-(4-methyl-3,4-dihydro-2H-pyrido-[3,2-b][1,4]-oxazin-7-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | 4-methyl-3,4-dihydro-2H-pyrido[3,2-b][1,4]oxazin-7-yl | (1S,4S)-5-methyl-2,5-diazabicyclo[2.2.1]heptan-2-yl | A |

TABLE 2-continued

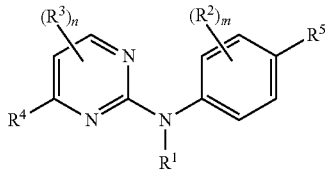

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 10 | 4-(6-(morpholin-4-yl)pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 6-(morpholin-4-yl)pyridin-3-yl | (1S,4S)-5-methyl-2,5-diazabicyclo[2.2.1]heptan-2-yl | A |
| 11 | 4-(6-(morpholin-4-yl)pyridin-3-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | 6-(morpholin-4-yl)pyridin-3-yl | (1S,4S)-5-methyl-2,5-diazabicyclo[2.2.1]heptan-2-yl | A |
| 12 | 4-(6-((1S,4S)-5-methyl-2,5-diazabicyclo-[2.2.1]-heptan-2-yl)pyridin-3-yl)-N-(3-methyl-4-(4-methyl-piperazin-1-yl)phenyl)-pyrimidin-2-amine | 0 | 1 | H | —CH$_3$ | — | 6-((1S,4S)-5-methyl-2,5-diazabicyclo[2.2.1]heptan-2-yl)pyridin-3-yl | 4-methylpiperazin-1-yl | B |
| 13 | 4-(6-((1S,4S)-5-(4-fluorophenyl)-2,5-diazabicyclo-[2.2.1]-heptan-2-yl)pyridin-3-yl)-N-(3-methyl-4-(4-methyl-piperazin-1-yl)phenyl)-pyrimidin-2-amine | 0 | 1 | H | —CH$_3$ | — | 6-((1S,4S)-5-(4-fluorophenyl)-2,5-diazabicyclo[2.2.1]heptan-2-yl)pyridin-3-yl | 4-methylpiperazin-1-yl | A |

TABLE 2-continued

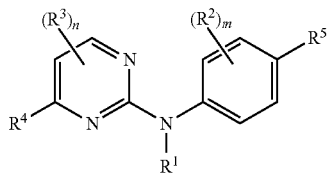

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 14 | 4-(4-(N,N-dimethylamino)-phenyl)-N-(3-methyl-4-((1S,4S)-5-methyl-2,5-diazabicyclo[2.2.1]-heptan-2-yl)phenyl)-pyrimidin-2-amine | 0 | 1 | H | —CH$_3$ | — | | | A |
| 15 | 4-(4-(N,N-dimethyl-amino)-phenyl)-N-(3-fluoro-4-((1S,4S)-5-methyl-2,5-diazabicyclo[2.2.1]-heptan-2-yl)phenyl)-pyrimidin-2-amine | 0 | 1 | H | —F | — | | | B |
| 16 | 4-(6-(4-acetylpiperazin-1-yl)pyridin-3-yl)-N-(3-fluoro-4-((1S,4S)-5-methyl-2,5-diazabicyclo[2.2.1]-heptan-2-yl)phenyl)-pyrimidin-2-amine | 0 | 1 | H | —F | — | | | A |
| 19 | 4-(2,2-dimethyl-3-oxo-3,4-dihydro-2H-pyrido[3,2-b][1,4]-oxazin-7-yl)-N-(3-fluoro-4-((1S,4S)-5-methyl-2,5-diazabicyclo[2.2.1]-heptan-2-yl)phenyl)-pyrimidin-2-amine | 0 | 1 | H | —F | — | | | A |

TABLE 2-continued

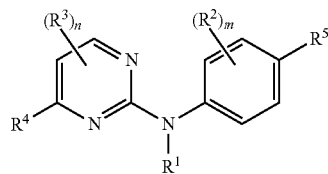

IC₅₀ activity: A = <1 µM
B = 1 to 10 µM
C = >10 to 20 µM
D = >20 µM

| Cpd # | Compound Name | n | m | R¹ | R² | R³ | R⁴ | R⁵ | IC₅₀ |
|---|---|---|---|---|---|---|---|---|---|
| 20 | 4-(2,2-dimethyl-3-oxo-3,4-dihydro-2H-pyrido-[3,2-b][1,4]-oxazin-7-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH₃ | — | 2,2-dimethyl-3-oxo-3,4-dihydro-2H-pyrido[3,2-b][1,4]oxazin-7-yl | (1S,4S)-5-methyl-2,5-diazabicyclo[2.2.1]heptan-2-yl | A |
| 21 | 4-(1H-indol-6-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH₃ | — | 1H-indol-6-yl | (1S,4S)-5-methyl-2,5-diazabicyclo[2.2.1]heptan-2-yl | A |
| 22 | 4-(1H-pyrrolo[2,3-b]-pyridin-5-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH₃ | — | 1H-pyrrolo[2,3-b]pyridin-5-yl | (1S,4S)-5-methyl-2,5-diazabicyclo[2.2.1]heptan-2-yl | A |
| 23 | 4-(1H-pyrrolo-[2,3-b]-pyridin-5-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | 1H-pyrrolo[2,3-b]pyridin-5-yl | (1S,4S)-5-methyl-2,5-diazabicyclo[2.2.1]heptan-2-yl | A |

TABLE 2-continued

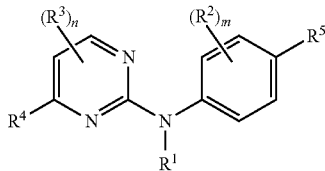

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 24 | 4-(6-(dimethyl-amino)-pyridin-3-yl)-N-(3-methyl-4-((1S,4S)-5-ethyl-2,5-diazbicyclo-[2.2.1]-heptan-2-yl)phenyl)-pyrimidin-2-amine | 0 | 1 | H | —CH$_3$ | — | 6-(dimethylamino)pyridin-3-yl | 5-ethyl-2,5-diazabicyclo[2.2.1]heptan-2-yl | A |
| 25 | 4-(6-(morpholin-4-yl)-pyridin-3-yl)-N-(3-methyl-4-((1S,4S)-5-ethyl-2,5-diazabicyclo-[2.2.1]-heptan-2-yl)phenyl)-pyrimidin-2-amine | 0 | 1 | H | —CH$_3$ | — | 6-(morpholin-4-yl)pyridin-3-yl | 5-ethyl-2,5-diazabicyclo[2.2.1]heptan-2-yl | A |
| 26 | 4-(6-(morpholin-4-yl)pyridin-3-yl)-N-(3-methyl-4-((1S,4S)-5-((ethylamino)-carbonyl)-2,5-diazabicyclo-[2.2.1]-heptan-2-yl)phenyl)-pyrimidin-2-amine | 0 | 1 | H | —CH$_3$ | — | 6-(morpholin-4-yl)pyridin-3-yl | 5-((ethylamino)carbonyl)-2,5-diazabicyclo[2.2.1]heptan-2-yl | A |
| 27 | 4-(2,2-dimethyl-3-oxo-3,4-dihydro-2H-pyrido[3,2-b][1,4]-oxazin-7-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | 2,2-dimethyl-3-oxo-3,4-dihydro-2H-pyrido[3,2-b][1,4]oxazin-7-yl | 5-oxa-2-azabicyclo[2.2.1]heptan-2-yl | A |

TABLE 2-continued

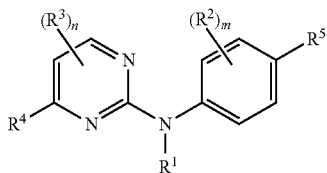

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 28 | 4-(2,2-dimethyl-3-oxo-3,4-dihydro-2H-pyrido-[3,2-b][1,4]-oxazin-7-yl)-N-(3-methyl-4-((1S,4S)-5-(ethyl-carbonyl)-2,5-diazabicyclo-[2.2.1]-heptan-2-yl)phenyl)-pyrimidin-2-amine | 0 | 1 | H | —CH$_3$ | — | (structure) | (structure) | A |
| 29 | 4-(2,2-dimethyl-3-oxo-3,4-dihydro-2H-pyrido-[3,2-b][1,4]-oxazin-7-yl)-N-(3-methyl-4-((1S,4S)-5-(methyl-sulfonyl)-2,5-diazabicyclo-[2.2.1]-heptan-2-yl)phenyl)-pyrimidin-2-amine | 0 | 1 | H | —CH$_3$ | — | (structure) | (structure) | A |
| 30 | 4-(2,2-dimethyl-3-oxo-3,4-dihydro-2H-pyrido-[3,2-b][1,4]-oxazin-7-yl)-N-(3-methyl-4-((1S,4S)-5-ethyl-2,5-diazabicyclo-[2.2.1]-heptan-2-yl)phenyl)-pyrimidin-2-amine | 0 | 1 | H | —CH$_3$ | — | (structure) | (structure) | A |

TABLE 2-continued

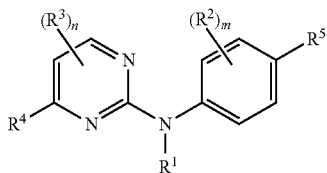

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 31 | 4-(3'-oxo-3',4'-dihydrospiro-[cyclobutane-1,2'-pyrido-[3,2-b][1,4]-oxazine]-7'-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (spiro cyclobutane pyrido-oxazinone) | (N-methyl-2,5-diazabicyclo[2.2.1]heptane) | A |
| 32 | 4-(3'-oxo-3',4'-dihydrospiro-[cyclobutane-1,2'-pyrido-[3,2-b][1,4]-oxazine]-7'-yl)-N-(3-methyl-4-((1S,4S)-5-ethyl-2,5-diazabicyclo-[2.2.1]-heptan-2-yl)phenyl)-pyrimidin-2-amine | 0 | 1 | H | —CH$_3$ | — | (spiro cyclobutane pyrido-oxazinone) | (N-ethyl-2,5-diazabicyclo[2.2.1]heptane) | A |
| 33 | 4-(1H-pyrrolo-[2,3-b]-pyridin-5-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | (1H-pyrrolo[2,3-b]pyridin-5-yl) | (5-oxa-2-azabicyclo[2.2.1]heptane) | A |

TABLE 2-continued

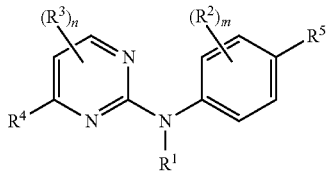

(Ia-1)

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 34 | 4-(1H-pyrrolo[2,3-b]-pyridin-5-yl)-N-(3-methyl-4-((1S,4S)-5-(2,2,2-trifluoro-ethyl)-2,5-diazabicyclo-[2.2.1]-heptan-2-yl)phenyl)-pyrimidin-2-amine | 0 | 1 | H | —CH$_3$ | — | 1H-pyrrolo[2,3-b]pyridin-5-yl | (1S,4S)-5-(2,2,2-trifluoroethyl)-2,5-diazabicyclo[2.2.1]heptan-2-yl with N-CH$_2$CH$_3$ | A |
| 35 | 4-(1H-pyrrolo-[2,3-b]pyridin-5-yl)-N-(3-methyl-4-((1S,4S)-5-(cyclopropyl)-methyl-2,5-diazabicyclo-[2.2.1]-heptan-2-yl)phenyl)-pyrimidin-2-amine | 0 | 1 | H | —CH$_3$ | — | 1H-pyrrolo[2,3-b]pyridin-5-yl | (1S,4S)-5-(cyclopropylmethyl)-2,5-diazabicyclo[2.2.1]heptan-2-yl | A |
| 36 | 4-(6-(morpholin-4-yl)pyridin-3-yl)-N-(3-methyl-4-((1S,4S)-5-(2,2,2-trifluoroethyl)-2,5-diazabicyclo-[2.2.1]-heptan-2-yl)phenyl)-pyrimidin-2-amine | 0 | 1 | H | —CH$_3$ | — | 6-(morpholin-4-yl)pyridin-3-yl | (1S,4S)-5-(2,2,2-trifluoroethyl)-2,5-diazabicyclo[2.2.1]heptan-2-yl | B |
| 37 | 4-(6-(morpholin-4-yl)pyridin-3-yl)-N-(3-methyl-4-((1S,4S)-5-(cyclopropyl)-methyl-2,5-diazabicyclo-[2.2.1]-heptan-2-yl)phenyl)-pyrimidin-2-amine | 0 | 1 | H | —CH$_3$ | — | 6-(morpholin-4-yl)pyridin-3-yl | (1S,4S)-5-(cyclopropylmethyl)-2,5-diazabicyclo[2.2.1]heptan-2-yl | A |

TABLE 2-continued

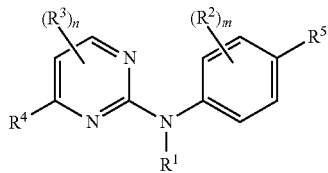

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 38 | 4-(2,2-dimethyl-3-oxo-3,4-dihydro-2H-pyrido-[3,2-n][1,4]-oxazin-7-yl)-N-(3-methyl-4-((1S,4S)-5-(amino-sulfonyl)-2,5-diazabicyclo-[2.2.1]-heptan-2-yl)phenyl)-pyrimidin-2-amine | 0 | 1 | H | —CH$_3$ | — | | | A |
| 39 | 4-(3-fluoro-2-(morpholin-4-yl)pyridin-4-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | | | B |
| 40 | 4-(2-(morpholin-4-yl)pyrimidin-5-yl)-N-(4-((1S,4S)-5-methyl-2,5-diazabicyclo-[2.2.1]-heptan-2-yl)phenyl)-pyrimidin-2-amine | 0 | 0 | H | — | — | | | B |
| 41 | 4-(2-(morpholin-4-yl)pyrimidin-5-yl)-N-(3-methyl-4-((1S,4S)-5-methyl-2,5-diazabicyclo-[2.2.1]heptan-2-yl)phenyl)-pyrimidin-2-amine | 0 | 1 | H | —CH$_3$ | — | | | A |

TABLE 2-continued

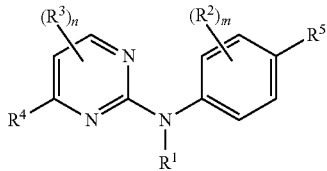

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 42 | 4-(2-(morpholin-4-yl)pyrimidin-5-yl)-N-(3-methyl-4-((1S,4S)-5-oxa-2-azabicyclo[2.2.1]-heptan-2-yl)phenyl)-pyrimidin-2-amine | 0 | 1 | H | —CH$_3$ | — | (2-morpholinopyrimidin-5-yl) | (5-oxa-2-azabicyclo[2.2.1]heptan-2-yl) | B |
| 43 | 4-(2-(morpholin-4-yl)pyrimidin-5-yl)-N-(3-fluoro-4-((1S,4S)-5-methyl-2,5-diazabicyclo[2.2.1]-heptan-2-yl)phenyl)-pyrimidin-2-amine | 0 | 1 | H | —F | — | (2-morpholinopyrimidin-5-yl) | (5-methyl-2,5-diazabicyclo[2.2.1]heptan-2-yl) | A |
| 44 | 4-(2-((cyclopropyl)-carbonyl-amino)-pyrimidin-5-yl)-N-(3-methyl-4-((1S,4S)-5-methyl-2,5-diazabicyclo[2.2.1]-heptan-2-yl)phenyl)-pyrimidin-2-amine | 0 | 1 | H | —CH$_3$ | — | (2-(cyclopropanecarboxamido)pyrimidin-5-yl) | (5-methyl-2,5-diazabicyclo[2.2.1]heptan-2-yl) | A |
| 45 | 4-(4-(4,5-dihydro-thiazol-2-ylcarbamoyl)-phenyl)-N-(3-methyl-4-((1S,4S)-5-methyl-2,5-diazabicyclo[2.2.1]-heptan-2-yl)phenyl)-pyrimidin-2-amine | 0 | 1 | H | —CH$_3$ | — | (4-(4,5-dihydrothiazol-2-ylcarbamoyl)phenyl) | (5-methyl-2,5-diazabicyclo[2.2.1]heptan-2-yl) | B |

TABLE 2-continued

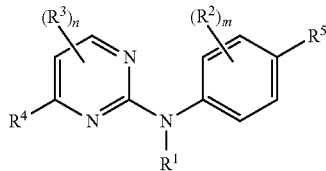

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 46 | 4-(4-(1,1-dimethyl-ethyl)-phenyl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 4-tert-butylphenyl | (1S,4S)-5-methyl-2,5-diazabicyclo[2.2.1]heptan-2-yl | A |
| 47 | 4-(4-(morpholin-4-yl)phenyl)-N-(3-fluoro-4-((1S,4S)-5-methyl-2,5-diazabicyclo-[2.2.1]-heptan-2-yl)phenyl)-pyrimidin-2-amine. TFA salt | 0 | 1 | H | —F | — | 4-morpholinophenyl | (1S,4S)-5-methyl-2,5-diazabicyclo[2.2.1]heptan-2-yl | B |
| 48 | 4-(4-((methyl)-amino-carbonyl-methyl)-phenyl)-N-(3-methyl-4-((1S,4S)-5-methyl-2,5-diazabicyclo-[2.2.1]-heptan-2-yl)phenyl)-pyrimidin-2-amine. TFA salt | 0 | 1 | H | —CH$_3$ | — | 4-(methylaminocarbonylmethyl)phenyl | (1S,4S)-5-methyl-2,5-diazabicyclo[2.2.1]heptan-2-yl | B |
| 49 | 4-(4-((cyclo-propyl)-amino-carbonyl-methyl)-phenyl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 4-(cyclopropylaminocarbonylmethyl)phenyl | (1S,4S)-5-methyl-2,5-diazabicyclo[2.2.1]heptan-2-yl | B |

TABLE 2-continued

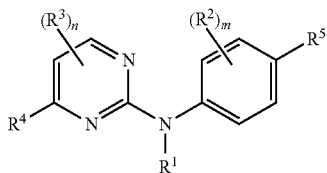

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 50 | 4-(6-(methylaminocarbonyl)-pyridin-3-yl)-N-(3-methyl-4-((1S,4S)-5-methyl-2,5-diazabicyclo[2.2.1]-heptan-2-yl)phenyl)-pyrimidin-2-amine | 0 | 1 | H | —CH$_3$ | — | (methylcarbamoyl-pyridinyl) | (5-methyl-2,5-diazabicyclo[2.2.1]heptan-2-yl) | A |
| 51 | 4-(7-oxo-, 5,6,7,8-tetrahydro-1,8-naphthyridin-3-yl)-N-(3-methyl-4-((1S,4S)-5-methyl-2,5-diazabicyclo[2.2.1]-heptan-2-yl)phenyl)-pyrimidin-2-amine. TFA salt | 0 | 1 | H | —CH$_3$ | — | (7-oxo-tetrahydro-naphthyridinyl) | (5-methyl-2,5-diazabicyclo[2.2.1]heptan-2-yl) | A |
| 52 | 4-(5-((morpholin-4-yl)carbonyl)-pyridin-3-yl)-N-(3-methyl-4-((1S,4S)-5-methyl-2,5-diazabicyclo[2.2.1]-heptan-2-yl)phenyl)-pyrimidin-2-amine. Bis TFA salt | 0 | 1 | H | —CH$_3$ | — | (5-(morpholin-4-ylcarbonyl)pyridin-3-yl) | (5-methyl-2,5-diazabicyclo[2.2.1]heptan-2-yl) | A |

TABLE 2-continued

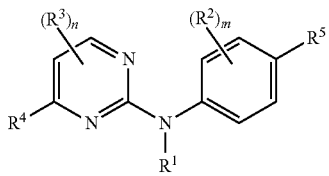

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 53 | 4-(2,2-dimethyl-3-oxo-3,4-dihydro-2H-pyrido-[3,2-b][1,4]-oxazin-7-yl)-N-(3-cyano-4-((1S,4S)-5-methyl-2,5-diazabicyclo-[2.2.1]-heptan-2-yl)phenyl)-pyrimidin-2-amine | 0 | 1 | H | -CN | — | 3,3-dimethyl-2-oxo-1,2,3,4-tetrahydro-1,8-naphthyridin-6-yl | (1S,4S)-5-methyl-2,5-diazabicyclo[2.2.1]heptan-2-yl | A |
| 59 | 4-(5-methyl-6-(morpholin-4-yl)pyridin-3-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | 5-methyl-6-morpholinopyridin-3-yl | (1S,4S)-5-methyl-2,5-diazabicyclo[2.2.1]heptan-2-yl | A |
| 60 | 4-(5-methyl-6-(morpholin-4-yl)pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 5-methyl-6-morpholinopyridin-3-yl | (1S,4S)-5-methyl-2,5-diazabicyclo[2.2.1]heptan-2-yl | A |
| 67 | 5-methyl-4-(6-(morpholin-4-yl)pyridin-3-yl)-N-(3-methyl-4-((1S,4S)-5-methyl-2,5-diazabicyclo-[2.2.1]-heptan-2-yl)phenyl)-pyrimidin-2-amine | 1 | 1 | H | —CH$_3$ | —CH$_3$ | 6-morpholinopyridin-3-yl | (1S,4S)-5-methyl-2,5-diazabicyclo[2.2.1]heptan-2-yl | A |

TABLE 2-continued

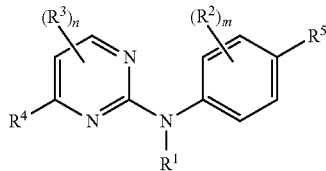

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 68 | 5-methyl-4-(6-(morpholin-4-yl)pyridin-3-yl)-N-(3-fluoro-4-((1S,4S)-5-methyl-2,5-diazabicyclo[2.2.1]heptan-2-yl)phenyl)-pyrimidin-2-amine | 1 | 1 | H | —F | —CH$_3$ | morpholin-4-yl-pyridin-3-yl | (1S,4S)-5-methyl-2,5-diazabicyclo[2.2.1]heptan-2-yl | A |
| 69 | 4-(6-(2-(morpholin-4-yl)ethyl)-aminopyridin-3-yl)-N-(4-((1S,4S)-5-methyl-2,5-diazabicyclo[2.2.1]heptan-2-yl)phenyl)-pyrimidin-2-amine | 0 | 0 | H | — | — | 6-(2-(morpholin-4-yl)ethyl)aminopyridin-3-yl | (1S,4S)-5-methyl-2,5-diazabicyclo[2.2.1]heptan-2-yl | B |
| 70 | 4-(6-(2-(morpholin-4-yl)ethyl)-aminopyridin-3-yl)-N-(3-fluoro-4-((1S,4S)-5-methyl-2,5-diazabicyclo[2.2.1]heptan-2-yl)phenyl)-pyrimidin-2-amine | 0 | 1 | H | —F | — | 6-(2-(morpholin-4-yl)ethyl)aminopyridin-3-yl | (1S,4S)-5-methyl-2,5-diazabicyclo[2.2.1]heptan-2-yl | A |
| 71 | 4-(2,2-dimethyl-3-oxo-3,4-dihydro-2H-pyrido[3,2-b][1,4]oxazin-7-yl)-N-(3-methyl-4-((1R,4R)-5-methyl-2,5-diazabicyclo[2.2.1]heptan-2-yl)phenyl)-pyrimidin-2-amine | 0 | 1 | H | —CH$_3$ | — | 2,2-dimethyl-3-oxo-3,4-dihydro-2H-pyrido[3,2-b][1,4]oxazin-7-yl | (1R,4R)-5-methyl-2,5-diazabicyclo[2.2.1]heptan-2-yl | A |

TABLE 2-continued

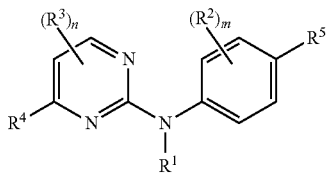

(Ia-1)

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 72 | 4-(6-(morpholin-4-yl)pyridin-3-yl)-N-(3-methyl-4-((1R,4R)-5-methyl-2,5-diazabicyclo-[2.2.1]-heptan-2-yl)phenyl)-pyrimidin-2-amine | 0 | 1 | H | —CH$_3$ | — | 6-(morpholin-4-yl)pyridin-3-yl | (1R,4R)-5-methyl-2,5-diazabicyclo[2.2.1]heptan-2-yl | A |
| 73 | 4-(2,2-dimethyl-3-oxo-3,4-dihydro-2H-pyrido[3,2-b][1,4]oxazin-7-yl)-N-(3-fluoro-4-((1R,4R)-5-methyl-2,5-diazabicyclo-[2.2.1]-heptan-2-yl)phenyl)-pyrimidin-2-amine | 0 | 1 | H | F | — | 2,2-dimethyl-3-oxo-3,4-dihydro-2H-pyrido[3,2-b][1,4]oxazin-7-yl | (1R,4R)-5-methyl-2,5-diazabicyclo[2.2.1]heptan-2-yl | A |
| 74 | 4-(6-(morpholin-4-yl)pyridin-3-yl)-N-(3-fluoro-4-((1R,4R)-5-methyl-2,5-diazabicyclo-[2.2.1]-heptan-2-yl)phenyl)-pyrimidin-2-amine | 0 | 1 | H | F | — | 6-(morpholin-4-yl)pyridin-3-yl | (1R,4R)-5-methyl-2,5-diazabicyclo[2.2.1]heptan-2-yl | A |
| 75 | 4-(6-(morpholin-4-yl)pyridin-3-yl)-N-(3-methyl-4-(1,5,7-trimethyl-3,7-diazabicyclo-[3.3.1]-nonan-3-yl)phenyl)-pyrimidin-2-amine | 0 | 1 | H | —CH$_3$ | — | 6-(morpholin-4-yl)pyridin-3-yl | 1,5,7-trimethyl-3,7-diazabicyclo[3.3.1]nonan-3-yl | A |

TABLE 2-continued

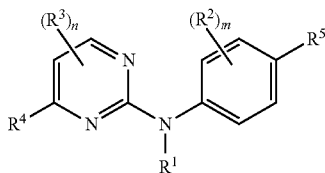

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 76 | 4-(6-(dimethylamino)-pyridin-3-yl)-N-(3-methyl-4-(1,5,7-trimethyl-3,7-diazabicyclo-[3.3.1]-nonan-3-yl)phenyl)-pyrimidin-2-amine | 0 | 1 | H | —CH$_3$ | — | 6-(dimethylamino)pyridin-3-yl | 1,5,7-trimethyl-3,7-diazabicyclo[3.3.1]nonan-3-yl | A |
| 77 | 4-(6-(cyclohexylamino)-pyridin-3-yl)-N-(3-methyl-4-(1,5,7-trimethyl-3,7-diazabicyclo-[3.3.1]-nonan-3-yl)phenyl)-pyrimidin-2-amine | 0 | 1 | H | —CH$_3$ | — | 6-(cyclohexylamino)pyridin-3-yl | 1,5,7-trimethyl-3,7-diazabicyclo[3.3.1]nonan-3-yl | A |
| 78 | 4-(6-(cyclohexylamino)-pyridin-3-yl)-N-(3-methyl-4-((1S,4S)-5-methyl-2,5-diazabicyclo-[2.2.1]heptan-2-yl)phenyl)-pyrimidin-2-amine | 0 | 1 | H | —CH$_3$ | — | 6-(cyclohexylamino)pyridin-3-yl | (1S,4S)-5-methyl-2,5-diazabicyclo[2.2.1]heptan-2-yl | A |
| 79 | 4-(6-(cyclohexylamino)-pyridin-3-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | 6-(cyclohexylamino)pyridin-3-yl | (1S,4S)-5-methyl-2,5-diazabicyclo[2.2.1]heptan-2-yl | A |

TABLE 2-continued

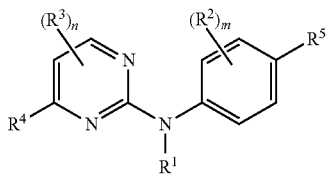

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 80 | 4-(6-(benzyl)-pyridin-3-yl)-N-(3-methyl-4-((1S,4S)-5-methyl-2,5-diazabicyclo[2.2.1]heptan-2-yl)phenyl)-pyrimidin-2-amine | 0 | 1 | H | —CH$_3$ | — | benzyl-NH-pyridinyl | N-methyl-2,5-diazabicyclo[2.2.1]heptanyl | A |
| 81 | 4-(6-(benzyl)-pyridin-3-yl)-N-(3-fluoro-4-((1S,4S)-5-methyl-2,5-diazabicyclo[2.2.1]heptan-2-yl)phenyl)-pyrimidin-2-amine | 0 | 1 | H | —F | — | benzyl-NH-pyridinyl | N-methyl-2,5-diazabicyclo[2.2.1]heptanyl | A |
| 82 | 4-(5-methyl-6-(morpholin-4-yl)pyridin-3-yl)-N-(3-fluoro-4-(1,5,7-trimethyl-3,7-diazabicyclo[3.3.1]nonan-3-yl)phenyl)-pyrimidin-2-amine | 0 | 1 | H | —F | — | 3-methyl-6-morpholinyl-pyridinyl | 1,5,7-trimethyl-3,7-diazabicyclo[3.3.1]nonanyl | A |
| 83 | 4-(6-(dimethylamino)-pyridin-3-yl)-N-(3-fluoro-4-(1,5,7-trimethyl-3,7-diazabicyclo[3.3.1]nonan-3-yl)phenyl)-pyrimidin-2-amine | 0 | 1 | H | —F | — | 6-(dimethylamino)pyridinyl | 1,5,7-trimethyl-3,7-diazabicyclo[3.3.1]nonanyl | A |

TABLE 2-continued

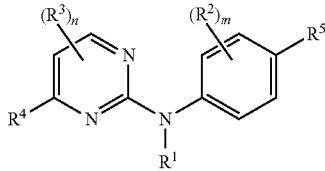

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 84 | 4-(4-(dimethyl-amino)-phenyl)-N-(3-fluoro-4-(1,5,7-trimethyl-3,7-diazabicyclo-[3.3.1]-nonan-3-yl)phenyl)-pyrimidin-2-amine | 0 | 1 | H | —F | — | 4-(dimethylamino)phenyl | 1,5,7-trimethyl-3,7-diazabicyclo[3.3.1]nonan-3-yl | A |
| 85 | 4-(6-(morpholin-4-yl)pyridin-3-yl)-N-(3-fluoro-4-(1,5,7-trimethyl-3,7-diazabicyclo-[3.3.1]-nonan-3-yl)phenyl)-pyrimidin-2-amine | 0 | 1 | H | —F | — | 6-(morpholin-4-yl)pyridin-3-yl | 1,5,7-trimethyl-3,7-diazabicyclo[3.3.1]nonan-3-yl | A |
| 86 | 4-(3,4-dihydro-2H-pyrido[3,2-b][1,4]-oxazin-7-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 3,4-dihydro-2H-pyrido[3,2-b][1,4]oxazin-7-yl | (1S,4S)-5-methyl-2,5-diazabicyclo[2.2.1]heptan-2-yl | A |
| 87 | 4-(3,4-dihydro-2H-pyrido-[3,2-b][1,4]-oxazin-7-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | 3,4-dihydro-2H-pyrido[3,2-b][1,4]oxazin-7-yl | (1S,4S)-5-methyl-2,5-diazabicyclo[2.2.1]heptan-2-yl | A |

TABLE 2-continued

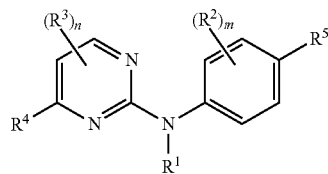

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 88 | 4-(3,4-dihydro-2H-pyrido-[3,2-b][1,4]-oxazin-7-yl)-N-(3-methyl-4-(1,5,7-trimethyl-3,7-diazabicyclo-[3.3.1]-nonan-3-yl)phenyl)-pyrimidin-2-amine | 0 | 1 | H | —CH$_3$ | — | (structure) | (structure) | A |
| 89 | 4-(3,4-dihydro-2H-pyrido-[3,2-b][1,4]-oxazin-7-yl)-N-(3-fluoro-4-(1,5,7-trimethyl-3,7-diazabicyclo-[3.3.1]-nonan-3-yl)phenyl)-pyrimidin-2-amine | 0 | 1 | H | —F | — | (structure) | (structure) | B |
| 90 | 4-(6-(benzyl)-pyridin-3-yl)-N-(3-methyl-4-(1,5,7-trimethyl-3,7-diazabicyclo-[3.3.1]-nonan-3-yl)phenyl)-pyrimidin-2-amine | 0 | 1 | H | —CH$_3$ | — | (structure) | (structure) | A |
| 91 | 4-(6-(benzyl)-pyridin-3-yl)-N-(3-fluoro-4-(1,5,7-trimethyl-3,7-diazabicyclo-[3.3.1]-nonan-3-yl)phenyl)-pyrimidin-2-amine | 0 | 1 | H | —F | — | (structure) | (structure) | A |

TABLE 2-continued

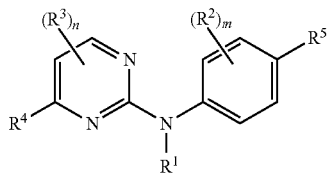

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 92 | 4-(2-(propyl)-amino-pyrimidin-5-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (2-propylamino-pyrimidin-5-yl) | ((1S,4S)-5-methyl-2,5-diazabicyclo[2.2.1]heptan-2-yl) | A |
| 93 | 4-(2-(propyl)-amino-pyrimidin-5-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | (2-propylamino-pyrimidin-5-yl) | ((1S,4S)-5-methyl-2,5-diazabicyclo[2.2.1]heptan-2-yl) | A |
| 94 | 4-(6-(cyclohexyl-amino)-pyridin-3-yl)-N-(3-trifluoro-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (6-cyclohexylamino-pyridin-3-yl) | ((1S,4S)-5-methyl-2,5-diazabicyclo[2.2.1]heptan-2-yl) | A |
| 95 | 4-(5-methyl)-sulfonyl-pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (5-methylsulfonyl-pyridin-3-yl) | ((1S,4S)-5-methyl-2,5-diazabicyclo[2.2.1]heptan-2-yl) | A |

TABLE 2-continued

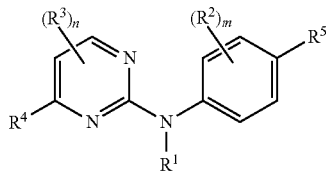

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 96 | 4-(6-(dimethylamino)-pyridin-3-yl)-N-(3-trifluoromethyl-4-((1S,4S)-5-methyl-2,5-diazabicyclo[2.2.1]-heptan-2-yl)phenyl)-pyrimidin-2-amine | 0 | 1 | H | —CF$_3$ | — | 6-(dimethylamino)pyridin-3-yl | (1S,4S)-5-methyl-2,5-diazabicyclo[2.2.1]heptan-2-yl | A |
| 97 | 4-(6-(morpholin-4-yl)pyridin-3-yl)-N-(3-trifluoromethyl-4-((1S,4S)-5-methyl-2,5-diazabicyclo[2.2.1]-heptan-2-yl)phenyl)-pyrimidin-2-amine | 0 | 1 | H | —CF$_3$ | — | 6-(morpholin-4-yl)pyridin-3-yl | (1S,4S)-5-methyl-2,5-diazabicyclo[2.2.1]heptan-2-yl | A |
| 98 | 4-(3,4-dihydro-2H-pyrido[3,2-b][1,4]oxazin-7-yl)-N-(3-trifluoromethyl-4-((1S,4S)-5-methyl-2,5-diazabicyclo[2.2.1]heptan-2-yl)phenyl)-pyrimidin-2-amine | 0 | 1 | H | —CF$_3$ | — | 3,4-dihydro-2H-pyrido[3,2-b][1,4]oxazin-7-yl | (1S,4S)-5-methyl-2,5-diazabicyclo[2.2.1]heptan-2-yl | A |
| 99 | 4-(6-((2-(cyclopropyl-sulfonyl)-aminoethyl)-amino)pyridin-3-yl)-N-(3-methyl-4-((1S,4S)-5-methyl-2,5-diazabicyclo[2.2.1]-heptan-2-yl)phenyl)-pyrimidin-2-amine | 0 | 1 | H | —CH$_3$ | — | 6-((2-(cyclopropylsulfonyl)aminoethyl)amino)pyridin-3-yl | (1S,4S)-5-methyl-2,5-diazabicyclo[2.2.1]heptan-2-yl | B |

TABLE 2-continued

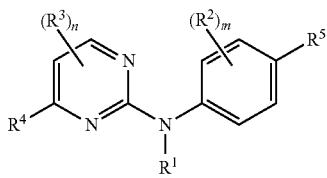

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 100 | 4-(6-((2-(cyclopropyl-sulfonyl)-aminoethyl)-amino)pyridin-3-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | (cyclopropylsulfonylamino-ethylamino)pyridinyl | oxa-azabicycloheptanyl | A |
| 101 | 4-(5-(methyl)-sulfonyl-pyridin-3-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | (methylsulfonyl)pyridinyl | N-methyl-diazabicycloheptanyl | A |
| 102 | 4-(5-(methyl)-sulfonyl-pyridin-3-yl)-N-(3-tri-fluoromethyl-4-((1S,4S)-5-methyl-2,5-diazabicyclo-[2.2.1]-heptan-2-yl)phenyl)-pyrimidin-2-amine | 0 | 1 | H | —CF$_3$ | — | (methylsulfonyl)pyridinyl | N-methyl-diazabicycloheptanyl | A |
| 103 | 4-(imidazo-[1,2-a]pyridin-6-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | imidazo[1,2-a]pyridinyl | N-methyl-diazabicycloheptanyl | A |

TABLE 2-continued

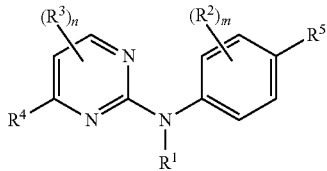

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 104 | 4-(4-(5-(4-dimethyl-aminophenyl)-oxazol-2-yl)phenyl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (4-(5-(4-dimethylaminophenyl)oxazol-2-yl)phenyl group) | (N-methyl-2,5-diazabicyclo[2.2.1]heptan-2-yl group) | B |
| 105 | 4-(6-methoxy-1H-indol-2-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (6-methoxy-1H-indol-2-yl group) | (N-methyl-2,5-diazabicyclo[2.2.1]heptan-2-yl group) | A |
| 106 | 4-(1-(3-chloro-phenyl)-1H-pyrazol-4-yl)-N-(3-methyl-4-((1S,4S)-5-methyl-2,5-diazabicyclo-[2.2.1]heptan-2-yl)phenyl)-pyrimidin-2-amine | 0 | 1 | H | —CH$_3$ | — | (1-(3-chlorophenyl)-1H-pyrazol-4-yl group) | (N-methyl-2,5-diazabicyclo[2.2.1]heptan-2-yl group) | B |
| 107 | 4-(1-methyl-benzimidazol-6-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (1-methylbenzimidazol-6-yl group) | (N-methyl-2,5-diazabicyclo[2.2.1]heptan-2-yl group) | A |

TABLE 2-continued

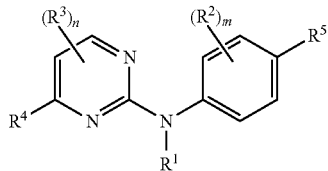

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 108 | 4-(5-cyano-1H-indol-2-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 5-cyano-1H-indol-2-yl | (1S,4S)-5-methyl-2,5-diazabicyclo[2.2.1]heptan-2-yl | A |
| 109 | 4-(1-(4-fluoro-phenyl)-1H-pyrazol-4-yl)-N-(3-methyl-4-((1S,4S)-5-methyl-2,5-diazabicyclo-[2.2.1]heptan-2-yl)phenyl)-pyrimidin-2-amine | 0 | 1 | H | —CH$_3$ | — | 1-(4-fluorophenyl)-1H-pyrazol-4-yl | (1S,4S)-5-methyl-2,5-diazabicyclo[2.2.1]heptan-2-yl | A |
| 110 | 4-(6-(morpholin-4-yl)pyridin-3-yl)-N-(3-methyl-4-(7-azabicyclo-[2.2.1]-heptan-7-yl)phenyl)-pyrimidin-2-amine | 0 | 1 | H | —CH$_3$ | — | 6-(morpholin-4-yl)pyridin-3-yl | 7-azabicyclo[2.2.1]heptan-7-yl | B |
| 111 | 4-(6-cyano-pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 6-cyano-pyridin-3-yl | (1S,4S)-5-methyl-2,5-diazabicyclo[2.2.1]heptan-2-yl | B |
| 112 | 4-(6-cyano-pyridin-3-yl)-N-(3-methyl-4-(7-azabicyclo-[2.2.1]heptan-7-yl)phenyl)-pyrimidin-2-amine | 0 | 1 | H | —CH$_3$ | — | 6-cyano-pyridin-3-yl | 7-azabicyclo[2.2.1]heptan-7-yl | B |

TABLE 2-continued (Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 113 | 4-(2-oxoindolin-5-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 2-oxoindolin-5-yl | 5-methyl-2,5-diazabicyclo[2.2.1]heptan-2-yl | A |
| 114 | 4-(5-cyano-pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 5-cyanopyridin-3-yl | 5-methyl-2,5-diazabicyclo[2.2.1]heptan-2-yl | B |
| 115 | 4-(6-(1H-tetrazol-5-yl)pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 6-(1H-tetrazol-5-yl)pyridin-3-yl | 5-methyl-2,5-diazabicyclo[2.2.1]heptan-2-yl | C |
| 116 | 4-(6-(morpholin-4-yl)pyridin-3-yl)-N-(3-cyano-4-((1S,4S)-5-acetyl-2,5-diazabicyclo-[2.2.1]-heptan-2-yl)phenyl)-pyrimidin-2-amine | 0 | 1 | H | —CN | — | 6-(morpholin-4-yl)pyridin-3-yl | 5-acetyl-2,5-diazabicyclo[2.2.1]heptan-2-yl | A |

TABLE 2-continued

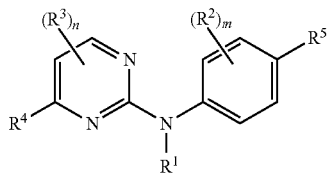

(Ia-1)

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 117 | 4-(6-(morpholin-4-yl)pyridin-3-yl)-N-(3-cyano-4-((1S,4S)-5-methyl-sulfonyl-2,5-diazabicyclo-[2.2.1]-heptan-2-yl)phenyl)-pyrimidin-2-amine | 0 | 1 | H | —CN | — | 6-(morpholin-4-yl)pyridin-3-yl | (1S,4S)-5-(methylsulfonyl)-2,5-diazabicyclo[2.2.1]heptan-2-yl | A |
| 118 | 4-(6-(morpholin-4-yl)pyridin-3-yl)-N-(3-cyano-4-((1S,4S)-5-methyl-2,5-diazabicyclo-[2.2.1]-heptan-2-yl)phenyl)-pyrimidin-2-amine | 0 | 1 | H | —CN | — | 6-(morpholin-4-yl)pyridin-3-yl | (1S,4S)-5-methyl-2,5-diazabicyclo[2.2.1]heptan-2-yl | A |
| 119 | 4-(6-(morpholin-4-yl)pyridin-3-yl)-N-(3-cyano-4-((1S,4S-5-cyclopentyl-2,5-diazabicyclo-[2.2.1]-heptan-2-yl)phenyl)-pyrimidin-2-amine | 0 | 1 | H | —CN | — | 6-(morpholin-4-yl)pyridin-3-yl | (1S,4S)-5-cyclopentyl-2,5-diazabicyclo[2.2.1]heptan-2-yl | A |
| 120 | 4-(6-(morpholin-4-yl)pyridin-3-yl)-N-(3-methyl-4-(1,4-diazabicyclo-[3.2.1]-octan-4-yl)phenyl)-pyrimidin-2-amine | 0 | 1 | H | —CH$_3$ | — | 6-(morpholin-4-yl)pyridin-3-yl | 1,4-diazabicyclo[3.2.1]octan-4-yl | A |

TABLE 2-continued

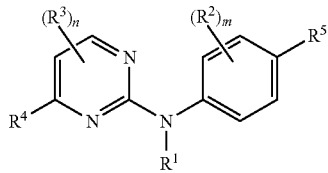

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 121 | 4-(2-oxoindolin-5-yl)-N-(3-methyl-4-(1,4-diazabicyclo-[3.2.1]octan-4-yl)phenyl)-pyrimidin-2-amine | 0 | 1 | H | —CH$_3$ | — | 2-oxoindolin-5-yl | 1,4-diazabicyclo[3.2.1]octan-4-yl | A |
| 122 | (1-methyl-benzimidazol-6-yl)-N-(3-methyl-4-(1,4-diazabicyclo-[3.2.1]-octan-4-yl)phenyl)-pyrimidin-2-amine | 0 | 1 | H | —CH$_3$ | — | 1-methylbenzimidazol-6-yl | 1,4-diazabicyclo[3.2.1]octan-4-yl | A |
| 123 | 4-(imidazo[1,2-a]pyridin-6-yl)-N-(3-methyl-4-(1,4-diazabicyclo-[3.2.1]-octan-4-yl)phenyl)-pyrimidin-2-amine | 0 | 1 | H | —CH$_3$ | — | imidazo[1,2-a]pyridin-6-yl | 1,4-diazabicyclo[3.2.1]octan-4-yl | A |
| 124 | 4-(2H-benzo[b][1,4]-oxazin-3(4H)-on-6-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | 2H-benzo[b][1,4]oxazin-3(4H)-on-6-yl | (1S,4S)-5-methyl-2,5-diazabicyclo[2.2.1]heptan-2-yl | A |
| 125 | 4-(2,2,4-trimethyl-3-oxo-3,4-dihydro-2H-pyrido-[3,2-b][1,4]-oxazin-7-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 2,2,4-trimethyl-3-oxo-3,4-dihydro-2H-pyrido[3,2-b][1,4]oxazin-7-yl | (1S,4S)-5-methyl-2,5-diazabicyclo[2.2.1]heptan-2-yl | A |

TABLE 2-continued

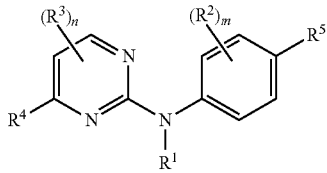

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 126 | 4-(2,2,4-trimethyl-3-oxo-3,4-dihydro-2H-pyrido-[3,2-b][1,4]-oxazin-7-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | (2,2,4-trimethyl-3-oxo-3,4-dihydro-2H-pyrido[3,2-b][1,4]oxazin-7-yl) | (5-methyl-2,5-diazabicyclo[2.2.1]heptan-2-yl) | A |
| 127 | 4-(5-(3-methyl-piperidin-1-yl)pyrazin-2-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | (5-(3-methylpiperidin-1-yl)pyrazin-2-yl) | (5-methyl-2,5-diazabicyclo[2.2.1]heptan-2-yl) | B |
| 128 | 4-(4-(t-butylcarbonyl-amino)-phenyl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | (4-(t-butylcarbonylamino)phenyl) | (5-methyl-2,5-diazabicyclo[2.2.1]heptan-2-yl) | A |
| 129 | 4-(4-(t-butylcarbonyl-amino)phenyl)-N-(3-methyl-4-((1S,4S)-5-methyl-2,5-diazabicyclo-[2.2.1]heptan-2-yl)phenyl)-pyrimidin-2-amine | 0 | 1 | H | —CH$_3$ | — | (4-(t-butylcarbonylamino)phenyl) | (5-methyl-2,5-diazabicyclo[2.2.1]heptan-2-yl) | A |

TABLE 2-continued

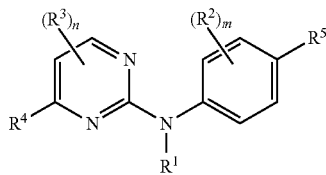

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 130 | 4-(2,2-dimethyl-3-oxo-3,4-dihydro-2H-pyrido-[3,2-b][1,4]-oxazin-7-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (2,2-dimethyl-3-oxo-3,4-dihydro-2H-pyrido[3,2-b][1,4]oxazin-7-yl) | (5-methyl-2,5-diazabicyclo[2.2.1]heptan-2-yl) | A |
| 132 | 4-(6-(acetamido)-pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (6-acetamidopyridin-3-yl) | (5-methyl-2,5-diazabicyclo[2.2.1]heptan-2-yl) | A |
| 133 | 4-(4-((pyridin-2-yl)amino-carbonyl)-phenyl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | (4-((pyridin-2-yl)aminocarbonyl)phenyl) | (5-methyl-2,5-diazabicyclo[2.2.1]heptan-2-yl) | B |
| 134 | 4-(4-((pyridin-2-yl)amino-carbonyl)-phenyl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (4-((pyridin-2-yl)aminocarbonyl)phenyl) | (5-methyl-2,5-diazabicyclo[2.2.1]heptan-2-yl) | A |

TABLE 2-continued

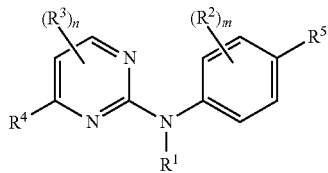

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 135 | 4-(4-(methyl-sulfonyl-amino)-phenyl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | | | A |
| 136 | 4-(4-(methyl-sulfonyl-amino)-phenyl)-N-(3-methyl-4-((1S,4S)-5-methyl-2,5-diazabicyclo-[2.2.1]heptan-2-yl)phenyl)-pyrimidin-2-amine | 0 | 1 | H | —CH$_3$ | — | | | A |
| 137 | 4-(2,2-dimethyl-3-oxo-3,4-dihydro-2H-pyrido-[3,2-b][1,4]-oxazin-7-yl)-N-(4-((1S,4S)-5-methyl-2,5-diazabicyclo-[2.2.1]-heptan-2-yl)phenyl)-pyrimidin-2-amine | 0 | 0 | H | — | — | | | A |
| 139 | 4-(4-(3-cyclopropyl-ureido)phenyl)-N-(4-((1S,4S)-5-methyl-2,5-diazabicyclo-[2.2.1]-heptan-2-yl)phenyl)-pyrimidin-2-amine | 0 | 0 | H | — | — | | | A |

TABLE 2-continued

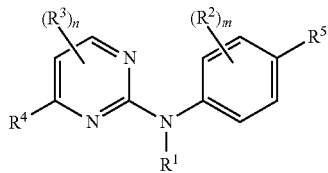

(Ia-1)

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 141 | 4-(6-(2-(morpholin-4-yl)acetamido)-pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | morpholinyl-CH$_2$-C(O)NH-pyridin-2-yl | N-methyl-diazabicycloheptane | A |
| 142 | 4-(6-(2-(morpholin-4-yl)acetamido)-pyridin-3-yl)-N-(4-((1S,4S)-5-methyl-2,5-diazabicyclo-[2.2.1]-heptan-2-yl)phenyl)-pyrimidin-2-amine | 0 | 0 | H | — | — | morpholinyl-CH$_2$-C(O)NH-pyridin-2-yl | N-methyl-diazabicycloheptane | B |
| 143 | 4-(6-(2-(morpholin-4-yl)acetamido)-pyridin-3-yl)-N-(3-fluoro-4-((1S,4S-5-methyl-2,5-diazabicyclo-[2.2.1]-heptan-2-yl)phenyl)-pyrimidin-2-amine | 0 | 1 | H | —F | — | morpholinyl-CH$_2$-C(O)NH-pyridin-2-yl | N-methyl-diazabicycloheptane | B |
| 147 | 4-(6-(acetamido)-pyridin-3-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | H$_3$C-C(O)NH-pyridin-2-yl | oxa-azabicycloheptane | A |

TABLE 2-continued

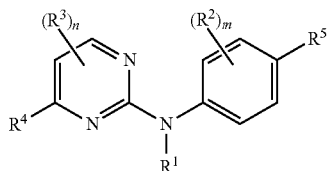

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 148 | 4-(6-aminopyridin-3-yl)-N-(3-methyl-4-((1S,4S)-5-ethyl-carbonyl-2,5-diazabicyclo-[2.2.1]-heptan-2-yl)phenyl)-pyrimidin-2-amine | 0 | 1 | H | —CH$_3$ | — | 6-aminopyridin-3-yl | 5-(ethylcarbonyl)-2,5-diazabicyclo[2.2.1]heptan-2-yl | A |
| 149 | 4-(6-(acetamido)-pyridin-3-yl)-N-(3-methyl-4-((1S,4S)-5-ethyl-carbonyl-2,5-diazabicyclo-[2.2.1]heptan-2-yl)phenyl)-pyrimidin-2-amine | 0 | 1 | H | —CH$_3$ | — | 6-acetamidopyridin-3-yl | 5-(ethylcarbonyl)-2,5-diazabicyclo[2.2.1]heptan-2-yl | A |
| 150 | 4-(6-amino-pyridin-3-yl)-N-(3-methyl-4-((1S,4S)-5-methyl-sulfonyl-2,5-diazabicyclo-[2.2.1]-heptan-2-yl)phenyl)-pyrimidin-2-amine | 0 | 1 | H | —CH$_3$ | — | 6-aminopyridin-3-yl | 5-(methylsulfonyl)-2,5-diazabicyclo[2.2.1]heptan-2-yl | A |
| 151 | 4-(6-(methyl-sulfonyl-amino)-pyridin-3-yl)-N-(3-methyl-4-((1S,4S)-5-methyl-2,5-diazabicyclo-[2.2.1]heptan-2-yl)phenyl)-pyrimidin-2-amine | 0 | 1 | H | —CH$_3$ | — | 6-(methylsulfonylamino)pyridin-3-yl | 5-methyl-2,5-diazabicyclo[2.2.1]heptan-2-yl | B |

TABLE 2-continued

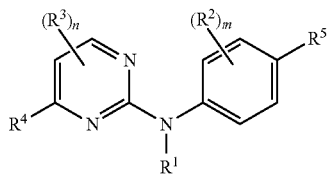

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 152 | 4-(6-(2-(dimethyl-amino)-acetamido)-pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (structure) | (structure) | A |
| 153 | 4-(6-(methyl-sulfonyl-amino)-pyridin-3-yl)-N-(3-fluoro-4-((1S,4S)-5-methyl-2,5-diazabicyclo-[2.2.1]heptan-2-yl)phenyl)-pyrimidin-2-amine | 0 | 1 | H | —F | — | (structure) | (structure) | B |
| 155 | 4-(6-(morpholin-4-yl)pyridin-3-yl)-N-(4-(8-methyl-3,8-diazabicyclo-[3.2.1]-octan-3-yl)phenyl)-pyrimidin-2-amine | 0 | 0 | H | — | — | (structure) | (structure) | A |
| 156 | 4-(6-(methyl-sulfonyl-amino)pyridin-3-yl)-N-(4-(8-methyl-3,8-diazabicyclo-[3.2.1]-octan-3-yl)phenyl)-pyrimidin-2-amine | 0 | 0 | H | — | — | (structure) | (structure) | B |

TABLE 2-continued

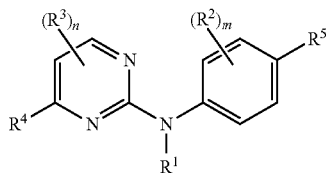

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 157 | 4-(2,2-dimethyl-3-oxo-3,4-dihydro-2H-pyrido-[3,2-b][1,4]-oxazin-7-yl)-N-(4-(8-methyl-3,8-diazabicyclo-[3.2.1]-octan-3-yl)phenyl)-pyrimidin-2-amine | 0 | 0 | H | — | — | 2,2-dimethyl-3-oxo-3,4-dihydro-2H-pyrido[3,2-b][1,4]oxazin-7-yl | 8-methyl-3,8-diazabicyclo[3.2.1]octan-3-yl | A |
| 158 | 4-(6-amino-pyridin-3-yl)-N-(4-(8-methyl-3,8-diazabicyclo-[3.2.1]-octan-3-yl)phenyl)-pyrimidin-2-amine | 0 | 0 | H | — | — | 6-aminopyridin-3-yl | 8-methyl-3,8-diazabicyclo[3.2.1]octan-3-yl | A |
| 159 | 4-(6-(morpholin-4-yl)pyridin-3-yl)-N-(3-methyl-4-(1,4-diazabicyclo-[3.2.2]-nonan-4-yl)phenyl)-pyrimidin-2-amine | 0 | 1 | H | —CH$_3$ | — | 6-(morpholin-4-yl)pyridin-3-yl | 1,4-diazabicyclo[3.2.2]nonan-4-yl | A |
| 160 | 4-(2,2-dimethyl-3-oxo-3,4-dihydro-2H-pyrido[3,2-b][1,4]oxazin-7-yl)-N-(3-methyl-4-(1,4-diazabicyclo-[3.2.2]-nonan-4-yl)phenyl)-pyrimidin-2-amine | 0 | 1 | H | —CH$_3$ | — | 2,2-dimethyl-3-oxo-3,4-dihydro-2H-pyrido[3,2-b][1,4]oxazin-7-yl | 1,4-diazabicyclo[3.2.2]nonan-4-yl | A |

TABLE 2-continued

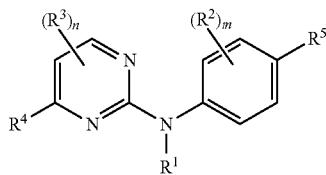

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 161 | 4-(4-((pyridin-2-yl)-aminocarbonyl)-phenyl)-N-(3-methyl-4-(1,4-diazabicyclo-[3.2.2]-nonan-4-yl)phenyl)-pyrimidin-2-amine | 0 | 1 | H | —CH$_3$ | — | | | A |
| 162 | 4-(4-(acetamido)-phenyl)-N-(4-(8-methyl-3,8-diazabicyclo-[3.2.1]-octan-3-yl)phenyl)-pyrimidin-2-amine | 0 | 0 | H | — | — | | | A |
| 163 | 4-(2-(diethylamino)-thiazol-4-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | | | A |
| 164 | 4-(2-(diethylamino)-thiazol-4-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | | | A |

TABLE 2-continued (Ia-1)

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 165 | 4-(2,2-dimethyl-3-oxo-3,4-dihydro-2H-pyrido[3,2-b][1,4]oxazin-7-yl)-N-(3-methyl-4-(8-methyl-3,8-diazabicyclo-[3.2.1]-octan-3-yl)phenyl)-pyrimidin-2-amine | 0 | 1 | H | —CH$_3$ | — | 2,2-dimethyl-3-oxo-3,4-dihydro-2H-pyrido[3,2-b][1,4]oxazin-7-yl | 8-methyl-3,8-diazabicyclo[3.2.1]octan-3-yl | A |
| 166 | 4-(6-(morpholin-4-yl)pyridin-3-yl)-N-(3-methyl-4-(8-methyl-3,8-diazabicyclo-[3.2.1]-octan-3-yl)phenyl)-pyrimidin-2-amine | 0 | 1 | H | —CH$_3$ | — | 6-(morpholin-4-yl)pyridin-3-yl | 8-methyl-3,8-diazabicyclo[3.2.1]octan-3-yl | A |
| 167 | 4-(6-(methyl-sulfonyl-amino)pyridin-3-yl)-N-(3-methyl-4-(8-methyl-3,8-diazabicyclo-[3.2.1]-octan-3-yl)phenyl)-pyrimidin-2-amine | 0 | 1 | H | —CH$_3$ | — | 6-(methylsulfonylamino)pyridin-3-yl | 8-methyl-3,8-diazabicyclo[3.2.1]octan-3-yl | A |
| 168 | 4-(4-(t-butylcarbonyl-amino)phenyl)-N-(3-methyl-4-(8-methyl-3,8-diazabicyclo-[3.2.1]-octan-3-yl)phenyl)-pyrimidin-2-amine | 0 | 1 | H | —CH$_3$ | — | 4-(t-butylcarbonylamino)phenyl | 8-methyl-3,8-diazabicyclo[3.2.1]octan-3-yl | A |

TABLE 2-continued

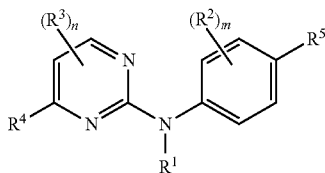

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 169 | 4-(1H-pyrrol-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | pyrrole | N-methyl diazabicycloheptane | B |
| 170 | 4-(1H-pyrrol-3-yl)-N-(4-((1S,4S)-5-methyl-2,5-diazabicyclo-[2.2.1]-heptan-2-yl)phenyl)-pyrimidin-2-amine | 0 | 0 | H | — | — | pyrrole | N-methyl diazabicycloheptane | B |
| 171 | 4-(1H-pyrrol-3-yl)-N-(3-trifluoro-methyl-4-((1S,4S)-5-methyl-2,5-diazabicyclo-[2.2.1]-heptan-2-yl)phenyl)-pyrimidin-2-amine | 0 | 1 | H | —CF$_3$ | — | pyrrole | N-methyl diazabicycloheptane | A |
| 172 | 4-(2,2-dimethyl-3-oxo-3,4-dihydro-2H-pyrido-[3,2-b][1,4]-oxazin-7-yl)-N-(3-trifluoromethyl-4-((1S,4S)-2,5-diazabicyclo-[2.2.1]-heptan-2-yl)phenyl)-pyrimidin-2-amine | 0 | 1 | H | —CF$_3$ | — | 2,2-dimethyl-pyrido-oxazinone | NH diazabicycloheptane | A |

TABLE 2-continued

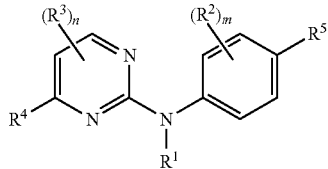

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 173 | 4-(6-ethoxypyridin-3-yl)-N-(3-methyl-4-((1S,4S)-5-methyl-2,5-diazabicyclo[2.2.1]heptan-2-yl)phenyl)pyrimidin-2-amine | 0 | 1 | H | —CH$_3$ | — | 6-ethoxypyridin-3-yl | (1S,4S)-5-methyl-2,5-diazabicyclo[2.2.1]heptan-2-yl | A |
| 174 | 4-(6-ethoxypyridin-3-yl)-N-(3-fluoro-4-((1S,4S)-5-methyl-2,5-diazabicyclo[2.2.1]heptan-2-yl)phenyl)pyrimidin-2-amine | 0 | 1 | H | —F | — | 6-ethoxypyridin-3-yl | (1S,4S)-5-methyl-2,5-diazabicyclo[2.2.1]heptan-2-yl | B |
| 175 | 4-(2-(dimethylamino)thiazol-4-yl)-N-(3-methyl-4-((1S,4S)-5-methyl-2,5-diazabicyclo[2.2.1]heptan-2-yl)phenyl)pyrimidin-2-amine | 0 | 1 | H | —CH$_3$ | — | 2-(dimethylamino)thiazol-4-yl | (1S,4S)-5-methyl-2,5-diazabicyclo[2.2.1]heptan-2-yl | B |
| 176 | 4-(2-(dimethylamino)thiazol-4-yl)-N-(3-fluoro-4-((1S,4S)-5-methyl-2,5-diazabicyclo[2.2.1]heptan-2-yl)phenyl)pyrimidin-2-amine | 0 | 1 | H | —F | — | 2-(dimethylamino)thiazol-4-yl | (1S,4S)-5-methyl-2,5-diazabicyclo[2.2.1]heptan-2-yl | B |

TABLE 2-continued

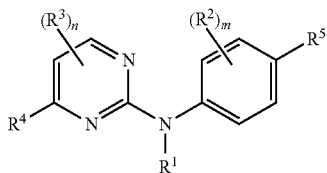

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 178 | 4-(5-(morpholin-4-yl)pyrazin-2-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 5-morpholinopyrazin-2-yl | (1S,4S)-5-methyl-2,5-diazabicyclo[2.2.1]heptan-2-yl | B |
| 179 | 4-(5-(morpholin-4-yl)pyrazin-2-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | 5-morpholinopyrazin-2-yl | (1S,4S)-5-methyl-2,5-diazabicyclo[2.2.1]heptan-2-yl | B |
| 181 | 4-(4-(1-ethoxyethyl)-phenyl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 6-(1-ethoxyethyl)pyridin-3-yl | (1S,4S)-5-methyl-2,5-diazabicyclo[2.2.1]heptan-2-yl | B |
| 182 | 4-(4-(1-ethoxyethyl)-phenyl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | 6-(1-ethoxyethyl)pyridin-3-yl | (1S,4S)-5-methyl-2,5-diazabicyclo[2.2.1]heptan-2-yl | B |

TABLE 2-continued

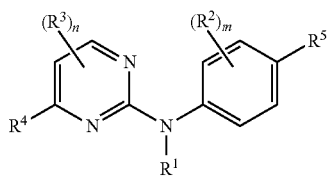

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 183 | 4-(6-(dimethyl-amino)-pyridin-3-yl)-N-(4-((1S,4S)-5-methyl-2,5-diazabicyclo-[2.2.1]-heptan-2-yl)phenyl)-pyrimidin-2-amine | 0 | 0 | H | — | — | 6-(dimethylamino)pyridin-3-yl | (1S,4S)-5-methyl-2,5-diazabicyclo[2.2.1]heptan-2-yl | A |
| 184 | 4-(6-(morpholin-4-yl)pyridin-3-yl)-N-(4-((1S,4S)-5-methyl-2,5-diazabicyclo-[2.2.1]-heptan-2-yl)phenyl)-pyrimidin-2-amine | 0 | 0 | H | — | — | 6-(morpholin-4-yl)pyridin-3-yl | (1S,4S)-5-methyl-2,5-diazabicyclo[2.2.1]heptan-2-yl | A |
| 185 | 4-(4-methyl-3,4-dihydro-2H-pyrido-[3,2-b][1,4]-oxazin-7-yl)-N-(4-((1S,4S)-5-methyl-2,5-diazabicyclo-[2.2.1]heptan-2-yl)phenyl)-pyrimidin-2-amine | 0 | 0 | H | — | — | 4-methyl-3,4-dihydro-2H-pyrido[3,2-b][1,4]oxazin-7-yl | (1S,4S)-5-methyl-2,5-diazabicyclo[2.2.1]heptan-2-yl | A |
| 186 | 4-(6-(3-ethoxypropyl)-aminopyridin-3-yl)-N-(3-methyl-4-((1S,4S)-5-methyl-2,5-diazabicyclo-[2.2.1]heptan-2-yl)phenyl)-pyrimidin-2-amine | 0 | 1 | H | —CH$_3$ | — | 6-(3-ethoxypropyl)aminopyridin-3-yl | (1S,4S)-5-methyl-2,5-diazabicyclo[2.2.1]heptan-2-yl | A |

TABLE 2-continued

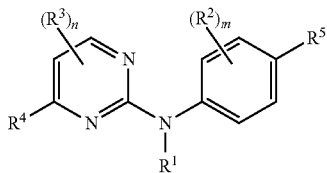

(Ia-1)

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 187 | 4-(6-(cis-2,6-dimethyl-morpholin-4-yl)pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 2,6-dimethylmorpholinyl-pyridinyl | N-methyl-diazabicycloheptyl | A |
| 188 | 4-(6-(propyl-amino)-pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 6-(propylamino)pyridinyl | N-methyl-diazabicycloheptyl | A |
| 189 | 4-(6-(2-(dimethyl-amino)-methyl-morpholin-4-yl)pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 6-(2-(dimethylamino)methyl-morpholinyl)pyridinyl | N-methyl-diazabicycloheptyl | A |
| 190 | 4-(6-(piperidin-1-yl)pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 6-(piperidin-1-yl)pyridinyl | N-methyl-diazabicycloheptyl | A |

TABLE 2-continued

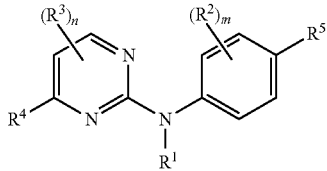

(Ia-1)

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 191 | 4-(6-(3-(amino carbonyl)-piperidin-1-yl)pyridin-3-yl)-N-(3-methyl-4-((1S,4S)-5-methyl-2,5-diazabicyclo[2.2.1]-heptan-2-yl)phenyl)-pyrimidin-2-amine | 0 | 1 | H | —CH$_3$ | — | | | B |
| 192 | 4-(6-(morpholin-4-yl)pyridin-3-yl)-N-(3-methyl-4-((1S,4S)-5-methyl sulfonyl-2,5-diazabicyclo[2.2.1]-heptan-2-yl)phenyl)-pyrimidin-2-amine | 0 | 1 | H | —CH$_3$ | — | | | A |
| 193 | 4-(4-methyl-3,4-dihydro-2H-pyrido[3,2-b][1,4]-oxazin-7-yl)-N-(3-methyl-4-((1S,4S)-5-methyl-sulfonyl-2,5-diaza-bicyclo[2.2.1]heptan-2-yl)phenyl)-pyrimidin-2-amine | 0 | 1 | H | —CH$_3$ | — | | | A |
| 194 | 4-(6-(morpholin-4-yl)pyridin-3-yl)-N-(3-methyl-4-((1S,4S)-5-oxa-2-azabicyclo[2.2.1]-heptan-2-yl)phenyl)-pyrimidin-2-amine | 0 | 1 | H | —CH$_3$ | — | | | A |

TABLE 2-continued

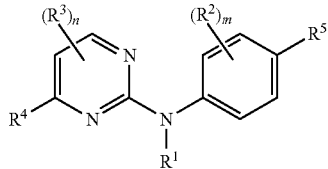

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 195 | 4-(4-methyl-3,4-dihydro-2H-pyrido[3,2-b][1,4]oxazin-7-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | (4-methyl-3,4-dihydro-2H-pyrido[3,2-b][1,4]oxazin-7-yl) | ((1S,4S)-5-oxa-2-azabicyclo[2.2.1]heptan-2-yl) | A |
| 196 | 4-(6-(morpholin-4-yl)pyridin-3-yl)-N-(3-methyl-4-((1S,4S)-5-ethylcarbonyl-2,5-diazabicyclo-[2.2.1]-heptan-2-yl)phenyl)-pyrimidin-2-amine | 0 | 1 | H | —CH$_3$ | — | (6-(morpholin-4-yl)pyridin-3-yl) | ((1S,4S)-5-ethylcarbonyl-2,5-diazabicyclo[2.2.1]heptan-2-yl) | A |
| 197 | 4-(6-(2-(morpholin-4-yl)ethyl)-aminopyridin-3-yl)-N-(3-methyl-4-((1S,4S)-5-ethylcarbonyl-2,5-diazabicyclo-[2.2.1]-heptan-2-yl)phenyl)-pyrimidin-2-amine | 0 | 1 | H | —CH$_3$ | — | (6-(2-(morpholin-4-yl)ethyl)-aminopyridin-3-yl) | ((1S,4S)-5-ethylcarbonyl-2,5-diazabicyclo[2.2.1]heptan-2-yl) | B |
| 198 | 4-(6-(3-dimethyl-amino)-propylamino-pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (6-(3-dimethylamino)propylaminopyridin-3-yl) | ((1S,4S)-5-methyl-2,5-diazabicyclo[2.2.1]heptan-2-yl) | B |

TABLE 2-continued

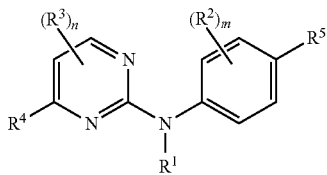

(Ia-1)

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 199 | 4-(6-(morpholin-4-yl)pyridin-3-yl)-N-(3-methyl-4-((1S,4S)-5-amidino-2,5-diazabicyclo-[2.2.1]-heptan-2-yl)phenyl)-pyrimidin-2-amine. TFA salt | 0 | 1 | H | —CH$_3$ | — | (6-(morpholin-4-yl)pyridin-3-yl) | (5-amidino-2,5-diazabicyclo[2.2.1]heptan-2-yl), TFA | B |
| 200 | 4-(6-(3-ethoxypropyl)-aminopyridin-3-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | (6-(3-ethoxypropyl)aminopyridin-3-yl) | (5-oxa-2-azabicyclo[2.2.1]heptan-2-yl) | A |
| 201 | 4-(6-cis-2,6-dimethyl-morpholin-4-yl)pyridin-3-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | (6-(cis-2,6-dimethylmorpholin-4-yl)pyridin-3-yl) | (5-oxa-2-azabicyclo[2.2.1]heptan-2-yl) | A |
| 202 | 4-(6-(propylamino)-pyridin-3-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | (6-(propylamino)pyridin-3-yl) | (5-oxa-2-azabicyclo[2.2.1]heptan-2-yl) | A |

TABLE 2-continued

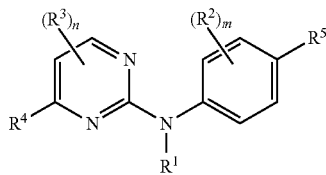

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 203 | 4-(6-(3-dimethyl-amino)-propylamino-pyridin-3-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | | | A |
| 204 | 4-(6-(1,4-oxazepan-4-yl)pyridin-3-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | | | A |
| 205 | 4-(6-(morpholin-4-yl)pyridin-3-yl)-N-(3-methyl-4-((1S,4S)-5-isobutyl-2,5-diazabicyclo-[2.2.1]-heptan-2-yl)phenyl)-pyrimidin-2-amine | 0 | 1 | H | —CH$_3$ | — | | | A |
| 206 | 4-(6-(1,4-oxazepan-4-yl)pyridin-3-yl)-N-(3-methyl-4-((1S,4S)-5-methyl-2,5-diazabicyclo-[2.2.1]heptan-2-yl)phenyl)-pyrimidin-2-amine | 0 | 1 | H | —CH$_3$ | — | | | A |

TABLE 2-continued

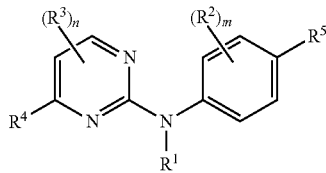

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 207 | 4-(2,2-dimethyl-3-oxo-3,4-dihydro-2H-pyrido[3,2-b][1,4]oxazin-7-yl)-N-(3-methyl-4-(1,5,7-trimethyl-3,7-diazabicyclo-[3.3.1]-nonan-3-yl)phenyl)-pyrimidin-2-amine | 0 | 1 | H | —CH$_3$ | — | 2,2-dimethyl-3-oxo-pyrido-oxazine | 1,5,7-trimethyl-diazabicyclo[3.3.1]nonane | A |
| 208 | 4-(2,2-dimethyl-3-oxo-3,4-dihydro-2H-pyrido[3,2-b][1,4]oxazin-7-yl)-N-(3-fluoro-4-(1,5,7-trimethyl-3,7-diazabicyclo-[3.3.1]-nonan-3-yl)phenyl)-pyrimidin-2-amine | 0 | 1 | H | —F | — | 2,2-dimethyl-3-oxo-pyrido-oxazine | 1,5,7-trimethyl-diazabicyclo[3.3.1]nonane | B |
| 209 | 4-(3-oxo-3,4-dihydro-2H-pyrido[3,2-b][1,4]-oxazin-7-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 3-oxo-pyrido-oxazine | (1S,4S)-5-methyl-2,5-diazabicyclo[2.2.1]heptane | A |

TABLE 2-continued

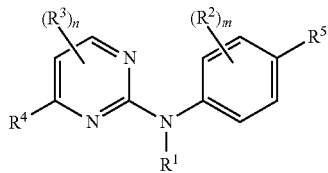

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 210 | 4-(3-oxo-3,4-dihydro-2H-pyrido[3,2-b][1,4]oxazin-7-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | | | A |
| 211 | 4-(6-(3-ethoxypropyl)-aminopyridin-3-yl)-N-(3-methyl-4-(1,5,7-trimethyl-3,7-diazabicyclo-[3.3.1]nonan-3-yl)phenyl)-pyrimidin-2-amine | 0 | 1 | H | —CH$_3$ | — | | | A |
| 212 | 4-(6-((2S,6R)-2,6-dimethyl-morpholin-4-yl)pyridin-3-yl)-N-(3-methyl-4-(1,5,7-trimethyl-3,7-diazabicyclo-[3.3.1]-nonan-3-yl)phenyl)-pyrimidin-2-amine | 0 | 1 | H | —CH$_3$ | — | | | A |
| 213 | 4-(6-(propyl-amino)-pyridin-3-yl)-N-(3-methyl-4-(1,5,7-trimethyl-3,7-diazabicyclo-[3.3.1]-nonan-3-yl)phenyl)-pyrimidin-2-amine | 0 | 1 | H | —CH$_3$ | — | | | A |

TABLE 2-continued

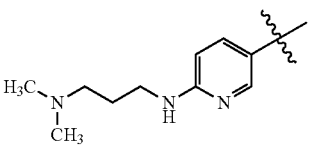 [SMILES: *c1ccc(NCCCN(C)C)nc1]

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 214 | 4-(6-(3-dimethyl-amino)-propylamino-pyridin-3-yl)-N-(3-methyl-4-(1,5,7-trimethyl-3,7-diazabicyclo-[3.3.1]nonan-3-yl)phenyl)-pyrimidin-2-amine | 0 | 1 | H | —CH$_3$ | — | 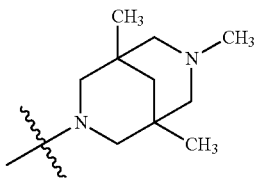 [SMILES: *N1CC2(C)CN(C)CC(C)(C1)C2] | 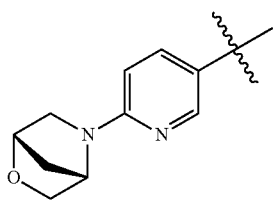 [SMILES: *c1ccc(N2C[C@@H]3C[C@H]2CO3)nc1] | B |
| 215 | 4-(6-((1S,4S)-2-oxa-5-azabicyclo-[2.2.1]-heptan-5-yl)pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 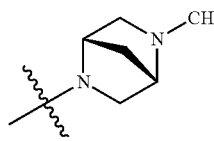 | 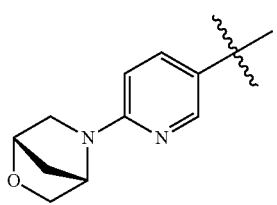 [SMILES: *c1ccc(N2C[C@@H]3C[C@H]2CO3)nc1] | A |
| 216 | 4-(6-((1S,4S)-5-oxa-2-azabicyclo-[2.2.1]-heptan-2-yl)pyridin-3-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | 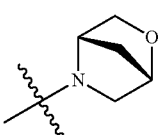 [SMILES: *N1C[C@@H]2C[C@H]1CO2] | 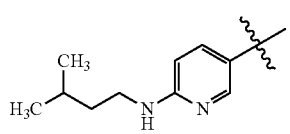 [SMILES: *c1ccc(NCCC(C)C)nc1] | A |
| 217 | 4-(6-(3-methyl-butyl)-aminopyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 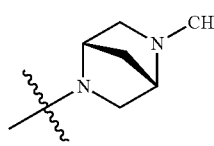 | 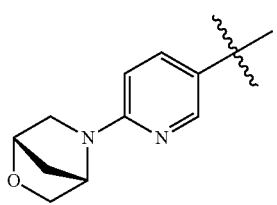 [SMILES: *c1ccc(N2C[C@@H]3C[C@H]2CO3)nc1] | A |

TABLE 2-continued

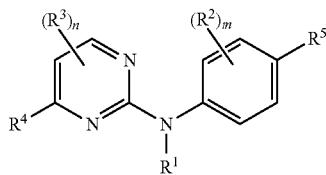

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 218 | 4-(6-(3,3-dimethyl-butyl)-aminopyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (3,3-dimethylbutyl)aminopyridin-5-yl | 5-methyl-2,5-diazabicyclo[2.2.1]heptan-2-yl | A |
| 219 | 4-(6-(2-methoxy-ethyl)-(methyl)-aminopyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (2-methoxyethyl)(methyl)aminopyridin-5-yl | 5-methyl-2,5-diazabicyclo[2.2.1]heptan-2-yl | A |
| 220 | 4-(6-(2-methoxy-ethyl)-(methyl)-amino-pyridin-3-yl)-N-(3-methyl-4-((1S,4S)-5-oxa-2-azabicyclo-[2.2.1]-heptan-2-yl)phenyl)-pyrimidin-2-amine | 0 | 1 | H | —CH$_3$ | — | (2-methoxyethyl)(methyl)aminopyridin-5-yl | 5-oxa-2-azabicyclo[2.2.1]heptan-2-yl | A |

TABLE 2-continued

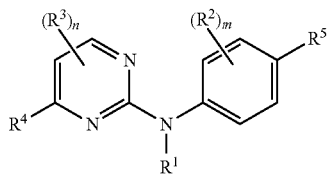

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 221 | 4-(6-(2-methoxy-ethyl)-(methyl)-amino-pyridin-3-yl)-N-(3-methyl-4-(1,5,7-trimethyl-3,7-diazabicyclo-[3.3.1]-nonan-3-yl)phenyl)-pyrimidin-2-amine | 0 | 1 | H | —CH$_3$ | — | (6-(2-methoxyethyl)(methyl)amino)pyridin-3-yl | 1,5,7-trimethyl-3,7-diazabicyclo[3.3.1]nonan-3-yl | A |
| 222 | 4-(6-(morpholin-4-yl)pyridin-3-yl)-N-(3-methyl-4-((1S,4R)-2-azabicyclo-[2.2.1]-heptan-2-yl)phenyl)-pyrimidin-2-amine | 0 | 1 | H | —CH$_3$ | — | 6-(morpholin-4-yl)pyridin-3-yl | (1S,4R)-2-azabicyclo[2.2.1]heptan-2-yl | A |
| 223 | 4-(2,2-dimethyl-3-oxo-3,4-dihydro-2H-pyrido-[3,2-b][1,4]-oxazin-7-yl)-N-(3-methyl-4-((1S,4R)-2-azabicyclo-[2.2.1]-heptan-2-yl)phenyl)-pyrimidin-2-amine | 0 | 1 | H | —CH$_3$ | — | 2,2-dimethyl-3-oxo-3,4-dihydro-2H-pyrido[3,2-b][1,4]oxazin-7-yl | (1S,4R)-2-azabicyclo[2.2.1]heptan-2-yl | A |

TABLE 2-continued

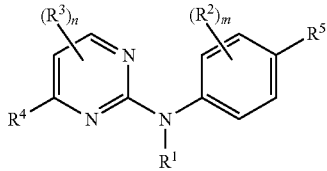

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 224 | 4-(2,2-dimethyl-3-oxo-3,4-dihydro-2H-pyrido-[3,2-b][1,4]-oxazin-7-yl)-N-(3-methyl-4-(2-methyl-sulfonyl-2-azabicyclo-[2.2.1]-heptan-5-yl)phenyl)-pyrimidin-2-amine and 4-(2,2-dimethyl-3-oxo-3,4-dihydro-2H-pyrido[3,2-b][1,4]oxazin-7-yl)-N-(3-methyl-4-(2-methyl-sulfonyl-2-azabicyclo-[2.2.1]-heptan-6-yl)phenyl)-pyrimidin-2-amine (68:31) | 0 | 1 | H | —CH$_3$ | — | (2,2-dimethyl-3-oxo-3,4-dihydro-2H-pyrido[3,2-b][1,4]oxazin-7-yl structure) | (2-methylsulfonyl-2-azabicyclo[2.2.1]heptan-5-yl and 6-yl structures) | A |
| 225 | 4-(6-(morpholin-4-yl)pyridin-3-yl)-N-(3-methyl-4-(2-methyl-sulfonyl-2-azabicyclo-[2.2.1]-heptan-5-yl)phenyl)-pyrimidin-2-amine and 4-(6-(morpholin-4-yl)pyridin-3-yl)-N-(3-methyl-4-(2-methyl-sulfonyl-2-azabicyclo-[2.2.1]-heptan-6-yl)phenyl)-pyrimidin-2-amine (85:15) | 0 | 1 | H | —CH$_3$ | — | (6-(morpholin-4-yl)pyridin-3-yl structure) | (2-methylsulfonyl-2-azabicyclo[2.2.1]heptan-5-yl and 6-yl structures) | B |

TABLE 2-continued

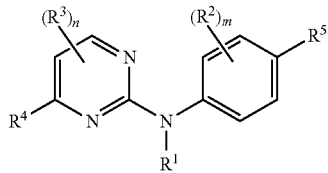

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 226 | 4-(2,2-dimethyl-3-oxo-3,4-dihydro-2H-pyrido[3,2-b][1,4]oxazin-7-yl)-N-(4-(2-methylsulfonyl-2-azabicyclo[2.2.1]heptan-5-yl)phenyl)-pyrimidin-2-amine | 0 | 0 | H | — | — | 2,2-dimethyl-3-oxo-3,4-dihydro-2H-pyrido[3,2-b][1,4]oxazin-7-yl | 2-(methylsulfonyl)-2-azabicyclo[2.2.1]heptan-5-yl | B and |
| 227 | 4-(6-(morpholin-4-yl)pyridin-3-yl)-N-(4-(2-methylsulfonyl-2-azabicyclo[2.2.1]heptan-5-yl)phenyl)-pyrimidin-2-amine | 0 | 0 | H | — | — | 6-(morpholin-4-yl)pyridin-3-yl | 2-(methylsulfonyl)-2-azabicyclo[2.2.1]heptan-5-yl | A and |
| 228 | 4-(2,2-dimethyl-3-oxo-3,4-dihydro-2H-pyrido[3,2-b][1,4]oxazin-7-yl)-N-(4-(2-methylsulfonyl-2-azabicyclo[2.2.1]heptan-6-yl)phenyl)-pyrimidin-2-amine | 0 | 0 | H | — | — | 2,2-dimethyl-3-oxo-3,4-dihydro-2H-pyrido[3,2-b][1,4]oxazin-7-yl | 2-(methylsulfonyl)-2-azabicyclo[2.2.1]heptan-6-yl | A |
| 229 | 4-(6-(morpholin-4-yl)pyridin-3-yl)-N-(4-(2-methylsulfonyl-2-azabicyclo[2.2.1]heptan-6-yl)phenyl)-pyrimidin-2-amine | 0 | 0 | H | — | — | 6-(morpholin-4-yl)pyridin-3-yl | 2-(methylsulfonyl)-2-azabicyclo[2.2.1]heptan-6-yl | B |

TABLE 2-continued

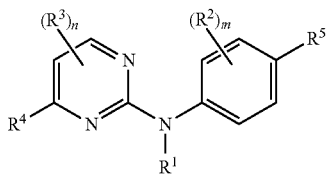

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 230 | 4-(6-(thiamorpholin-4-yl)pyridin-3-yl)-N-(3-methyl-4-((1S,4S)-5-methyl-2,5-diazabicyclo-[2.2.1]heptan-2-yl)phenyl)-pyrimidin-2-amine | 0 | 1 | H | —CH$_3$ | — | thiomorpholinyl-pyridinyl | methyl-diazabicycloheptyl | A |
| 231 | 4-(6-(morpholin-4-yl)pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | morpholinyl-pyridinyl | methyl-diazabicycloheptyl | A |
| 232 | 4-(1-(pyridin-4-yl)-1H-indol-5-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | 1-(pyridin-4-yl)-indolyl | methyl-diazabicycloheptyl | A |
| 233 | 4-(1-(pyridin-4-yl)-1H-indol-5-yl)-N-(3-fluoro-4-((1S,4S)-5-methyl-2,5-diazabicyclo-[2.2.1]-heptan-2-yl)phenyl)-pyrimidin-2-amine | 0 | 1 | H | —F | — | 1-(pyridin-4-yl)-indolyl | methyl-diazabicycloheptyl | A |

TABLE 2-continued

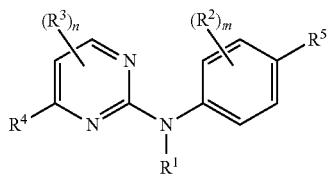

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 234 | 4-(1-(pyridin-4-yl)-1H-indol-5-yl)-N-(3-methyl-4-((1S,4S)-5-ethyl-2,5-diazabicyclo-[2.2.1]-heptan-2-yl)phenyl)-pyrimidin-2-amine | 0 | 1 | H | —CH$_3$ | — | 1-(pyridin-4-yl)-1H-indol-5-yl | 5-ethyl-2,5-diazabicyclo[2.2.1]heptan-2-yl | A |
| 235 | 4-(1-(pyridin-4-yl)-1H-indol-5-yl)-N-(3-methyl-4-((1S,4S)-5-isobutyl-2,5-diazabicyclo-[2.2.1]-heptan-2-yl)phenyl)-pyrimidin-2-amine | 0 | 1 | H | —CH$_3$ | — | 1-(pyridin-4-yl)-1H-indol-5-yl | 5-isobutyl-2,5-diazabicyclo[2.2.1]heptan-2-yl | A |
| 237 | 4-(7-oxo-5,6,7,8-tetrahydro-1,8-naphthyridin-3-yl)-N-(3-methyl-4-((1S,4S)-5-methyl-sulfonyl-2,5-diazabicyclo-[2.2.1]-heptan-2-yl)phenyl)-pyrimidin-2-amine | 0 | 1 | H | —CH$_3$ | — | 7-oxo-5,6,7,8-tetrahydro-1,8-naphthyridin-3-yl | 5-methylsulfonyl-2,5-diazabicyclo[2.2.1]heptan-2-yl | A |
| 238 | 4-(6-(propylamino)-pyridin-3-yl)-N-(3-methyl-4-((1S,4S)-5-methyl-sulfonyl-2,5-diazabicyclo-[2.2.1]heptan-2-yl)phenyl)-pyrimidin-2-amine | 0 | 1 | H | —CH$_3$ | — | 6-(propylamino)pyridin-3-yl | 5-methylsulfonyl-2,5-diazabicyclo[2.2.1]heptan-2-yl | A |

TABLE 2-continued

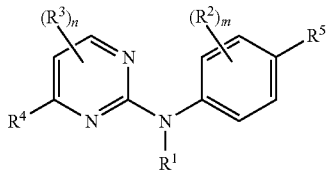

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 239 | 4-(3-oxo-3,4-dihydro-2H-benzo[b][1,4]-thiazin-7-yl)-N-(4-((1S,4S)-5-methyl-2,5-diazabicyclo-[2.2.1]-heptan-2-yl)phenyl)-pyrimidin-2-amine | 0 | 0 | H | — | — | (3-oxo-3,4-dihydro-2H-benzo[b][1,4]thiazin-7-yl) | (5-methyl-2,5-diazabicyclo[2.2.1]heptan-2-yl) | A |
| 240 | 4-(2,2-dimethyl-3-oxo-3,4-dihydro-2H-benzo[b][1,4]-oxazin-7-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (2,2-dimethyl-3-oxo-3,4-dihydro-2H-benzo[b][1,4]oxazin-7-yl) | (5-methyl-2,5-diazabicyclo[2.2.1]heptan-2-yl) | A |
| 241 | 4-(2,2-dimethyl-3-oxo-3,4-dihydro-2H-benzo[b][1,4]-oxazin-7-yl)-N-(3-methyl-4-((1S,4S)-5-methylsulfonyl-2,5-diazabicyclo-[2.2.1]-heptan-2-yl)phenyl)-pyrimidin-2-amine | 0 | 1 | H | —CH$_3$ | — | (2,2-dimethyl-3-oxo-3,4-dihydro-2H-benzo[b][1,4]oxazin-7-yl) | (5-methylsulfonyl-2,5-diazabicyclo[2.2.1]heptan-2-yl) | A |
| 242 | 4-(2-oxo-2,3,4,5-tetrahydro-1H-benzo[b]-azepin-7-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (2-oxo-2,3,4,5-tetrahydro-1H-benzo[b]azepin-7-yl) | (5-methyl-2,5-diazabicyclo[2.2.1]heptan-2-yl) | A |

TABLE 2-continued

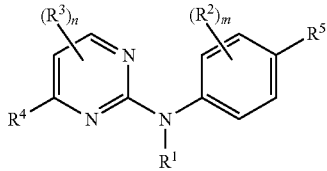
(Ia-1)

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 243 | 4-(2-oxo-2,3,4,5-tetrahydro-1H-benzo[b]-azepin-7-yl)-N-(3-methyl-4-((1S,4S)-5-methylsulfonyl-2,5-diazabicyclo-[2.2.1]-heptan-2-yl)phenyl)-pyrimidin-2-amine | 0 | 1 | H | —CH$_3$ | — | | | A |
| 244 | 4-(2,2-dimethyl-3-oxo-3,4-dihydro-2H-benzo[b][1,4]-oxazin-7-yl)-N-(3-methyl-4-((6R,9S)-6,9-methano-octahydro-1H-pyrido[1,2-a]pyrazin-2-yl)phenyl)-pyrimidin-2-amine | 0 | 1 | H | —CH$_3$ | — | | | A |
| 245 | 4-(6-(morpholin-4-yl)pyridin-3-yl)-N-(3-methyl-4-((6R,9S)-6,9-methano-octahydro-1H-pyrido[1,2-a]pyrazin-2-yl)phenyl)-pyrimidin-2-amine | 0 | 1 | H | —CH$_3$ | — | | | A |
| 246 | 4-(2,2-dimethyl-3-oxo-3,4-dihydro-2H-pyrido[3,2-b][1,4]-oxazin-7-yl)-N-(3-methyl-4-((1S,4S)-5-(1-methyl-ethyl)-2,5-diazabicyclo-[2.2.1]-heptan-2-yl)phenyl)-pyrimidin-2-amine | 0 | 1 | H | —CH$_3$ | — | | | A |

TABLE 2-continued

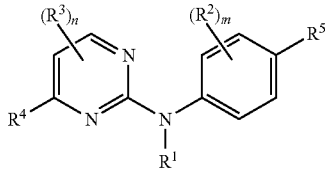
(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 247 | 4-(2,2-dimethyl-3-oxo-3,4-dihydro-2H-pyrido[3,2-b][1,4]oxazin-7-yl)-N-(3-methyl-4-((1S,4S)-5-cyclopropyl-2,5-diazabicyclo-[2.2.1]heptan-2-yl)phenyl)-pyrimidin-2-amine | 0 | 1 | H | —CH$_3$ | — | 2,2-dimethyl-3-oxo-3,4-dihydro-2H-pyrido[3,2-b][1,4]oxazin-7-yl | 5-cyclopropyl-2,5-diazabicyclo[2.2.1]heptan-2-yl | A |
| 248 | 4-(2,2-dimethyl-3-oxo-3,4-dihydro-2H-pyrido[3,2-b][1,4]oxazin-7-yl)-N-(3-chloro-4-((1S,4S)-5-methyl-2,5-diazabicyclo-[2.2.1]-heptan-2-yl)phenyl)-pyrimidin-2-amine | 0 | 1 | H | —Cl | — | 2,2-dimethyl-3-oxo-3,4-dihydro-2H-pyrido[3,2-b][1,4]oxazin-7-yl | 5-methyl-2,5-diazabicyclo[2.2.1]heptan-2-yl | A |
| 249 | 4-(2,2-dimethyl-3-oxo-3,4-dihydro-2H-pyrido[3,2-b][1,4]oxazin-7-yl)-N-(3-chloro-4-((1S,4S)-5-(methylsulfonyl)-2,5-diazabicyclo-[2.2.1]-heptan-2-yl)phenyl)-pyrimidin-2-amine | 0 | 1 | H | —Cl | — | 2,2-dimethyl-3-oxo-3,4-dihydro-2H-pyrido[3,2-b][1,4]oxazin-7-yl | 5-(methylsulfonyl)-2,5-diazabicyclo[2.2.1]heptan-2-yl | A |

TABLE 2-continued

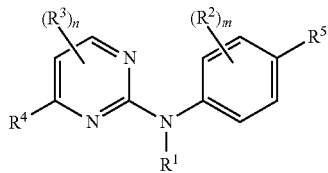

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 250 | 4-(2,2-dimethyl-3-oxo-3,4-dihydro-2H-pyrido[3,2-b][1,4]oxazin-7-yl)-N-(3-methyl-4-((1S,4S)-5-cyclopentyl-2,5-diazabicyclo-[2.2.1]heptan-2-yl)phenyl)-pyrimidin-2-amine | 0 | 1 | H | —CH$_3$ | — | (2,2-dimethyl-3-oxo-pyrido-oxazine) | (5-cyclopentyl-2,5-diazabicyclo[2.2.1]heptane) | A |
| 251 | 4-(2,2-dimethyl-3-oxo-3,4-dihydro-2H-pyrido[3,2-b][1,4]oxazin-7-yl)-N-(3-methyl-4-((1S,4S)-5-acetyl-2,5-diazabicyclo-[2.2.1]-heptan-2-yl)phenyl)-pyrimidin-2-amine | 0 | 1 | H | —CH$_3$ | — | (2,2-dimethyl-3-oxo-pyrido-oxazine) | (5-acetyl-2,5-diazabicyclo[2.2.1]heptane) | A |
| 252 | 4-(2,2-dimethyl-3-oxo-3,4-dihydro-2H-pyrido[3,2-b][1,4]oxazin-7-yl)-N-(3-methyl-4-(1,4-diazabicyclo-[3.2.1]-octan-4-yl)phenyl)-pyrimidin-2-amine | 0 | 1 | H | —CH$_3$ | — | (2,2-dimethyl-3-oxo-pyrido-oxazine) | (1,4-diazabicyclo[3.2.1]octane) | A |

TABLE 2-continued

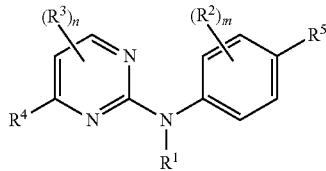

(Ia-1)

IC₅₀ activity: A = <1 μM
B = 1 to 10 μM
C = >10 to 20 μM
D = >20 μM

| Cpd # | Compound Name | n | m | R¹ | R² | R³ | R⁴ | R⁵ | IC₅₀ |
|---|---|---|---|---|---|---|---|---|---|
| 253 | 4-(5-(1-methyl-ethoxy)-carbonyl-propyl-6-amino-pyridin-3-yl)-N-(3-methyl-4-((1S,4S)-5-methyl-2,5-diazabicyclo-[2.2.1]-heptan-2-yl)phenyl)-pyrimidin-2-amine; | 0 | 1 | H | —CH₃ | — | (isopropyl ester butyl-aminopyridine) | (N-methyl-diazabicyclo[2.2.1]heptane) | A |
| 254 | 4-(6-(morpholin-4-yl)pyridin-3-yl)-N-(3-methyl-4-((1S,4S)-5-cyclopropyl-2,5-diazabicyclo-[2.2.1]heptan-2-yl)phenyl)-pyrimidin-2-amine | 0 | 1 | H | —CH₃ | — | (6-morpholinopyridin-3-yl) | (N-cyclopropyl-diazabicyclo[2.2.1]heptane) | A |
| 255 | 4-(6-(morpholin-4-yl)pyridin-3-yl)-N-(3-chloro-4-((1S,4S)-5-methyl-2,5-diazabicyclo-[2.2.1]-heptan-2-yl)phenyl)-pyrimidin-2-amine | 0 | 1 | H | —Cl | — | (6-morpholinopyridin-3-yl) | (N-methyl-diazabicyclo[2.2.1]heptane) | A |
| 256 | 4-(2-(tri-fluoromethyl)-pyridin-4-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH₃ | — | (2-CF₃-pyridin-4-yl) | (N-methyl-diazabicyclo[2.2.1]heptane) | A |

TABLE 2-continued

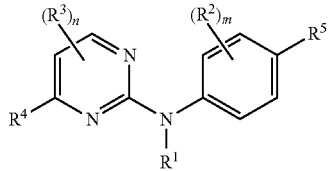

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 257 | 4-(6-(morpholin-4-yl)pyridin-3-yl)-N-(3-chloro-4-((1S,4S)-5-(methyl-sulfonyl)-2,5-diazabicyclo-[2.2.1]-heptan-2-yl)phenyl)-pyrimidin-2-amine | 0 | 1 | H | —Cl | — | 6-(morpholin-4-yl)pyridin-3-yl | (1S,4S)-5-(methylsulfonyl)-2,5-diazabicyclo[2.2.1]heptan-2-yl | A |
| 258 | 4-(6-(tetrahydro-pyran-4-yloxy)pyridin-3-yl)-N-(3-chloro-4-((1S,4S)-5-(methyl-sulfonyl)-2,5-diazabicyclo-[2.2.1]-heptan-2-yl)phenyl)-pyrimidin-2-amine | 0 | 1 | H | —Cl | — | 6-(tetrahydropyran-4-yloxy)pyridin-3-yl | (1S,4S)-5-(methylsulfonyl)-2,5-diazabicyclo[2.2.1]heptan-2-yl | B |
| 259 | 4-(6-(morpholin-4-yl)pyridin-3-yl)-N-(3-chloro-4-((1S,4S)-5-acetyl-2,5-diazabicyclo-[2.2.1]-heptan-2-yl)phenyl)-pyrimidin-2-amine | 0 | 1 | H | —Cl | — | 6-(morpholin-4-yl)pyridin-3-yl | (1S,4S)-5-acetyl-2,5-diazabicyclo[2.2.1]heptan-2-yl | A |
| 260 | 4-(6-(tetrahydro-pyran-4-yloxy)-pyridin-3-yl)-N-(3-chloro-4-((1S,4S)-5-acetyl-2,5-diazabicyclo-[2.2.1]-heptan-2-yl)phenyl)-pyrimidin-2-amine | 0 | 1 | H | —Cl | — | 6-(tetrahydropyran-4-yloxy)pyridin-3-yl | (1S,4S)-5-acetyl-2,5-diazabicyclo[2.2.1]heptan-2-yl | B |

TABLE 2-continued

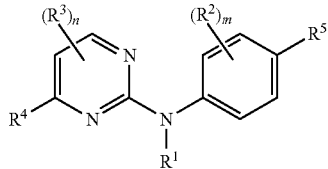

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 261 | 4-(6-(tetra-hydropyran-4-yloxy)pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH$_3$ | — | (tetrahydropyran-4-yloxy)pyridin-3-yl | 5-methyl-2,5-diazabicyclo[2.2.1]heptan-2-yl | A |
| 262 | 4-(6-(tetrahydro-pyran-4-yloxy)pyridin-3-yl)-N-(3-methyl-4-((1S,4S)-5-cyclopentyl-2,5-diazabicyclo-[2.2.1]-heptan-2-yl)phenyl)-pyrimidin-2-amine | 0 | 1 | H | —CH$_3$ | — | (tetrahydropyran-4-yloxy)pyridin-3-yl | 5-cyclopentyl-2,5-diazabicyclo[2.2.1]heptan-2-yl | A |
| 263 | 4-(6-(morpholin-4-yl)pyridin-3-yl)-N-(3-chloro-4-((1S,4S)-5-(1-methylethyl)-2,5-diazabicyclo-[2.2.1]-heptan-2-yl)phenyl)-pyrimidin-2-amine | 0 | 1 | H | —CH$_3$ | — | 6-(morpholin-4-yl)pyridin-3-yl | 5-(1-methylethyl)-2,5-diazabicyclo[2.2.1]heptan-2-yl | A |
| 264 | 4-(6-((1S,4S)-2-oxa-5-azabicyclo-[2.2.1]-heptan-5-yl)pyridin-3-yl)-N-(3-methyl-4-((1S,4S)-5-(methyl-sulfonyl)-2,5-diazabicyclo-[2.2.1]-heptan-2-yl)phenyl)-pyrimidin-2-amine | 0 | 1 | H | —CH$_3$ | — | 6-((1S,4S)-2-oxa-5-azabicyclo[2.2.1]heptan-5-yl)pyridin-3-yl | 5-(methylsulfonyl)-2,5-diazabicyclo[2.2.1]heptan-2-yl | A |

TABLE 2-continued

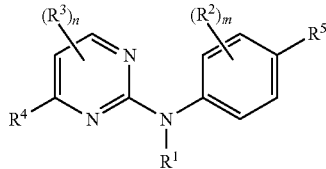

IC₅₀ activity: A = <1 μM
B = 1 to 10 μM
C = >10 to 20 μM
D = >20 μM

| Cpd # | Compound Name | n | m | R¹ | R² | R³ | R⁴ | R⁵ | IC₅₀ |
|---|---|---|---|---|---|---|---|---|---|
| 265 | 4-(6-((1R,4R)-2-oxa-5-azabicyclo-[2.2.1]-heptan-5-yl)pyridin-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH₃ | — | | | A |
| 267 | 4-(6,7,8,9-tetrahydro-5H-pyrido-[2,3-b]indol-3-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH₃ | — | | | B |
| 268 | 4-(6,7,8,9-tetrahydro-5H-pyrido-[2,3-b]indol-3-yl)-N-(3-methyl-4-((1S,4S)-5-(methylsulfonyl)-2,5-diazabicyclo-[2.2.1]-heptan-2-yl)phenyl)-pyrimidin-2-amine | 0 | 1 | H | —CH₃ | — | | | B |
| 269 | 4-(4-(trifluoromethyl)-phenyl)-N-(3-methyl-4-((1S,4S)-5-methyl-2,5-diazabicyclo-[2.2.1]-heptan-2-yl)phenyl)-pyrimidin-2-amine | 0 | 1 | H | —CH₃ | — | | | A |

TABLE 2-continued

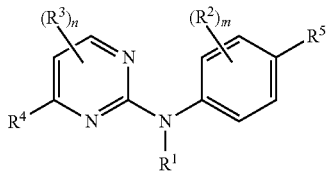

(Ia-1)

IC$_{50}$ activity: A = <1 µM
B = 1 to 10 µM
C = >10 to 20 µM
D = >20 µM

| Cpd # | Compound Name | n | m | R$^1$ | R$^2$ | R$^3$ | R$^4$ | R$^5$ | IC$_{50}$ |
|---|---|---|---|---|---|---|---|---|---|
| 270 | 4-(7,8,9,9a-tetrahydro-5H-pyrido[2,3-e]pyrrolo[1,2-a][1,4]diazepin-10(11H)-on-3-yl)-N-(3-methyl-4-((1S,4S)-5-methyl-2,5-diazabicyclo[2.2.1]heptan-2-yl)phenyl)pyrimidin-2-amine | 0 | 1 | H | —CH$_3$ | — | | | A |
| 271 | 4-(2,2-dimethyl-3-oxo-3,4-dihydro-2H-benzo[b][1,4]oxazin-7-yl)-N-(3-cyano-4-((1S,4S)-5-methyl-2,5-diazabicyclo[2.2.1]heptan-2-yl)phenyl)pyrimidin-2-amine | 0 | 1 | H | —CN | — | | | A |
| 272 | 4-(2-oxo-2,3,4,5-tetrahydro-1H-benzo[b]azepin-7-yl)-N-(3-cyano-4-((1S,4S)-5-methyl-2,5-diazabicyclo[2.2.1]heptan-2-yl)phenyl)pyrimidin-2-amine | 0 | 1 | H | —CN | — | | | A |

TABLE 2-continued

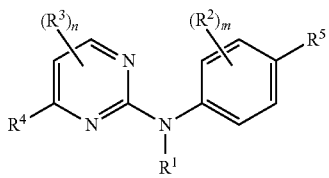

(Ia-1)

IC₅₀ activity: A = <1 µM
B = 1 to 10 µM
C = >10 to 20 µM
D = >20 µM

| Cpd # | Compound Name | n | m | R¹ | R² | R³ | R⁴ | R⁵ | IC₅₀ |
|---|---|---|---|---|---|---|---|---|---|
| 273 | 4-(3-oxo-3,4-dihydro-2H-benzo[b][1,4]-thiazin-7-yl)-N-(3-cyano-4-((1S,4S)-5-methyl-2,5-diazabicyclo-[2.2.1]-heptan-2-yl)phenyl)-pyrimidin-2-amine | 0 | 1 | H | —CN | — | (benzothiazinone) | (methyl-diazabicycloheptane) | A |
| 274 | 4-(3-oxo-3,4-dihydro-2H-benzo[b][1,4]-thiazin-7-yl)-N-(3-methyl-4-((1S,4S)-5-methyl-2,5-diazabicyclo-[2.2.1]-heptan-2-yl)phenyl)-pyrimidin-2-amine | 0 | 1 | H | —CH₃ | — | (benzothiazinone) | (methyl-diazabicycloheptane) | A |
| 275 | 4-(6-(tetrahydropyran-4-yloxy)-pyridin-3-yl)-N-(3-methyl-4-(1,4-diazabicyclo-[3.2.1]octan-4-yl)phenyl)-pyrimidin-2-amine | 0 | 1 | H | —CH₃ | — | (tetrahydropyranyloxy-pyridine) | (diazabicyclooctane) | A |
| 276 | 4-(6-(morpholin-4-yl)-pyridin-3-yl)-N-(3-methyl-4-((R)-1,4-diazabicyclo-[3.2.1]-octan-4-yl)phenyl)-pyrimidin-2-amine | 0 | 1 | H | —CH₃ | — | (morpholinyl-pyridine) | (diazabicyclooctane) | A |

TABLE 2-continued

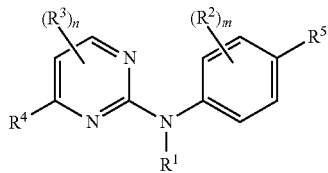

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 277 | 4-(6-(morpholin-4-yl)pyridin-3-yl)-N-(3-methyl-4-((S)-1,4-diazabicyclo-[3.2.1]-octan-4-yl)phenyl)-pyrimidin-2-amine | 0 | 1 | H | —CH$_3$ | — | | | A |
| 278 | 4-(2-oxo-2,3,4,5-tetrahydro-1H-benzo[b]-azepin-7-yl)-N-(3-methyl-4-((6R,9S)-6,9-methano-octahydro-1H-pyrido[1,2-a]-pyrazin-2-yl)phenyl)-pyrimidin-2-amine | 0 | 1 | H | —CH$_3$ | — | | | A |
| 279 | 4-(3-oxo-3,4-dihydro-2H-benzo[b][1,4]-thiazin-7-yl)-N-(3-methyl-4-((6R,9S)-6,9-methano-octahydro-1H-pyrido[1,2-a]pyrazin-2-yl)phenyl)-pyrimidin-2-amine | 0 | 1 | H | —CH$_3$ | — | | | A |
| 280 | 4-(6-((1S,4S)-2-oxa-5-azabicyclo-[2.2.1]-heptan-5-yl)pyridin-3-yl)-N-(3-methyl-4-(1,4-diazabicyclo-[3.2.2]-nonan-4-yl)phenyl)-pyrimidin-2-amine | 0 | 1 | H | —CH$_3$ | — | | | A |

TABLE 2-continued

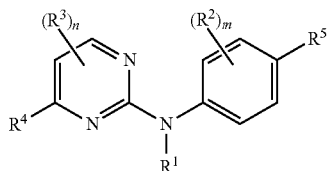

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 281 | 4-(6-(morpholin-4-yl)pyridin-3-yl)-N-(3-cyano-4-(3,9-diazabicyclo-[3.3.2]-decan-10-on-3-yl)phenyl)-pyrimidin-2-amine | 0 | 1 | H | —CN | — | 6-(morpholin-4-yl)pyridin-3-yl | 3,9-diazabicyclo[3.3.2]decan-10-on-3-yl | — |
| 282 | 4-(2,2-dimethyl-3-oxo-3,4-dihydro-2H-pyrido[3,2-b][1,4]oxazin-7-yl)-N-(3-cyano-4-(3,9-diazabicyclo-[3.3.2]-decan-10-on-3-yl)phenyl)-pyrimidin-2-amine | 0 | 1 | H | —CN | — | 2,2-dimethyl-3-oxo-3,4-dihydro-2H-pyrido[3,2-b][1,4]oxazin-7-yl | 3,9-diazabicyclo[3.3.2]decan-10-on-3-yl | — |
| 283 | 4-(6-(tetrahydropyran-4-yloxy)pyridin-3-yl)-N-(3-methyl-4-(3-(dimethyl-amino)-8-azabicyclo-[3.2.1]-octan-8-yl)phenyl)-pyrimidin-2-amine | 0 | 1 | H | —CH$_3$ | — | 6-(tetrahydropyran-4-yloxy)pyridin-3-yl | 3-(dimethylamino)-8-azabicyclo[3.2.1]octan-8-yl | A |
| 284 | 4-(6-(morpholin-4-yl)pyridin-3-yl)-N-(3-methyl-4-(3-(morpholin-4-yl)-8-azabicyclo-[3.2.1]-octan-8-yl)phenyl)-pyrimidin-2-amine | 0 | 1 | H | —CH$_3$ | — | 6-(morpholin-4-yl)pyridin-3-yl | 3-(morpholin-4-yl)-8-azabicyclo[3.2.1]octan-8-yl | A |

TABLE 2-continued

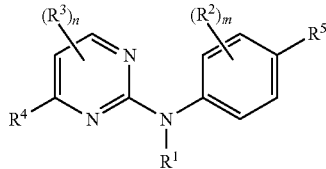

(Ia-1)

IC$_{50}$ activity: A = <1 μM
B = 1 to 10 μM
C = >10 to 20 μM
D = >20 μM

| Cpd # | Compound Name | n | m | R$^1$ | R$^2$ | R$^3$ | R$^4$ | R$^5$ | IC$_{50}$ |
|---|---|---|---|---|---|---|---|---|---|
| 285 | 4-(6-(tetra-hydropyran-4-yloxy)-pyridin-3-yl)-N-(3-methyl-4-(3-(morpholin-4-yl)-8-azabicyclo-[3.2.1]-octan-8-yl)phenyl)-pyrimidin-2-amine | 0 | 1 | H | —CH$_3$ | — | (tetrahydropyran-4-yloxy-pyridin-3-yl) | (3-(morpholin-4-yl)-8-azabicyclo[3.2.1]octan-8-yl) | A |
| 286 | 4-(6-(morpholin-4-yl)pyridin-3-yl)-N-(3-methyl-4-(3-(dimethyl-amino)-8-azabicyclo-[3.2.1]-octan-8-yl)phenyl)-primidin-2-amine | 0 | 1 | H | —CH$_3$ | — | (6-(morpholin-4-yl)pyridin-3-yl) | (3-(dimethylamino)-8-azabicyclo[3.2.1]octan-8-yl) | A |

TABLE 3

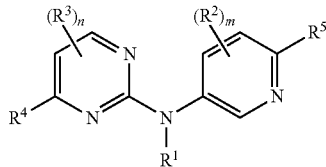

(Ia-2)

| Cpd # | Compound Name | n | m | R$^1$ | R$^2$ | R$^3$ | R$^4$ | R$^5$ | IC$_{50}$ |
|---|---|---|---|---|---|---|---|---|---|
| 54 | 4-(6-(dimethylamino)pyridin-3-yl)-N-(6-((1S,4S)-5-methyl-2,5-diazabicyclo[2.2.1]heptan-2-yl)pyridin-3-yl)pyrimidin-2-amine | 0 | 0 | H | — | — | (6-(dimethylamino)pyridin-3-yl) | ((1S,4S)-5-methyl-2,5-diazabicyclo[2.2.1]heptan-2-yl) | B |
| 55 | 4-(6-(methylcarbonylamino)pyridin-3-yl)-N-(4-((1S,4S)-5-methyl-2,5-diazabicyclo[2.2.1]heptan-2-yl)pyridin-3-yl)pyrimidin-2-amine | 0 | 0 | H | — | — | (6-(methylcarbonylamino)pyridin-3-yl) | ((1S,4S)-5-methyl-2,5-diazabicyclo[2.2.1]heptan-2-yl) | B |

TABLE 3-continued (Ia-2)

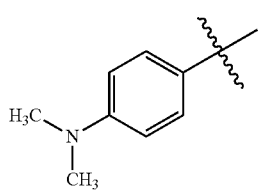

| Cpd # | Compound Name | n | m | R¹ | R² | R³ | R⁴ | R⁵ | IC$_{50}$ |
|---|---|---|---|---|---|---|---|---|---|
| 56 | 4-(4-(dimethylamino)phenyl)-N-(6-((1S,4S)-5-methyl-2,5-diazabicyclo[2.2.1]heptan-2-yl)pyridin-3-yl)pyrimidin-2-amine | 0 | 0 | H | — | — | 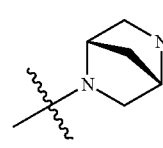 | 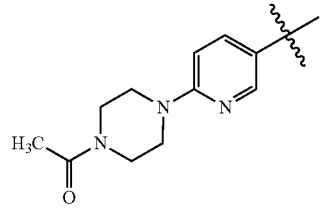 [SMILES: *c1ccc(N2CCN(C(C)=O)CC2)nc1] | B |
| 57 | 4-(6-(4-acetylpiperazin-1-yl)pyridin-3-yl)-N-(6-((1S,4S)-5-methyl-2,5-diazabicyclo[2.2.1]heptan-2-yl)pyridin-3-yl)pyrimidin-2-amine | 0 | 0 | H | — | — | 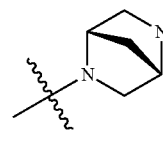 | 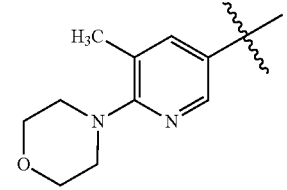 [SMILES: *c1cnc(N2CCOCC2)c(C)c1] | B |
| 58 | 4-(5-methyl-6-(morpholin-4-yl)pyridin-3-yl)-N-(6-((1S,4S)-5-methyl-2,5-diazabicyclo[2.2.1]heptan-2-yl)pyridin-3-yl)pyrimidin-2-amine | 0 | 0 | H | — | — | 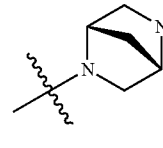 | 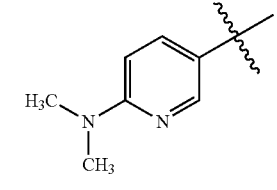 [SMILES: *c1ccc(N(C)C)nc1] | B |
| 61 | 4-(6-(dimethylamino)pyridin-3-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH₃ | — | 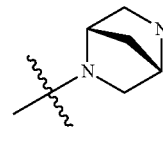 | 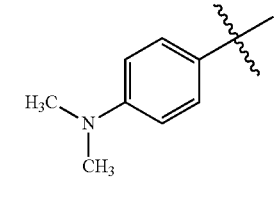 | A |
| 62 | 4-(4-(dimethylamino)phenyl)-N-(5-methyl-6-((1S,4S)-(5-methyl-2,5-diazabicyclo[2.2.1]heptan-2-yl)pyridin-3-yl)pyrimidin-2-amine | 0 | 1 | H | —CH₃ | — | 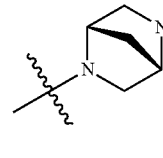 | 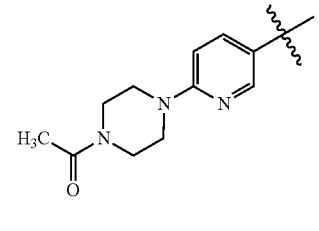 [SMILES: *c1ccc(N2CCN(C(C)=O)CC2)nc1] | B |
| 63 | 4-(6-(4-acetylpiperazin-1-yl)pyridin-3-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH₃ | — | 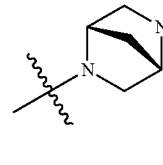 | | B |

TABLE 3-continued

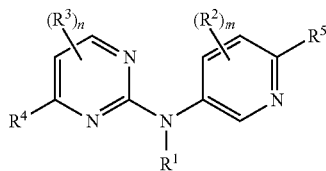

(Ia-2)

| Cpd # | Compound Name | n | m | R¹ | R² | R³ | R⁴ | R⁵ | IC$_{50}$ |
|---|---|---|---|---|---|---|---|---|---|
| 64 | 4-(5-methyl-6-(morpholin-4-yl)pyridin-3-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH$_3$ | — | 3-methyl-6-morpholinopyridin-5-yl | (1S,4S)-5-methyl-2,5-diazabicyclo[2.2.1]heptan-2-yl | A |
| 65 | 4-(4-methyl-3,4-dihydro-2H-pyrido[3,2-b][1,4]oxazin-7-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH$_3$ | — | 4-methyl-3,4-dihydro-2H-pyrido[3,2-b][1,4]oxazin-7-yl | (1S,4S)-5-methyl-2,5-diazabicyclo[2.2.1]heptan-2-yl | A |
| 66 | 4-(6-(morpholin-4-yl)pyridin-3-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH$_3$ | — | 6-morpholinopyridin-3-yl | (1S,4S)-5-methyl-2,5-diazabicyclo[2.2.1]heptan-2-yl | B |
| 131 | 4-(4-(t-butylcarbonylamino)phenyl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH$_3$ | — | 4-(pivaloylamino)phenyl | (1S,4S)-5-methyl-2,5-diazabicyclo[2.2.1]heptan-2-yl | A |
| 138 | 4-(2,2-dimethyl-3-oxo-3,4-dihydro-2H-pyrido[3,2-b][1,4]oxazin-7-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH$_3$ | — | 2,2-dimethyl-3-oxo-3,4-dihydro-2H-pyrido[3,2-b][1,4]oxazin-7-yl | (1S,4S)-5-methyl-2,5-diazabicyclo[2.2.1]heptan-2-yl | A |
| 140 | 4-(4-(3-cyclopropylureido)phenyl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH$_3$ | — | 4-(3-cyclopropylureido)phenyl | (1S,4S)-5-methyl-2,5-diazabicyclo[2.2.1]heptan-2-yl | B |

TABLE 3-continued

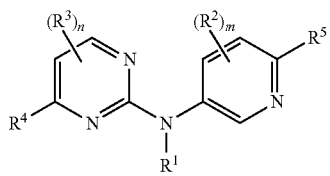

(Ia-2)

| Cpd # | Compound Name | n | m | R¹ | R² | R³ | R⁴ | R⁵ | IC₅₀ |
|---|---|---|---|---|---|---|---|---|---|
| 144 | 4-(6-(2-(morpholin-4-yl)acetamido)pyridin-3-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH₃ | — | morpholinyl-CH₂-C(O)NH-pyridinyl | N-methyl-diazabicycloheptanyl | B |
| 145 | 4-(6-aminopyridin-3-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH₃ | — | 6-aminopyridin-3-yl | N-methyl-diazabicycloheptanyl | A |
| 146 | 4-(6-(acetamido)pyridin-3-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH₃ | — | 6-acetamidopyridin-3-yl | N-methyl-diazabicycloheptanyl | B |
| 154 | 4-(6-(methylsulfonylamino)pyridin-3-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH₃ | — | 6-(methylsulfonylamino)pyridin-3-yl | N-methyl-diazabicycloheptanyl | D |
| 177 | 4-(2-(dimethylamino)thiazol-4-yl)-N-(6-((1S,4S)-5-methyl-2,5-diazabicyclo[2.2.1]heptan-2-yl)pyridin-3-yl)pyrimidin-2-amine | 0 | 0 | H | — | — | 2-(dimethylamino)thiazol-4-yl | N-methyl-diazabicycloheptanyl | D |
| 180 | 4-(5-(morpholin-4-yl)pyrazin-2-yl)-N-(6-((1S,4S)-5-methyl-2,5-diazabicyclo[2.2.1]heptan-2-yl)pyridin-3-yl)pyrimidin-2-amine | 0 | 0 | H | — | — | 5-(morpholin-4-yl)pyrazin-2-yl | N-methyl-diazabicycloheptanyl | B |
| 236 | 4-(1-(pyridin-4-yl)-1H-indol-5-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH₃ | — | 1-(pyridin-4-yl)-1H-indol-5-yl | N-methyl-diazabicycloheptanyl | A |

TABLE 3-continued (Ia-2)

| Cpd # | Compound Name | n | m | R¹ | R² | R³ | R⁴ | R⁵ | IC₅₀ |
|---|---|---|---|---|---|---|---|---|---|
| 266 | 4-(6-((1S,4S)-2-oxa-5-azabicyclo[2.2.1]heptan-5-yl)pyridin-3-yl)-N-(5-methyl-6-((1S,4S)-5-methyl-2,5-diazabicyclo[2.2.1]heptan-2-yl)pyridin-3-yl)pyrimidin-2-amine | 0 | 1 | H | —CH₃ | — | 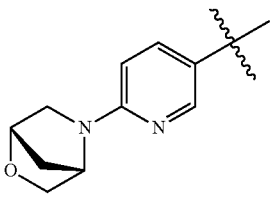 [SMILES: *c1ccc(N2C[C@@H]3C[C@H]2CO3)nc1] | 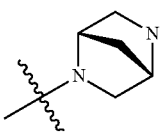 | A |

IC₅₀ activity:
A = <1 μM
B = 1 to 10 μM
C = >10 to 20 μM
D = >20 μM

All of the U.S. patents, U.S. patent application publications, U.S. patent applications, foreign patents, foreign patent applications and non-patent publications referred to in this specification and/or listed in the Application Data Sheet are incorporated herein by reference, in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method of treating, but not preventing, a disease or condition associated with JAK2 activity in a mammal, wherein the method comprises administering to the mammal a therapeutically effective amount of 4-(6-(morpholin-4-yl)pyridin-3-yl)-N-(3-methyl-4-((1S,4S)-5-methyl-2,5-diazabicyclo[2.2.1]heptan-2-yl)phenyl)pyrimidin-2-amine, or a pharmaceutically acceptable salt thereof, and the disease or condition is polycythemia vera disorder, essential thrombocythemia disorder or primary myelofibrosis.

2. A method of treating, but not preventing, a disease or condition associated with JAK2 activity in a mammal, wherein the method comprises administering to the mammal a pharmaceutical composition comprising a pharmaceutically acceptable excipient and a therapeutically effective amount of 4-(6-(morpholin-4-yl)pyridin-3-yl)-N-(3-methyl-4-((1S,4S)-5-methyl-2,5-diazabicyclo[2.2.1]heptan-2-yl)phenyl)pyrimidin-2-amine, or a pharmaceutically acceptable salt thereof, and the disease or condition is polycythemia vera disorder, essential thrombocythemia disorder or primary myelofibrosis.

3. The method of claim 1 wherein the disease or condition is polycythemia vera disorder.

4. The method of claim 1 wherein the disease or condition is essential thrombocythemia disorder.

5. The method of claim 1 wherein the disease or condition is primary myelofibrosis.

6. The method of claim 2 wherein the disease or condition is polycythemia vera disorder.

7. The method of claim 2 wherein the disease or condition is essential thrombocythemia disorder.

8. The method of claim 2 wherein the disease or condition is primary myelofibrosis.

* * * * *